United States Patent
Zhang et al.

(10) Patent No.: US 12,263,171 B2
(45) Date of Patent: Apr. 1, 2025

(54) 7-, 8-, AND 10-SUBSTITUTED AMINO TRIAZOLO QUINAZOLINE DERIVATIVES AS ADENOSINE RECEPTOR ANTAGONISTS, PHARMACEUTICAL COMPOSITIONS AND THEIR USE

(71) Applicant: Merck Sharp & Dohme LLC, Rahway, NJ (US)

(72) Inventors: Yonglian Zhang, East Brunswick, NJ (US); Amjad Ali, Freehold, NJ (US); Jared Cumming, Winchester, MA (US); Duane DeMong, Hanover, MA (US); Qiaolin Deng, Edison, NJ (US); Thomas H. Graham, Somerville, MA (US); Elisabeth Hennessy, Cambridge, MA (US); Matthew A. Larsen, Dedham, MA (US); Kun Liu, Needham, MA (US); Ping Liu, Westfield, NJ (US); Umar Faruk Mansoor, Hopkinton, MA (US); Jianping Pan, Monmouth Junction, NJ (US); Christopher W. Plummer, Westfield, NJ (US); Aaron Sather, Melrose, MA (US); Uma Swaminathan, Auburndale, MA (US); Huijun Wang, Westfield, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 866 days.

(21) Appl. No.: 17/294,836

(22) PCT Filed: Nov. 26, 2019

(86) PCT No.: PCT/US2019/063146
§ 371 (c)(1),
(2) Date: May 18, 2021

(87) PCT Pub. No.: WO2020/112706
PCT Pub. Date: Jun. 4, 2020

(65) Prior Publication Data
US 2023/0054411 A1  Feb. 23, 2023

Related U.S. Application Data

(60) Provisional application No. 62/774,069, filed on Nov. 30, 2018.

(51) Int. Cl.
| | | |
|---|---|---|
| *A61K 31/519* | (2006.01) | |
| *A61K 31/55* | (2006.01) | |
| *A61K 39/395* | (2006.01) | |
| *C07D 471/04* | (2006.01) | |
| *C07D 519/00* | (2006.01) | |

(52) U.S. Cl.
CPC .......... *A61K 31/519* (2013.01); *A61K 31/55* (2013.01); *A61K 39/3955* (2013.01); *C07D 471/04* (2013.01); *C07D 519/00* (2013.01)

(58) Field of Classification Search
CPC .. A61K 31/519; A61K 31/55; A61K 39/3955; C07D 471/04; C07D 519/00
USPC ....................................................... 514/217.06
See application file for complete search history.

(56) References Cited

U.S. PATENT DOCUMENTS

| | | | |
|---|---|---|---|
| 3,957,766 A | 5/1976 | Berger et al. | |
| 4,713,383 A | 12/1987 | Francis et al. | |
| 6,358,964 B1 | 3/2002 | Baraldi | |
| 10,822,338 B2 * | 11/2020 | Ali ..................... | C07D 491/153 |

(Continued)

FOREIGN PATENT DOCUMENTS

| | | |
|---|---|---|
| DE | 2109577 A1 | 9/1972 |
| WO | 2003032996 A1 | 4/2003 |

(Continued)

OTHER PUBLICATIONS

PubChem CID 6623104, create date: Jun. 5, 2006 (Jun. 5, 2006) entire document, 12 pages.

(Continued)

*Primary Examiner* — Kristin A Vajda
(74) *Attorney, Agent, or Firm* — Sanjeev K. Mahanta; Anna L. Cocuzzo

(57) ABSTRACT

In its many embodiments, the present invention provides certain 7-, 8-, and 10-substituted amino triazolo quinazoline derivatives of Formula (I): or a pharmaceutically acceptable salt thereof, wherein ring A, R1, R2, and R4 are as defined herein, pharmaceutical compositions comprising one or more such compounds (alone and in combination with one or more other therapeutic agents), and methods for their preparation and use, alone and in combination with other therapeutic agents, as antagonists of A2a and/or A2b receptors, and their use in the treatment of a variety of diseases, conditions, or disorders that are mediated, at least in part, by the adenosine A2a receptor and/or the adenosine A2b receptor.

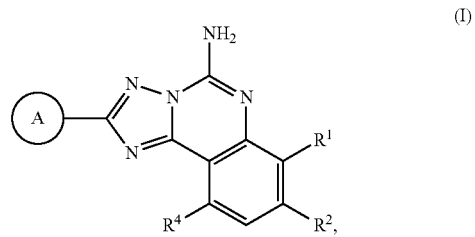

20 Claims, No Drawings

(56) References Cited

U.S. PATENT DOCUMENTS

| | | | |
|---|---|---|---|
| 11,312,719 B2* | 4/2022 | Larsen | A61P 35/00 |
| 2001/0016954 A1 | 8/2001 | Atkinson et al. | |
| 2004/0012471 A1 | 1/2004 | Kojima et al. | |
| 2006/0037003 A1 | 2/2006 | Long et al. | |
| 2006/0058320 A1 | 3/2006 | Iida et al. | |
| 2016/0194330 A1 | 7/2016 | Ali et al. | |
| 2022/0220117 A1* | 7/2022 | Larsen | C07D 487/04 |

FOREIGN PATENT DOCUMENTS

| | | |
|---|---|---|
| WO | 2003048164 A2 | 6/2003 |
| WO | 2003048165 A1 | 6/2003 |
| WO | 2004029056 A1 | 4/2004 |
| WO | 2004092177 A1 | 10/2004 |
| WO | 2005044819 A1 | 5/2005 |
| WO | 2005103055 A1 | 11/2005 |
| WO | 2006068954 A2 | 6/2006 |
| WO | 2007035542 A1 | 3/2007 |
| WO | 2008002596 A2 | 1/2008 |
| WO | 2009077741 A2 | 6/2009 |
| WO | 2009111442 A1 | 9/2009 |
| WO | 2011060207 A1 | 5/2011 |
| WO | 2014101113 A1 | 7/2014 |
| WO | 2014101120 A1 | 7/2014 |
| WO | 2014101373 A1 | 7/2014 |
| WO | 2014105664 A1 | 7/2014 |
| WO | 2014105666 A1 | 7/2014 |
| WO | 2015027431 A1 | 3/2015 |
| WO | 2015031221 A1 | 3/2015 |
| WO | 2016081290 A1 | 5/2016 |
| WO | 2016089796 A1 | 6/2016 |
| WO | 2016126570 A1 | 8/2016 |
| WO | 2016/209787 A1 | 12/2016 |
| WO | 2016200717 A1 | 12/2016 |
| WO | 2017008205 A1 | 1/2017 |
| WO | 2017011214 A1 | 1/2017 |
| WO | 2019118313 A1 | 6/2019 |
| WO | 2020106558 A1 | 5/2020 |
| WO | 2020106560 A1 | 5/2020 |

OTHER PUBLICATIONS

Neustadt, B.R. et al., Potent and selective adeonsine A2A receptor antagonists: 1,2,4-Triazolo[1,5-c]pyrimidines, Bioorganic & Medicinal Chemistry Letters, 2009, 967-971, 19.

Vu, C.B. et al., Tramino derivatives of triazolotriazine and triazolopyrimidine as adenosine A2A receptor antagonists, Bioorganic & Medicinal Chemistry Letters, 2004, 4835-4838, 14.

* cited by examiner

7-, 8-, AND 10-SUBSTITUTED AMINO TRIAZOLO QUINAZOLINE DERIVATIVES AS ADENOSINE RECEPTOR ANTAGONISTS, PHARMACEUTICAL COMPOSITIONS AND THEIR USE

CROSS-REFERENCE TO RELATED APPLICATIONS

This application is a U.S. National Phase application under 35 U.S.C. § 371 of PCT Application No. PCT/US2019/063146, filed Nov. 26, 2019, which published as WO2020/112706 A1 on Jun. 4, 2020, and claims priority under 35 U.S.C. § 365(b) from U.S. provisional patent application No. 62/774,069, filed Nov. 30, 2018.

FIELD OF THE INVENTION

The present invention relates to novel compounds that inhibit at least one of the A2a and A2b adenosine receptors, and pharmaceutically acceptable salts thereof, and compositions comprising such compound(s) and salts, methods for the synthesis of such compounds, and their use in the treatment of a variety of diseases, conditions, or disorders that are mediated, at least in part, by the adenosine A2a receptor and/or the adenosine A2b receptor. Such diseases, conditions, and disorders include but are not limited to cancer and immune-related disorders. The invention further relates to combination therapies, including but not limited to a combination comprising a compound of the invention and a PD-1 antagonist.

BACKGROUND OF THE INVENTION

Adenosine is a purine nucleoside compound comprised of adenine and ribofuranose, a ribose sugar molecule. Adenosine occurs naturally in mammals and plays important roles in various biochemical processes, including energy transfer (as adenosine triphosphate and adenosine monophosphate) and signal transduction (as cyclic adenosine monophosphate). Adenosine also plays a causative role in processes associated with vasodilation, including cardiac vasodilation. It also acts as a neuromodulator (e.g., it is thought to be involved in promoting sleep). In addition to its involvement in these biochemical processes, adenosine is used as a therapeutic antiarrhythmic agent to treat supraventricular tachycardia and other indications.

The adenosine receptors are a class of purinergic G protein-coupled receptors with adenosine as the endogenous ligand. The four types of adenosine receptors in humans are referred to as A1, A2a, A2b, and A3. Modulation of A1 has been proposed for the management and treatment of neurological disorders, asthma, and heart and renal failure, among others. Modulation of A3 has been proposed for the management and treatment of asthma and chronic obstructive pulmonary diseases, glaucoma, cancer, stroke, and other indications. Modulation of the A2a and A2b receptors are also believed to be of potential therapeutic use.

In the central nervous system, A2a antagonists are believed to exhibit antidepressant properties and to stimulate cognitive functions. A2a receptors are present in high density in the basal ganglia, known to be important in the control of movement. Hence, A2a receptor antagonists are believed to be useful in the treatment of depression and to improve motor impairment due to neurodegenerative diseases such as Parkinson's disease, senile dementia (as in Alzheimer's disease), and in various psychoses of organic origin.

In the immune system, adenosine signaling through A2a receptors and A2b receptors, expressed on a variety of immune cells and endothelial cells, has been established as having an important role in protecting tissues during inflammatory responses. In this way (and others), tumors have been shown to evade host responses by inhibiting immune function and promoting tolerance. (See, e.g., Fishman, P., et al., Handb, Exp. Pharmacol. (2009) 193:399-441). Moreover, A2a and A2b cell surface adenosine receptors have been found to be upregulated in various tumor cells. Thus, antagonists of the A2a and/or A2b adenosine receptors represent a new class of promising oncology therapeutics. For example, activation of A2a adenosine receptors results in the inhibition of the immune response to tumors by a variety of cell types, including but not limited to: the inhibition of natural killer cell cytotoxicity, the inhibition of tumor-specific CD4+/CD8+ activity, promoting the generation of LAG-3 and Foxp3+ regulatory T-cells, and mediating the inhibition of regulatory T-cells. Adenosine A2a receptor inhibition has also been shown to increase the efficacy of PD-1 inhibitors through enhanced anti-tumor T cell responses. As each of these immunosuppressive pathways has been identified as a mechanism by which tumors evade host responses, a cancer immunotherapeutic regimen that includes an antagonist of the A2a and/or A2b receptors, alone or together with one or more other therapeutic agents designed to mitigate immune suppression, may result in enhanced tumor immunotherapy. (See, e.g., P. Beavis, et al., Cancer Immunol. Res. DOI: 10.1158/2326-6066. CIR-14-0211, Feb. 11, 2015; Willingham, S B., et al., Cancer Immunol. Res., 6(10), 1136-49; and Leone R D, et al., Cancer Itrimunol, Immunother., August 2018, Vol. 67, Issue 8, 1271-1284).

Cancer cells release ATP into the tumor microenvironment when treated with chemotherapy and radiation therapy, which is subsequently converted to adenosine. (See Martins, I., et al., Cell Cycle, vol. 8, issue 22, pp. 3723 to 3728.) The adenosine can then bind to A2a receptors and blunt the anti-tumor immune response through mechanisms such as those described above. The administration of A2a receptor antagonists during chemotherapy or radiation therapy has been proposed to lead to the expansion of the tumor-specific T-cells while simultaneously preventing the induction of tumor-specific regulatory T-cells. (Young, A., et al., Cancer Discovery (2014) 4:879-888).

The combination of an A2a receptor antagonist with anti-tumor vaccines is believed to provide at least an additive therapeutic effect in view of their different mechanisms of action. Further, A2a receptor antagonists may be useful in combination with checkpoint blockers. By way of example, the combination of a PD-1 inhibitor and an adenosine A2a receptor inhibitor is thought to mitigate the ability of tumors to inhibit the activity of tumor-specific effector T-cells. (See, e.g., Willingham, S B., et al., Cancer Immunol. Res.; 6(10), 1136-49; Leone, R D., et al., Cancer Immunol. Immunother., August 2018, Vol. 67, Issue 8, pp. 1271-1284, Fishman, P., et al., Handb. Exp. Pharmacol. (2009) 193:399-441; and Sitkovsky, M V., et al., (2014) Cancer Immunol. Res 2:598-605.)

The A2b receptor is a G protein-coupled receptor found in various cell types. A2b receptors require higher concentrations of adenosine for activation than the other adenosine receptor subtypes, including A2a (Fredholm, B B., et al., Biochem. Pharmacol. (2001) 61:443-448). Conditions which activate A2b have been seen, for example, in tumors where hypoxia is observed. The A2b receptor may thus play an important role in pathophysiological conditions associated with massive adenosine release. While the pathway(s) associated with A2b receptor-mediated inhibition are not well understood, it is believed that the inhibition of A2b receptors (alone or together with A2a receptors) may block pro-tumorigenic functions of adenosine in the tumor microenvironment, including suppression of T-cell function and angiogenesis, and thus expand the types of cancers treatable by the inhibition of these receptors.

A2b receptors are expressed primarily on myeloid cells. The engagement of A2b receptors on myeloid derived suppressor cells (MDSCs) results in their expansion in vitro (Ryzhov, S. et al., J. Immunol. 2011, 187:6120-6129). MDSCs suppress T-cell proliferation and anti-tumor immune responses. Selective inhibitors of A2b receptors and A2b receptor knockouts have been shown to inhibit tumor growth in mouse models by increasing MDSCs in the tumor microenvironment (Iannone, R., et al., Neoplasia Vol. 13 No. 12, (2013) pp. 1400-1409; Ryzhov, S., et al., Neoplasia (2008) 10: 987-995). Thus, A2b receptor inhibition has become an attractive biological target for the treatment of a variety of cancers involving myeloid cells. Examples of cancers that express A2b receptors can be readily obtained through analysis of the publicly available TCGA database. Such cancers include lung colorectal, head and neck, and cervical cancer, among others, and are discussed in further detail below.

Angiogenesis plays an important role in tumor growth. The angiogenesis process is highly regulated by a variety of factors and is triggered by adenosine under particular circumstances that are associated with hypoxia. The A2b receptor is expressed in human microvascular endothelial cells, where it plays an important role in the regulation of the expression of angiogenic factors such as the vascular endothelial growth factor (VEGF). In certain tumor types, hypoxia has been observed to cause an upregulation of the A2b receptors, suggesting that inhibition of A2b receptors may limit tumor growth by limiting the oxygen supply to the tumor cells. Furthermore, experiments involving adenylate cyclase activation indicate that A2b receptors are the sole adenosine receptor subtype in certain tumor cells, suggesting that A2b receptor antagonists may exhibit effects on particular tumor types. (See, e.g., Feoktistov, I., et al., (2003) Circ. Res. 92:485-492; and P. Fishman, P., et al., Handb. Exp. Pharmacol. (2009) 193:399-441).

In view of their promising and varied therapeutic potential, there remains a need in the art for potent and selective inhibitors of the A2a and/or A2b adenosine receptors, for use alone or in combination with other therapeutic agents. The present invention addresses this and other needs.

SUMMARY OF THE INVENTION

In one aspect, the present invention provides compounds (hereinafter referred to as compounds of the invention) which, surprisingly and advantageously, have been found to be inhibitors of the adenosine A2a receptor and/or the adenosine A2b receptor. The compounds of the invention have a structure in accordance with Formula (I):

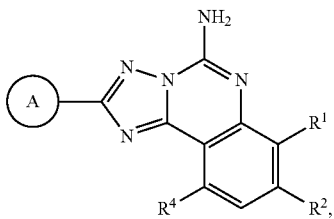

or a pharmaceutically acceptable salt thereof, wherein ring A, $R^1$, $R^2$, and $R^4$ are as defined below.

In another aspect, the present invention provides pharmaceutical compositions comprising at least one compound of the invention, or a pharmaceutically acceptable salt thereof, in a pharmaceutically acceptable carrier or diluent. Such compositions according to the invention may optionally further include one or more additional therapeutic agents as described herein.

In another aspect, the present invention provides a method for treating or preventing a disease, condition, or disorder that is mediated, at least in part, by the adenosine A2a receptor and/or the adenosine A2b receptor in a subject (e.g., an animal or human) in need thereof, said method comprising administering to the subject a therapeutically effective amount of at least one compound of the invention, or a pharmaceutically acceptable salt thereof, alone or in combination with one or more additional therapeutic agents. These and other aspects and embodiments of the invention are described more fully below.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted.

In one embodiment the compounds of the invention have the structural Formula (I):

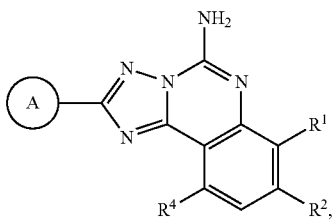

or a pharmaceutically acceptable salt thereof, wherein:
$R^1$ is selected from H, F, Cl, Br, CN, OH, $(C_1$-$C_6)$alkyl, $O(C_1$-$C_6)$alkyl, and $O(C_1$-$C_6)$haloalkyl;
$R^2$ is selected from H, F, Cl, Br, CN, OH, $(C_1$-$C_6)$alkyl, $(C_1$-$C_6)$haloalkyl, $O(C_1$-$C_6)$alkyl, $O(C_1$-$C_6)$haloalkyl, $(C_3$-$C_4)$cycloalkyl, $S(O)_2(C_1$-$C_6)$alkyl, $S(O)_2(C_1$-$C_6)$haloalkyl, and 4-5 membered monocyclic heterocycloalkyl comprising 1 or 2 ring nitrogen atoms;
$R^4$ is selected form H, F, Cl, Br, $(C_1$-$C_6)$alkyl, and $(C_1$-$C_6)$haloalkyl,
with the proviso that at least one of $R^1$, $R^2$, or $R^4$ is not H; and ring A is a moiety selected from:

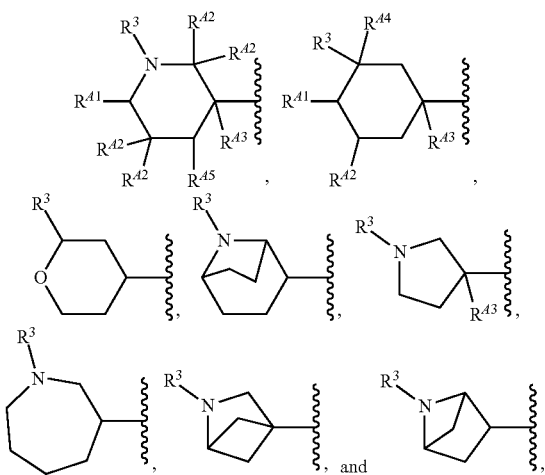

wherein:
R³ is selected from: pyrazolyl, pyridinyl, pyrazinyl, phenyl, oxadiazolyl, thiazolyl, triazolyl, pyrimidinyl, pyridazinyl, and imidazolyl,
wherein said pyridinyl, said pyrazinyl, and said phenyl are substituted with 1, 2, 3, or 4 $R^{3A}$ groups
wherein said pyrazolyl, pyridazinyl, imidazolyl, and said pyrimidinyl are substituted with 1, 2, or 3 $R^{3A}$ groups,
wherein said triazolyl and said thiazolyl are substituted with 1 or 2 $R^{3A}$ groups, and
wherein said oxadiazolyl is substituted with 1 $R^{3A}$ group;
each $R^{3A}$ is independently selected from H, F, Cl, $(C_1\text{-}C_6)$alkyl, $(C_1\text{-}C_6)$alkyl-OH, $(C_1\text{-}C_6)$haloalkyl, $(C_1\text{-}C_6)$alkyl$NH_2$, $O(C_1\text{-}C_6)$alkyl, $O(C_1\text{-}C_6)$haloalkyl, $C(O)(C_1\text{-}C_3)$alkyl, $(C_1\text{-}C_4)$alkylC(O)$(C_1\text{-}C_3)$alkyl, $(C_1\text{-}C_4)$alkylO$(C_1\text{-}C_3)$alkyl, $(C_1\text{-}C_4)$alkylCH(OH)$(C_1\text{-}C_3)$alkyl, $(C_1\text{-}C_4)$alkylS(O)$_2(C_1\text{-}C_3)$alkyl, $(C_1\text{-}C_6)$alkylC(O)NH$(C_1\text{-}C_6)$alkyl, $(C_1\text{-}C_6)$alkylC(O)OH, $(C_1\text{-}C_6)$alkylC(O)NH$(C_3\text{-}C_6)$cycloalkyl,

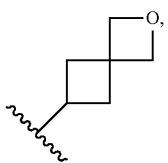 [SMILES: *C1CC2(COC2)C1]

—(CH$_2$)$_n$(C$_3$-C$_7$)cycloalkyl, and —(CH$_2$)$_n$4-7 membered monocyclic heterocycloalkyl comprising 1 or 2 ring heteroatoms selected from O, N, S, and S(O)$_2$,
wherein said (C$_3$-C$_7$)cycloalkyl, and said 4-7 membered monocyclic heterocycloalkyl are each unsubstituted or substituted with 1, 2, or 3 groups independently selected from F, Cl, OH, oxo, (C$_1$-C$_6$)alkyl, O(C$_1$-C$_6$)alkyl, (C$_1$-C$_6$)haloalkyl, and O(C$_1$-C$_6$)haloalkyl;
n is 0, 1, or 2;
each $R^{3Aa}$ is independently selected from H, (C$_1$-C$_4$)alkyl, O(C$_1$-C$_4$)alkyl, (C$_1$-C$_4$)haloalkyl, O(C$_1$-C$_4$)haloalkyl, and (C$_3$-C$_4$)cycloalkyl;
$R^{A1}$ is selected from H, and (C$_1$-C$_4$)alkyl;
each $R^{A2}$ is independently selected from H, F, and (C$_1$-C$_4$)alkyl;
$R^{A3}$ is selected from H, F, and (C$_1$-C$_4$)alkyl;
$R^{A4}$ is selected from H and OH; and
$R^{A5}$ is selected from H, F, and (C$_1$-C$_4$)alkyl.

In another embodiment, the compounds of the invention have the structural Formula (I.1):

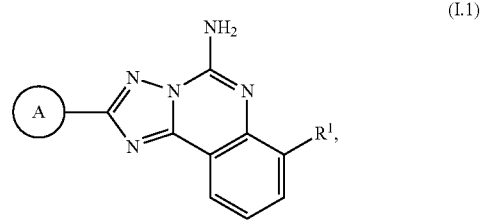

or a pharmaceutically acceptable salt thereof, wherein ring A and R¹ are as defined in Formula (I).

In an alternative of the immediately preceding embodiment of Formula (I.1):
R¹ is selected from F, Cl, Br, CN, OH, CH$_3$, CH$_2$CH$_3$, OCH$_3$, OCH$_2$CH$_3$ and O(C$_1$-C$_6$)haloalkyl.

In an alternative of the immediately preceding embodiment of Formula (I.1):
R¹ is selected from F, Cl, Br, CN, OH, CH$_3$, CH$_2$CH$_3$, OCH$_3$, OCH$_2$CH$_3$, and OCHF$_2$.

In another alternative of the immediately preceding embodiment of Formula (I.1):
R¹ is selected from F, Cl, OH, CH$_3$, CH$_2$CH$_3$, OCH$_3$, and OCHF$_2$.

In another alternative of the immediately preceding embodiment of Formula (I.1):
R¹ is OCH$_3$.

In another alternative of the immediately preceding embodiment of Formula (I.1).
R¹ is F.

In another embodiment, the compounds of the invention have the structural Formula (I.2):

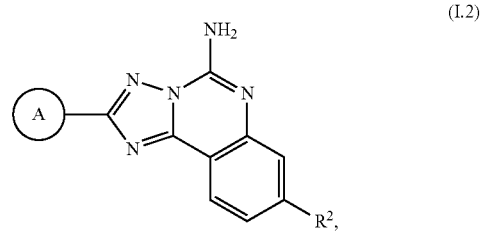

or a pharmaceutically acceptable salt thereof, wherein ring A and R² are as defined in Formula (I).

In an alternative of the immediately preceding embodiment of Formula (I.2):
R² is selected from F, Cl, Br, CN, OH, CH$_3$, CHF$_2$, CF$_3$, CH$_2$CH$_3$, OCH$_3$, OCH$_2$CH$_3$, OCHF, S(O)$_2$CH$_3$,

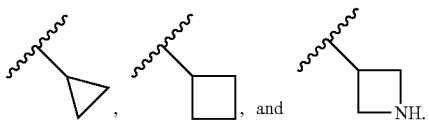

In another alternative of the immediately preceding embodiment of Formula (I.2):
R² is OCH₃.
In another alternative of the immediately preceding embodiment of Formula (I.2):
R² is F.
In another alternative of the immediately preceding embodiment of Formula (I.2):
R² is Cl.
In another alternative of the immediately preceding embodiment of Formula (I.2):
R² is Br.
In another alternative of the immediately preceding embodiment of Formula (I.2):
R² is CH₃.
In another alternative of the immediately preceding embodiment of Formula (I.2):
R² is CH₂CH₃.
In another alternative of the immediately preceding embodiment of Formula (I.2):
R² is selected from CHF₂ and CF₃.
In another alternative of the immediately preceding embodiment of Formula (I.2):
R² is

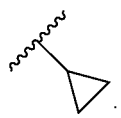 [SMILES: *C1CC1]

In another alternative of the immediately preceding embodiment of Formula (I.2):
R² is

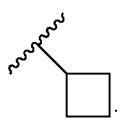

In another alternative of the immediately preceding embodiment of Formula (I.2):
R² is

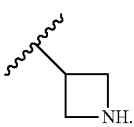

In another embodiment, the compounds of the invention have the structural Formula (I.3):

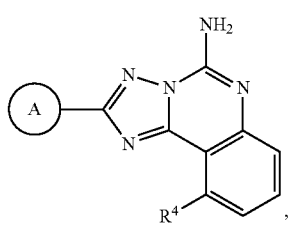

(I.3)

or a pharmaceutically acceptable salt thereof, wherein ring A and R⁴ are as defined in Formula (I).
In an alternative of the immediately preceding embodiment of Formula (I.3):
R⁴ is selected from F, Cl, Br, (C₁-C₆)alkyl, and (C₁-C₆)haloalkyl.
In another alternative of the immediately preceding embodiment of Formula (I.3):
R⁴ is F.
In another alternative of the immediately preceding embodiment of Formula (I.3):
R⁴ is Cl.
In another alternative of the immediately preceding embodiment of Formula (I.3):
R⁴ is CF₃.
In another embodiment, the compounds of the invention have the structural Formula (I.4):

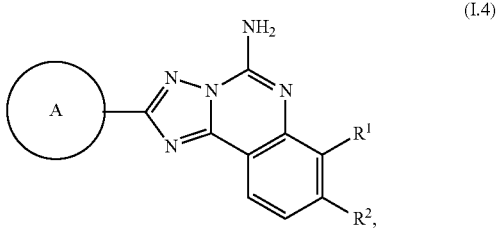

(I.4)

or a pharmaceutically acceptable salt thereof, wherein ring A, R¹, and R² are as defined in Formula (I).
In an alternative of the immediately preceding embodiment, in Formula (I.4):
R¹ is selected from F, Cl, Br, CN, OH, CH₃, OCH₃, CF₃, and OCHF₂; and
R² is selected from F, Cl, Br, CN, OH, CH₃, OCH₃, CF₃, and OCHF₂.
In another alternative of the immediately preceding embodiment, in Formula (I.4):
R¹ is F; and
R² is OCH₃.
In another alternative of the immediately preceding embodiment, in Formula (I.4):
R¹ is CH₃; and
R² is CH₃.
In another alternative of the immediately preceding embodiment, in Formula (I.4).
R¹ is OCH₃; and
R² is Cl.
In another alternative of the immediately preceding embodiment, in Formula (I.4):
R¹ is F; and
R² is F.
In another embodiment, the compounds of the invention have the structural Formula (I.5):

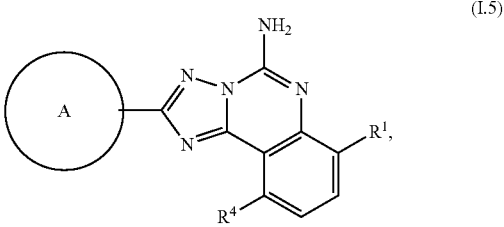

(I.5)

or a pharmaceutically acceptable salt thereof, wherein ring A, R¹, and R⁴ are as define Formula (I).

In an alternative of the immediately preceding embodiment, in Formula (I.5):
R¹ is selected from F, Cl, Br, CN, OH, $CH_3$, $OCH_3$, $CF_3$, and $OCHF_2$; and
R⁴ is selected from F, Cl, Br, CN, OH, $CH_3$, $OCH_3$, and $CF_3$.

In another alternative of the immediately preceding embodiment, in Formula (I.5):
R¹ is F; and
R⁴ is $OCH_3$.

In another alternative of the immediately preceding embodiment, in Formula (I.5):
R¹ is $CH_3$; and
R⁴ is $CH_3$.

In another alternative of the immediately preceding embodiment, in Formula (I.5):
R¹ is $OCH_3$; and
R⁴ is Cl.

In another alternative of the immediately preceding embodiment, in Formula (I.5):
R¹ is F; and
R⁴ is F.

In another alternative of the immediately preceding embodiment, in Formula (I.5):
R¹ is Cl; and
R⁴ is Cl.

In another embodiment, in each of Formulas (I), (I.1), (I.2), (I.3), (I.4), and (I.5):
ring A is:

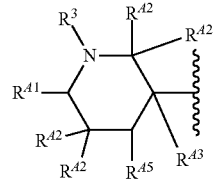

wherein $R^3$, $R^{A1}$, each $R^{A2}$, $R^{A3}$, and $R^{A5}$ are as defined in Formula (I); and wherein R¹, R², and R⁴ are as defined in Formula (I), or wherein R¹ is as defined in Formula (I.1) or as in any of the alternative embodiments of Formula (I.1), or wherein R² is defined in Formula (I.2) or as in any of the alternative embodiments of Formula (I.2), or wherein R⁴ is as defined in Formula (I.3) or as in any of the alternative embodiments of Formula (I.3), or wherein R¹ and R² are as defined in Formula (I.4) or as in any of the alternative embodiments of Formula (I.4), or wherein R¹ and R⁴ are as defined in Formula (I.5) or as in any of the alternative embodiments of Formula (I.5).

In another embodiment, in each of Formulas (I), (I.1), (I.2), (I.3), (I.4), and (I.5):
ring A is:

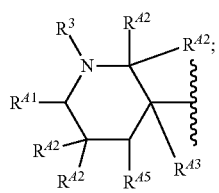

$R^3$ is a moiety selected from:

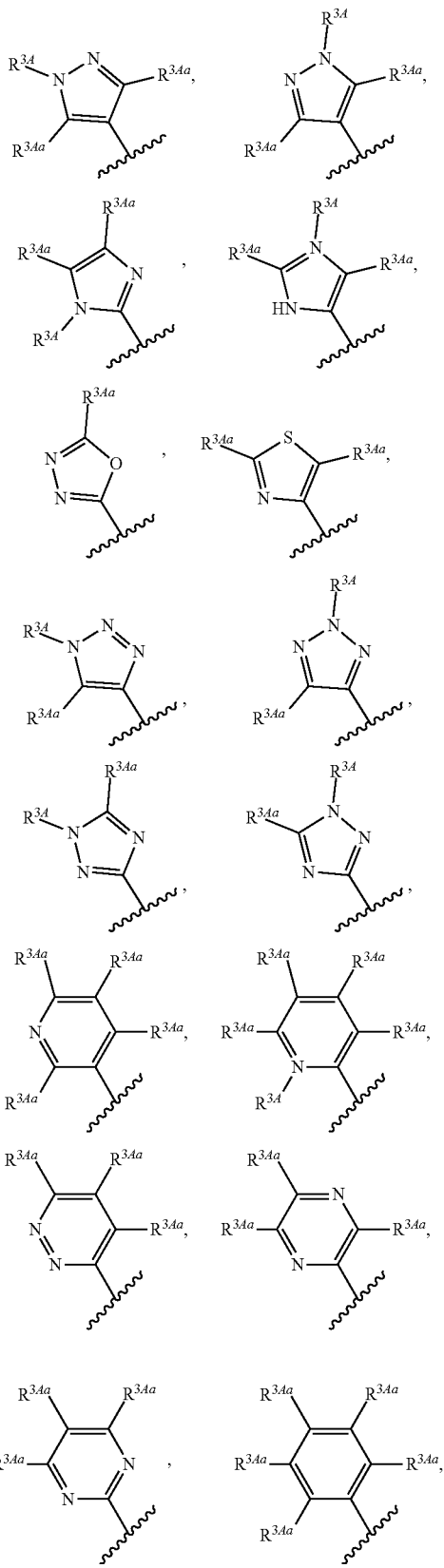

-continued

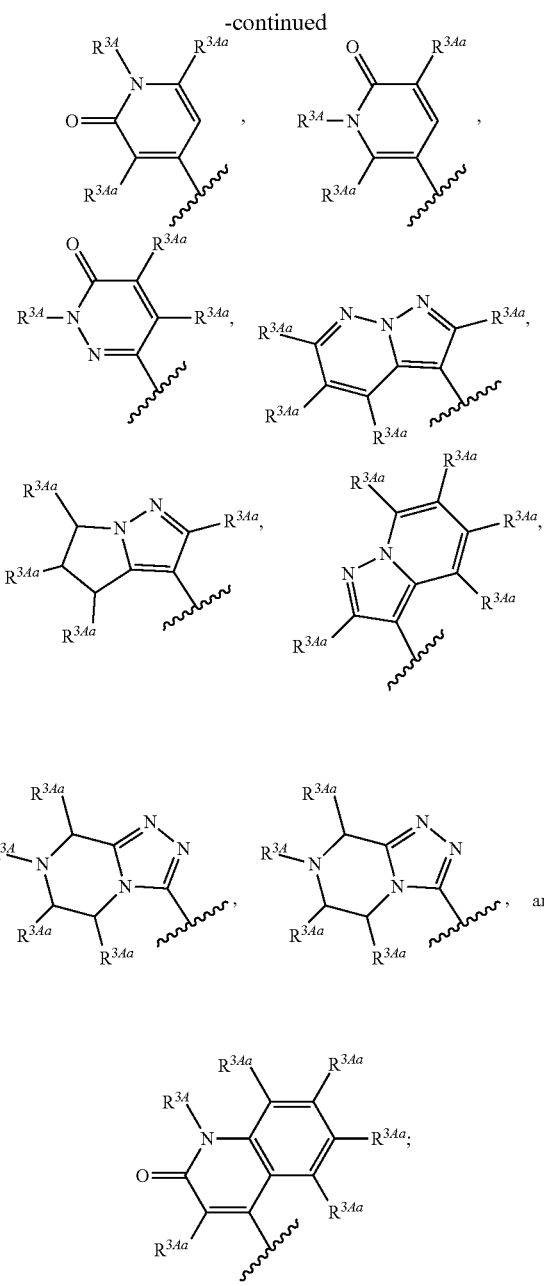

each $R^{3Aa}$, $R^{A1}$, each $R^{A2}$, $R^{A3}$, and $R^{A5}$ are as defined in Formula (I); and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):
ring A is:

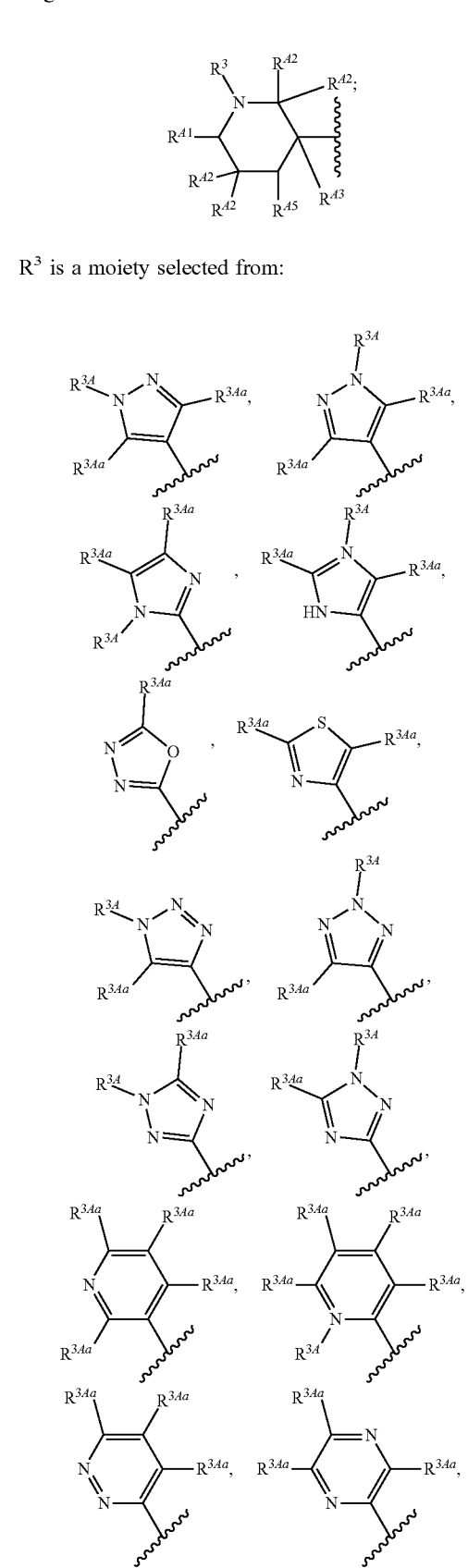

$R^3$ is a moiety selected from:

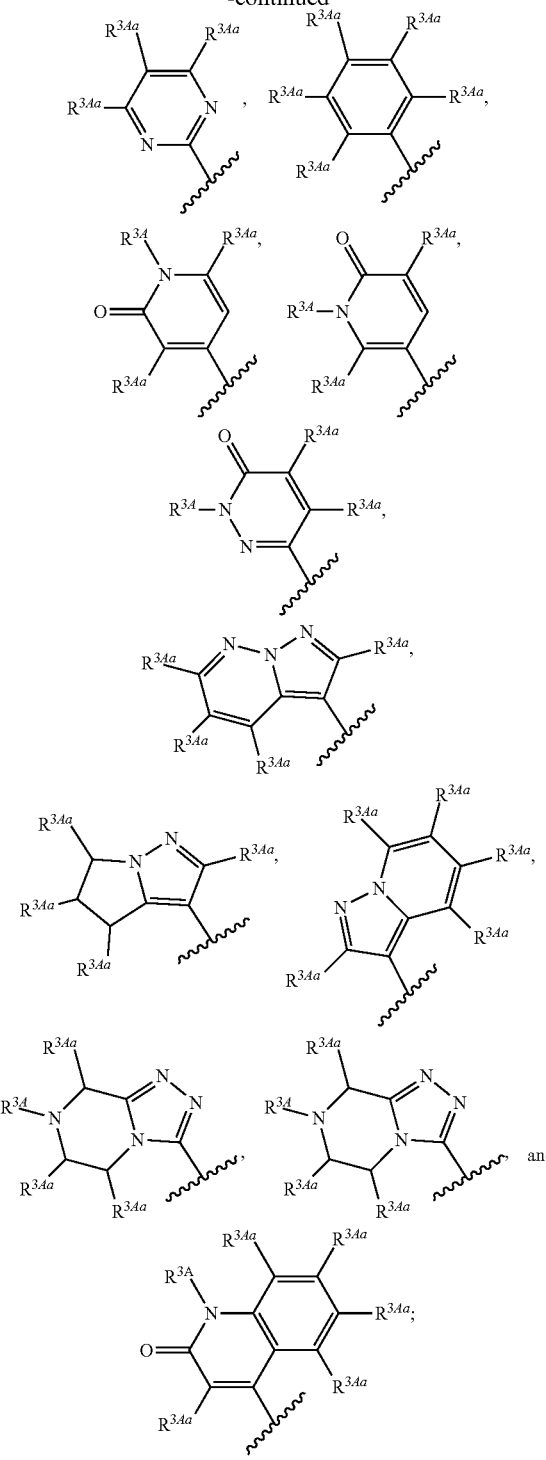
R³ᴬ is a moiety selected from:
H, CH₃, CH₂CH₃,
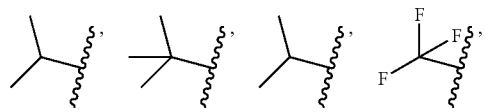
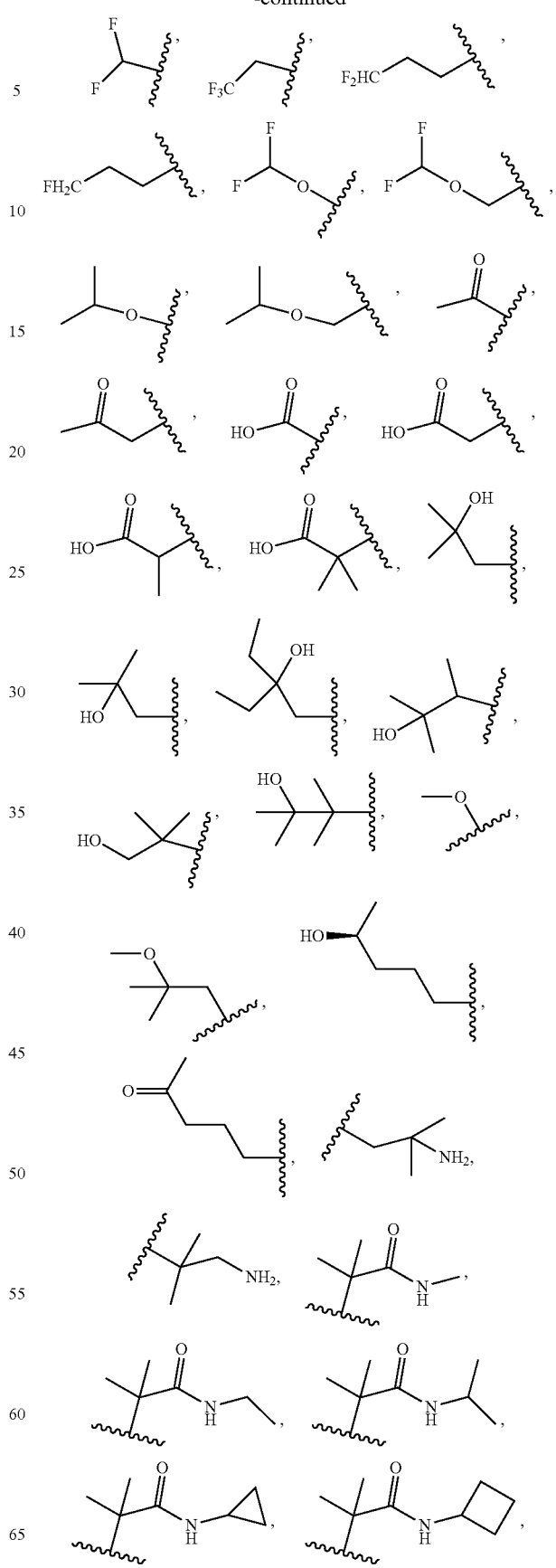

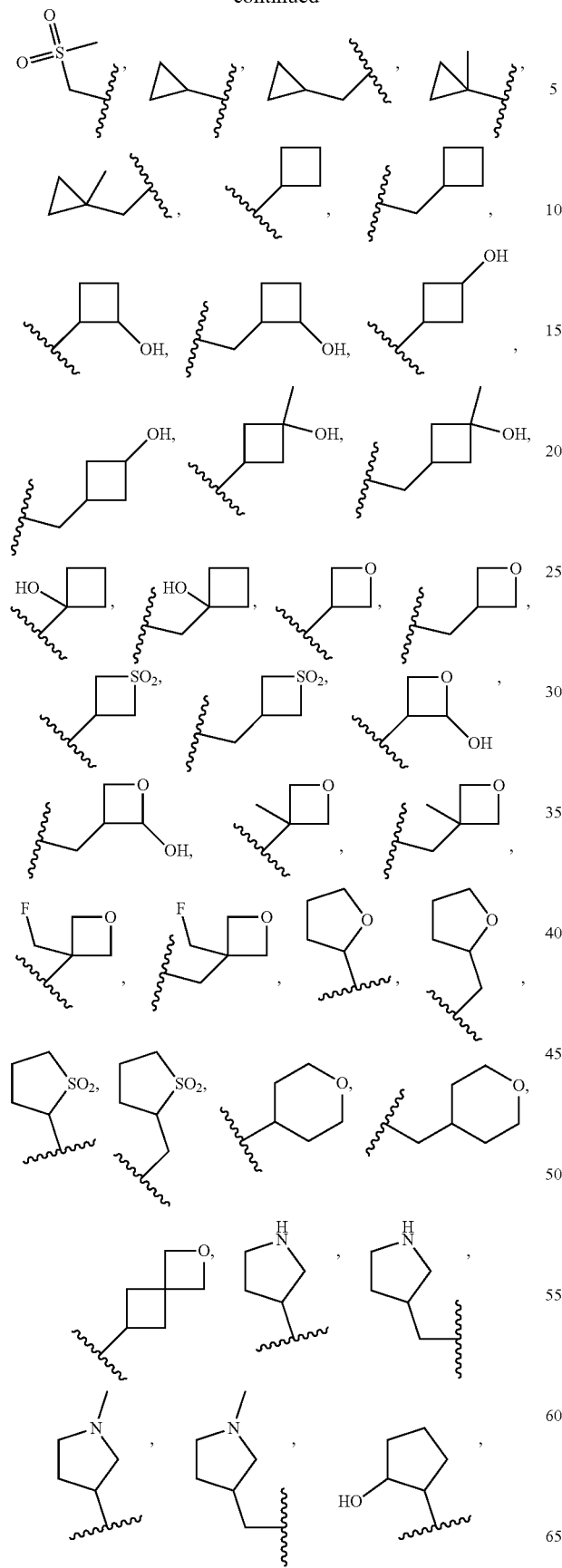
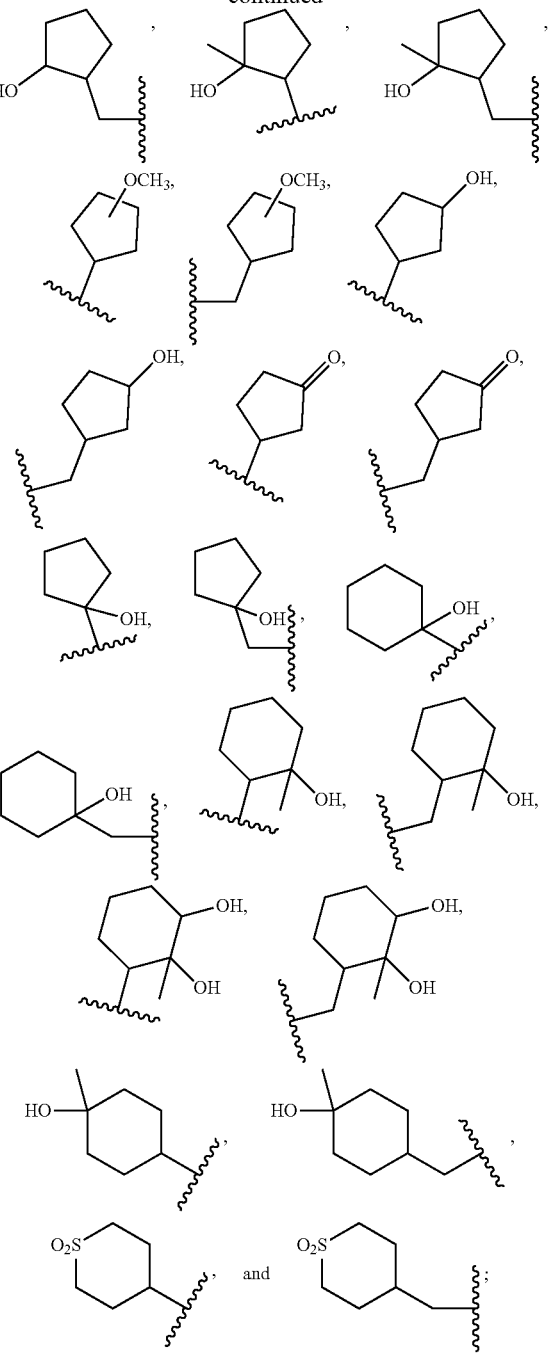

each $R^{3Aa}$, $R^{A1}$, each $R^{A2}$, $R^{A3}$, and $R^{A5}$ are as defined in Formula (I); and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In an alternative of any of the preceding embodiments:
$R^{41}$ is selected from H, $CH_3$, and $CH_2CH_3$;
each $R^{42}$ is independently selected from H, F, $CH_3$, and $CH_2CH_3$;
$R^{43}$ is selected from H and F; and
$R^{45}$ is H.

In another alternative of any of the preceding embodiments:
$R^{41}$ is selected from H and $CH_3$;
each $R^{42}$ is independently selected from H and $CH_3$;
$R^{43}$ is H; and
$R^{45}$ is H.

In another alternative of any of the preceding embodiments:
$R^{41}$ is H;
each $R^{42}$ is H;
$R^{43}$ is H; and
$R^{45}$ is H.

In another alternative of any of the preceding embodiments:
$R^3$ is a moiety selected from:

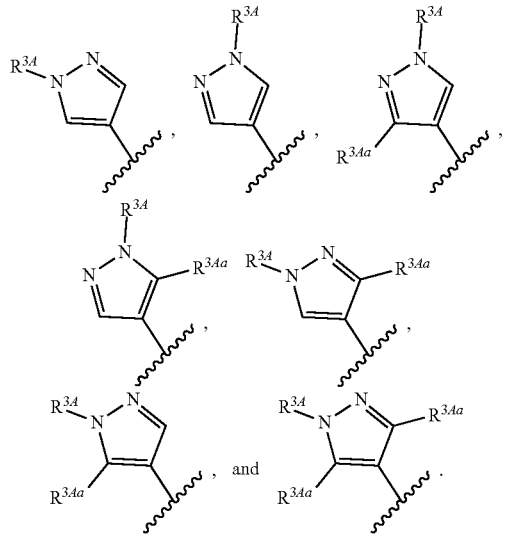

In another embodiment, in each of Formulas (I), (I.1), (I.2), (I.3), (I.4), and (I.5):
ring A is:

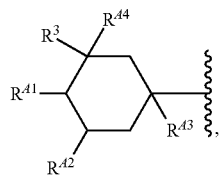

wherein $R^3$, $R^{41}$, $R^{42}$, $R^{43}$, and $R^{44}$ are as defined in Formula (I); and wherein $R^1$, $R^2$, and $R^4$ are as defined in Formula (I), or wherein $R^1$ is as defined in Formula (I.1) or as in any of the alternative embodiments of Formula (I.1), or wherein $R^2$ is as defined in Formula (I.2) or as in any of the alternative embodiments of Formula (I.2), or wherein $R^4$ is as defined in Formula (I.3) or as in any of the alternative embodiments of Formula (I.3), or wherein $R^1$ and $R^2$ are as defined in Formula (I.4) or as in any of the alternative embodiments of Formula (I.4), or wherein $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):
ring A is:

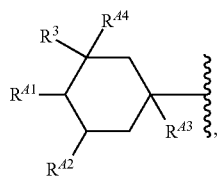

wherein:
$R^3$ is a moiety selected from:

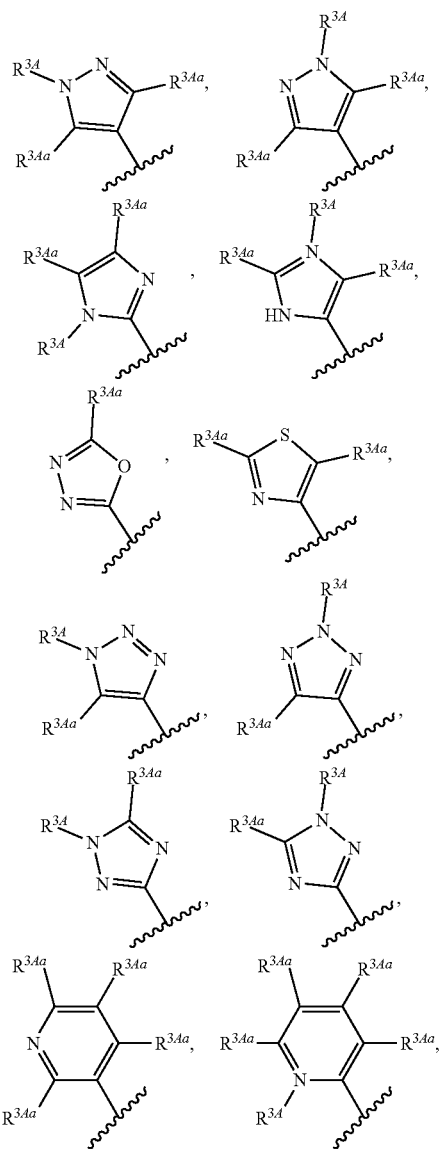

-continued

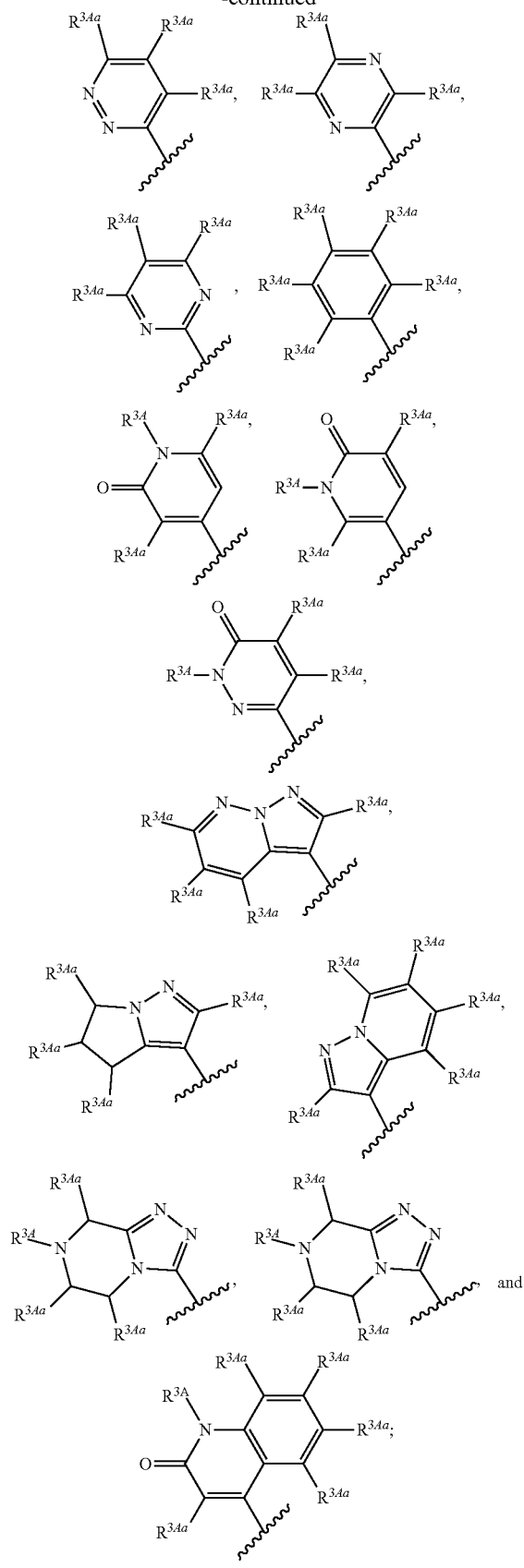

each $R^{3Aa}$, $R^{A1}$, $R^{A2}$, $R^{A3}$, and $R^{A4}$ are as defined in Formula (I);

$R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):

ring A is:

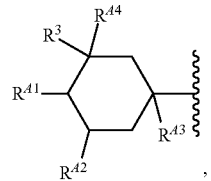

wherein:

$R^3$ is a moiety selected from:

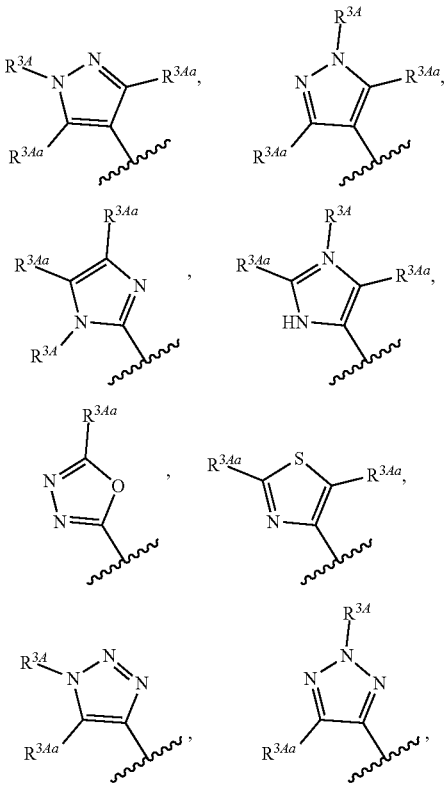

-continued
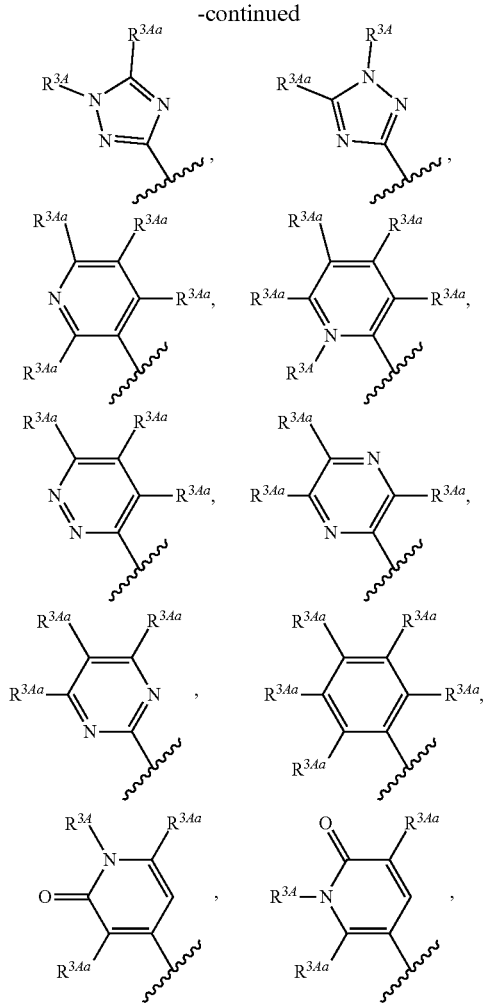
$R^{3A}$ is a moiety selected from:
H, $CH_3$, $CH_2CH_3$,
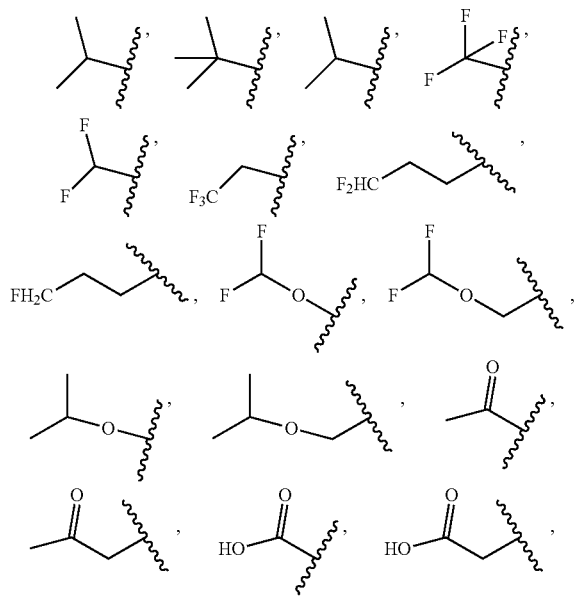
-continued
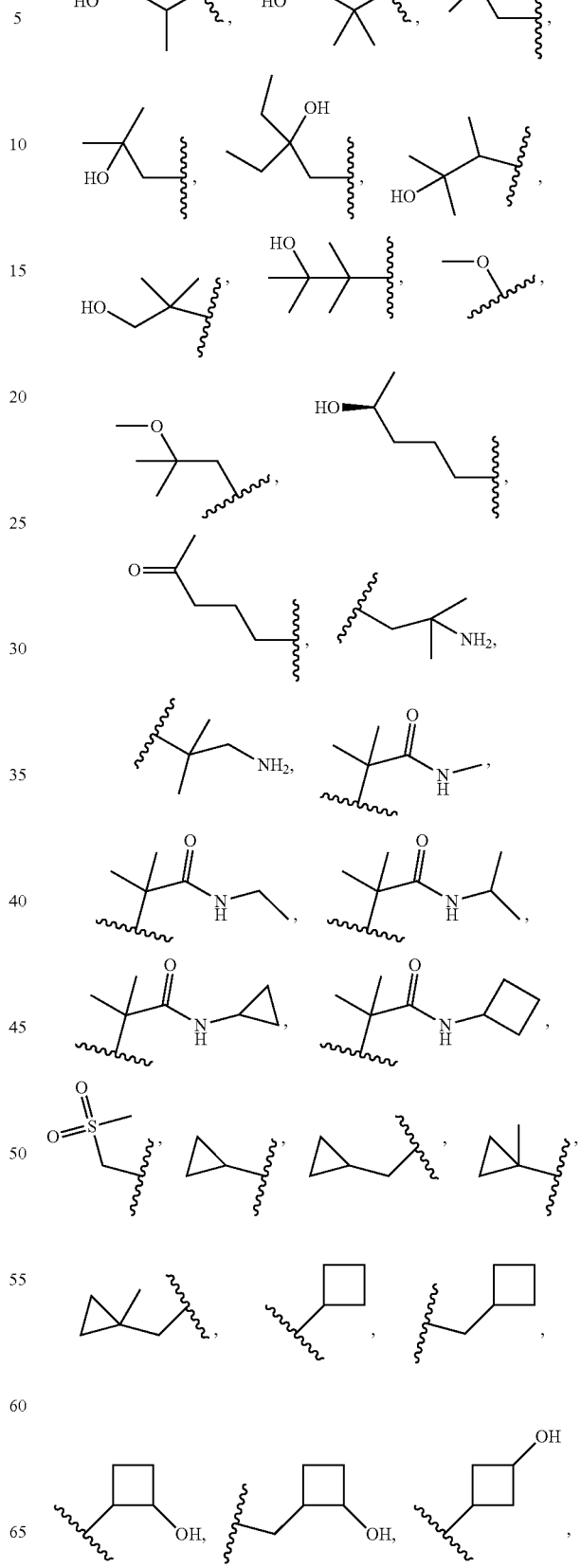

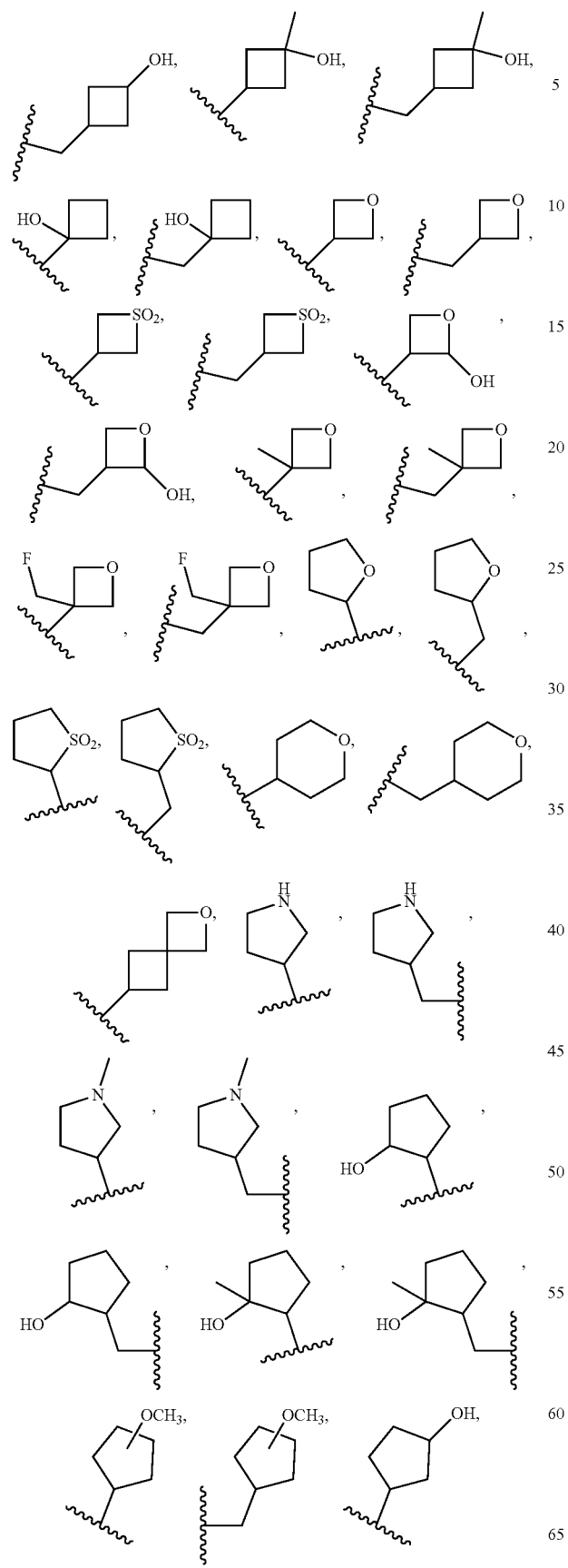
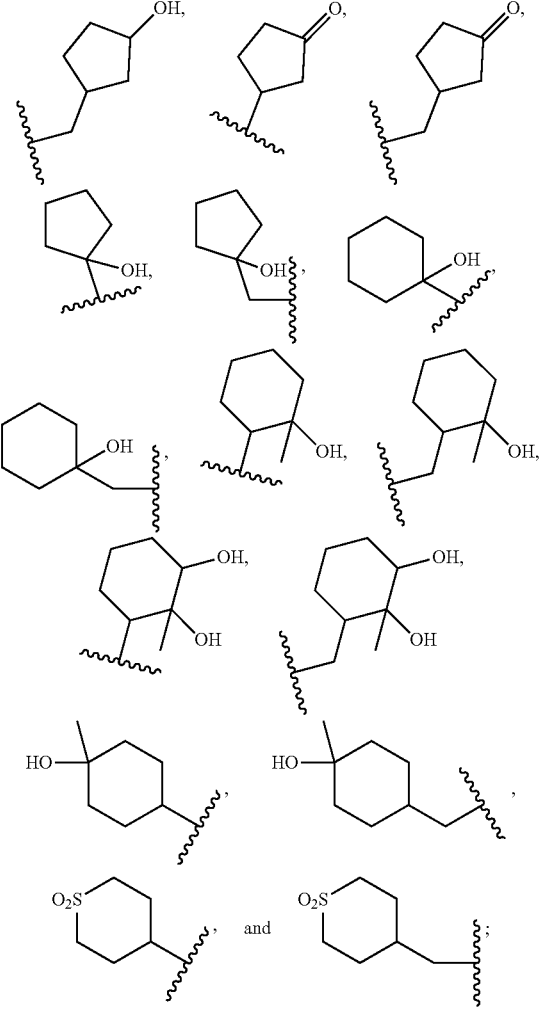

each $R^{3Aa}$, $R^{A1}$, $R^{A2}$, $R^{A3}$, and $R^{A4}$ are as defined in Formula (I); and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In an alternative of any of the preceding embodiments:
$R^{A1}$ is selected from H, $CH_3$, and $CH_2CH_3$;
$R^{A2}$ is selected from H, F, $CH_3$, and $CH_2CH_3$;
$R^{A3}$ is selected from H and F; and
$R^{A4}$ is selected from H, $CH_3$, and OH.

In another alternative of any of the preceding embodiments:
$R^{A1}$ is H:
$R^{A2}$ is H:
$R^{A3}$ is H; and $R^{A4}$ is selected from H, $CH_3$, and OH.

In another alternative of any of the preceding embodiments:

$R^3$ is a moiety selected from:

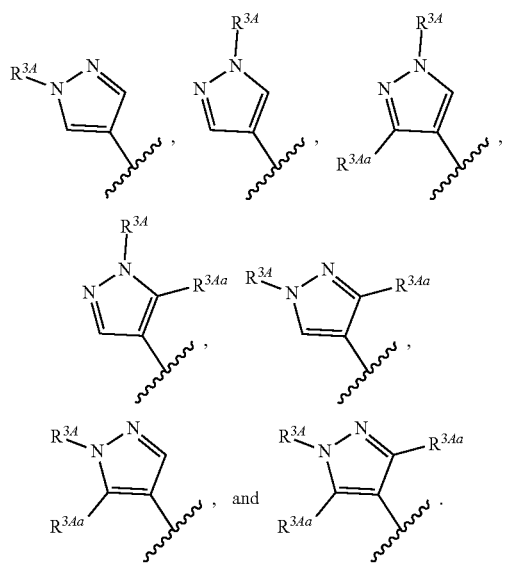

In another embodiment, in each of Formulas (I), (I.1), (I.2), (I.3), (I.4), and (I.5):

ring A is:

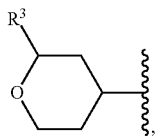

wherein $R^3$ is as defined in Formula (I); and wherein $R^1$, $R^2$, and $R^4$ are as defined in Formula (I), or wherein $R^1$ is as defined in Formula (I.1) or as in any of the alternative embodiments of Formula (I.1), or wherein $R^2$ is as defined in Formula (I.2) or as in any of the alternative embodiments of Formula (I.2), or wherein $R^4$ is as defined in Formula (I.3) or as in any of the alternative embodiments of Formula (I.3), or wherein $R^1$ and $R^2$ are as defined in Formula (I.4) or as in any of the alternative embodiments of Formula (I.4), or wherein $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):

ring A is:

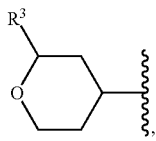

wherein:

$R^3$ is a moiety selected from:

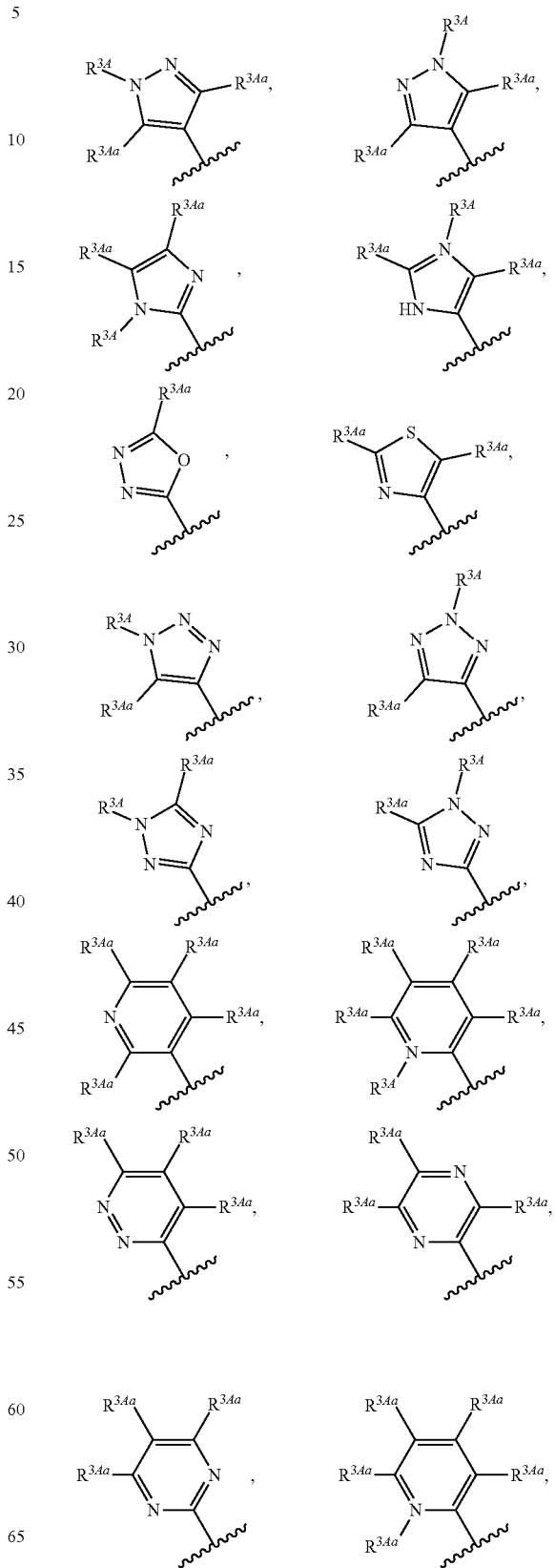

-continued

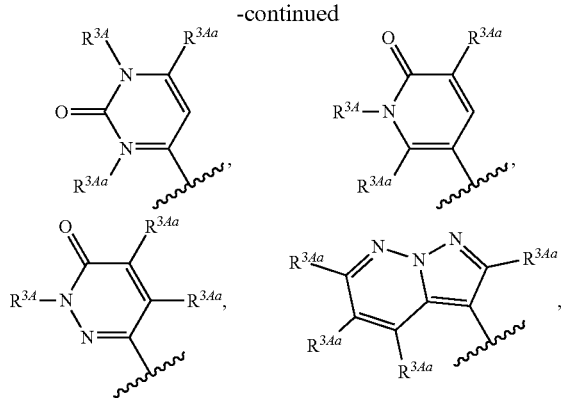

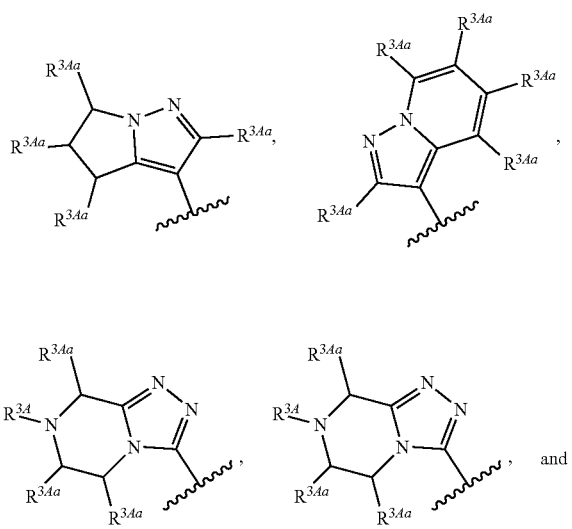

each $R^{3Aa}$ is as defined in Formula (I); and
$R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):
ring A is:

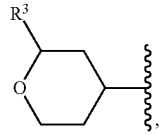

wherein:
$R^3$ is a moiety selected from:

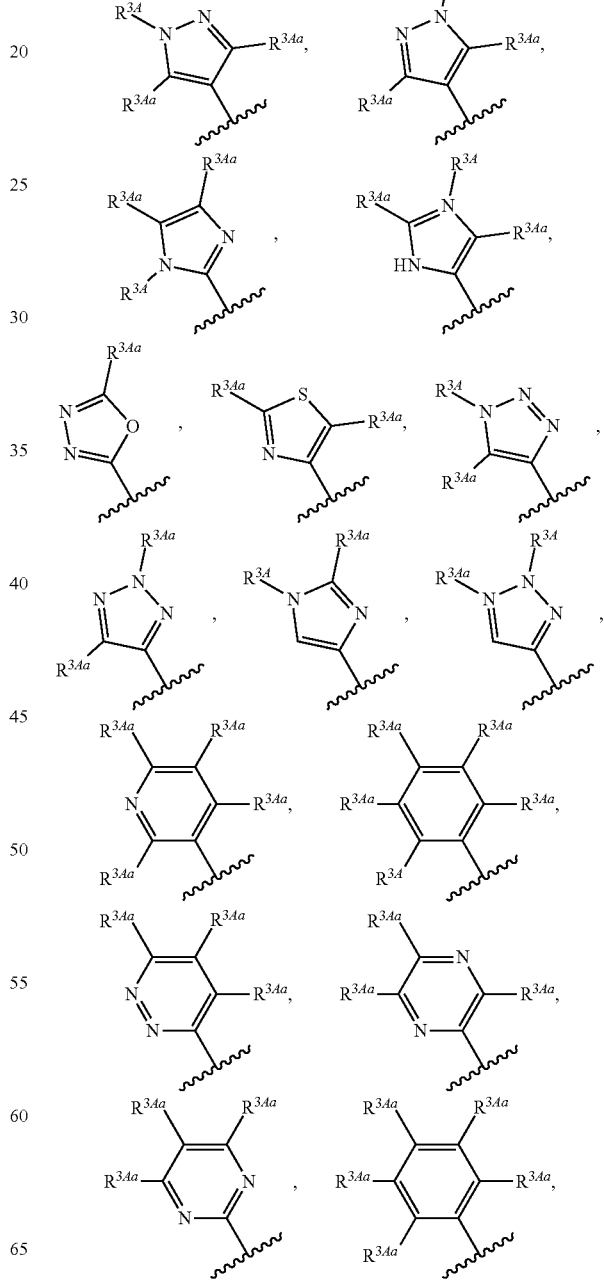

-continued
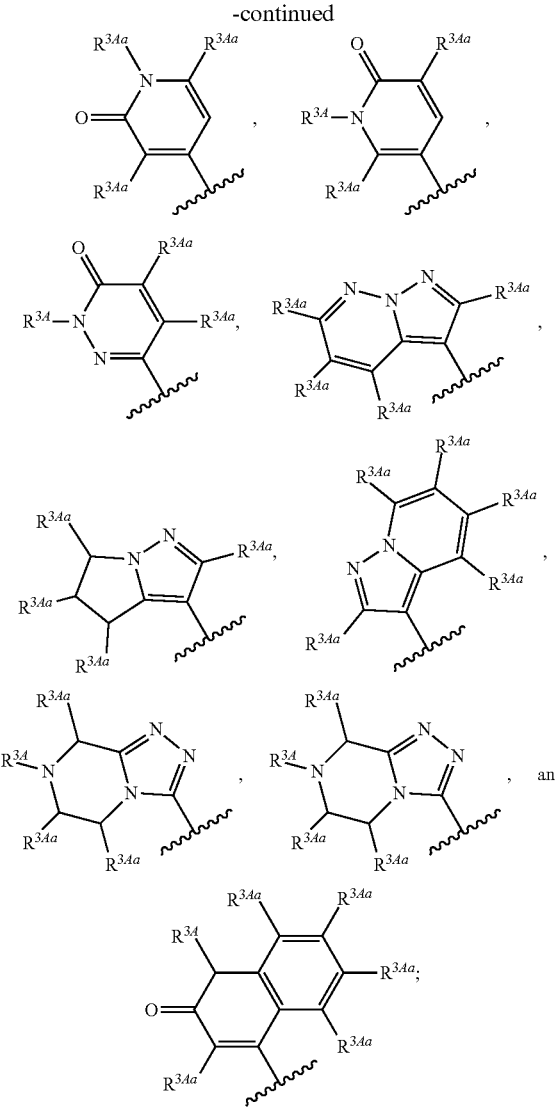
$R^{3A}$ is a moiety selected from:
H, CH₃, CH₂CH₃,
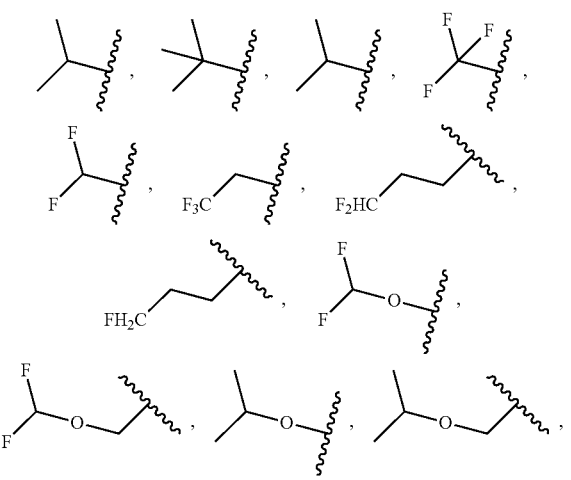
-continued
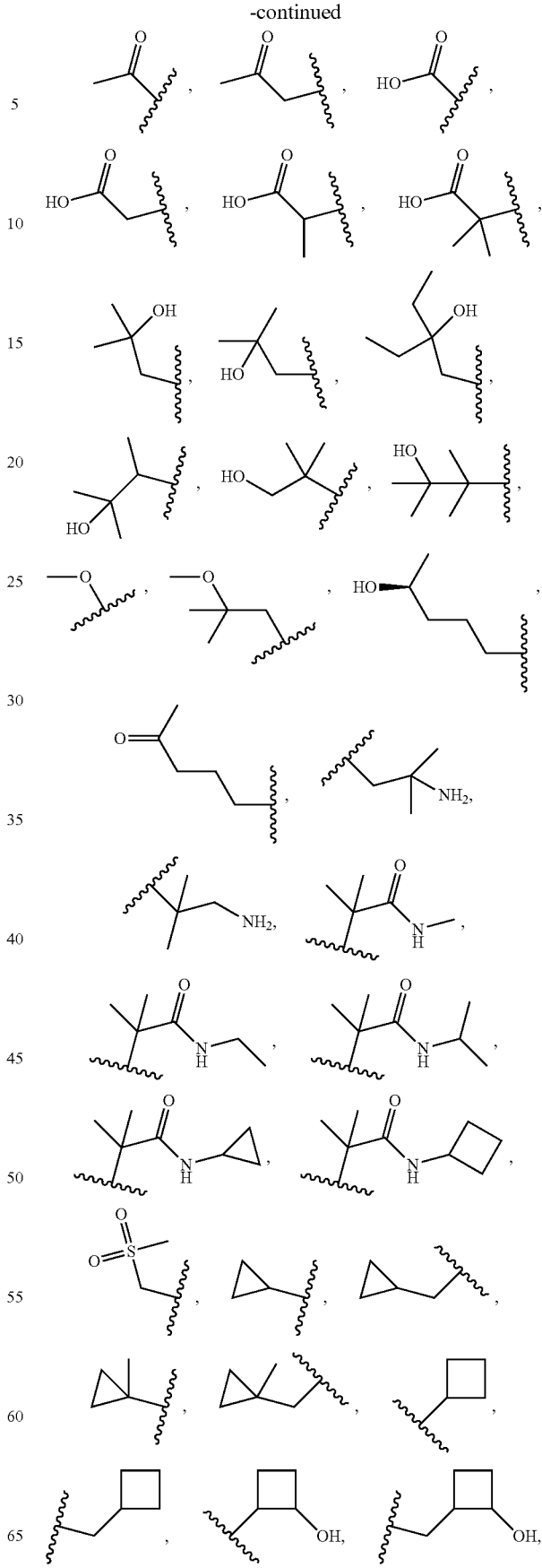

-continued

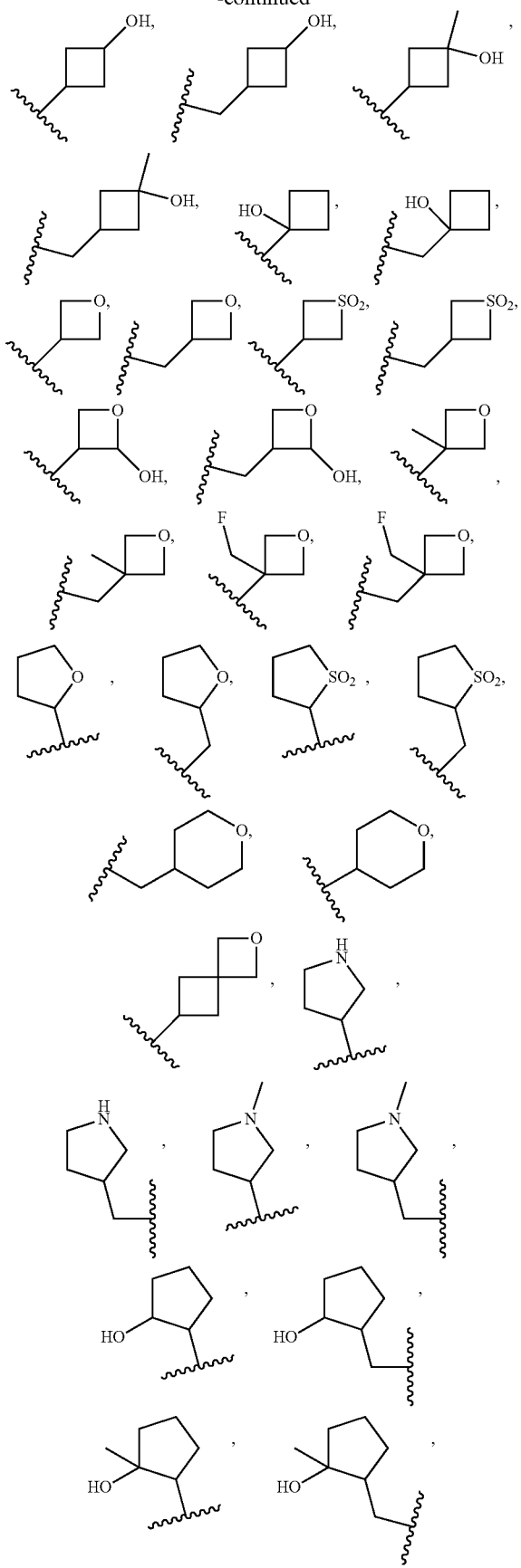
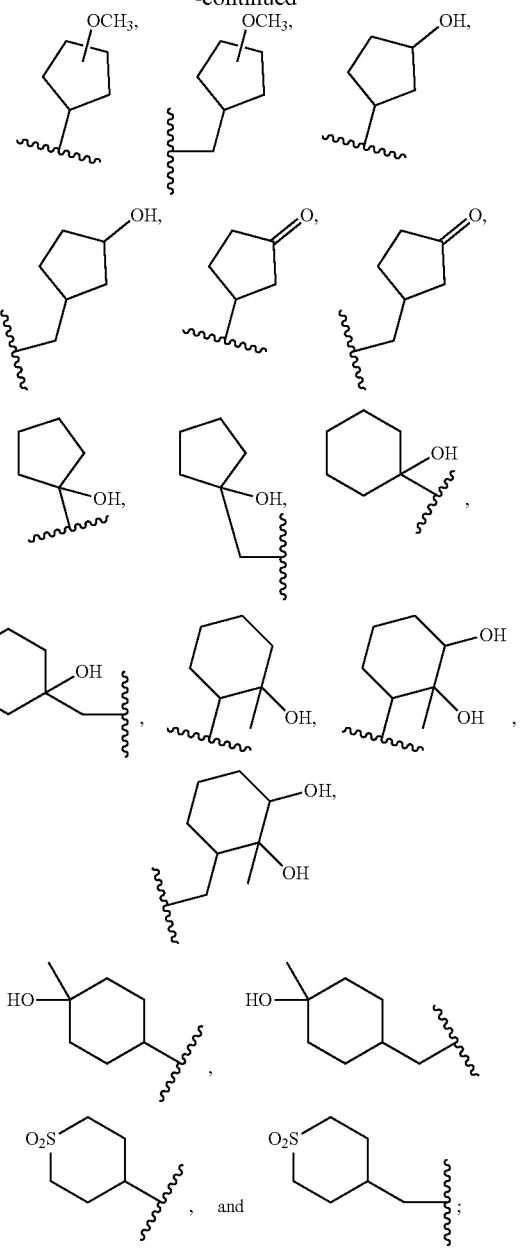

each $R^{3Aa}$ is as defined in Formula (I); and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another alternative of any of the preceding embodiments:

R³ is a moiety selected from:

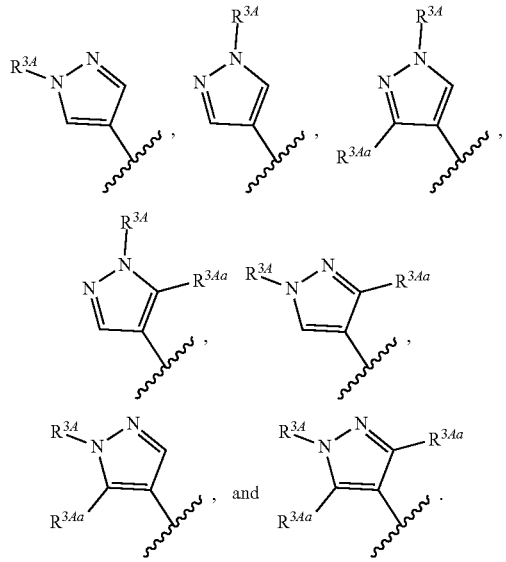

In another embodiment, in each of Formulas (I), (I.1), (I.2), (I.3), (I.4), and (I.5):

ring A is:

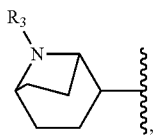

wherein R³ is as defined in Formula (I); and wherein R¹, R², and R⁴ are as defined in Formula (I), or wherein R¹ is as defined in Formula (I.1) or as in any of the alternative embodiments of Formula (I.1), or wherein R² is as defined in Formula (I.2) or as in any of the alternative embodiments of Formula (I.2), or wherein R⁴ is as defined in Formula (I.3) or as in any of the alternative embodiments of Formula (I.3), or wherein R¹ and R² are as defined in Formula (I.4) or as in any of the alternative embodiments of Formula (I.4), or wherein R¹ and R⁴ are as defined in Formula (I.5) or as in any of the alternative embodiments of Formula (I.5).

In another embodiment, in each of Formulas (I), (I.1), (I.2), (I.3), (I.4), and (I.5):

ring A is:

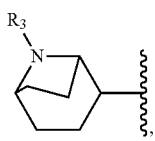

wherein:

R³ is a moiety selected from:

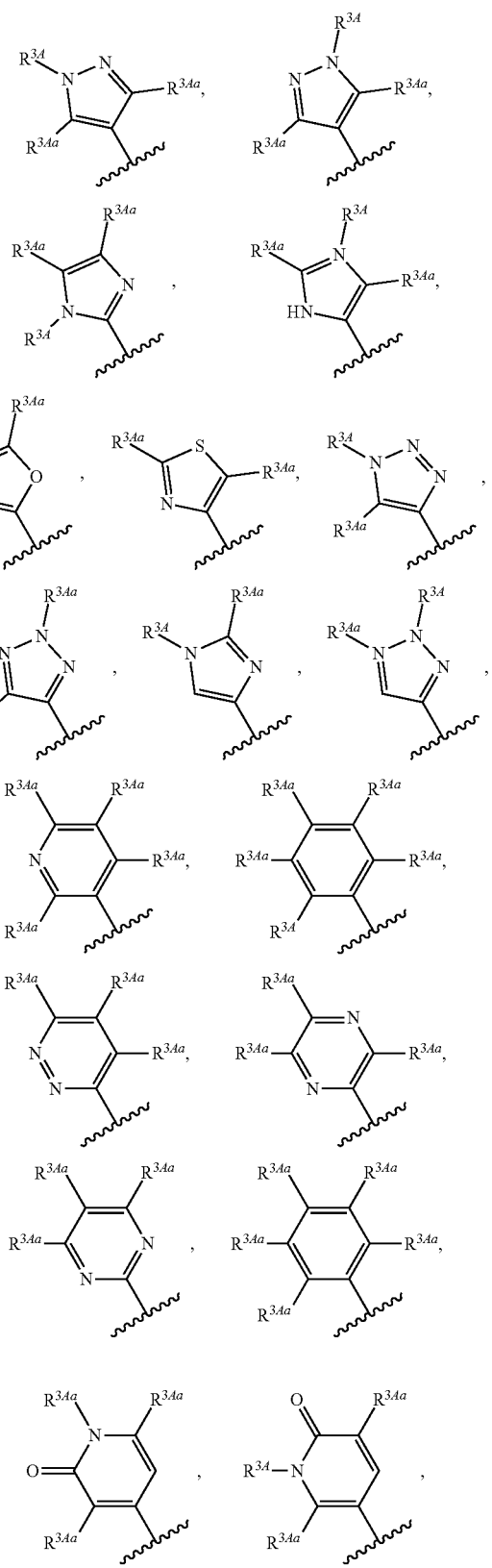

-continued

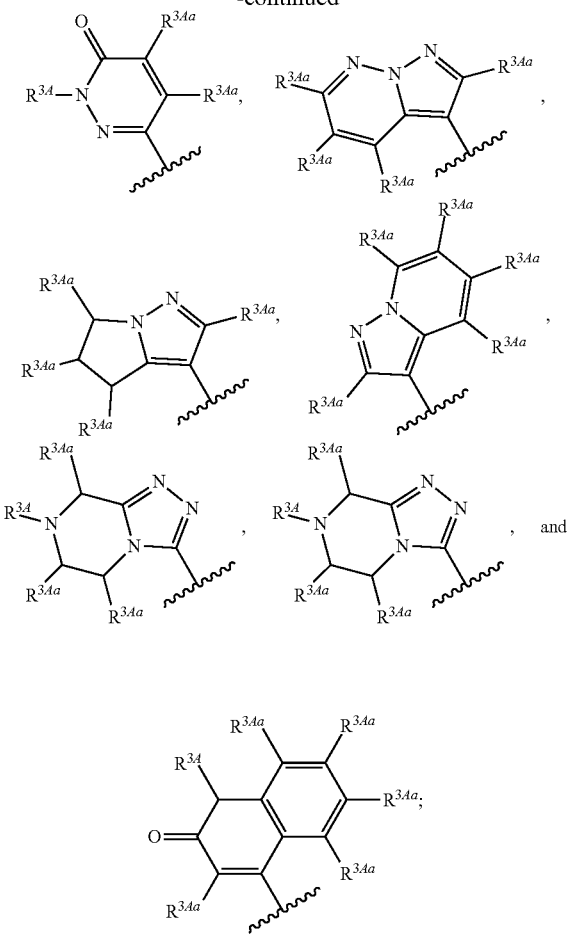

each $R^{3Aa}$ is as defined in Formula (I); and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):

ring A is:

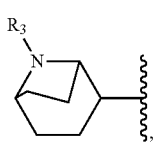

wherein:

$R^3$ is a moiety selected from:

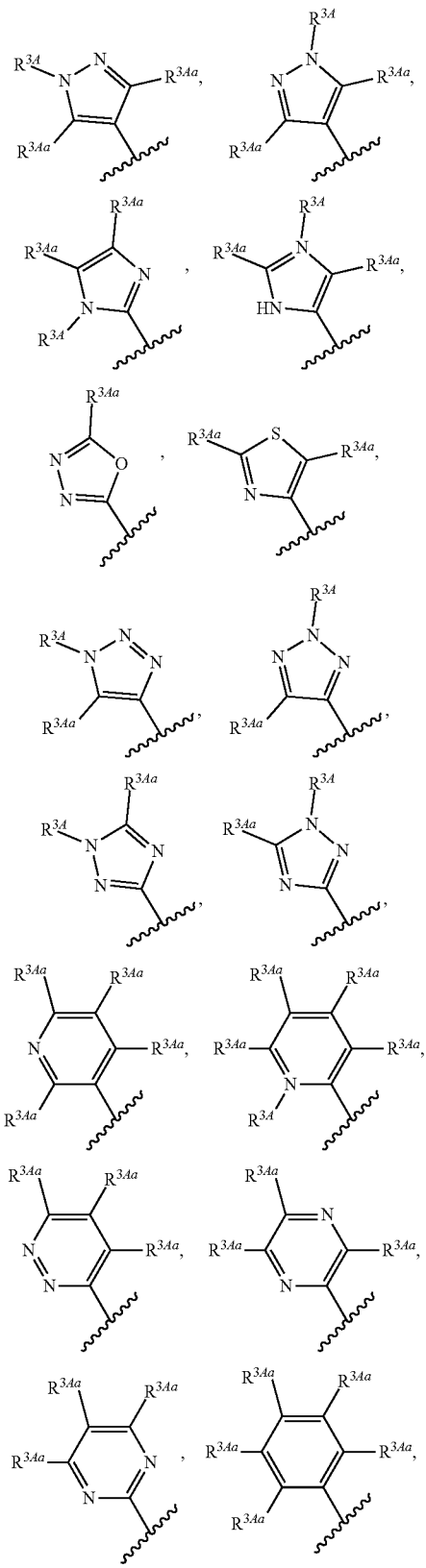

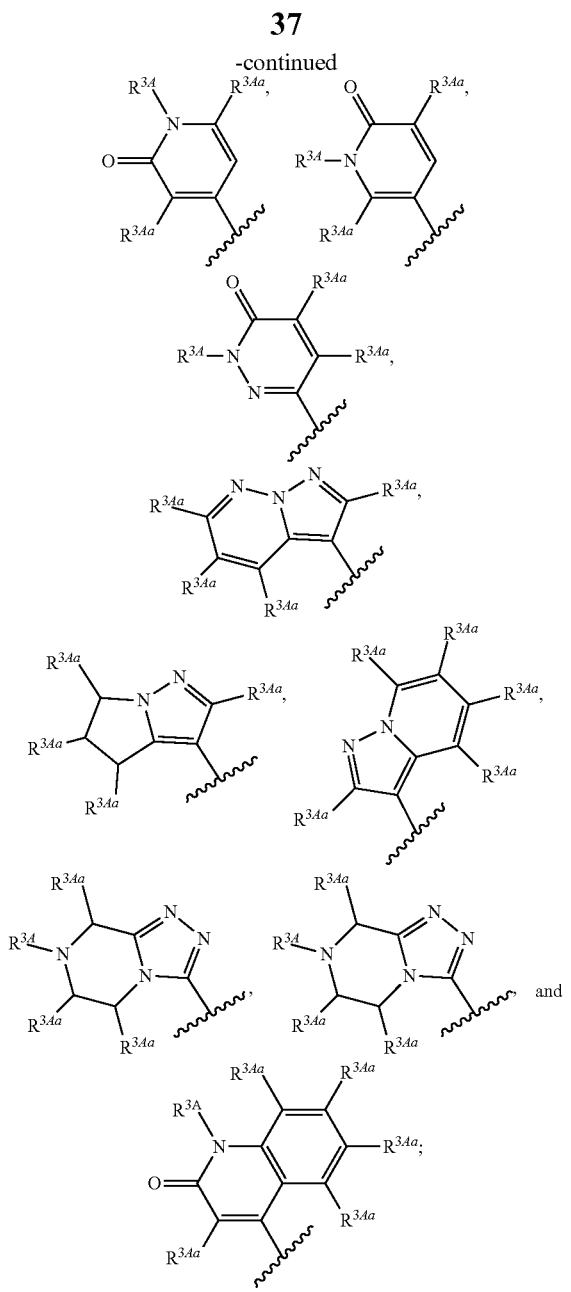
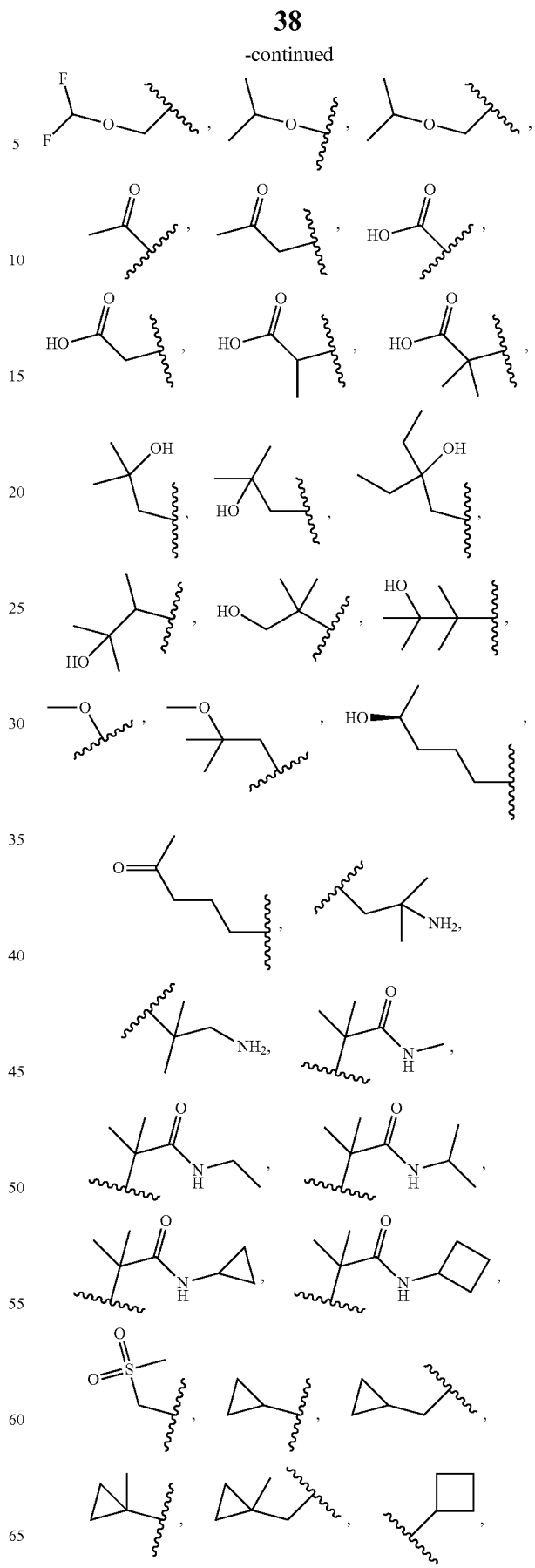
R$^{3A}$ is a moiety selected from:
H, CH$_3$, CH$_2$CH$_3$,
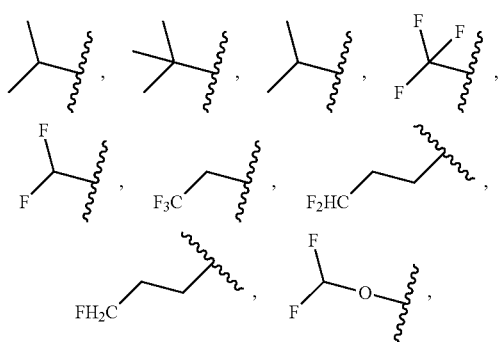

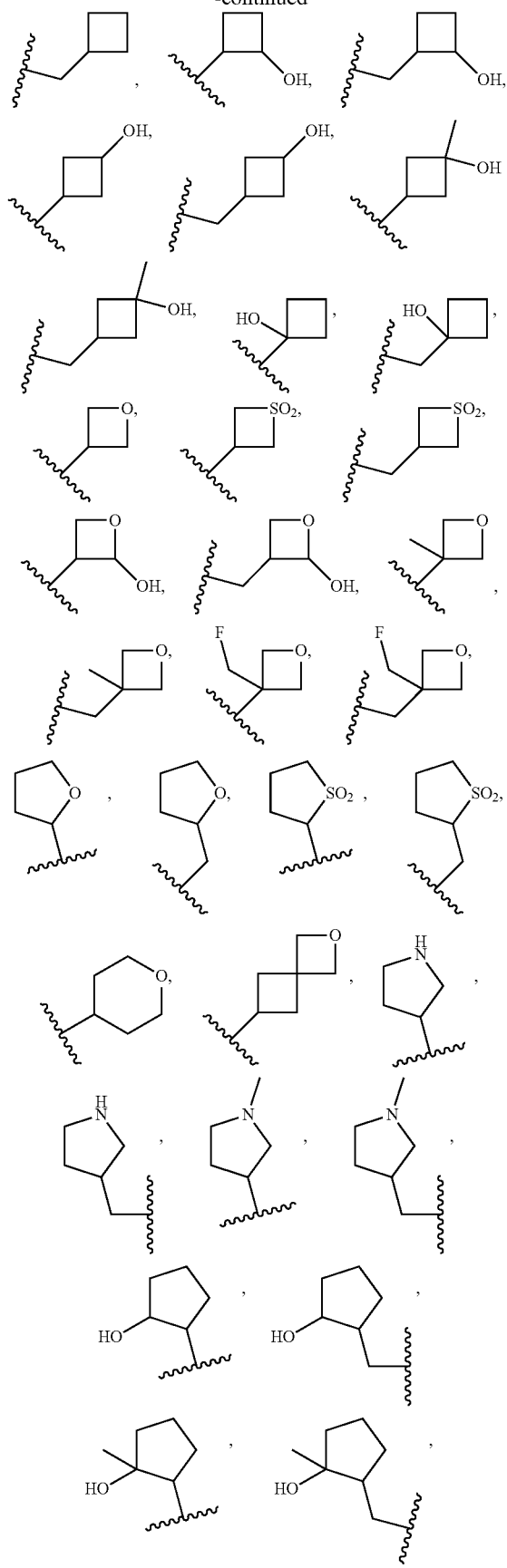
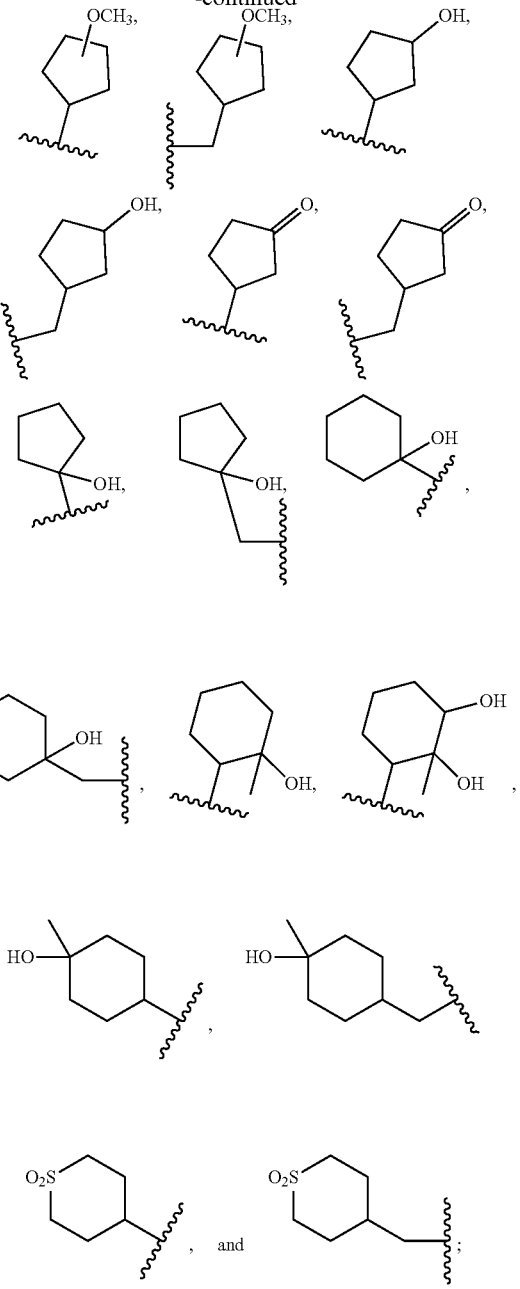

each $R^{3Aa}$ is as defined in Formula (I); and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another alternative of any of the preceding embodiments:
R³ is a moiety selected from:

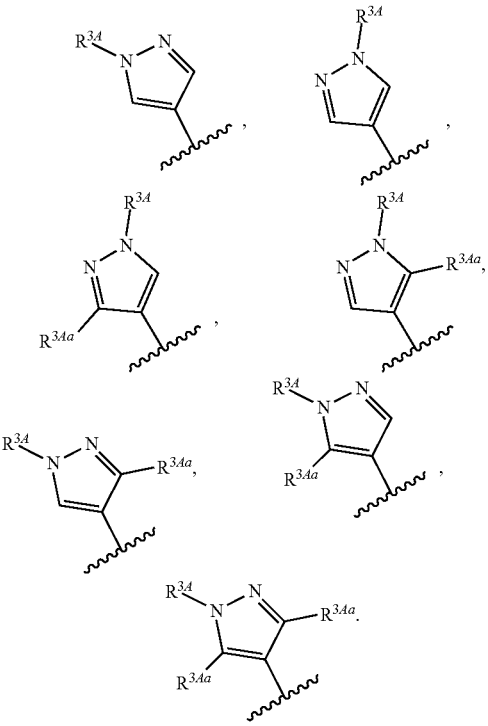

In another embodiment, in each of Formulas (I), (I.1), (I.2), (I.3), (I.4), and (I.5):
ring A is:

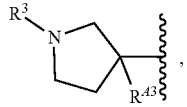

wherein R³ and R^{A3} are as defined in Formula (I); and wherein R¹, R², and R⁴ are as defined in Formula (I), or wherein R¹ is as defined in Formula (I.1) or as in any of the alternative embodiments of Formula (I.1), or wherein R² is as defined in Formula (I.2) or as in any of the alternative embodiments of Formula (I.2), or wherein R⁴ is as defined in Formula (I.3) or as in any of the alternative embodiments of Formula (I.3), or wherein R¹ and R² are as defined in Formula (I.4) or as in any of the alternative embodiments of Formula (I.4), or wherein R¹ and R⁴ are as defined in Formula (I.5) or as in any of the alternative embodiments of Formula (I.5).

In another embodiment, in each of Formulas (I), (I.1), (I.2), (I.3), (I.4), and (I.5):
ring A is:

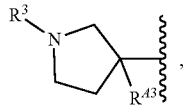

wherein:
R³ is a moiety selected from:

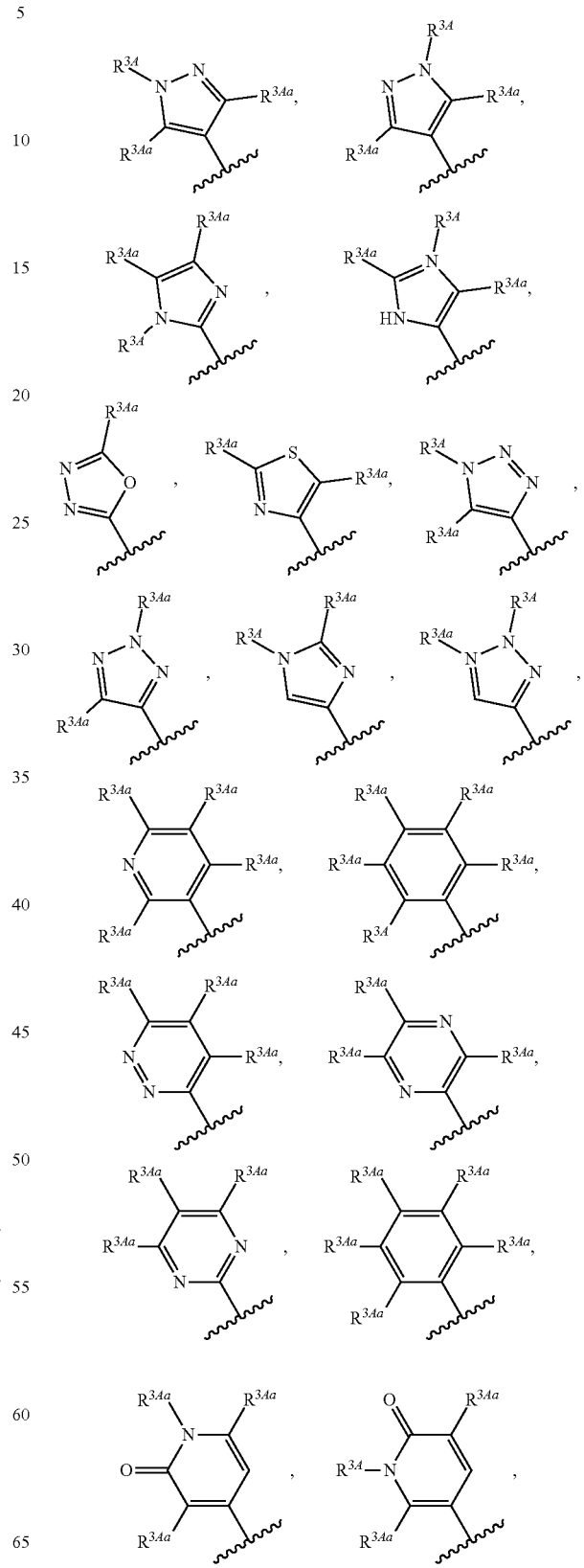

-continued

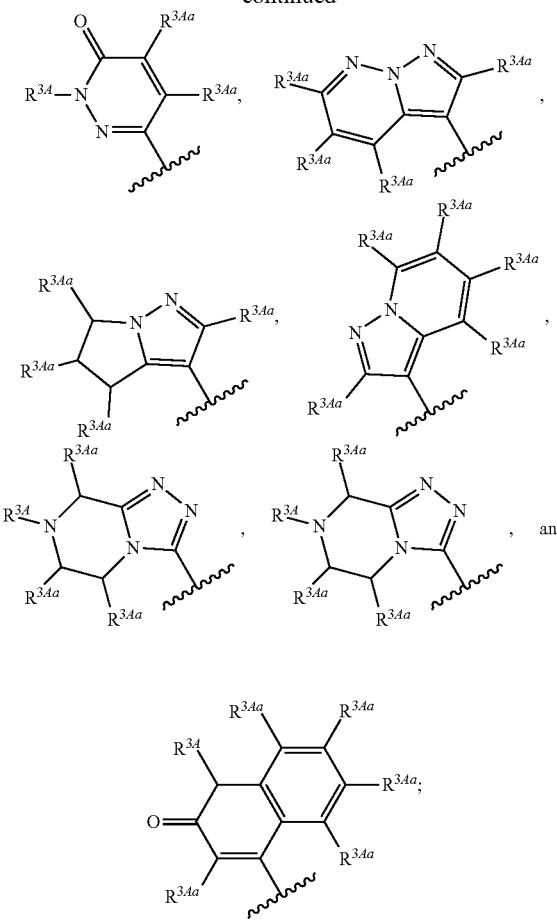

each $R^{3Aa}$ is as defined in Formula (I);

$R^{A3}$ is selected from H, F, and $(C_1-C_4)$alkyl; and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):

ring A is:

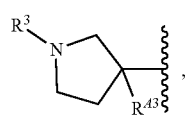

wherein:

$R^3$ is a moiety selected from:

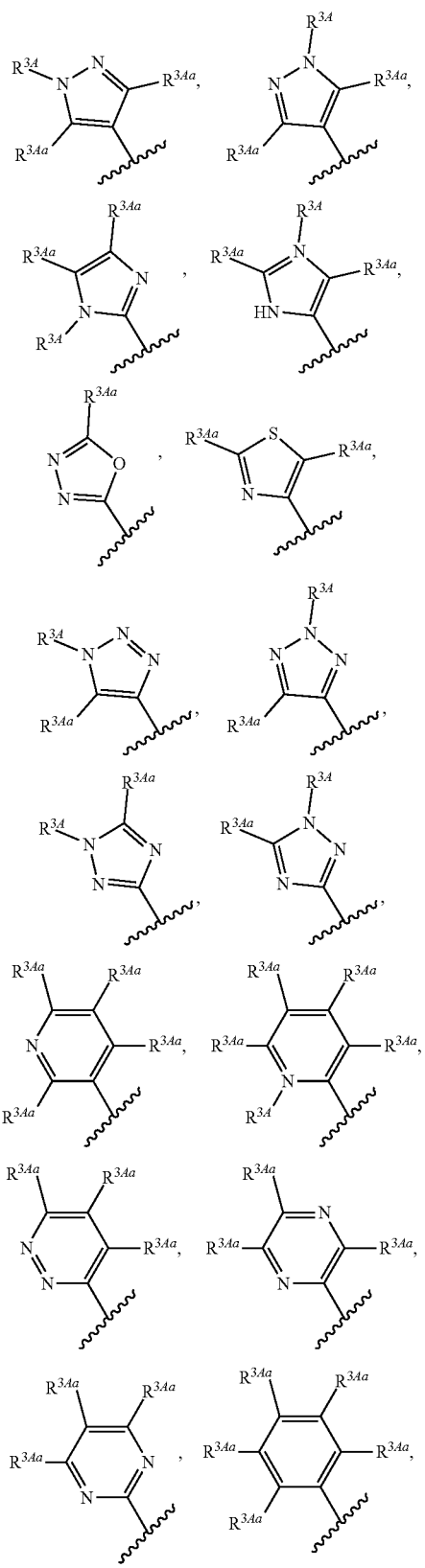

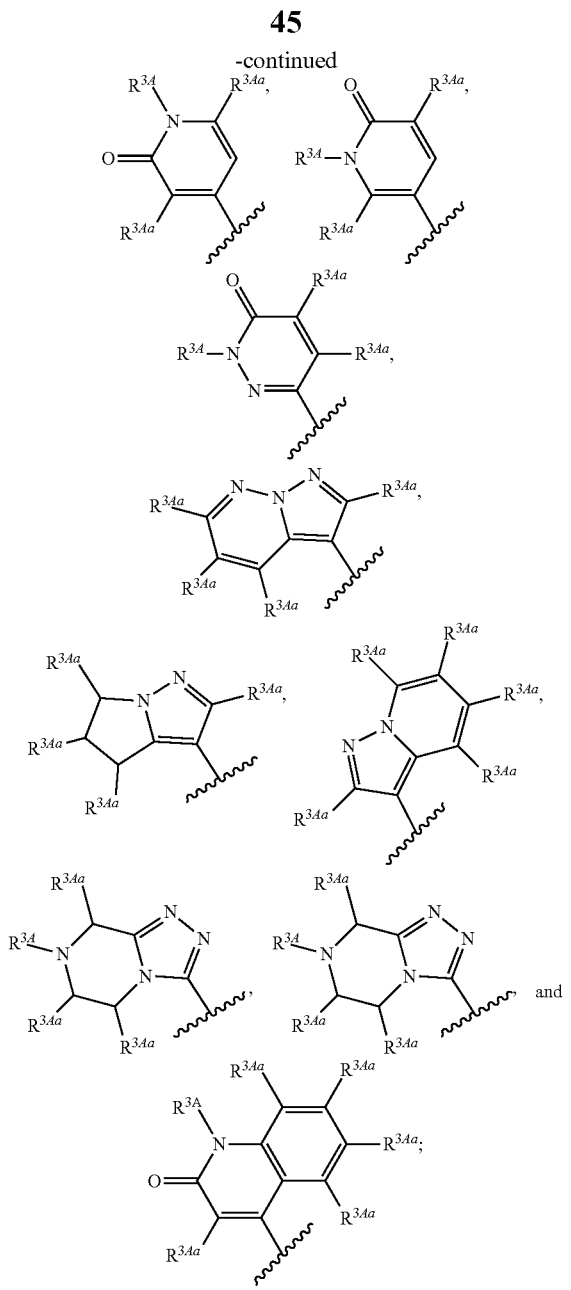
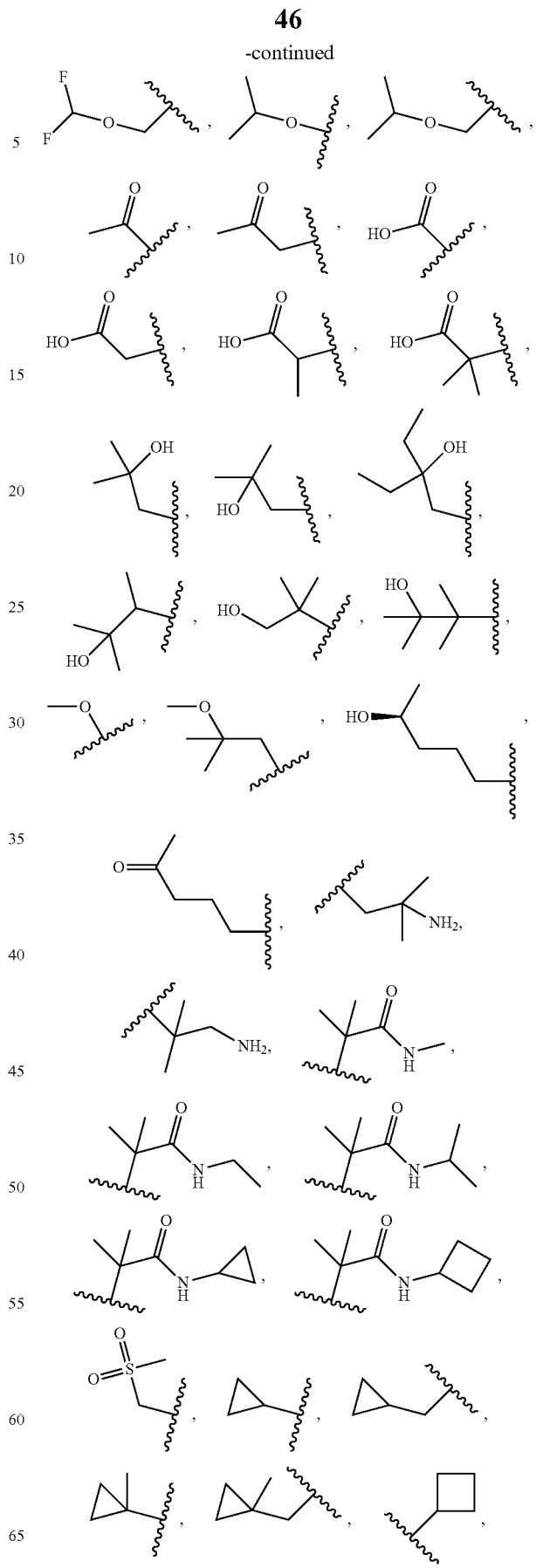
$R^{3A}$ is a moiety selected from:
H, $CH_3$, $CH_2CH_3$,
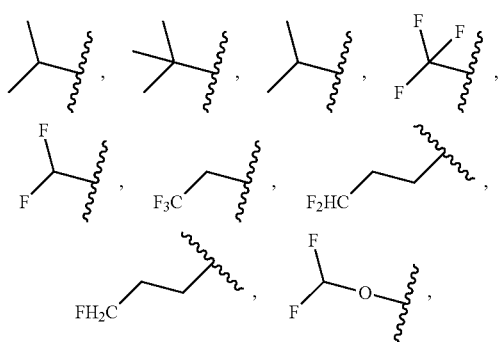

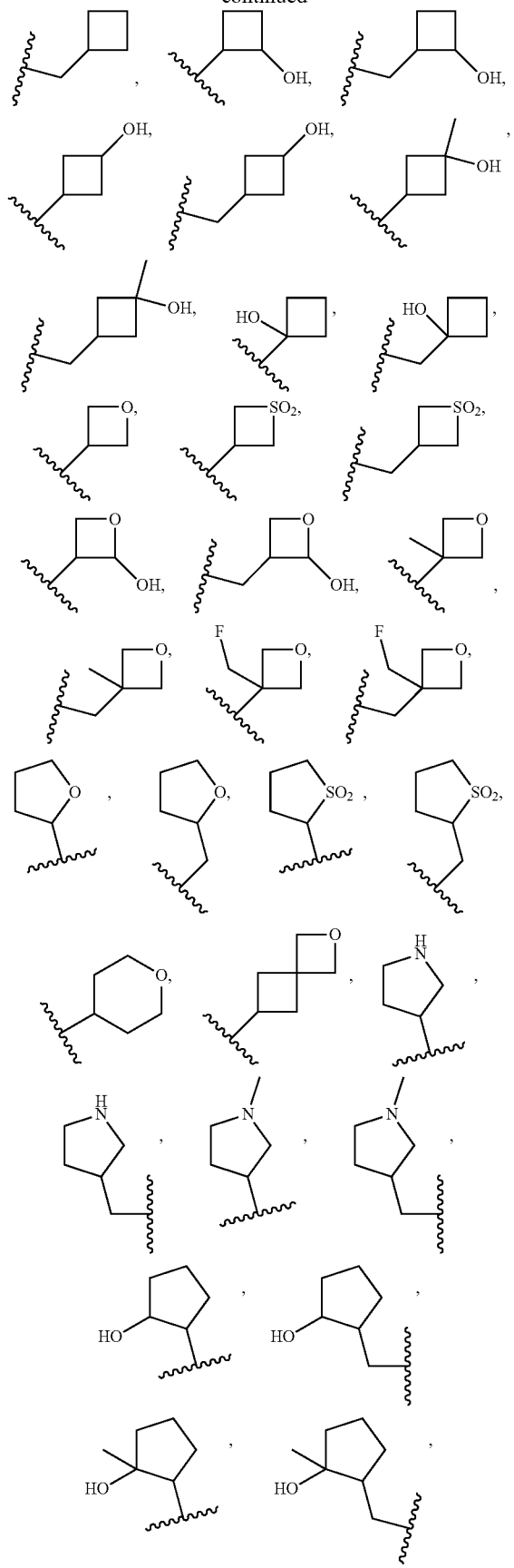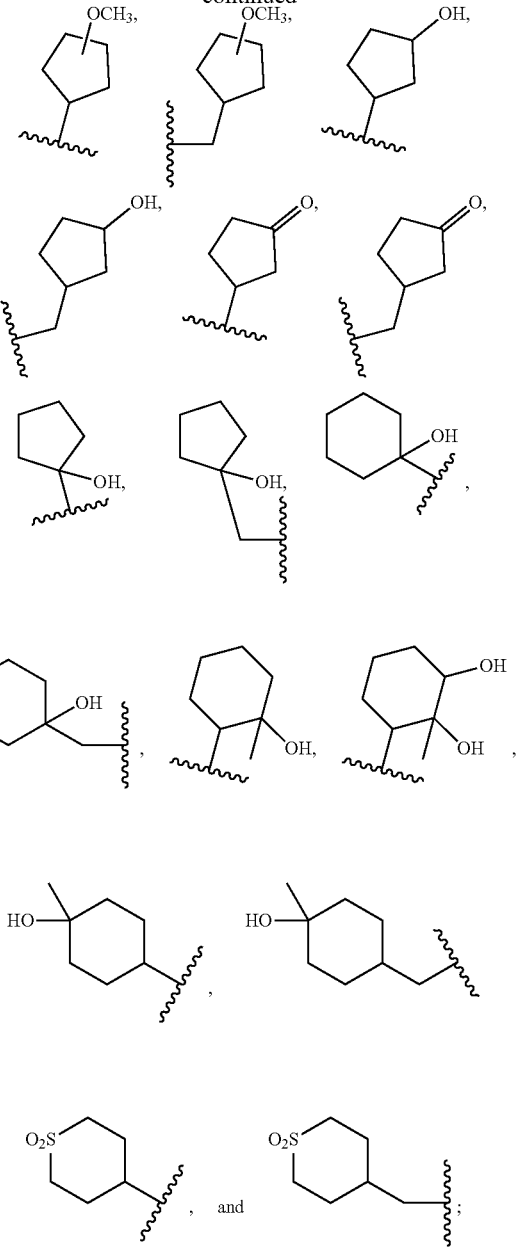

each $R^{3Aa}$ is as defined in Formula (I);

$R^{43}$ is selected from H, F, and $CH_3$; and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another alternative of any of the preceding embodiments:

R³ is a moiety selected from:

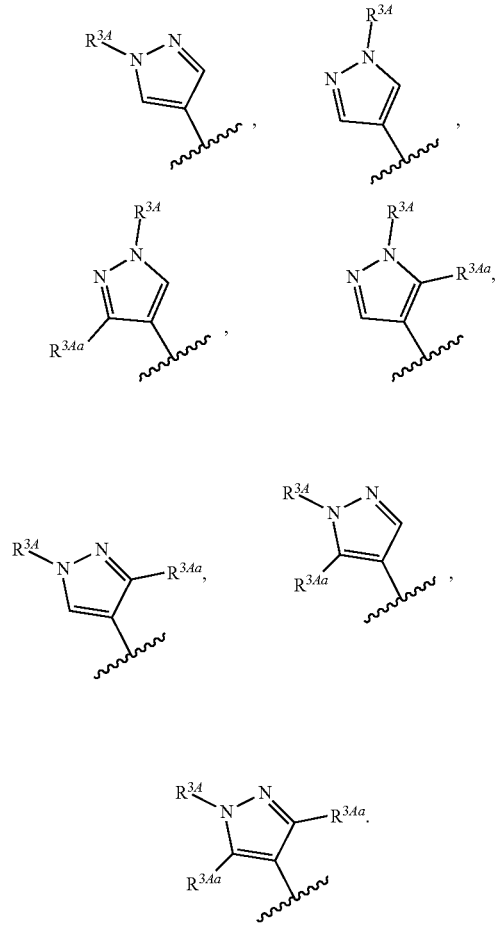

In another embodiment, in each of Formulas (I), (I.1), (I.2), (I.3), (I.4), and (I.5):

ring A is:

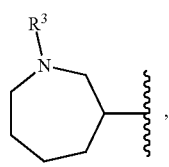

wherein R³ is as defined in Formula (I); and wherein R¹, R², and R⁴ are as defined in Formula (I), or wherein R¹ is as defined in Formula (I.1) or as in any of the alternative embodiments of Formula (I.1), or wherein R² is as defined in Formula (I.2) or as in any of the alternative embodiments of Formula (I.2), or wherein R⁴ is as defined in Formula (I.3) or as in any of the alternative embodiments of Formula (I.3), or wherein R¹ and R² are as defined in Formula (I.4) or as in any of the alternative embodiments of Formula (I.4), or wherein R¹ and R⁴ are as defined in Formula (I.5) or as in any of the alternative embodiments of Formula (I.5).

In another embodiment, in each of Formulas (I), (I.1), (I.2), (I.3), (I.4), and (I.5):

ring A is:

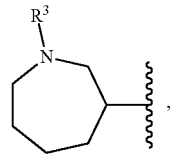

wherein:

R³ is a moiety selected from:

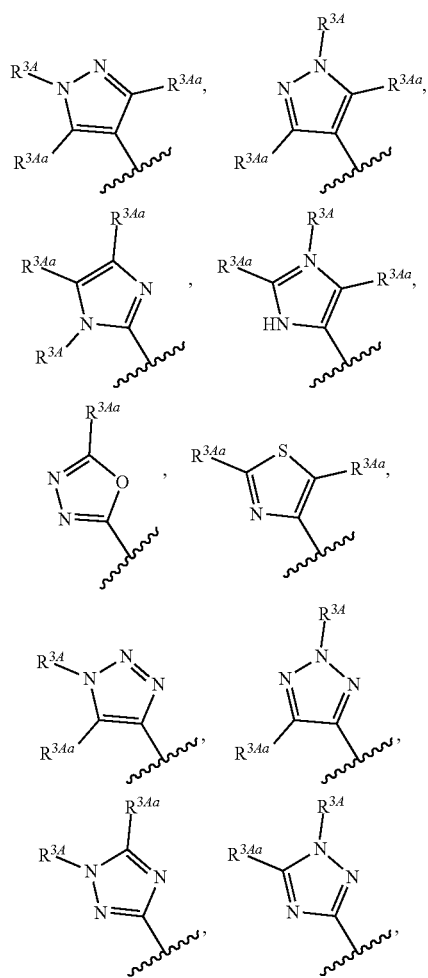

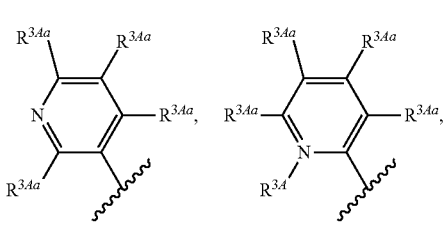

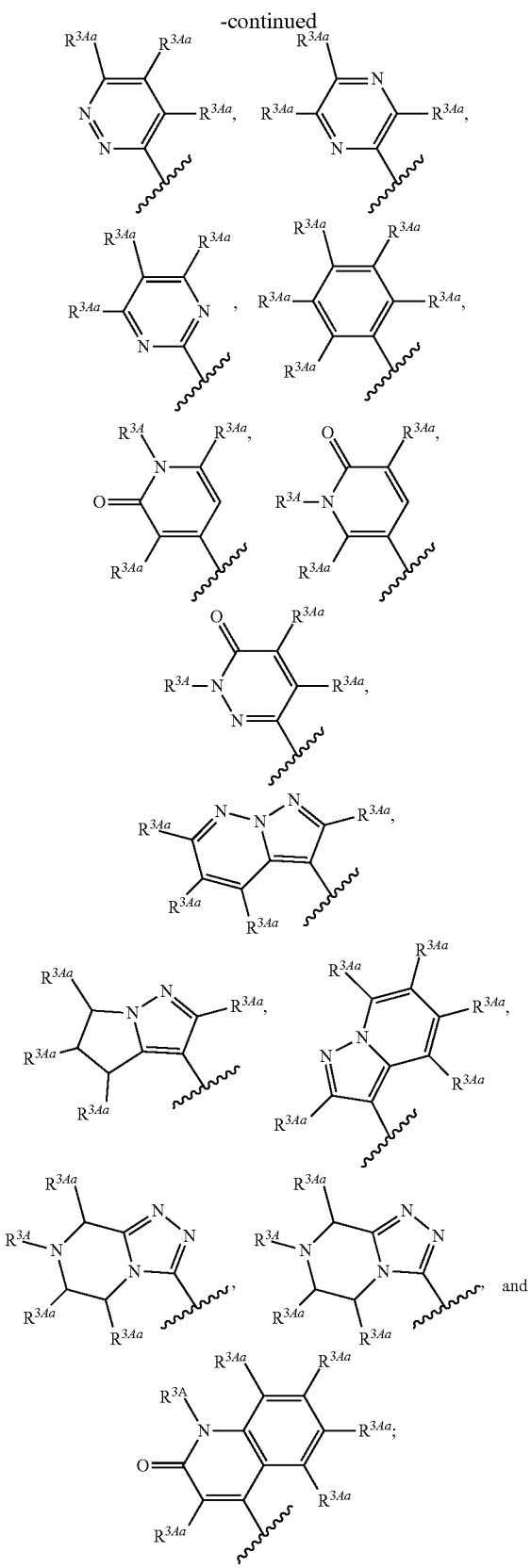

each $R^{3Aa}$ is as defined in Formula (I); and
$R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):

ring A is:

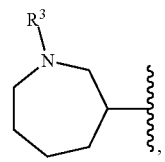

wherein:

$R^3$ is a moiety selected from:

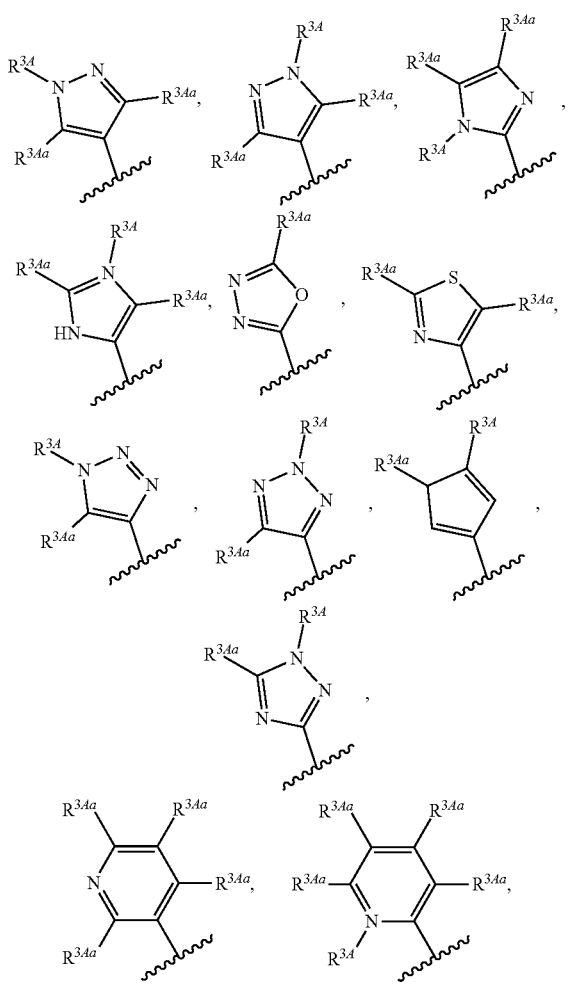

-continued
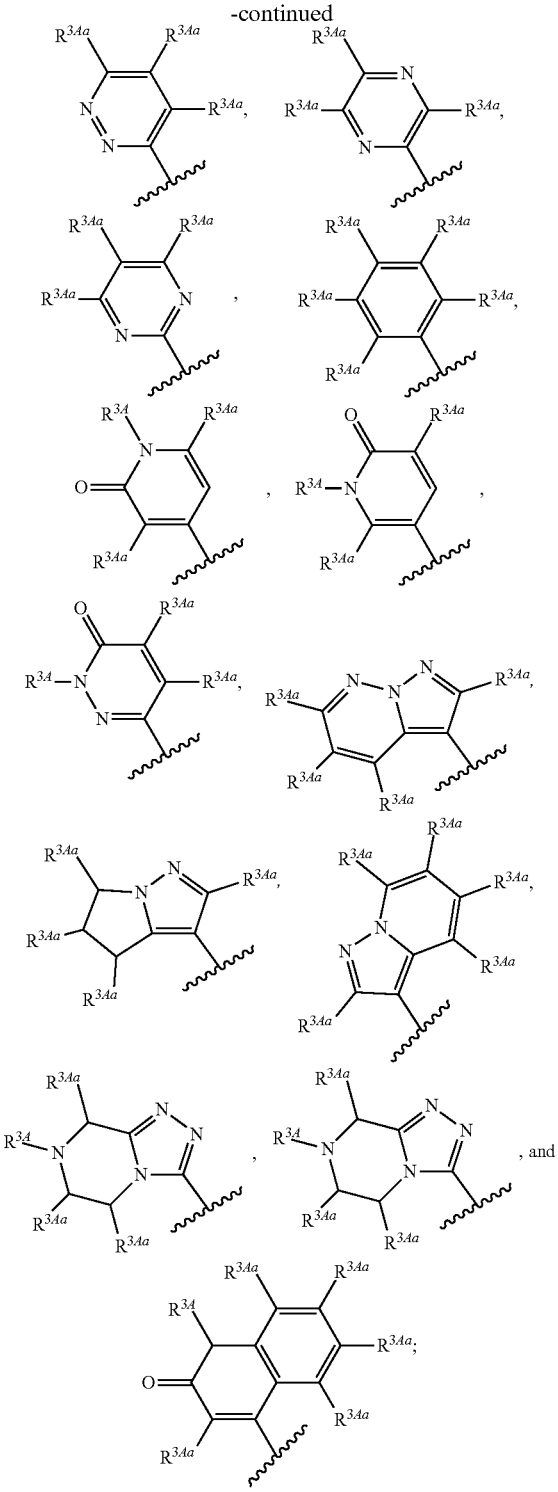
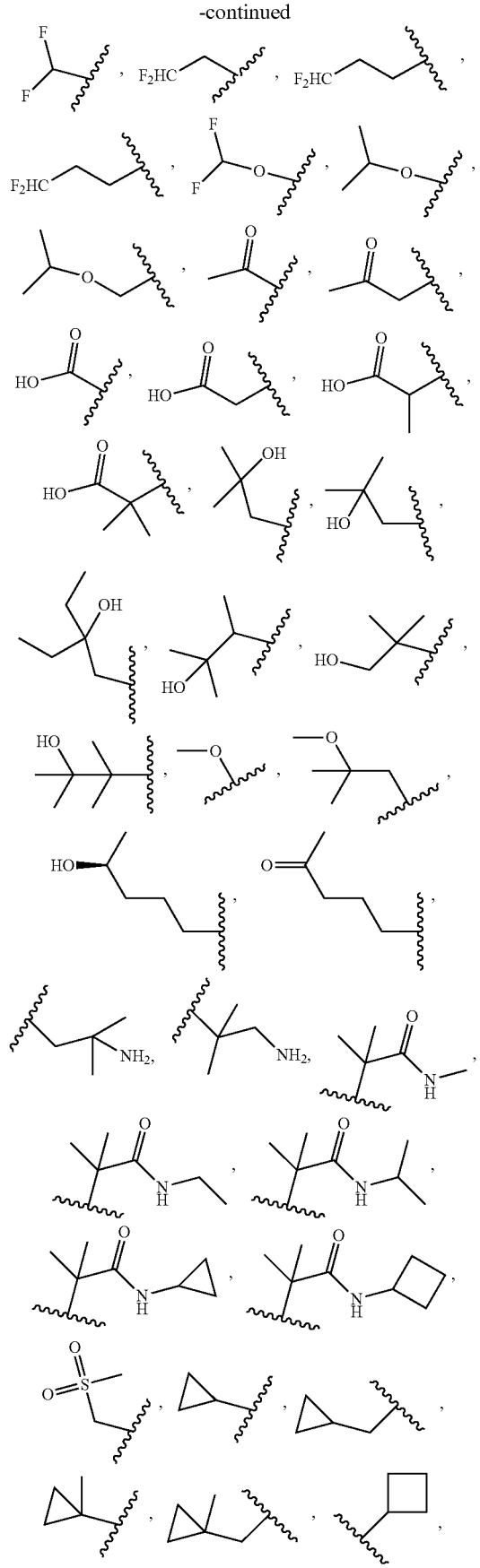
R³ᴬ is a moiety selected from:
H, CH₃, CH₂CH₃,

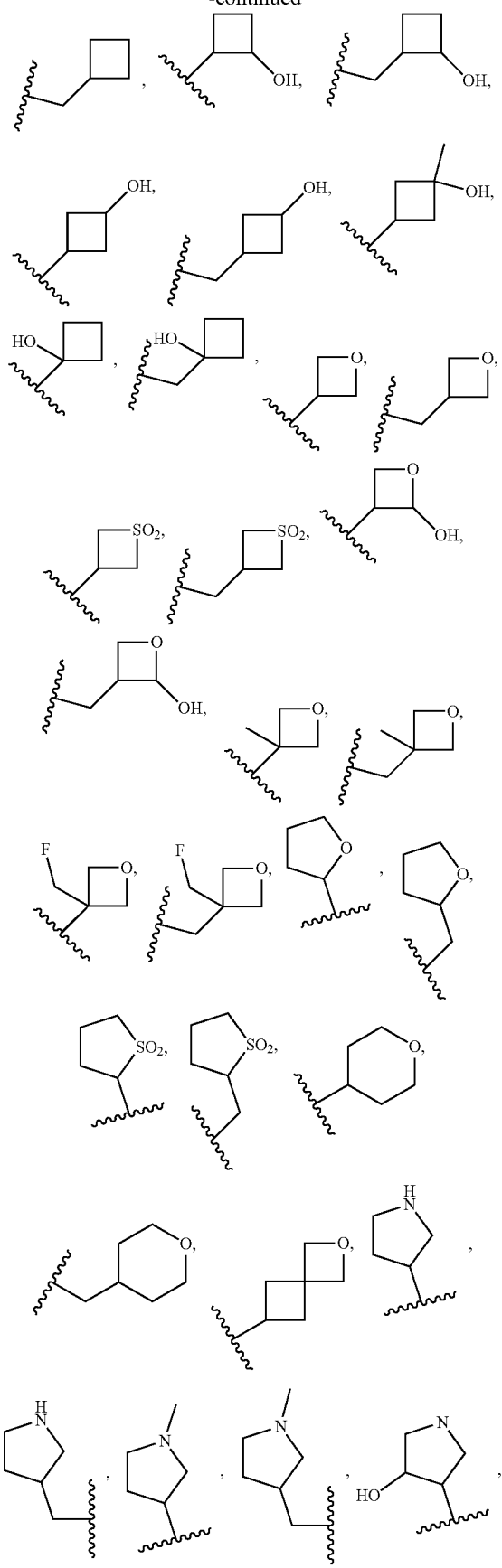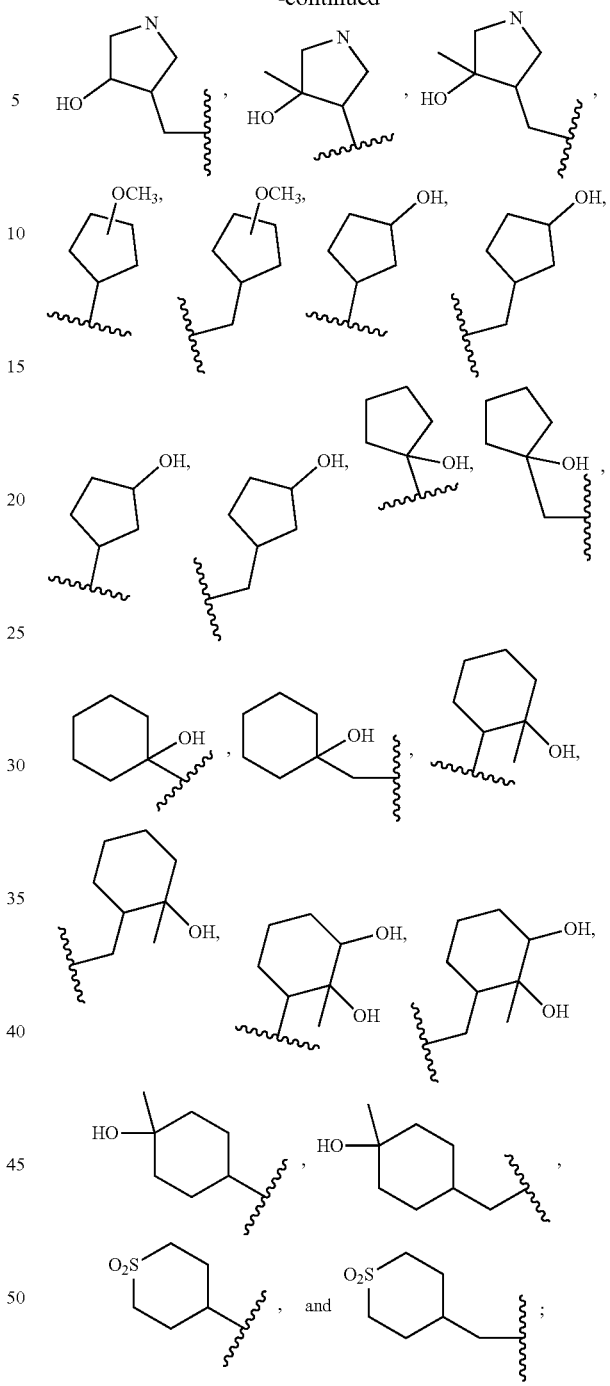

each $R^{3Aa}$ is as defined in Formula (I); and
$R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another alternative of any of the preceding embodiments:

$R^3$ is a moiety selected from:

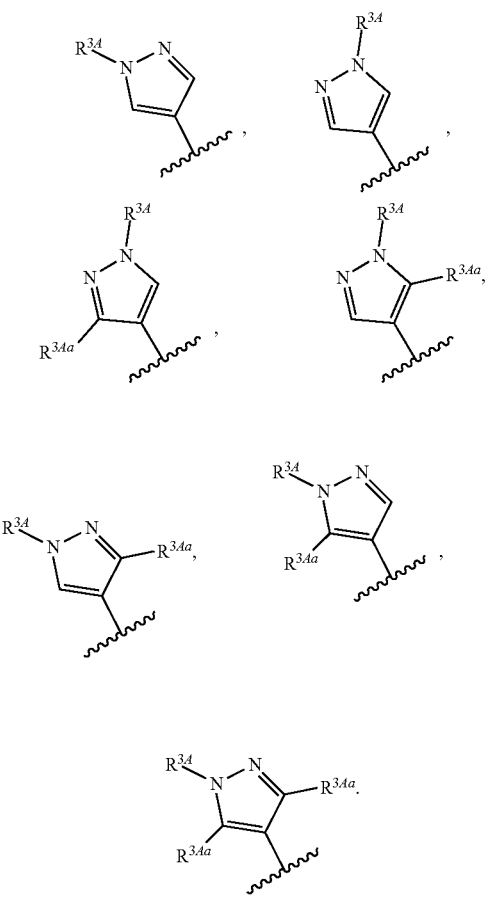

In another embodiment, in each of Formulas (I), (I.1), (I.2), (I.3), (I.4) and (I.5):

ring A is a moiety selected from:

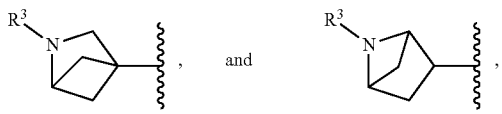

wherein $R^3$ is as defined in Formula (I); and wherein $R^1$, $R^2$, and $R^4$ are as defined in Formula (I), or wherein $R^1$ is as defined in Formula (I.1) or as in any of the alternative embodiments of Formula (I.1), or wherein $R^2$ is as defined in Formula (I.2) or as in any of the alternative embodiments of Formula (I.2), or wherein $R^4$ is as defined in Formula (I.3) or as in any of the alternative embodiments of Formula (I.3), or wherein $R^1$ and $R^2$ are as defined in Formula (I.4) or as in any of the alternative embodiments of Formula (I.4), or wherein $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):

ring A is a moiety selected from:

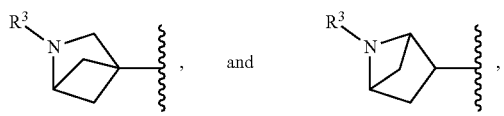

wherein:

$R^3$ is a moiety selected from:

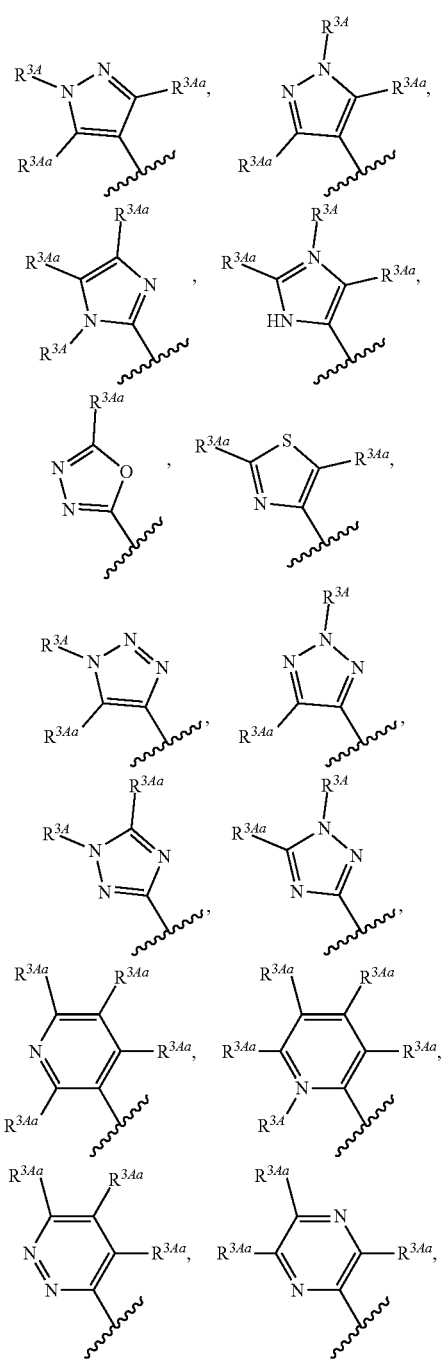

-continued

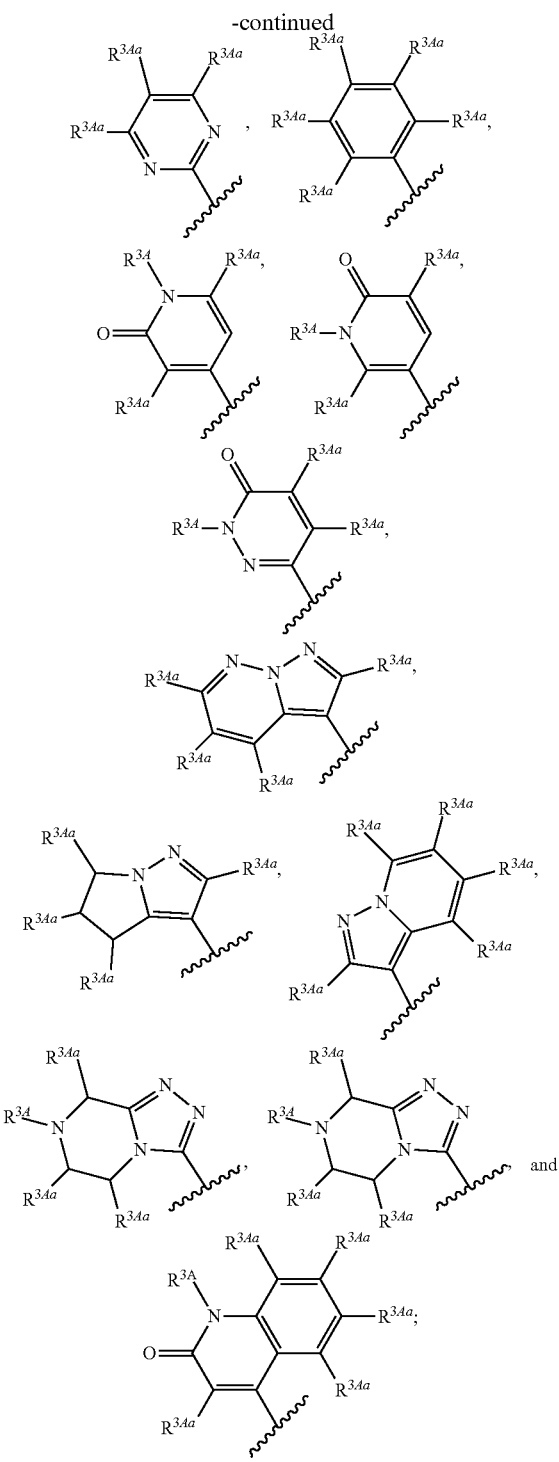

each $R^{3Aa}$ is as defined in Formula (I); and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another embodiment, in each of Formulas (I), (I.1), (I.2), (I.3), (I.4), and (I.5):

ring A is a moiety selected from:

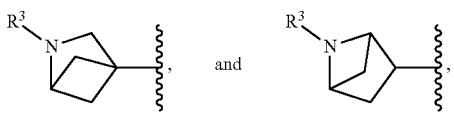

wherein:

$R^3$ is a moiety selected from:

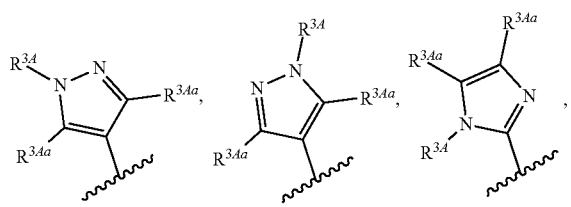

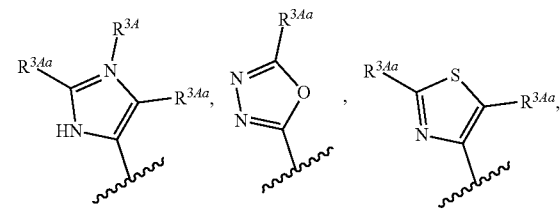

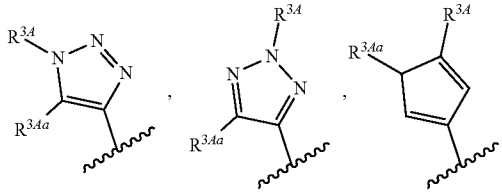

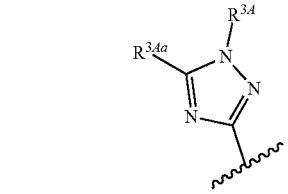

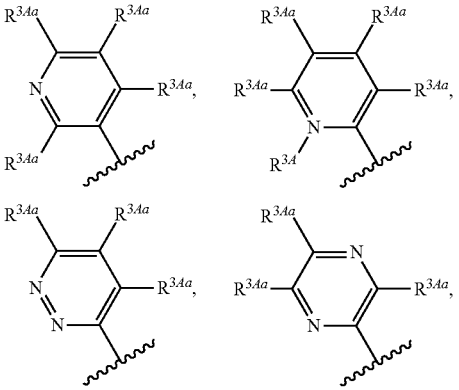

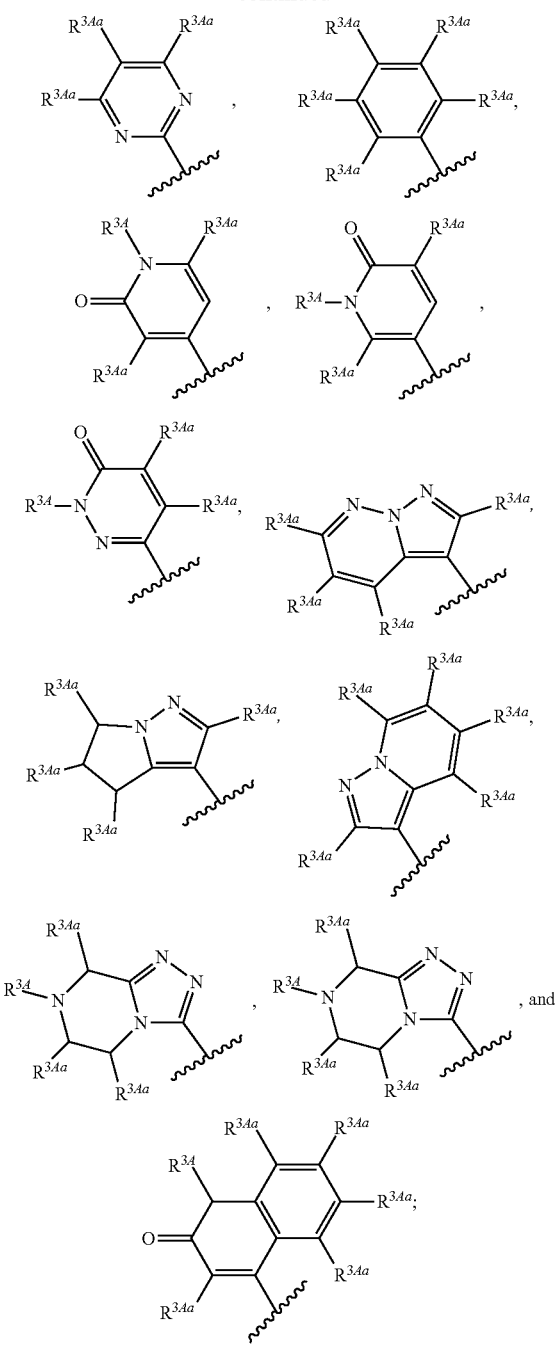
$R^{3A}$ is a moiety selected from:
H, $CH_3$, $CH_2CH_3$,
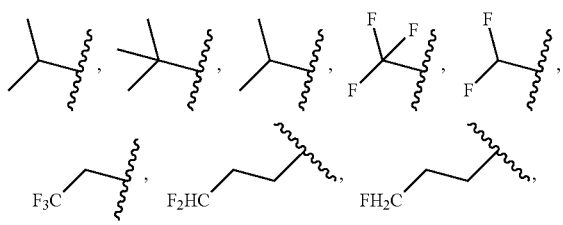
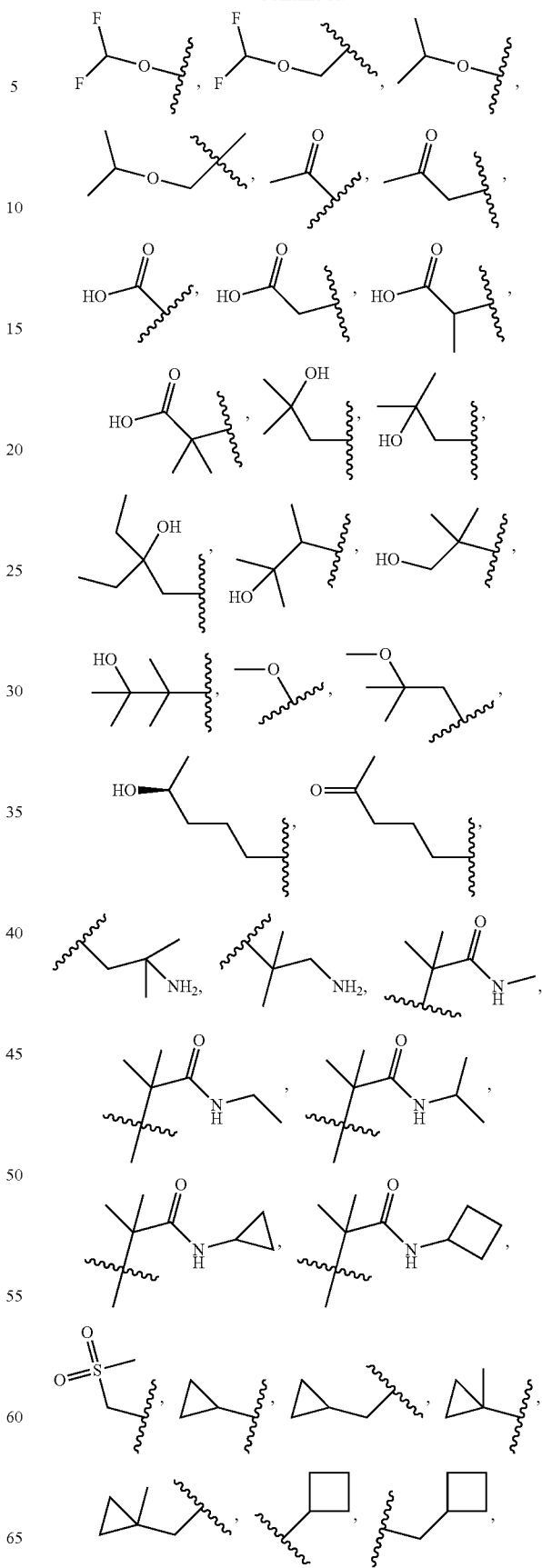

-continued

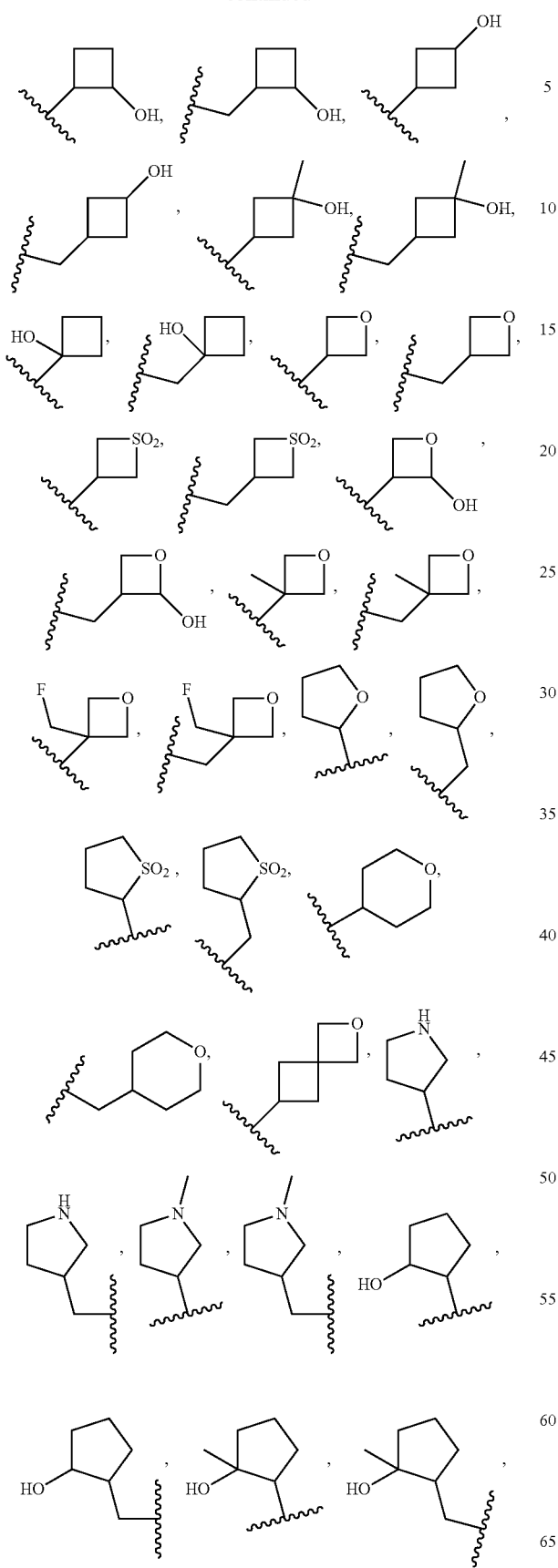
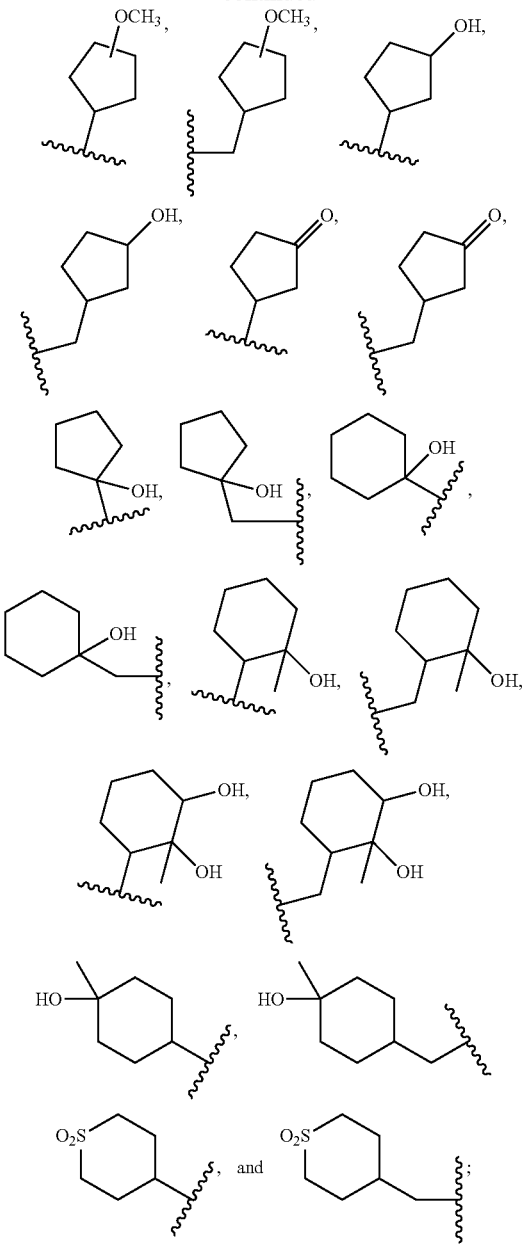

each $R^{3Aa}$ is as defined in Formula (I), and $R^1$, $R^2$, and $R^4$ are as defined in Formula (I) or, alternatively, $R^2$ and $R^4$ are absent and $R^1$ is as defined in Formula (I.1) or as in any of the alternative embodiments of Formula (I.1), or, alternatively, $R^1$ and $R^4$ are absent and $R^2$ is as defined in Formula (I.2) or as in any of the alternative embodiments of Formula (I.2), or, alternatively, $R^1$ and $R^2$ are absent and $R^4$ is as defined in Formula (I.3) or as in any of the alternative embodiments of Formula (I.3), or, alternatively, $R^4$ is absent and $R^1$ and $R^2$ are as defined in Formula (I.4) or as in any of the alternative embodiments of Formula (I.4), or, alternatively, $R^2$ is absent and $R^1$ and $R^4$ are as defined in Formula (I.5) or as in any of the alternative embodiments of Formula (I.5).

In another alternative of any of the preceding embodiments:

R³ is a moiety selected from:

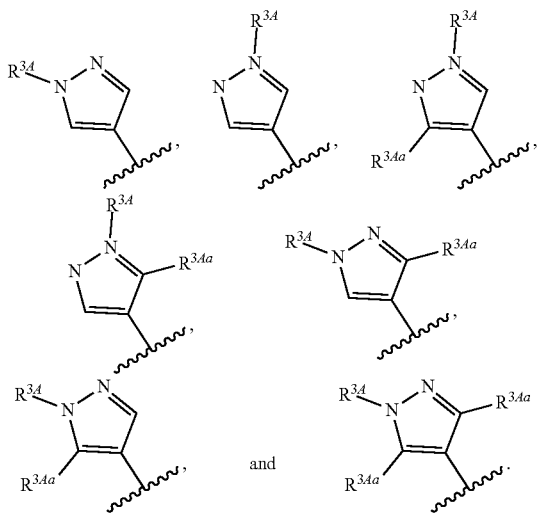

In another embodiment, the compounds of the invention comprise those compounds identified herein as examples in the tables below, and pharmaceutically acceptable salts thereof.

In another aspect, the present invention provides pharmaceutical compositions comprising a pharmaceutically acceptable carrier and a compound of the invention or a pharmaceutically acceptable salt thereof. Such compositions according to the invention may optionally further include one or more additional therapeutic agents as described herein.

In another aspect, the present invention provides a method for the manufacture of a medicament or a composition which may be useful for treating diseases, conditions, or disorders that are mediated, at least in part, by the adenosine A2a receptor and/or the adenosine A2b receptor, comprising combining a compound of the invention with one or more pharmaceutically acceptable carriers.

In another aspect, the present invention provides a method for treating or preventing a disease, condition, or disorder that is mediated, at least in part, by the adenosine A2a receptor and/or the adenosine A2b receptor in a subject (e.g., an animal or human) in need thereof, said method comprising administering to the subject in need thereof a therapeutically effective amount of at least one compound of the invention, or a pharmaceutically acceptable salt thereof, alone or in combination with one or more additional therapeutic agents. Specific non-limiting examples of such diseases, conditions, and disorders are described herein.

Oncology

In some embodiments, the disease, condition or disorder is a cancer. Any cancer for which a PD-1 antagonist and/or an A2a and/or A2b inhibitor are thought to be useful by those of ordinary skill in the art are contemplated as cancers treatable by this embodiment, either as a monotherapy or in combination with other therapeutic agents discussed below. Cancers that express high levels of A2a receptors or A2b receptors are among those cancers contemplated as treatable by the compounds of the invention. Examples of cancers that express high levels of A2a and/or A2b receptors may be discerned by those of ordinary skill in the art by reference to The Cancer Genome Atlas (TCGA) database. Non-limiting examples of cancers that express high levels of A2a receptors include cancers of the kidney, breast, lung, and liver. Non-limiting examples of cancers that express high levels of the A2b receptor include lung, colorectal, head & neck cancer, and cervical cancer.

Thus, one embodiment provides a method of treating cancer comprising administering an effective amount of a compound of the invention, or a pharmaceutically acceptable salt thereof, to a subject in need of such treatment, wherein said cancer is a cancer that expresses a high level of A2a receptor. A related embodiment provides a method of treating cancer comprising administering an effective amount of a compound of the invention, or a pharmaceutically acceptable salt thereof, to a subject in need of such treatment, wherein said cancer is selected from kidney (or renal) cancer, breast cancer, lung cancer, and liver cancer.

Another embodiment provides a method of treating cancer comprising administering an effective amount of a compound of the invention, or a pharmaceutically acceptable salt thereof, to a subject in need of such treatment, wherein said cancer is a cancer that expresses a high level of A2b receptor. A related embodiment provides a method of treating cancer comprising administering an effective amount of a compound of the invention, or a pharmaceutically acceptable salt thereof, to a subject in need of such treatment, wherein said cancer is selected from lung cancer, colorectal cancer, head & neck cancer, and cervical cancer.

Additional non-limiting examples of cancers which may be treatable by administration of a compound of the invention (alone or in combination with one or more additional agents described below) include cancers of the prostate (including but not limited to metastatic castration resistant prostate cancer), colon, rectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including but not limited to small cell lung cancer, non-small cell lung cancer, and lung adenocarcinoma), adrenal gland, thyroid, kidney, or bone. Additional cancers treatable by a compound of the invention include glioblastoma, mesothelioma, renal cell carcinoma, gastric carcinoma, sarcoma, choriocarcinoma, cutaneous basocellular carcinoma, and testicular seminoma, and Kaposi's sarcoma.

CNS and Neurological Disorders

In other embodiments, the disease, condition or disorder is a central nervous system or a neurological disorder. Non-limiting examples of such diseases, conditions or disorders include movement disorders such as tremors, bradykinesias, gait disorders, dystonias, dyskinesias, tardive dyskinesias, other extrapyramidal syndromes, Parkinson's disease, and disorders associated with Parkinson's disease. The compounds of the invention also have the potential, or are believed to have the potential, for use in preventing or reducing the effect of drugs that cause or worsen such movement disorders.

Infections

In other embodiments, the disease, condition or disorder is an infective disorder. Non-limiting examples of such diseases, conditions or disorders include an acute or chronic viral infection, a bacterial infection, a fungal infection, or a parasitic infection. In one embodiment, the viral infection is human immunodeficiency virus. In another embodiment, the viral infection is cytomegalovirus.

Immune Disease

In other embodiments, the disease, condition or disorder is an immune-related disease, condition or disorder. Non-limiting examples of immune-related diseases, conditions, or disorders include multiple sclerosis and bacterial infections. (See, e.g., Safarzadeh, E. et al., Inflamm Res 2016 65(7):511-20, and Antoniou, L., et al., Immunol Lett S0165-2478(18)30172-X 2018).

Additional Indications

Other diseases, conditions, and disorders that have the potential to be treated or prevented, in whole or in part, by the inhibition of the A2a and/or A2b adenosine receptor(s) are also candidate indications for the compounds of the invention and salts thereof. Non-limiting examples of other diseases, conditions or disorders in which a compound of the invention, or a pharmaceutically acceptable salt thereof, may be useful include the treatment of hypersensitivity reaction to a tumor antigen and the amelioration of one or more complications related to bone marrow transplant or to a peripheral blood stem cell transplant. Thus, in another embodiment, the present invention provides a method for treating a subject receiving a bone marrow transplant or a peripheral blood stem cell transplant by administering to said subject a therapeutically effective amount of a compound of the invention, or a pharmaceutically acceptable salt thereof, sufficient to increase the delayed-type hypersensitivity reaction to tumor antigen, to delay the time-to-relapse of post-transplant malignancy, to increase relapse-free survival time post-transplant, and/or to increase long-term post-transplant survival.

Combination Therapy

In another aspect, the present invention provides methods for the use of a compound of the invention, or a pharmaceutically acceptable salt thereof, (or a pharmaceutically acceptable composition comprising a compound of the invention or pharmaceutically acceptable salt thereof) in combination with one or more additional agents. Such additional agents may have some adenosine A2a and/or A2b receptor activity, or, alternatively, they may function through distinct mechanisms of action. The compounds of the invention may be used in combination with one or more other drugs in the treatment, prevention, suppression or amelioration of diseases or conditions for which the compounds of the invention or the other drugs described herein may have utility, where the combination of the drugs together are safer or more effective than either drug alone. The combination therapy may have an additive or synergistic effect. Such other drug(s) may be administered in an amount commonly used therefore, contemporaneously or sequentially with a compound of the invention or a pharmaceutically acceptable salt thereof. When a compound of the invention is used contemporaneously with one or more other drugs, the pharmaceutical composition may in specific embodiments contain such other drugs and the compound of the invention or its pharmaceutically acceptable salt in separate doses or in unit dosage form. However, the combination therapy may also include therapies in which the compound of the invention or its pharmaceutically acceptable salt and one or more other drugs are administered sequentially, on different or overlapping schedules. It is also contemplated that when used in combination with one or more other active ingredients, the compounds of the invention and the other active ingredients may be used in lower doses than when each is used singly. Accordingly, the pharmaceutical compositions comprising the compounds of the invention include those that contain one or more other active ingredients, in addition to a compound of the invention or a pharmaceutically acceptable salt thereof.

The weight ratio of the compound of the present invention to the second active ingredient may be varied and will depend upon the effective dose of each ingredient. Generally, an effective dose of each will be used. Thus, for example, when a compound of the invention is used in combination with another agent, the weight ratio of the compound of the present invention to the other agent may generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should generally be used.

Given the immunosuppressive role of adenosine, the administration of an A2a receptor antagonist, an A2b receptor antagonist, and/or an A2a/A2b receptor dual antagonist according to the invention may enhance the efficacy of immunotherapies such as PD-1 antagonists. Thus, in one embodiment, the additional therapeutic agent comprises an anti-PD-1 antibody. In another embodiment, the additional therapeutic agent is an anti-PD-L1 antibody.

As noted above, PD-1 is recognized as having an important role in immune regulation and the maintenance of peripheral tolerance. PD-1 is moderately expressed on naive T-cells, B-cells and NKT-cells and up-regulated by T-cell and B-cell receptor signaling on lymphocytes, monocytes and myeloid cells (Sharpe et al., Nature Immunology (2007); 8:239-245).

Two known ligands for PD-1, PD-L1 (B7-H1) and PD-L2 (B7-DC) are expressed in human cancers arising in various tissues. In large sample sets of, for example, ovarian, renal, colorectal, pancreatic, and liver cancers, and in melanoma, it was shown that PD-L1 expression correlated with poor prognosis and reduced overall survival irrespective of subsequent treatment. (Dong et al., Nat Med. 8(8):793-800 (2002); Yang et al., Invest Ophthalmol Vis Sci. 49: 2518-2525 (2008); Ghebeh et al., Neoplasia 8:190-198 (2006); Hamanishi et al., Proc. Natl. Acad. USA 104: 3360-3365 (2007); Thompson et al., Cancer 5: 206-211 (2006); Nomi et al., Clin. Cancer Research 13:2151-2157 (2007); Ohigashi et al., Clin. Cancer Research 11: 2947-2953; Inman et al., Cancer 109: 1499-1505 (2007); Shimauchi et al., Int. J. Cancer 121:2585-2590 (2007); Gao et al., Clin. Cancer Research 15: 971-979 (2009); Nakanishi J., Cancer Immunol immunother. 56: 1173-1182 (2007); and Hino et al., Cancer 00: 1-9 (2010)).

Similarly, PD-1 expression on tumor infiltrating lymphocytes was found to mark dysfunctional T-cells in breast cancer and melanoma (Gheheh et al., BMC Cancer. 2008 8:5714-15 (2008); and Ahmadzadeh et al., Blood 114: 1537-1544 (2009)) and to correlate with poor prognosis in renal cancer (Thompson et al., Clinical Cancer Research 15: 1757-1761(2007)). Thus, it has been proposed that PD-L1 expressing tumor cells interact with PD-1 expressing T-cells to attenuate T-cell activation and to evade immune surveillance, thereby contributing to an impaired immune response against the tumor.

Immune checkpoint therapies targeting the PD-1 axis have resulted in groundbreaking improvements in clinical response in multiple human cancers (Brahmer, et al., N Engl J Med 2012, 366: 2455-65; Garon et al., N Engl J Med 2015, 372: 2018-28; Hamid et al., N Engl J Med 2013, 369: 134-44; Robert et al., Lancet 2014, 384: 1109-17; Robert et al., N Engl J Med 2015, 372: 2521-32; Robert et al., N Engl J Med 2015, 372: 320-30; Topalian et al., N Engl J Med 2012, 366: 2443-54; Topalian et al., J Clin Oncol 2014, 32: 1020-30; and Wolchok et al., N Engl J Med 2013, 369: 122-33).

"PD-1 antagonist" means any chemical compound or biological molecule that blocks binding of PD-L1 expressed on a cancer cell to PD-1 expressed on an immune cell (T-cell, B-cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment methods, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP 005009. Human PD-L1 and PD-L2 amino acid sequences can be found in NCBI Locus No.: NP_054862 and NP_079515, respectively.

PD-1 antagonists useful in any of the treatment methods, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, say and Fv fragments. Examples of PD-1 antagonists include, but are not limited to, pembrolizumab (KEYTRUDA®, Merck and Co., Inc., Kenilworth, N.J., USA). "Pembrolizumab" (formerly known as MK-3475, SCH 900475 and lambrolizumab and sometimes referred to as "pembro") is a humanized IgG4 mAb with the structure described in WHO Drug Information, Vol. 27, No. 2, pages 161-162 (2013). Additional examples of PD-1 antagonists include nivolumab (OPDIVO®, Bristol-Myers Squibb Company, Princeton, N.J., USA), atezolizumab (MPDL3280A; TECENTRIQ®, Genentech, San Francisco, Calif., USA), durvalumab (IMFINZI®, Astra Zeneca Pharmaceuticals, LP, Wilmington, Del., and avelumab (BAVENCIO®, Merck KGaA, Darmstadt, Germany and Pfizer, Inc., New York, N.Y.).

Examples of monoclonal antibodies (mAbs) that bind to human PD-1, and useful in the treatment methods, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment methods, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment methods, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010/027827 and WO2011/066342. Specific fusion proteins useful as the PD-1 antagonist in the treatment methods, medicaments and uses of the present invention include AMP-224 (also known as B7-DCIg), which is a PD-L2-FC fusion protein that binds to human PD-1.

Thus, one embodiment provides for a method of treating cancer comprising administering an effective amount of a compound of the invention, or a pharmaceutically acceptable salt thereof, in combination with a PD-1 antagonist to a subject in need thereof. In such embodiments, the compounds of the invention, or a pharmaceutically acceptable salt thereof, and PD-1 antagonist are administered concurrently or sequentially.

Specific non-limiting examples of such cancers in accordance with this embodiment include melanoma (including unresectable or metastatic melanoma), head & neck cancer (including recurrent or metastatic head and neck squamous cell cancer (HNSCC)), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, and salivary cancer.

In one embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from unresectable or metastatic melanoma, recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma. In one such embodiment, the agent is a PD-1 antagonist. In one such embodiment, the agent is pembrolizumab. In another such embodiment, the agent is nivolumab. In another such embodiment, the agent is atezolizumab.

Pembrolizumab is approved by the U.S. FDA for the treatment of patients with unresectable or metastatic melanoma and for the treatment of certain patients with recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma, as described in the Prescribing Information for KEYTRUDA™ (Merck & Co., Inc., Whitehouse Station, N.J. USA; initial U.S. approval 2014, updated November 2018). In another embodiment, there is provided a method of treating cancer comprising administering an effective amount of a compound of the invention, or a pharmaceutically acceptable salt thereof, to a person in need thereof, in combination with pembrolizumab, wherein said cancer is selected from unresectable or metastatic melanoma, recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma.

In another embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from melanoma, non-small cell lung cancer, head and neck squamous cell cancer (HNSCC), Hodgkin lymphoma, primary mediastinal large B-cell lymphoma, urothelial carcinoma, microsatellite instability-high cancer, gastric cancer, Merkel cell carcinoma, hepatocellular carcinoma, esophageal cancer and cervical cancer. In one such embodiment, the agent is a PD-1 antagonist. In one such embodiment, the agent is pembrolizumab. In another such embodiment, the agent is nivolumab. In another such embodiment, the agent is atezolizumab. In another such embodiment, the agent is durvalumab. In another such embodiment, the agent is avelumab.

In another embodiment, there is provided a method of treating cancer comprising administering an effective amount of a compound of the invention, or a pharmaceutically acceptable salt thereof, to a person in need thereof, in a combination with a PD-1 antagonist, wherein said cancer is selected from melanoma, non-small cell lung cancer, small cell lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, and salivary cancer. In one such embodiment, the agent is a PD-1 antagonist. In one such embodiment, the agent is pembrolizumab. In another such embodiment, the agent is nivolumab. In another such embodiment, the agent is atezolizumab. In another such embodiment, the agent is durvalumab. In another such embodiment, the agent is avelumab.

In one embodiment, there is provided a method of treating unresectable or metastatic melanoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating recurrent or metastatic head and neck squamous cell cancer (HNSCC) comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating classical Hodgkin lymphoma (cHL) comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating urothelial carcinoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating gastric cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating cervical cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating primary mediastinal large-B-cell lymphoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating microsatellite instability-high (MSI-H) cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating non-small cell lung cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating hepatocellular carcinoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In another embodiment, the additional therapeutic agent is at least one immunomodulator other than an A2a or A2b receptor inhibitor. Non-limiting examples of immunomodulators include CD40L, B7, B7RP1, anti-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-a/-13, M-CSF, IL-3, GM-CSF, IL-13, anti-IL-10 and indolamine 2,3-dioxygenase 1 (IDO1) inhibitors.

In another embodiment, the additional therapeutic agent comprises radiation. Such radiation includes localized radiation therapy and total body radiation therapy.

In another embodiment, the additional therapeutic agent is at least one chemotherapeutic agent. Non-limiting examples of chemotherapeutic agents contemplated for use in combination with the compounds of the invention include: pemetrexed, alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine), nitroso ureas such as carmustine, lomustine, and streptozocin; topoisomerase 1 inhibitors (e.g., irinotecan); platinum complexes such as cisplatin, carboplatin and oxaliplatin; bioreductive alkylators such as mitomycin, procarbazine, dacarbazine and altretamine); anthracycline-based therapies (e.g., doxorubicin, daunorubicin, epirubicin and idarubicin); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethynyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); luteinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide).

In another embodiment, the additional therapeutic agent is at least one signal transduction inhibitor (STI). Non-limiting examples of signal transduction inhibitors include BCR/ABL kinase inhibitors, epidermal growth factor (EGF) receptor inhibitors, HER-2/neu receptor inhibitors, and farnesyl transferase inhibitors (FTIs).

In another embodiment, the additional therapeutic agent is at least one anti-infective agent. Non-limiting examples of anti-infective agents include cytokines, non-limiting examples of which include granulocyte-macrophage colony stimulating factor (GM-CSF) and an flt3-ligand.

In another embodiment, the present invention provides a method for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackievirus, and human immunodeficiency virus (HIV).

In another embodiment, the present invention provides a method for the treatment of an infective disorder, said method comprising administering to a subject in need thereof an effective amount of a compound of the invention, or a pharmaceutically acceptable salt thereof, in combination with a vaccine. In some embodiments, the vaccine is an anti-viral vaccine, including, for example, an anti-HTV vaccine. Other antiviral agents contemplated for use include an anti-HIV, anti-HPV, anti HCV, anti HSV agents and the like. In other embodiments, the vaccine is effective against tuberculosis or malaria. In still other embodiments, the vaccine is a tumor vaccine (e.g., a vaccine effective against melanoma) the tumor vaccine may comprise genetically modified tumor cells or a genetically modified cell line, including genetically modified tumor cells or a genetically modified cell line that has been transfected to express granulocyte-macrophage stimulating factor (GM-CSF). In another embodiment, the vaccine includes one or more immunogenic peptides and/or dendritic cells.

In another embodiment, the present invention provides for the treatment of an infection by administering a compound of the invention, or a pharmaceutically acceptable salt thereof, and at least one additional therapeutic agent, wherein a symptom of the infection observed after administering both the compound of the invention (or a pharmaceutically acceptable salt thereof) and the additional therapeutic agent is improved over the same symptom of infection observed after administering either alone. In some embodiments, the symptom of infection observed can be reduction in viral load, increase in CD4+ T cell count, decrease in opportunistic infections, increased survival time, eradication of chronic infection, or a combination thereof.

Definitions

As used herein, unless otherwise specified, the following terms have the following meanings.

Unsatisfied valences in the text, schemes, examples, structural formulae, and any Tables herein are assumed to have a hydrogen atom or atoms of sufficient number to satisfy the valences.

When a variable appears more than once in any moiety or in any compound of the invention (e.g., aryl, heterocycle, $N(R)_2$), the selection of moieties defining that variable for each occurrence is independent of its definition at every other occurrence unless specified otherwise in the local variable definition.

As used herein, unless otherwise specified, the term "A2a receptor antagonist" (equivalently, A2a antagonist) and/or "A2b receptor antagonist" (equivalently, A2b antagonist) means a compound exhibiting a potency ($IC_{50}$) of less than about 1 μM with respect to the A2a and/or A2b receptors, respectively, when assayed in accordance with the procedures described herein. Preferred compounds exhibit at least 10-fold selectivity for antagonizing the A2a receptor and/or the A2b receptor over any other adenosine receptor (e.g., A1 or A3).

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administrations.

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

Whether used in reference to a substituent on a compound or a component of a pharmaceutical composition the phrase "one or more", means the same as "at least one".

"Concurrently" and "contemporaneously" both include in their meaning (1) simultaneously in time (e.g., at the same time); and (2) at different times but within the course of a common treatment schedule.

"Consecutively" means one following the other.

"Sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component.

"Effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating a cancer as described herein with one or more of the compounds of the invention optionally in combination with one or more additional agents, "effective amount" (or "therapeutically effective amount") means, for example, providing the amount of at least one compound of the invention that results in a therapeutic response in a patient afflicted with the disease, condition, or disorder, including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition.

"Patient" and "subject" means an animal, such as a mammal a human being) and is preferably a human being.

"Prodrug" means compounds that are rapidly transformed, for example, by hydrolysis in blood, in vivo to the parent compound, e.g., conversion of a prodrug of a compound of the invention to a compound of the invention, or to a salt thereof. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and. Pergamon Press, 1987, both of which are incorporated herein by reference; the scope of this invention includes prodrugs of the novel compounds of this invention.

The term "substituted" means that one or more of the moieties enumerated as substituents (or, where a list of substituents are not specifically enumerated, the substituents specified elsewhere in this application) for the particular type of substrate to which said substituent is appended, provided that such substitution does not exceed the normal valence rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution by a moiety is described (e.g. "optionally substituted") the term means that if substituents are present, one or more of the enumerated (or default) moieties listed as optional substituents for the specified substrate can be present on the substrate in a bonding position normally occupied by the default substituent, for example, a hydrogen atom on an alkyl chain can be substituted by one of the optional substituents, in accordance with the definition of "substituted" presented herein.

"Alkyl" means an aliphatic hydrocarbon group, which may be straight or branched, comprising 1 to 10 carbon atoms. "$(C_1-C_6)$alkyl" means an aliphatic hydrocarbon group, which may be straight or branched, comprising 1 to 6 carbon atoms. Branched means that one or more lower alkyl groups such as methyl, ethyl or propyl, are attached to a linear alkyl chain. Non-limiting examples of alkyl groups include methyl, ethyl, n-propyl, isopropyl, n-butyl, i-butyl, and t-butyl.

"Haloalkyl" means an alkyl as defined above wherein one or more hydrogen atoms on the alkyl (up to and including each available hydrogen group) is replaced by a halogen atom. As appreciated by those of skill in the art, "halo" or "halogen" as used herein is intended to include chloro (Cl), fluoro (F), bromo (Br) and iodo (I). Chloro (Cl) and fluoro (F) halogens are generally preferred.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazol, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridinyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic fully saturated monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyl groups contain 4, 5 or 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide, "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

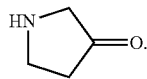

As used herein, the term "monocyclic heterocycloalkyl" refers to monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

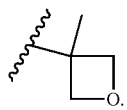

It is noted that in hetero-atom containing ring systems of this invention, there are no hydroxyl groups on carbon atoms adjacent to a N, O or S, as well as there are no N or S groups on carbon adjacent to another heteroatom.

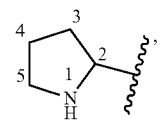

there is no —OH attached directly to carbons marked 2 and 5.

The line ———, as a bond generally indicates a mixture of, or either of, the possible isomers, e.g., containing (R)- and (S)-stereochemistry. For example:

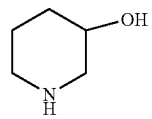

means containing both

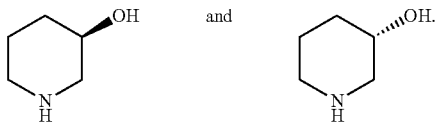

The wavy line, ~~~, as used herein, indicates a point of attachment to the rest of the compound. Lines drawn into the ring systems, such as, for example:

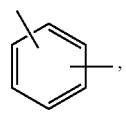

indicate that the indicated line (bond) may be attached to any of the substitutable ring atoms.

"Oxo" is defined as an oxygen atom that is double bonded to a ring carbon in a cycloalkyl, cycloalkenyl, heterocyclyl, heterocyclenyl, or other ring described herein, e.g.,

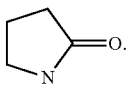

As well known in the art, a bond drawn from a particular atom wherein no moiety is depicted at the terminal end of the bond indicates a methyl group bound through that bond to the atom, unless stated otherwise. For example:

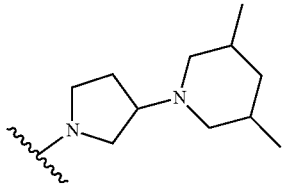 [SMILES: *N1CCC(N2CC(C)CC(C)C2)C1]

represents

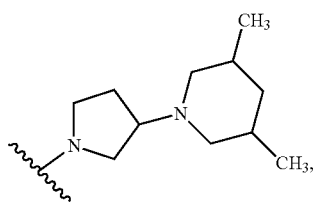 [SMILES: *N1CCC(N2CC(C)CC(C)C2)C1]

One or more compounds of the invention may also exist as, or optionally be converted to, a solvate. Preparation of solvates is generally known. Thus, for example, M. Caira et al., J. Pharmaceutical Sci., 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al., AAPS PharmSciTech., 5(1), article 12 (2004); and A. L. Bingham et al., Chem. Commun., 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I. R. spectroscopy, show the presence of the solvent (including water) in the crystals as a solvate (or hydrate in the case where water is incorporated into the crystalline form).

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

This invention also includes the compounds of the invention in isolated and purified form obtained by routine techniques. Polymorphic forms of the compounds of the invention, and of the salts, solvates and prodrugs thereof, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In similar manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

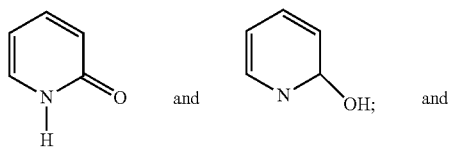

and

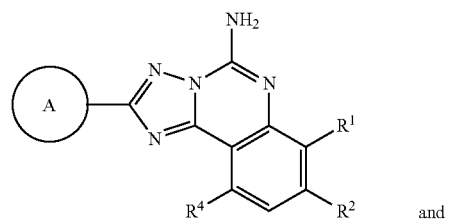

and

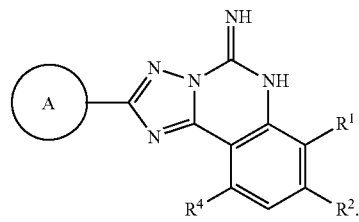

Where a reaction scheme appearing in an example employs a compound having one or more stereocenters, the stereocenters are indicated with an asterisk, as shown below:

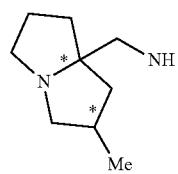 [SMILES: CC1CN2CCCC2(CN)C1]

Accordingly, the above depiction consists of the following pairs of isomers: (i) Trans-isomers ((2R,7aS)-2-methyl-hexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl) methanamine (Compound ABC-3) and ((2S,7aS)-2-methylhexahydro-1H-pyrrolizin-7a-yl)methanamine (Compound ABC-4).

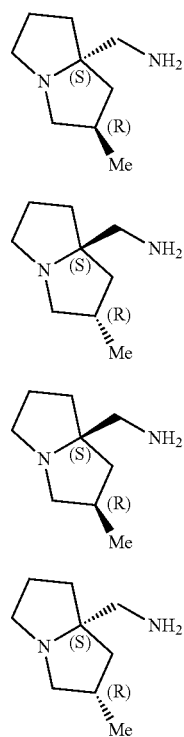

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al., The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Intl. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), arylalkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the scope of the invention.

A functional group in a compound termed "protected" means that the group is in modified form to preclude undesired side reactions at the protected site when the protected compound is subjected to particular reaction conditions aimed at modifying another region of the molecule. Suitable protecting groups are known, for example, as by reference to standard textbooks, for example, T. W. Greene et al., Protective Groups in organic Synthesis (1991), Wiley, New York.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the Schemes and Examples herein using appropriate isotopically-enriched reagents and/or intermediates.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, and $^{36}$Cl, $^{123}$I, and $^{125}$I. It will be appreciated that other isotopes also nay be incorporated by known means.

Certain isotopically-labeled compounds of the invention (e.g., those labeled with $^3$H, $^{11}$C and $^{14}$C) are recognized as being particularly useful in compound and/or substrate tissue distribution assays using a variety of known techniques. Tritiated (i.e., $^3$H) and carbon-14 (i.e., $^{14}$C) isotopes are particularly preferred for their ease of preparation and detection. Further, substitution of a naturally abundant isotope with a heavier isotope, for example, substitution of protium with deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

The term "composition" is intended to encompass a product comprising the specified ingredients in the specified amounts, and any product which results, directly or indirectly, from combination of the specified ingredients in the specified amounts.

The term "pharmaceutical composition" as used herein encompasses both the bulk composition and individual dosage units comprised of one, or more than one (e.g., two), pharmaceutically active agents such as, for example, a compound of the present invention (optionally together with an additional agent as described herein), along with any pharmaceutically inactive excipients. As will be appreciated by those of ordinary skill in the art, excipients are any constituent which adapts the composition to a particular route of administration or aids the processing of a composition into a dosage form without itself exerting an active pharmaceutical effect. The bulk composition and each individual dosage unit can contain fixed amounts of the aforesaid one, or more than one, pharmaceutically active agents. The bulk composition is material that has not yet been formed into individual dosage units.

It will be appreciated that pharmaceutical formulations of the invention may comprise more than one compound of the invention (or a pharmaceutically acceptable salt thereof), for example, the combination of two or three compounds of the invention, each present in such a composition by adding to the formulation the desired amount of the compound in a pharmaceutically acceptably pure form. It will be appreciated also that in formulating compositions of the invention, a composition may comprise, in addition to one or more of compounds of the invention, one or more other agents which also have pharmacological activity, as described herein.

While formulations of the invention may be employed in bulk form, it will be appreciated that for most applications the inventive formulations will be incorporated into a dosage form suitable for administration to a patient, each dosage form comprising an amount of the selected formulation which contains an effective amount of one or more compounds of the invention. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions comprising compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20th Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In accordance with the present invention, antagonism of adenosine A2a and/or A2b receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, or a salt thereof, and at least one pharmaceutically acceptable carrier (described herein). It will be appreciated that pharmaceutically formulations of the invention may comprise more than one compound of the invention, or a salt thereof, for example, the combination of two or three compounds of the invention, or, additionally or alternatively, another therapeutic agent such as those described herein, each present by adding to the formulation the desired amount of the compound or a salt thereof (or agent, where applicable) which has been isolated in a pharmaceutically acceptably pure form.

As mentioned above, administration of a compound of the invention to effect antagonism of A2a and/or A2b receptors is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof. Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the invention can be administered at a total daily dosage of up to 1,000 mg, which can be administered in one daily dose or can be divided into multiple doses per 24 hour period, for example, two to four doses per day.

As those of ordinary skill in the art will appreciate, an appropriate dosage level for a compound (or compounds) of the invention will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 200, 25.0, 50.0, 75.0, 100.0, 150.0, 200.0, 2500, 300.0, 400.0, 500.0, 600.0, 750.0, 800.0, 9000, and 1000.0 milligrams of the active ingredient for the symptomatic adjustment of the dosage to the patient to be treated. The compounds may be administered on a regimen of 1 to 4 times per day, or may be administered once or twice per day.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during a treatment cycle.

In general, in whatever form administered, the dosage form administered will contain an amount of at least one compound of the invention, or a salt thereof, which will provide a therapeutically effective serum level of the compound in some form for a suitable period of time such as at least 2 hours, more preferably at least four hours or longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active agents as may be additionally needed or desired in the course of providing treatment. As will be appreciated, the dosage form administered may also be in a form providing an extended release period for the pharmaceutically active compound which will provide a therapeutic serum level for a longer period, necessitating less frequent dosage intervals.

Preparative Examples

The compounds of the present invention can be prepared readily according to the following schemes and specific examples, or modifications thereof, using readily available starting materials, reagents and conventional synthetic procedures. In these reactions, it is also possible to make use of variants which are themselves known to those of ordinary skill in this art but are not mentioned in detail. The general procedures for making the compounds claimed in this invention can be readily understood and appreciated by one skilled in the art from viewing the following Schemes and descriptions.

General Scheme A

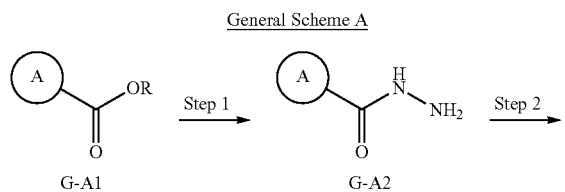

G-A1   G-A2

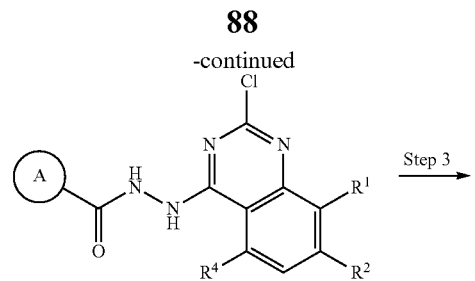

G-A3

DMB = 2,4-Dimethoxybenzyl

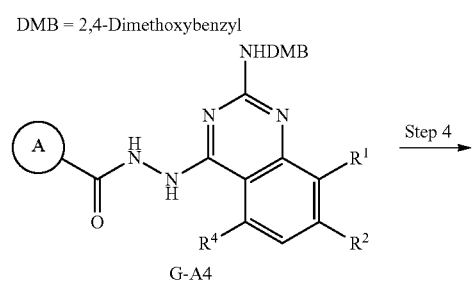

G-A4

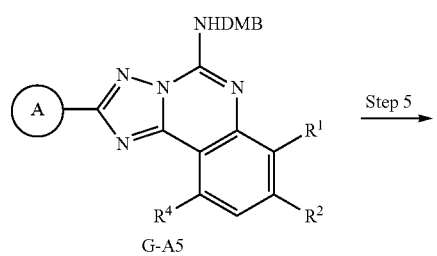

G-A5

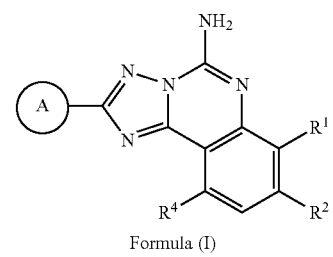

Formula (I)

One general strategy for the synthesis of compounds of type G-A5 is via the five-step procedure shown in General Scheme A, wherein OR is an alkoxy group and wherein ring A, $R^1$, $R^2$, and $R^4$ are as defined in Formula (I). Esters G-A1 can be treated with hydrazine hydrate in solvents such as MeOH to form intermediate hydrazides G-A2. In the second step, these hydrazides can then be combined with dichloropyrimidines in the presence of a base such as DIPEA in a solvent such as dioxane to produce the coupled products G-A3. In the third step, 2, 4-dimethoxybenzyl amine is added with a base such as DIPEA in a solvent such as dioxane to generate pyrimidines G-A4. In the fourth step, pyrimidines G-A4 are heated in BSA to generate tricyclic pyrimidines G-A5. In Step 5, treatment of G-A5 with acids such as TFA, HCl, and the like will afford compounds of Formula (I).

General Scheme B

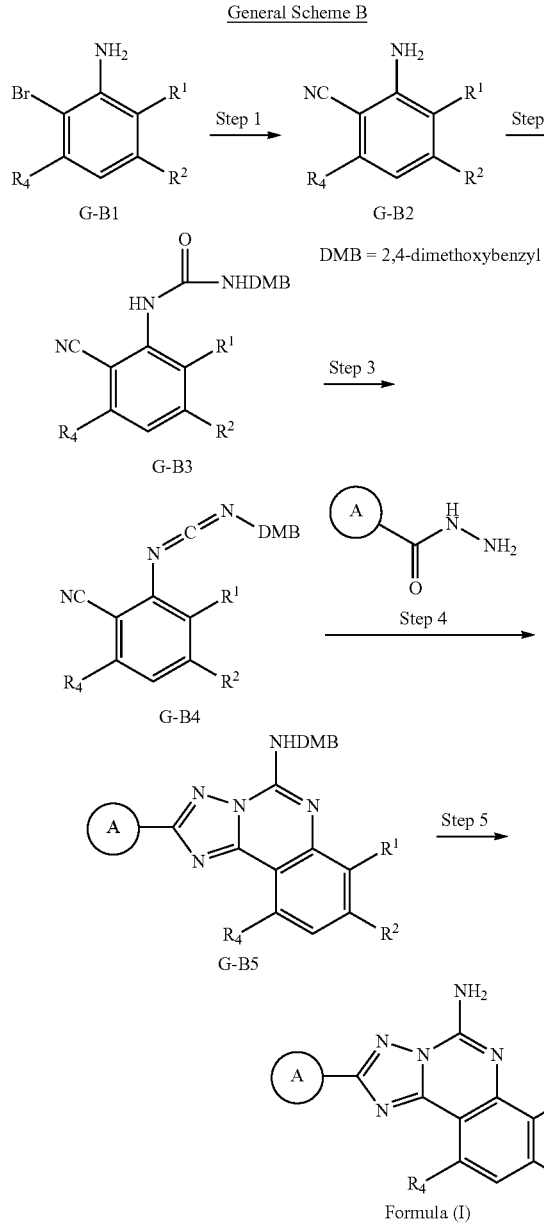

One general strategy for the synthesis of compounds of type G-B5 is via the five-step procedure shown in General Scheme B, wherein $R^1$, $R^2$, and $R^4$ are defined in Formula (I). Bromides G-B1 can be treated with dicyano zinc, the appropriate palladium catalyst, solvent, and base (when necessary) to form intermediate nitrites G-B2. In the second step, these nitrites can then be combined with 1-(isocyanatomethyl)-2,4-dimethoxybenzene in the presence of a base such as pyridine in a solvent such as DCM to produce the coupled products G-B3. In the third step, triphenylphosphine, DEA are added in along with carbon tetrabromide in a solvent such as DCM to generate nitriles G-B4. In the fourth step, nitrites G-A4 can be combined with hydrazides in the presence of an acid such as AcOH in a solvent such as DCM to generate tricyclic pyrimidines G-B5. In Step 5, treatment of G-B5 with acids such as TFA, HCl, and the like will afford compounds of Formula (I).

Experimentals

The following abbreviations may be used in the following experimentals:

| | |
|---|---|
| ° C. | Degrees Celsius |
| AcOH | Acetic acid |
| aq. | Aqueous |
| Atm | Atmospheres |
| BHT | 3,5-Di-tert-4-butylhydroxytoluene |
| BSA | N,O-Bis(trimethylsilyl)acetamide |
| CDI | 1,1'-Carbonyldiimidazole |
| $CD_3OD$ | Deuterated Methanol-d4 |
| CPME | Cyclopentyl methyl ether |
| DBU | Diazabicycloundecene |
| DCE | 1,2-Dichloroethane |
| DCM | Dichloromethane |
| DDQ | 2,3-Dichloro-5,6-dicyano-p-benzoquinone |
| DEA | Diethylamine |
| DIBAL | Diisobutylaluminium hydride |
| DIEA | N,N-Diisopropylethylamine |
| DIPA | Diisopropylamine |
| DIPEA | N,N-Diisopropylethylamine |
| DMA | N,N-Dimethylacetamide |
| DMAP | 4-Dimethylaminopyridine |
| DME | Dimethoxyethane |
| DMF | Dimethylformamide |
| DMP | Dess-Martin periodinane |
| DMPU | 1,3-Dimethyl-3,4,5,6-tetrahydro-2(1H)-pyrimidinone |
| DMSO | Dimethyl Sulfoxide |
| DMSO-d6 | Deuterated Dimethyl Sulfoxide |
| DPP | Diphenylphosphine |
| Dppf | Bis(diphenylphosphino)ferrocene |
| ESI | Electrospray Ionization |
| $ET_3N$ | Triethylamine |
| $Et_2O$ | Diethylether |
| EtOAc | Ethyl Acetate |
| EtOH | Ethanol |
| H | Hours |
| HPLC | High Performance Liquid Chromatography |
| IPA | Isopropyl alcohol |
| LED | Light-emitting diode |
| LiHMDS | Lithium bis(trimethylsilyl)amide |
| M | Molar |
| MeCN | Acetonitrile |
| MeOD-d4 | Deuterated Methanol |
| MeOH | Methanol |
| MHz | Megahertz |
| Min | Minutes |
| MI | Milliliters |
| MP TMT resin | Macroporous polystyrene-bound trimercaptotriazine, a resin bound equivalent of 2,4,6-trimercaptotriazine |
| MS | Mass Spectroscopy |
| MsCl | p-Toluenesulfonyl chloride |
| NBS | N-Bromosuccinimide |
| Nm | Nanometers |
| NMP | N-Methyl-2-pyrrolidone |
| NMR | Nuclear Magnetic Resonance |
| N-XantPhos | 4,6-Bis(diphenylphosphino)-10H-phenoxazine |
| Pd/C | Palladium on Carbon |
| Prep SFC | Preparative Super Critical Fluid (CO2) |
| p-TsOH | 4-Methylbenzenesulfonic acid |
| rac- | racemic |
| RT | Retention Time |
| sat. | Saturated |
| TBAF | Tetrabutylammonium fluoride |
| TBME | Methyl tert-butyl ether |

| | |
|---|---|
| t-BuXPhos Pc G3 | 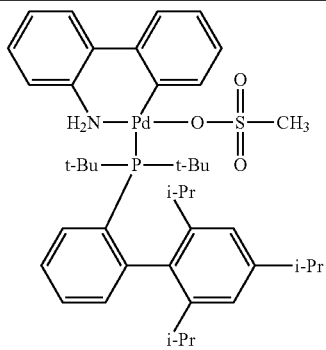 |
| | [(2-di-tert-butylphosphino-2',4',6'-triisopropyl-1,1'-biphenyl)-2-(2'-amino-1,1'-biphenyl)]palladium(II) methansulfonate CAS# 1447963-75-8 |
| TFA | Trifluoroacetic acid |
| TFE | 2,2,2-Trifluoroethanol |
| TF$_2$O | Trifluoromethanesulfonic anhydride |
| THF | Tetrahydrofuran |
| TLC | Thin Layer Chromatography |
| XPhos Pd G2 | 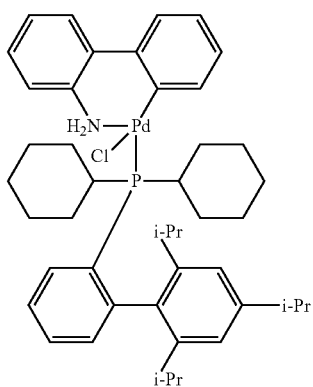 |
| | Chloro(2-dicyclohexylphosphino-2',4',6'-triisopropyl-1,1'-biphenyl)[2-(2'-amino-1,1'-biphenyl)]palladium(II) CAS# 1310584-14-5 |
| cataCXium ® A PD G3 | Mesylate[(di(1-adamantyl)-n-butylphosphine)-2-(2'-amino-1,1'-biphenyl)]palladium(II), [Di(1-adamantyl)-butylphosphine)-2-(2'-amino-1,1'-biphenyl)]palladium(II) methanesulfonate CAS# 321921-71-5 |
| Pd-BINAP G3 | PubChem Substance ID: 329824403 |
| XPhos Pd G3 | 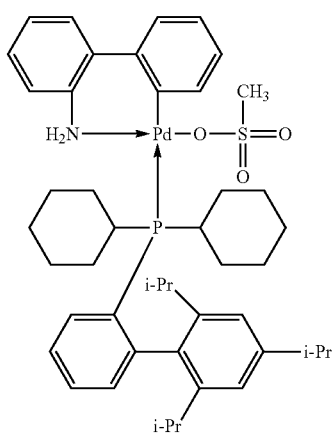 |

| | |
|---|---|
| CPhos Pd G4 | (2-Dicyclohexylphosphino-2',4',6'-triisopropyl-1,1'-biphenyl)[2-(2'-amino-1,1'-biphenyl)]palladium(II) methanesulfonate CAS# 1445085-55-1 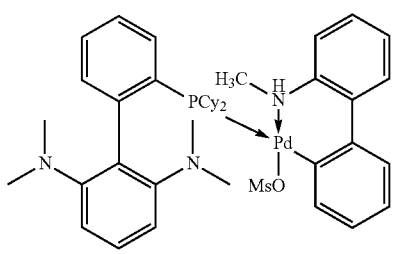 |
| | Product Number: 900471 (Sigma Aldrich) |

General Experimental Information

Unless otherwise noted, all reactions were magnetically stirred and performed under an inert atmosphere such as nitrogen or argon.

Unless otherwise noted, diethyl ether used in the experiments described below was Fisher ACS certified material and stabilized with BHT.

Unless otherwise noted, "degassed" refers to a solvent from which oxygen has been removed, generally by bubbling an inert gas such as nitrogen or argon through the solution for 10 to 15 minutes with an outlet needle to normalize pressure. Unless otherwise noted, "concentrated" means evaporating the solvent from a solution or mixture using a rotary evaporator or vacuum pump.

Unless otherwise noted, silica gel chromatography was carried out on an ISCO®, Analogix®, or Biotage® automated chromatography system using a commercially available cartridge as the column. Columns were usually filled with silica gel as the stationary phase. Reverse phase preparative HPLC conditions can be found at the end of the experimental section. Aqueous solutions were concentrated on a Genevac® evaporator or were lyophilized.

Unless otherwise noted, proton nuclear magnetic resonance ($^1$H NMR) spectra and proton-decoupled carbon nuclear magnetic resonance ($^{13}$C{$^1$H} NMR) spectra were recorded on 400, 500, or 600 MHz Bruker or Varian NMR spectrometers at ambient temperature. All chemical shifts (δ) were reported in parts per million (ppm). Proton resonances were referenced to residual protium in the NMR solvent, which can include, but is not limited to, CDCl$_3$, DMSO-d$_6$, and MeOD-d$_4$. Carbon resonances are referenced to the carbon resonances of the NMR solvent. Data are represented as follows: chemical shift, multiplicity (br=broad, br s=broad singlet, s=singlet, d=doublet, dd=doublet of doublets, ddd=doublet of doublet of doublets, t=triplet, q=quartet, m=multiplet), coupling constants (J) in Hertz (Hz), integration.

Intermediate A1

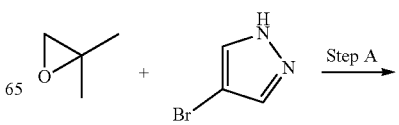

-continued

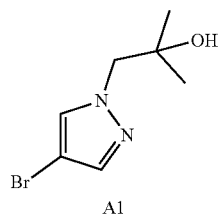

A1

Step A Synthesis of Intermediate A1. 1-(4-bromo-1H-pyrazol-1-yl)-2-methylpropan-2-ol A mixture of 4-bromo-1H-pyrazole (5 g, 34.0 mmol) in DRIP (4.5 mL) was treated with cesium carbonate (16.63 g, 51.0 mmol) and 2,2-dimethyloxirane (7.36 g, 102 mmol). The resulting mixture was stirred at 25° C. for 14 hours. Upon completion, the reaction mixture was diluted with EtOAc (100 mL) and water (100 mL). The organic layer was separated, washed with brine (50 mL), dried over $Na_2SO_4$, and concentrated. The crude residue was purified by silica gel column chromatography with 0-15% EtOAc/petroleum ether as eluent to provide A1. LC/MS (ES, m/z)=219, 221 $[M+H]^+$.

Compounds in Table A were prepared using a similar procedure to INTERMEDIATE A1, in some cases using a higher reaction temperature, starting from commercially available bromoheterocycles and epoxides.

TABLE A

| Entry | Structure Name | Observed m/z $[M + H]^+$ |
|---|---|---|
| A2 | 1-(4-bromo-3-methyl-1H-pyrazol-1-yl)-2-methylpropan-2-ol | 233, 235 |
| A3 | 1-(4-bromo-5-methyl-1H-pyrazol-1-yl)-2-methylpropan-2-ol | 233, 235 |
| A4 | 3-(4-bromo-1H-pyrazol-1-yl)-2-methylbutan-2-ol | 233, 235 |

TABLE A-continued

| Entry | Structure Name | Observed m/z $[M + H]^+$ |
|---|---|---|
| A5 | 1-(3-bromo-1H-1,2,4-triazol-1-yl)-2-methylpropan-2-ol | 220, 222 |
| A6 | 1-(3-bromo-5-methyl-1H-1,2,4-triazol-1-yl)-2-methylpropan-2-ol | 234, 236 |
| A7 | rac, trans-2-(4-bromo-1H-pyrazol-1-yl)cyclopentan-1-ol | 231, 233 |
| A8 | rac, trans-2-(4-bromo-1H-pyrazol-1-yl)-1-methylcyclopentan-1-ol | 245, 247 |
| A9 | rac-3-(4-bromo-5-methyl-1H-pyrazol-1-yl)-2-methylbutan-2-ol | 247, 249 |
| A10 | rac-3-(4-bromo-3-methyl-1H-pryazol-1-yl)-2-methylbutan-2-ol | 247, 249 |

TABLE A-continued

| Entry | Structure Name | Observed m/z [M + H]+ |
|---|---|---|
| A11 | 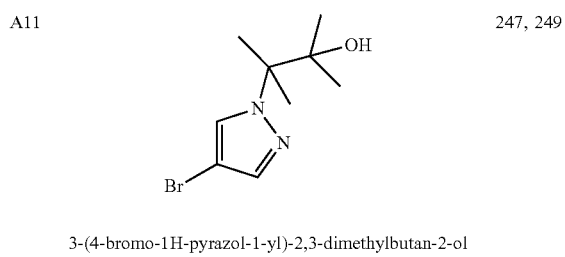<br>3-(4-bromo-1H-pyrazol-1-yl)-2,3-dimethylbutan-2-ol | 247, 249 |
| A12 | 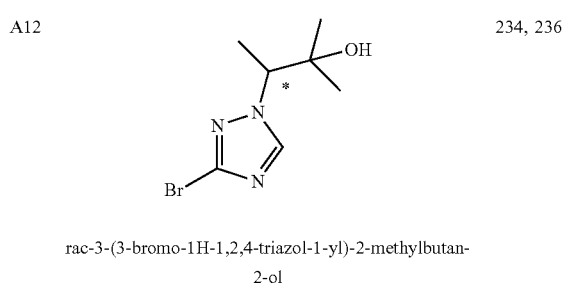<br>rac-3-(3-bromo-1H-1,2,4-triazol-1-yl)-2-methylbutan-2-ol | 234, 236 |
| A13 | 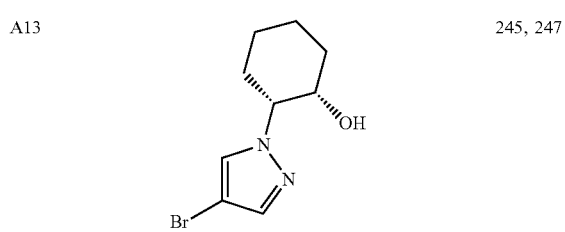<br>(1S,2R)-2-(4-bromo-1H-pyrazol-1-yl)cyclohexan-1-ol | 245, 247 |
| A14 | 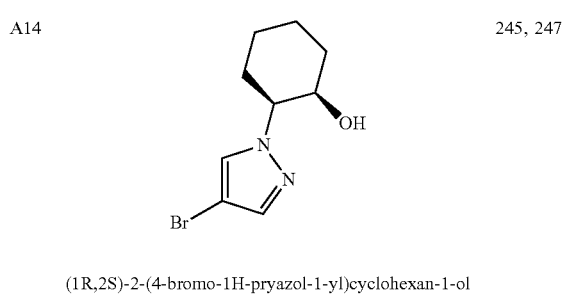<br>(1R,2S)-2-(4-bromo-1H-pryazol-1-yl)cyclohexan-1-ol | 245, 247 |
| A15 | 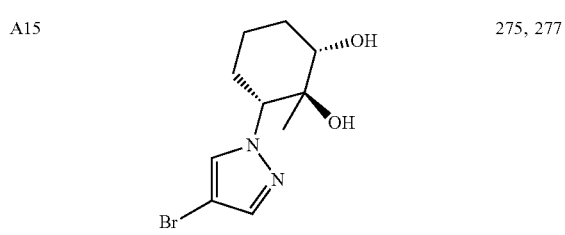<br>(1S,2S,6R)-6-(4-bromo-1H-pyrazol-1-yl)-1-methylcyclohexane-1,2-diol | 275, 277 |
| A16 | 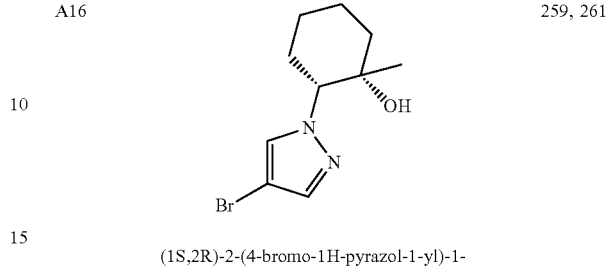<br>(1S,2R)-2-(4-bromo-1H-pyrazol-1-yl)-1-methylcyclohexan-1-ol | 259, 261 |
| A17 | 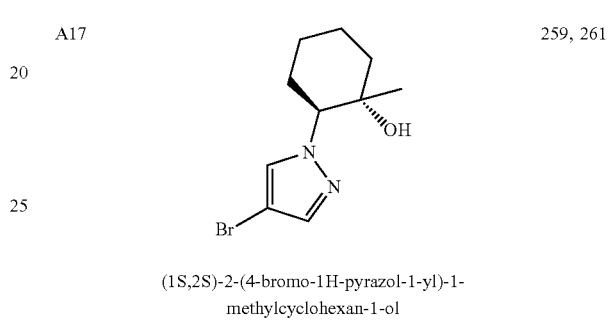<br>(1S,2S)-2-(4-bromo-1H-pyrazol-1-yl)-1-methylcyclohexan-1-ol | 259, 261 |
| A18 | 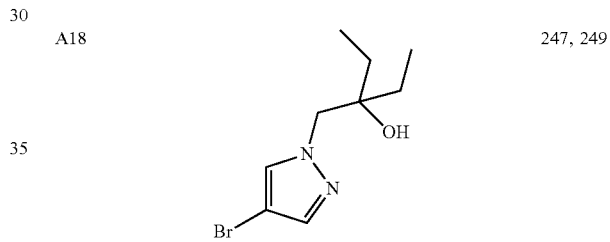<br>3-((4-bromo-1H-pyrazol-1-yl)methyl)pentan-3-ol | 247, 249 |
| A19 | 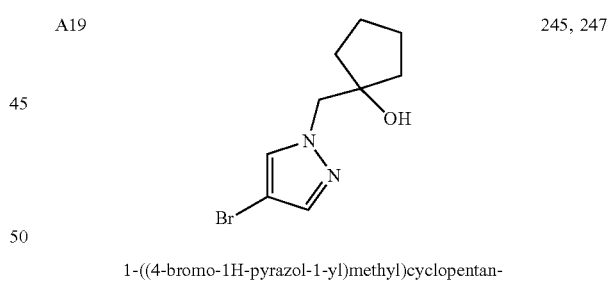<br>1-((4-bromo-1H-pyrazol-1-yl)methyl)cyclopentan-1-ol | 245, 247 |
| A20 | 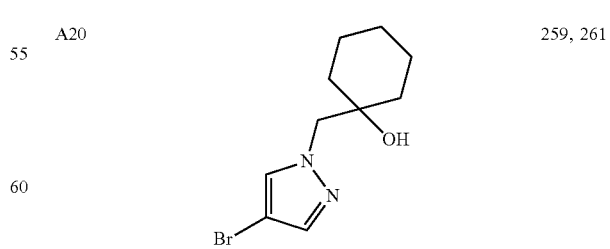<br>1-((4-bromo-1H-pryazol-1-yl)methyl)cyclohexan-1-ol | 259, 261 |

TABLE A-continued

| Entry | Structure Name | Observed m/z [M + H]⁺ |
|---|---|---|
| A21 | 1-(4-bromo-3-(difluoromethyl)-1H-pryazol-1-yl)-2-methylpropan-2-ol | 269, 271 |
| A22 | 1-(4-bromo-3-(trifluoromethyl)-1H-pryazol-1-yl)-2-methylpropan-2-ol | 287, 289 |
| A23 | 1-(3-bromo-4-(trifluoromethyl)-1H-pyrazol-1-yl)-2-methylpropan-2-ol | 287, 289 |
| A24 | 1-(4-bromo-1H-1,2,3-triazol-1-yl)-2-methylpropan-2-ol | 220, 222 |
| A25 | 1-(3-bromo-1H-pyrazol-1-yl)-2-methylpropan-2-ol | 219, 221 |

Intermediates A4A and A4B

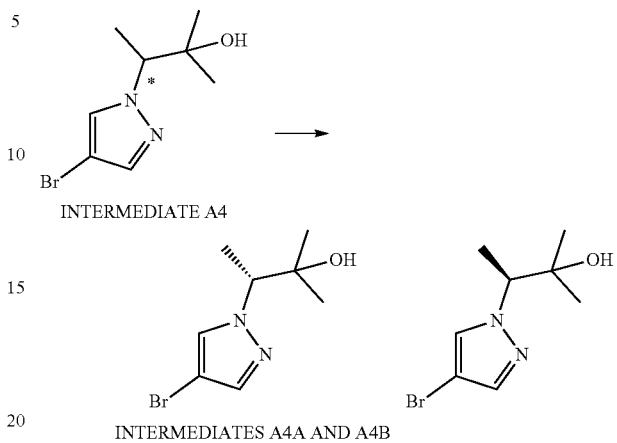

INTERMEDIATE A4

INTERMEDIATES A4A AND A4B

Synthesis of Intermediates A4A and A4B: (R)-3-(4-bromo-1H-pyrazol-1-yl)-2-methylbutan-2-ol and (S)-3-(4-bromo-1H-pyrazol-1-yl)-2-methylbutan-2-ol Intermediate A4 was subjected to chiral SFC (AD-H, Chiraltech, 50+250 mm, Co-Solvent: 45% (MeOH)) to afford Intermediate A4A (faster eluting isomer) and Intermediate A4B (slower eluting isomer).

Intermediate A26

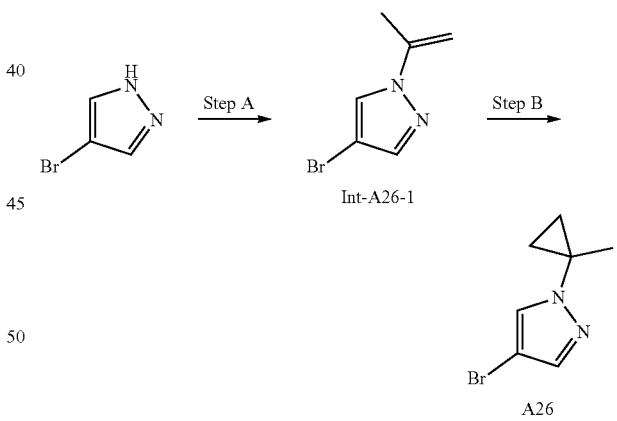

Step A—Synthesis of Compound Int-A26-1: 4-bromo-1-(prop-1-en-2-yl)-1H-pyrazole

A mixture of copper acetate (3.09 g, 17 mmol) and 2,2'-bipyridine (5.31 g, 34 mmol) were suspended in DCE (15 ml) and heated to 70° C. for 30 minutes. The resulting turquoise suspension was added to a stirred suspension of 4-bromo-1H-pyrazole (2.499 g, 17 mmol), potassium trifluoro(prop-1-en-2-yl)borate (5.03 g, 34 mmol) and Na₂CO₃ (3.60 g, 34.0 mmol) in DCE (10 ml). The resulting reaction mixture was stirred at 70° C. for 48 hours. Upon completion, the reaction mixture was partitioned between EtOAc and 1N HCl aqueous solution. The layers were separated, and the aqueous layer was extracted with ethyl acetate twice. The combined organic layers were washed with brine, dried over anhydrous $Na_2SO_4$, filtered and evaporated to afford a crude residue, then purified by silica gel column chromatography with 0% to 10% EtOAc in hexanes as eluent to provide the title compound Int-A26-1. LC/MS (ES, m/z)=187, 189 $[M+H]^+$.

Step B—Synthesis of 4-bromo-1-(1-methylcyclopropyl)-1H-pyrazole (Intermediate A26)

A 25 mL round bottomed flask with a magnetic stir bar was evacuated then backfilled with nitrogen three times. DCM (3208 μL) and 1M diethylzinc in toluene (4277 μl, 4.28 mmol) were added to the flask with stirring and the solution was cooled in an ice water bath. TFA (330 μl, 4.28 mmol) in DCM (1069 μl) was added dropwise with stirring. A precipitate formed. The suspension was stirred for 20 min at 0° C. Diiodomethane (345 μl, 4.28 mmol) in DCM (713 μl) was added dropwise with stirring at 0° C. The resulting mixture was stirred for 20 min, then 4-bromo-1-(prop-1-en-2-yl)-1H-pyrazole (400 mg, 2.139 mmol) in DCM (356 μl) was added dropwise, and the ice water bath was removed. The reaction mixture was stirred at room temperature for 4 hours then quenched with saturated aqueous $NH_4Cl$ solution. The layers were separated, and the aqueous layer was extracted with dichloromethane. The combined organic layers were washed with brine, dried over anhydrous $Na_2SO_4$, filtered, and evaporated to afford a crude residue. The crude residue was then purified by silica gel column chromatography with 0% to 30% EtOAc in hexanes as eluent to afford Intermediate A26. LC/MS (ES, m/z)=201, 203 $[M+H]^+$.

Intermediate A27

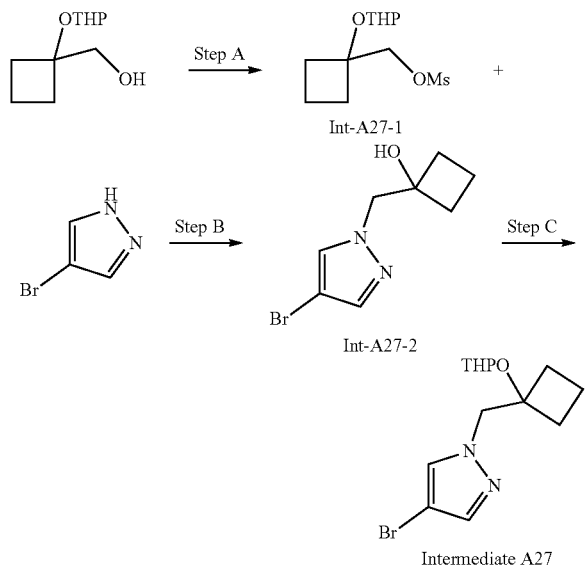

Step A—Synthesis of Compound Int-A27-1. (1-((tetrahydro-2H-pyran-2-yl)oxy)cyclobutyl)methyl methanesulfonate A mixture of (1-((tetrahydro-2H-pyran-2-yl)oxy)cyclobutyl)methanol (200 mg, 1.074 mmol) and $Et_3N$ (0.210 mL, 1.503 mmol) in DCM (2 mL) was cooled to 0° C. and treated with MSCl (0.211 mL, 2.71 mmol). The resulting mixture was stirred at 0° C. for 1 hour. Water (10 mL) was then added and the mixture was extracted with ethyl acetate (3×5 mL). The combined organic layers were dried over anhydrous $Na_2SO_4$, filtered, and concentrated to provide Int-A27-1, which was used in the next step without further purification.

Step B—Synthesis of Compound Int-A27-2. 1-((4-bromo-1H-pyrazol-1-yl)methyl)cyclobutanol A mixture of Int-A27-1 (39.6 mg, 0.150 mmol), $Cs_2CO_3$ (133 mg, 0.408 mmol) and 4-bromo-1H-pyrazole (20 mg, 0.136 mmol) in DMF (2 mL) was stirred at 90° C. for 12 hours. After cooling, water (10 mL) was added and the mixture was extracted with ethyl acetate (3×5 mL). The combined organic layers were dried over anhydrous $Na_2SO_4$, filtered, and concentrated. The crude residue was purified by preparative silica gel TLC plate with 50% EtOAc/petroleum ether as eluent to provide Int-A27-2. LC/MS (ES, m/z)=231, 233 $[M+H]^+$.

Step C—Synthesis Intermediate A27. 4-bromo-1-((1-((tetrahydro-2H-pyran-2-yl) oxy)cyclobutyl) methyl)-1H-pyrazole p-TsOH (4.94 mg, 0.026 mmol) and 3,4-dihydro-2H-pyran (21.54 mg, 0.260 mmol) were added to a stirred solution of 1-((4-bromo-1H-pyrazol-1-yl)methyl)cyclobutanol (60 mg, 0.260 mmol) in DCM (2 mL) at 0° C. The resulting mixture was stirred at 40° C. for 12 hours. After cooling, water (20 mL) was added, and then the mixture was extracted with ethyl acetate (3×10 mL). The combined organic layers were dried over anhydrous $Na_2SO_4$, filtered, and concentrated. The crude residue was purified by silica gel column chromatography with 0-10% EtOAc/Petroleum Ether as eluent to provide Intermediate A27. LC/MS (ES, m/z)=315, 317 $[M+H]^+$.

Intermediate A28

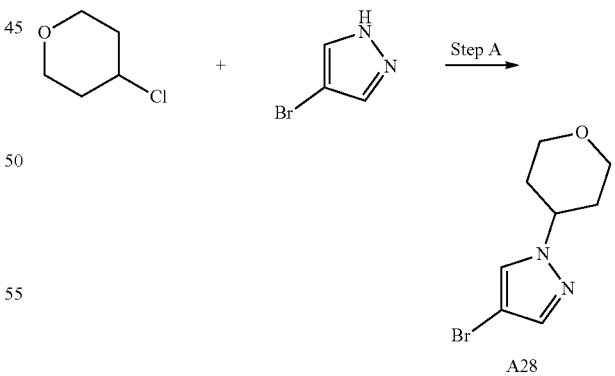

Step A—Synthesis of Intermediate A28. 4-bromo-1-(tetrahydro-2H-pyran-4-yl)-1H-pyrazole A solution of 4-bromo-1H-pyrazole (200 mg, 1.361 mmol) in DMF (2 mL) was treated with 4-chlorotetrahydro-2H-pyran (656 mg, 5.44 mmol) and $K_2CO_3$ (564 mg, 4.08 mmol). The resulting reaction mixture was stirred at 100° C.

for 3 h. After cooling, the mixture was filtered and the filtrate concentrated. The resulting residue was purified by silica gel column chromatography with 0-80% EtOAc/hexane as eluent to afford Intermediate A28. LC/MS (ES, m/z)=231, 233 [M+H]⁺.

Intermediate A29

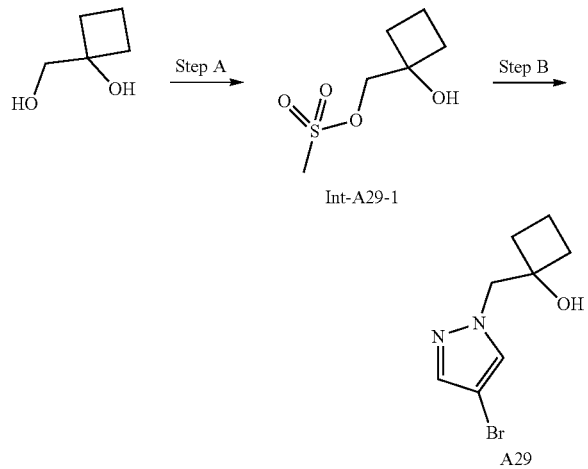

Step A—Synthesis of Compound Int-A29-1. 1-((4 (4-bromo-1H-pyrazol-1-yl)methyl)cyclobutan-1-ol To a stirred solution of 1-(hydroxymethyl) cyclobutan-1-ol (9.00 g, 88.0 mmol) in DCM (260 mL) at 0° C. was added triethylamine (17.2 ml, 123 mmol), followed by methanesulfonyl chloride (7.0 mL, 90 mmol). The mixture was stirred at 0° C. for 10 minutes and then at room temperature for 15 minutes. Upon completion, the mixture was washed with water, followed by brine. The organic layer was dried over anhydrous MgSO₄, filtered, and concentrated to provide Int-A29-1, which was used directly in the next step.

Step B—Synthesis of Intermediate A29. 1-((4-bromo-1H-pyrazol-1-yl)methyl)cyclobutan-1-ol To a solution of 4-bromo-1H-pyrazole (7.7 g, 52.4 mmol) in DMF (60 ml) at 0° C. was added NaH (60% in mineral oil, 2.30 g, 57.6 mmol) portionwise. The mixture was stirred at 0° C. under nitrogen for 30 minutes. To the mixture was added a solution of Int-A29-1 (13.1 g, 72.8 mmol) in DMF (20 ml). The mixture was heated at 90° C. for 16 hours to completion, then cooled and quenched with water (70 ml). The mixture was extracted with EtOAc three times. The combined organic layers were dried over anhydrous MgSO₄, filtered, and concentrated. The resulting residue was purified by silica gel column chromatography with 0-30% EtOAc in petroleum ether as eluent to afford Intermediate A29. LC/MS (ES, m/z)=231, 233 [M+H]⁺.

Compounds in Table B were prepared using a similar procedure to INTERMEDIATES A28 and A29, in some cases using a higher reaction temperature, starting from commercially available bromoheterocycles and alkyl alcohols or alkyl halides.

TABLE B

| Entry | Structure Name | Observed m/z [M + H]⁺ |
|---|---|---|
| A30 | 4-bromo-1-(2-oxaspiro[3.3]heptan-6-yl)-1H-pyrazole | 243, 245 |
| A31 | 4-bromo-1-(oxetan-3-yl)-1H-pyrazole | 202, 204 |
| A32 | rac-4-bromo-1-(tetrahydrofuran-3-yl)-1H-pyrazole | 216, 218 |
| A33 | 4-bromo-3-(difluoromethyl)-1-(tetrahydro-2H-pyran-4-yl)-1H-pyraozle | 281, 283 |
| A34 | 4-bromo-5-(difluoromethyl)-1-(tetrahydro-2H-pryan-4-yl)-1H-pyrazole | 281, 283 |

TABLE B-continued

| Entry | Structure Name | Observed m/z [M + H]+ |
|---|---|---|
| A35 | 4-bromo-3-methyl-1-(tetrahydro-2H-pryan-4-yl)-1H-pyrazole | 245, 247 |
| A36 | 4-bromo-5-methyl-1-(tetrahydro-2H-pryan-4-yl)-1H-pyrazole | 245, 247 |
| A37 | 4-bromo-2-(tetrahydro-2H-pyran-4-yl)-2H-1,2,3-triazole | 232, 234 |
| A38 | 3-bromo-1-(tetrahydro-2H-pyran-4-yl)-1H-1,2,4-triazole | 232, 234 |
| A39 | 4-bromo-1-((3-(fluoromethyl)oxetan-3-yl)methyl)-1H-pyrazole | 249, 251 |
| A40 | 1-((4-bromo-5-methyl-1H-pyrazol-1-yl)methyl)cyclobutan-1-ol | 245, 247 |
| A41 | 1-((4-bromo-3-methyl-1H-pyrazol-1-yl)methyl)cyclobutan-1-ol | 245, 247 |

Intermediate A42

Step A—Synthesis of Compound Int-A42-1. 2-(benzyloxy)cyclobutanone

To a mixture of phenylmethanol (1.2 mL, 12.50 mmol) and HCl-dioxane (25 mL) at 0° C. was added 1,2-bis((trimethylsilyl)oxy)cyclobut-1-ene (2.3 g, 9.98 mmol) dropwise with stirring at room temperature. After completion, the mixture was heated at 80° C. for 16 h, then concentrated. The resulting residue was purified by silica gel column chromatography with 0~15% ethyl acetate/petroleum ether as eluent to provide the title compound Int-A42-

1. $^1$H NMR (400 MHz, CDCl$_3$) δ 7.29-7.39 (m, 5H), 4.70-4.80 (m, 2H), 4.64 (d, J=11.40 Hz, 1H), 2.69-2.86 (m, 2H), 2.32 (dtd, J=5.48, 9.76, 10.96 Hz, 1H), 1.91-2.02 (m, 1H).

Step B—Synthesis of Compound Int-A42-2. 2-(benzyloxy)cyclobutanol

To a stirred solution of Int-A42-1 (1708 mg, 7.75 mmol) in MeOH (12 mL) was added NaBH$_4$ (734 mg, 19.40 mmol) portionwise at 0° C. The resulting mixture was stirred at room temperature for 1 hour. Upon completion, the reaction mixture was quenched with water (2 mL), and then diluted with DCM (20 mL). The organic layer was separated, dried over anhydrous Na$_2$SO$_4$, and filtered. The solvents of filtrate were concentrated to provide Int-A42-2. $^1$H NMR (400 MHz, CDCl$_3$) δ 7.28-7.39 (m, 6H), 4.49-4.62 (m, 2H), 4.09-4.33 (m, 1H), 3.75-4.09 (m, 1H), 1.92-2.13 (m, 3H), 1.31-1.43 (m, 1H).

Step C—Synthesis of Compound Int-A42-3. 2-(benzyloxy)cyclobutyl 4-(trifluoromethyl)benzenesulfonate To a stirred mixture of Int-A42-2 (1407 mg, 6.32 mmol), 4-(trifluoromethyl)benzene-1-sulfonyl chloride (3090 mg, 12.63 mmol) and DMAP (154 mg, 1.263 mmol) in DCM (25 mL) was added DIPEA (4.5 mL, 25.8 mmol) at room temperature. The resulting mixture was stirred at room temperature for 14 h. Upon completion, the reaction mixture was concentrated. The resulting crude residue was purified by silica gel column chromatography with 0-20% EtOAc in petroleum ether as eluent to provide Int-A42-3. $^1$H NMR (400 MHz, CDCl$_3$) δ 7.99-8.09 (m, 2H), 7.80 (d, J=8.33 Hz, 1H), 7.74 (d, J=8.33 Hz, 1H), 7.28-7.39 (m, 4H), 7.21-7.26 (m, 1H), 4.68-5.11 (m, 1H), 4.37-4.48 (m, 2H), 3.98-4.19 (m, 1H), 2.21-2.33 (m, 1H), 2.06-2.20 (m, 2H), 1.96-2.06 (m, 1H).

Step C—Synthesis of Intermediate A42. 1-(2-(benzyloxy)cyclobutyl)-4-bromo-1H-pyrazole To a stirred mixture of 4-bromo-1H-pyrazole (263 mg, 1.789 mmol) in DMSO (6.5 mL) was added potassium 2-methylpropan-2-plate (355 mg, 3.17 mmol) and 2 Int-A42-3 (755 mg, 1.583 mmol). The mixture was heated at 120° C. for 1 h under microwave conditions. The resulting mixture was cooled, filtered, and then concentrated. The residue was purified by reverse phase HPLC using a Boston Green ODS column and 10-100% MeCN/water (0.1% TFA) as eluent to provide Intermediate A42. LC/MS (ES, m/z)=307, 309 [M+H]$^+$.

Intermediate A43

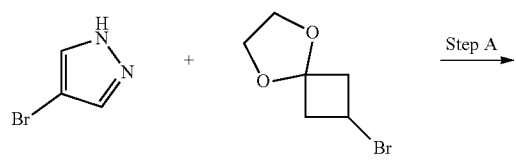

Step A—Synthesis of Compound Int-A43-1. 4-bromo-1-(5,8-dioxaspiro[3.4]octan-2-yl)-1H-pyrazole To a solution of 2-promo-5,8-dioxaspiro[3.4]octane (0.500 g, 2.59 mmol) and 4-bromo-1H-pyrazole (0.761 g, 5.18 mmol) in DMF (2.6 mL) was added potassium carbonate (1.074 g, 7.77 mmol) and 18-crown-6 (1,4,7,10,13,16-hexaoxacyclooctadecane, 0.137 g, 0.518 mmol). The mixture was stirred, and heated at 90° C. After 5 min, the mixture was cooled to room temperature, and to the mixture was added additional 4-bromo-1H-pyrazole (400 mg, 2.72 mmol). The resulting mixture was stirred and heated at 90° C. for 48 hours. The mixture was cooled to room temperature and partitioned between EtOAc (25 mL) and water (25 mL). The layers were separated, and then the aqueous layer was extracted with EtOAc (15 mL). The combined organic layers were washed with brine twice, dried over anhydrous Na$_2$SO$_4$, filtered, and then the solvents of the filtrate were evaporated. The resulting residue was purified by silica gel column chromatography with 0-50% EtOAc in hexanes as eluent to afford the title compound. Int-A43-1. LC/MS (ES, m/z)=259, 261 [M+H]$^+$.

Step B—Synthesis of Compound Int-A43-2. 3-(4-bromo-1H-pyrazol-1-yl)cyclobutanone To a solution of Int-A43-1 (270 mg, 1.042 mmol) and PPTS (131 mg, 0.521 mmol) in dioxane (2.6 mL) was added water (2.6 mL). The mixture was stirred and heated at 85° C. for 95 h. The mixture was cooled to room temperature. The mixture was then partitioned between EtOAc and saturated aqueous sodium bicarbonate. The layers were separated and the aqueous layer was extracted with EtOAc. The combined organic layers were washed with brine, dried over anhydrous Na$_2$SO$_4$, filtered, and the solvents were evaporated. The resulting residue was purified by silica gel column chromatography with 0-100% EtOAc in hexanes as eluent to afford Int-A43-2. LC/MS (ES, m/z)=215, 217 [M+H]$^+$.

Step C—Synthesis of Intermediates A43. (1S,3S)-3-(4-bromo-1H-pyrazol-1-yl)-1-methylcyclobutanol A solution of Int-A43-2 (129 mg, 0.600 mmol) in diethyl ether (3.5 ml) was cooled to 0° C. To the stirred mixture was added methylmagnesium bromide (3 M in diethyl ether, 0.240 ml, 0.720 mmol) dropwise. The mixture was stirred for 16 h, allowing the ice bath to expire. Upon completion, the mixture was partitioned between EtOAc and 20% aqueous citric acid and stirred for 2 h. The layers were separated, and then the aqueous layer was extracted with EtOAc. The combined organic layers were washed with brine, dried over anhydrous $Na_2SO_4$, filtered, and the solvents of the filtrate were evaporated. The resulting residue was purified by silica gel column chromatography with 0-60% EtOAc in hexanes as eluent to afford the title compound A43. LC/MS (ES, m/z)=231, 233 $[M+H]^+$.

Intermediate A44

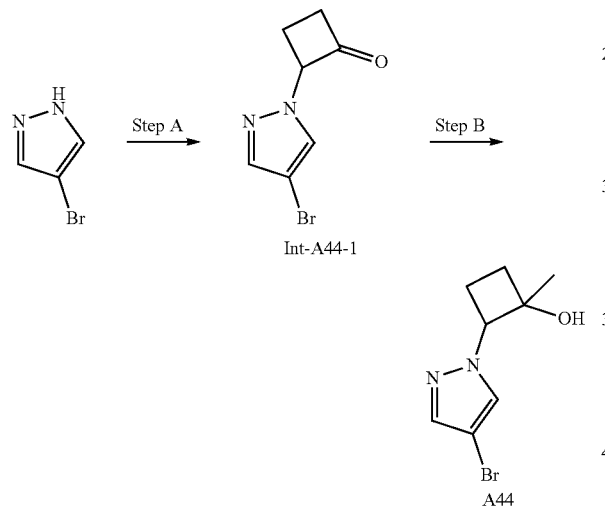

Step A—Synthesis of Compound Int-A44-1. 2-(4-Bromo-1H-pyrazol-1-yl)cyclobutan-1-one To a solution of 2-bromocyclobutanone (16.2 g, 109 mmol) in MeCN (30 mL) was added 4-bromo-1H-pyrazole (8.00 g, 54.4 mmol) and potassium carbonate (30.1 g, 218 mmol). The mixture was stirred at 20° C. for 10 h. The mixture was filtered, and then the solvents of the filtrate were evaporated. The resulting residue was purified by reversed-phase HPLC using a C18 column and MeCN/water (with 0.1% TEA modifier) as eluent to afford the title compound Int-A44-1. LC/MS (ES, m/z)=215, 217 $[M+H]^+$.

Step B—Synthesis of Intermediate A44. 2-(4-Bromo-1H-pyrazol-1-yl)-1-methylcyclobutan-1-ol Methylmagnesium bromide (0.248 ml, 0.744 mmol, 3 M in diethyl ether) was added to a stirred mixture of Int-A44-1 (80.0 mg, 0.372 mmol) in THF (2 mL) at −78° C. The resulting mixture was stirred at this temperature for 3 h. Upon completion, the reaction mixture was quenched with saturated $NH_4Cl$ (2 mL) aqueous solution and extracted with EtOAc (2×20 mL). The combined organic layers were dried over anhydrous $Na_2SO_4$, filtered, and the solvents of the filtrate were evaporated. The resulting residue was purified by preparative silica gel TLC with 30% EtOAc in petroleum ether as eluent to afford intermediate A44. LC/MS (ES, m/z)=231, 233 $[M+H]^+$.

Intermediate A45

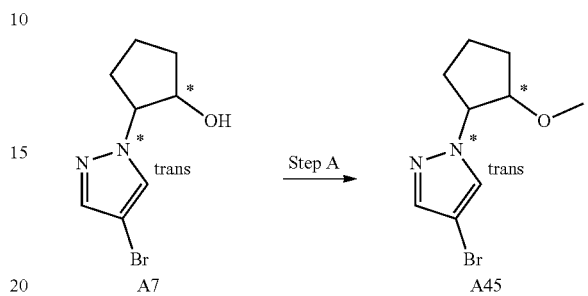

Step A—Synthesis if Intermediate A45. 4-bromo-1-((1R,2R or 1S,2S)-2-methoxycyclopentyl)-1H-pyrazole To a mixture of MeI (0.027 ml, 0.433 mmol) and Intermediate A7 (50 mg, 0.216 mmol) in DMF (2 mL) was added NaH (17.31 mg, 0.433 mmol) at room temperature. The resulting mixture was stirred at this temperature for 2 h. Upon completion, the mixture was quenched with water (10 mL), extracted with EtOAc (15 mL×3). The combined organic layers were dried over anhydrous $Na_2SO_4$ and filtered. The filtrate was concentrated to afford Intermediate A45, which was used in the next step without further purification. LC/MS (ES, m/z)=245, 247 $[M+H]^+$.

Intermediate A46

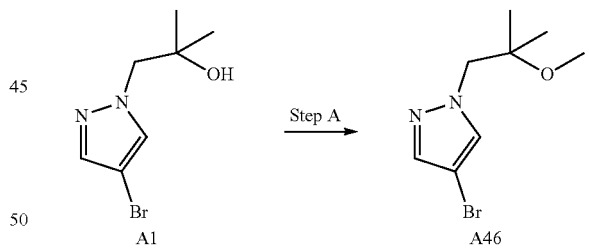

Step A—Synthesis of Intermediate A46. 4-bromo-1-(2-methoxy-2-methylpropyl)-1H-pyrazole To a mixture of MeI (0.027 ml, 0.433 mmol) and Intermediate A1 (47 mg, 0.216 mmol) in DMF (2 mL) was added NaH (17.31 mg, 0.433 mmol) at room temperature. The resulting mixture was stirred at this temperature for 2 h. Upon completion, the mixture was quenched with water (10 mL), and then extracted with EtOAc (15 mL×3). The combined organic layers were dried over anhydrous $Na_2SO_4$ and then filtered. The filtrate was concentrated in vacuum to afford Intermediate A46, which was used in the next step without further purification. LC/MS (ES, m/z)=233, 235 $[M+H]^+$.

Intermediate A47

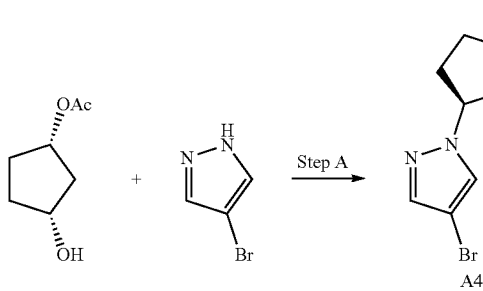

Step A—Synthesis of Intermediate A47. (1S,3S)-3-(4-bromo-1H-pyrazol-1-yl)cyclopentyl acetate To a stirred solution of (1S,3R)-3-hydroxycyclopentyl acetate (2.0 g, 13.87 mmol), 4-bromo-1H-pyrazole (2039 mg, 13.87 mmol), and triphenylphosphine (3639 mg, 13.87 mmol) in THF (10.20 ml) was added (E)-diisopropyl diazene-1,2-dicarboxylate (2.8 g, 13.87 mmol). The mixture was stirred at 60° C. for overnight. Upon completion, the reaction mixture was concentrated, and the resulting residue was purified by silica gel column chromatography with 0-80% EtOAc in hexane as eluent to provide Intermediate A47. LC/MS (ES, m/z)=273, 275 [M+H]+.

Intermediates A48, A49

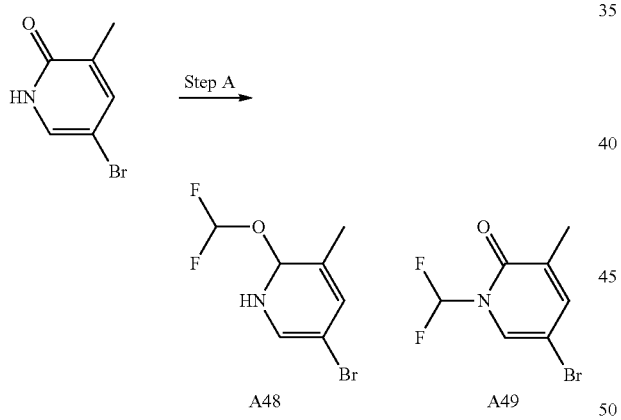

Step A—Synthesis of Intermediates A48 and A49. 5-bromo-1-(difluoromethyl)-3-methylpyridin-2(1H)-one and 5-bromo-2-(difluoromethoxy)-3-methyl-1,2-dihydropyridine To a stirred solution of 5-bromo-3-methylpyridin-2(1H)-one (5 g, 26.6 mmol) and lithium bromide (4.62 g, 53.2 mmol) in DMF (50 ml) was added sodium 2-chloro-2,2-difluoroacetate (8.11 g, 53.2 mmol) and NaH (1.170 g, 29.3 mmol) at 0° C. The resulting mixture was heated at 80° C. for 16 h. Upon completion, the reaction mixture was concentrated. The residue was partitioned between ethyl acetate and saturated NH4Cl aqueous solution. The organic layer was separated, washed with brine, dried over Na2SO4, filtered, and concentrated. The residue was purified by silica gel column chromatography with 0~25% ethyl acetate in petroleum ether as eluent to provide a mixture of Intermediates A48 and A49, LC/MS (ES, m/z)=240, 242 [M+H]+.

Intermediates B1, B2

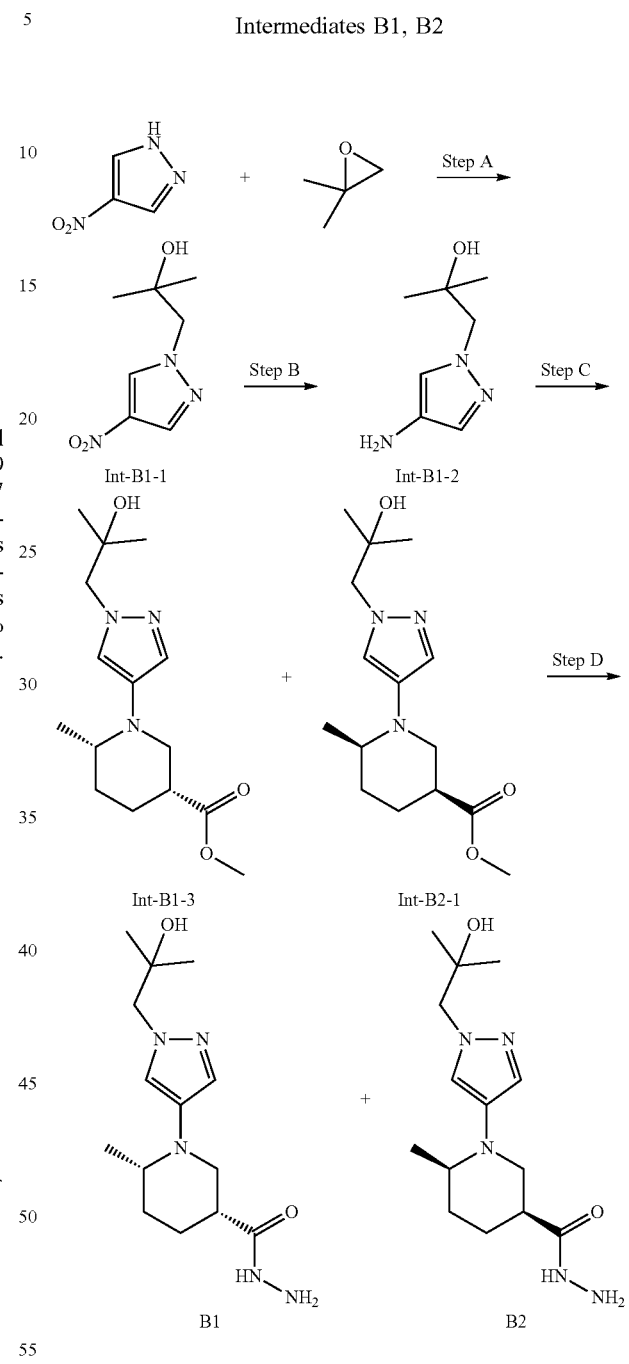

Step A—Synthesis of Compound Int-B1-1. 2-methyl-1-(4-nitro-1H-pyrazol-1-yl)propan-2-ol To a 500 mL round bottom flask was added 4-nitro-1H-pyrazole (15.0 g, 133 mmol), cesium carbonate (64.8 g, 199 mmol), DMF (195 ml) and 2,2-dimethyloxirane (23.56 ml, 265 mmol.). The mixture was heated at 80° C. for 16 hours. The mixture was cooled, filtered, and washed with EtOAc. The solvents of the filtrate were evaporated. The resulting residue was then purified by silica gel column chromatography with 0-80% EtOAc in hexanes as eluent, yielding Int-B1-1. LC/MS (ES, m/z)=186 [M+H]⁺.

Step B—Synthesis of Compound Int-B1-2. 1-(4-amino-1H-pyrazol-1-yl)-2-methylpropan-2-ol To a solution of Int-B1-1 (18.8 g, 102 mmol) in ethyl acetate (300 mL) was added 10% palladium on carbon under $N_2$ atmosphere. The mixture was degassed and stirred under a balloon of hydrogen for 21 hours. The mixture was filtered through Celite® (diatomaceous earth). The solvents of the filtrate were evaporated, yielding Int-B1-2. LC/MS (ES, m/z)=156 [M+H]⁺.

Step C—Synthesis of Compounds Int-B1-3: Methyl (3R,6S)-1-(1-(2-hydroxy-2-methylpropyl)-1H-pyrazol-4-yl)-6-i-3-carboxylate and Int-B2-1: methyl (3S,6R)-1-(1-(2-hydroxy-2-methylpropyl)-1H-pyrazol-4-yl)-6-methylpiperidine-3-carboxylate A 100 mL flask was charged with Int-B1-2 (4.66 g, 30.0 mmol), methyl 2-methylene-5-oxohexanoate (3.12 g, 20.0 mmol), and LiBF₄ (1.88 g, 20.0 mmol). To the flask was added TFE (31.2 mL). The flask was fitted with a reflux condenser, which had an inlet for nitrogen. The mixture was heated at reflux for 48 hours. The reaction mixture was cooled to room temperature and 10% palladium on carbon (0.639 g, 6.00 mmol) was added. The mixture was placed under an atmosphere of hydrogen and stirred at room temperature for 6 hours. The mixture was filtered, and then the solvents of the filtrate were evaporated. The residue was purified by silica gel column chromatography with 0-4% MeOH in DCM as eluent, yielding a racemic, cis mixture that was resolved by chiral SFC using AD-H column and 15% MeOH (with 0.1% NH₄OH modifier) as cosolvent, yielding Int-B1-3 (first eluting peak) and Int-B2-1 (second eluting peak). LC/MS (ES, m/z)=296 [M+H]⁺.

Step D—Synthesis of Intermediate B1: (3R,6S)-1-(1-(2-hydroxy-2-methylpropyl)-1H-pyrazol-4-yl)-6-methylpiperidine-3-carbohydrazide and Intermediate B2: (3S,6R)-1-(1-(2-hydroxy-2-methylpropyl)-1H-pyrazol-4-yl)-6-methylpiperidine-3-carbohydrazide To a 20 mL microwave vial was added methyl Int-B1-3 (300 mg, 1.016 mmol), ethanol (5 ml), and hydrazine hydrate (0.305 ml, 6.09 mmol). The vial was sealed and heated in a microwave at 180° C. for 3 hours. Upon completion, the mixture was concentrated, and the residue was subjected to 3 co-evaporations with toluene, yielding Intermediate B1. LC/MS (ES, m/z)=296 [M+H]⁺. The absolute stereochemistry of Intermediate B1 was assigned based on the stereochemical determination, via vibrational circular dichroism, of an intermediate prepared from Intermediate B1.

Intermediate B2 was prepared in a manner similar to that described for the preparation of Intermediate B1 but substituting intermediate Int-B2-1 for Int-B1-3. LC/MS (ES, m/z) =296 [M+H]⁺.

Intermediate B3

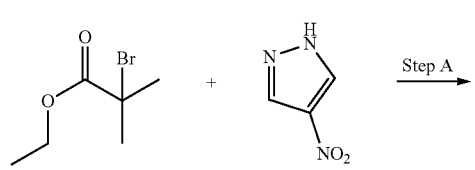

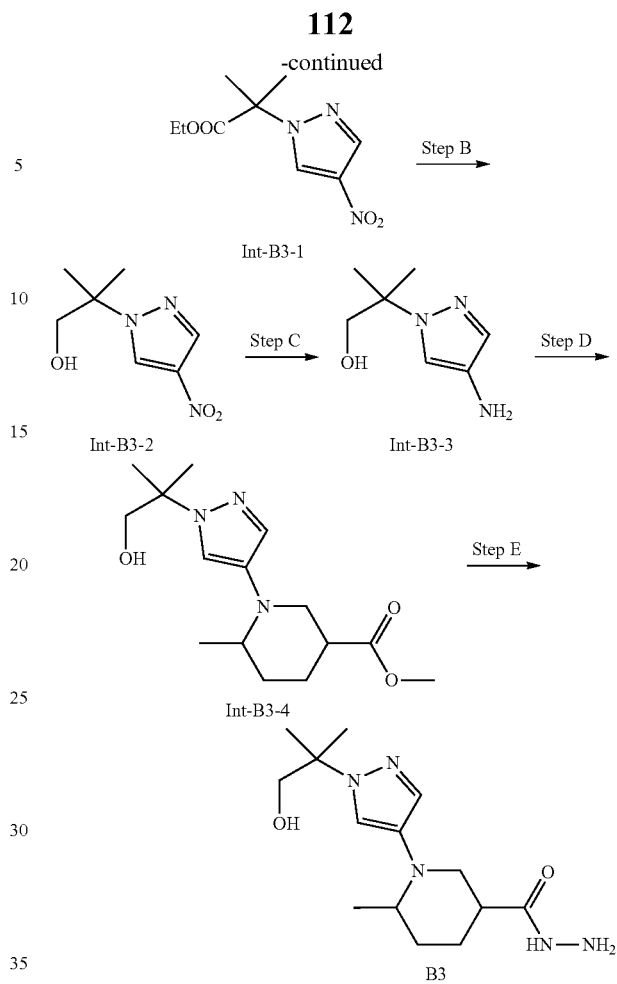

Step A—Synthesis of Compound Int-B3-1. ethyl 2-methyl-2-(4-nitro-1H-pyrazol-1-yl)propanoate To a stirred mixture of 4-nitro-1H-pyrazole (3.00 g, 26.5 mmol) and ethyl 2-bromo-2-methylpropanoate (5.69 g, 29.2 mmol) in DMF (50 mL) was added K₂CO₃ (11.00 g, 80.00 mmol). The mixture was stirred and heated at 80° C. for 10 h. The mixture was cooled, filtered, and the solvents of the filtrate were evaporated. The resulting residue was purified by silica gel column chromatography with 5-20% EtOAc in petroleum ether as eluent to afford the title compound Int-B3-1. LC/MS (ES, m/z)=228 [M+H]⁺.

Step B—Synthesis of Compound Int-B3-2. 2-Methyl-2-(4-nitro-4H-pyrazol-4-yl)propan-1-ol To a stirred mixture of Int-B3-1 (3.00 g, 13.2 mmol) in EtOH (50 mL) was added NaBH₄ (0.999 g, 26.4 mmol). The mixture was stirred at room temperature for 2 h. Upon completion, the mixture was diluted with water (40 mL) and extracted with EtOAc (2×50 mL). The combined organic layers were dried over anhydrous Na₁SO₄, filtered, and the solvents of the filtrate were evaporated to afford Int-B3-2. LC/MS (ES, m/z)=186 [M+H]⁺.

Step C—Synthesis of Compound Int-B3-3. 2-(4-Amino-1H-pyrazol-1-yl)-2-methylpropan-1-ol Step C of the synthesis of Int-B3-3 was conducted using a procedure similar to that of step B of the synthesis of Int-B1-2, to afford the title compound Int-B3-3. LC/MS (ES, m/z)=156 [M+H]$^+$.

Step D—Synthesis of Compound Int-B3-4. methyl 1-(1-(1-hydroxy-2-methylpropan-2-yl)-1H-pyrazol-4-yl)-6-methylpiperidine-3-carboxylate Step D of the synthesis of Int-B3-4 was conducted using a procedure similar to that of step C of the synthesis of Int-B1-3 and Int-B2-1, with the exception that Int-B3-4 was isolated as a mixture of racemic diastereomers. LC/MS (ES, m/z)=296 [M+H]$^+$.

Step D—Synthesis Intermediate B3: (3R,6S and 3S,6R)1-(1-(1-hydroxy-2-methylpropan-2-yl)-1H-pyrazol-4-yl)-6-methylpiperidine-3-carbohydrazide and (3S,6S and 3R,6R)1-(1-(1-hydroxy-2-methyl-propan-2-yl)-1H-pyrazol-4-yl)-6-methylpiperidine-3-carbohydrazide Step D of the synthesis of Intermediate B3 was conducted using a procedure similar to that of step D of the synthesis of Intermediate B1. LC/MS (ES, m/z)=296 [M+H]$^+$.

The intermediates in the following Table C were prepared using a procedure similar to that described for the synthesis of Intermediate B3, substituting the appropriate intermediates and starting materials.

TABLE C

| Intermediate | Structure Name | Observed m/z [M + H]$^+$ |
|---|---|---|
| B4 | 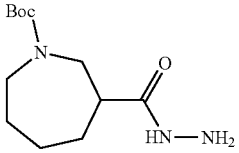<br>rac-tert-butyl 3-(hydrazinecarbonyl)azepane-1-carboxylate | 258 |
| B5 | 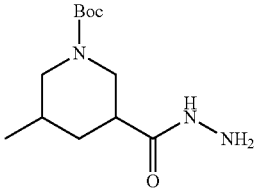 [SMILES: CC1CC(C(=O)NN)CN(C(=O)OC(C)(C)C)C1]<br>tert-butyl 3-(hydrazinecarbonyl)-5-methylpiperidine-1-carboxylate | 258 |
| B6 | 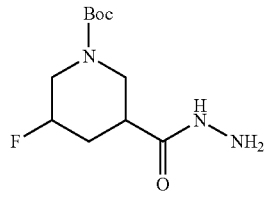 [SMILES: CC(C)(C)OC(=O)N1CC(F)CC(C(=O)NN)C1]<br>tert-butyl 3-fluoro-5-(hydrazinecarbonyl)piperidine-1-carboxylate | 206 [M + H − C$_4$H$_8$]$^+$ |
| B7 | 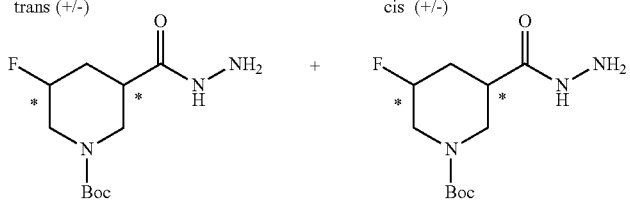 [SMILES: CC(C)(C)OC(=O)N1CC(F)CC(C(=O)NN)C1 ; CC(C)(C)OC(=O)N1CC(F)CC(C(=O)NN)C1]<br>mixture of tert-butyl (3R,5R and 3S,5S)-3-fluoro-5-(hydrazinecarbonyl)piperidine-1-carboxylate and tert-butyl (3S,5R and 3R,5S)-3-fluoro-5-(hydrazinecarobnyl)piperidine-1-carboxylate | 206 [M + H − C$_4$H$_8$]$^+$ |

TABLE C-continued
| Intermediate | Structure Name | Observed m/z [M + H]+ |
|---|---|---|
| B8 | 1-(1-(2-hydroxy-2-methylpropyl)-3-methyl-1H-pyrazol-4-yl)-6-methylpiperidine-3-carbohydrazide | 310 |
| B9 | 3-hydroxycyclohexane-1-carbohydrazide | 159 |
| B10 | 3-hydroxycyclohexane-1-carbohydrazide | 258 |
Intermediate B11
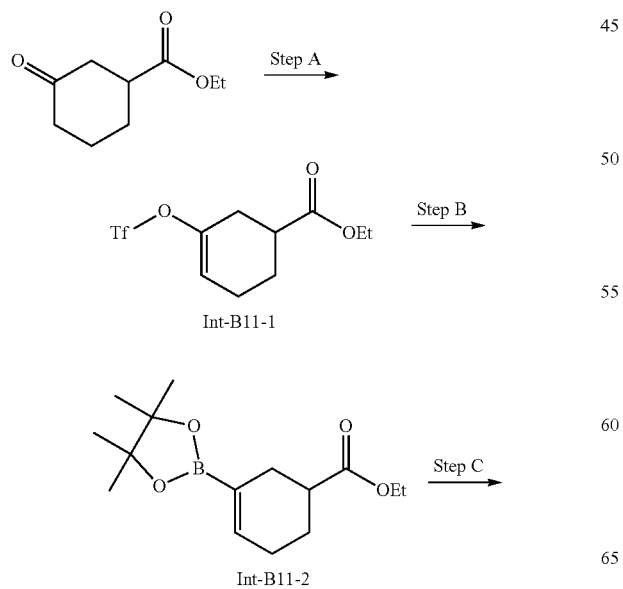
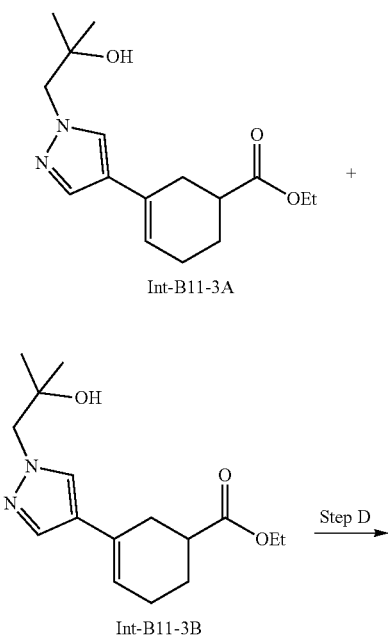

117

-continued

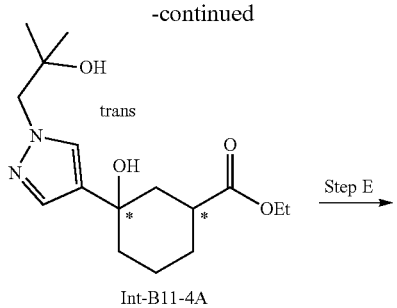

Int-B11-4A

Step E →

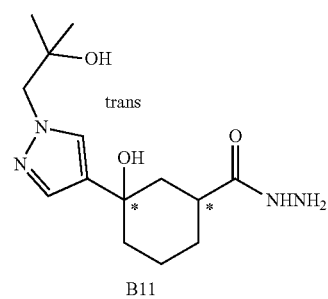

B11

Step A—Synthesis of Compound Int-B11-1. ethyl 3-(((trifluoromethyl)sulfonyl)oxy)cyclohex-3-ene-1-carboxylate To a 100 mL round bottom flask was added 2,6-di-tert-butylpyridine (11.1 ml, 49.4 mmol), ethyl 3-oxocyclohexane-1-carboxylate (6.32 ml, 35.3 mmol), and DCE (70.5 mL). The mixture was stirred and cooled at 0° C. To the mixture was added Tf$_2$O (45.8 mL, 45.8 mmol, 1 M in THF) dropwise over 5 minutes. The mixture was stirred for 30 minutes and then warmed to room temperature for 2 hours. Upon completion, the reaction mixture was concentrated, and then to the residue was added 1:1 DCM:hexanes (20 mL), and then solids precipitated. The solids were removed by filtration. The filter cake was washed with 1:1 DCM: hexanes. The solvents of the filtrate were evaporated. The resulting residue was purified by silica gel column chromatography with 0-100% EtOAc in hexanes as eluent, yielding the title compound Int-B11-1.

Step B—Synthesis of Compound Int-B11-2. ethyl 3-(4,4,5,5-tetramethyl-1,3,2-dioxaborolan-2-yl)cyclohex-3-ene-1-carboxylate To a 100 mL round bottom flask was added potassium acetate (3.96 g, 40.4 mmol), Pd(dppf)Cl$_2$ (0.660 g, 0.808 mmol), bis(pinacolato)diboron (8.21 g, 32.3 mmol), and ethyl 3-(((trifluoromethyl)sulfonyl)oxy)cyclohex-3-ene-1-carboxylate (7.08 mL, 26.9 mmol). The flask was evacuated and refilled with nitrogen three times. To the flask was added DMA (40 mL). The mixture was stirred and heated at 90° C. for 16 hours. The mixture was cooled to room temperature and poured into a flask containing diethyl ether (150 mL). The mixture was stirred for 15 min. The solids were removed by filtration. The filtrate was washed with water

118

(3×100 mL). The organic layer was dried over anhydrous magnesium sulfate, filtered, and the solvents were evaporated. The resulting residue was purified by silica gel chromatography with 0-30% EtOAc in hexanes as eluent, to afford the title compound Int-B11-2. LC/MS (ES, m/z)=281 [M+H]$^+$.

Step C—Synthesis of Compound Int-B11-3A and Int-D11-3B. ethyl (R or S)-3-(1-(2-hydroxy-2-methylpropyl)-1H-pyrazol-4-yl)cyclohex-3-ene-1-carboxylate and ethyl (S or R)-3-(1-(2-hydroxy-2-methylpropyl)-1H-pyrazol-4-yl)cyclohex-3-ene-1-carboxylate To a 100 mL flask was added Pd(dppf)Cl$_2$ (0.708 g, 0.968 mmol), K$_3$PO$_4$ (15.4 g, 72.6 mmol), ethyl 3-(4,4,5,5-tetramethyl-1,3,2-dioxaborolan-2-yl)cyclohex-3-ene-1-carboxylate (7.12 g, 25.4 mmol), 1-(4-bromo-1H-pyrazol-1-yl)-2-methylpropan-2-ol (5.30 g, 24.2 mmol) and 1,4-dioxane (60 mL) and water (12 mL). The mixture was degassed with nitrogen for 5 minutes. The resulting mixture was stirred and heated at 90° C. for 2 hours. Upon completion, the mixture was diluted in EtOAc (10 mL) and filtered through Celite® (diatomaceous earth) topped with sodium sulfate. The solvents of the filtrate were evaporated. The resulting residue was purified by silica gel chromatography with 0-70% EtOAc in hexanes as eluent to afford the racemate. The racemate was resolved by chiral SFC using CCA column and 15% MeOH with NH$_4$OH modifier as cosolvent to afford Int-B11-3A (first eluting peak) and Int-B11-3B (second eluting peak), respectively. LC/MS (ES, m/z)=293 [M+H]$^+$.

Step D—Synthesis of Compound Int-B11-4A. ethyl (1R,3R or 1S,3S)-3-hydroxy-3-(1-(2-hydroxy-2-methylpropyl)-1H-pyrazol-4-yl)cyclohexane-1-carboxylate To a 250 mL round bottom was added (R or S)-3-(1-(2-hydroxy-2-methylpropyl)-pyrazol-4-yl)cyclohex-3-ene-1-carboxylate (Int-B11-3A) (933 mg, 3.19 mmol), cobalt(II) acetylacetonate hydrate (220 mg, 0.798 mmol) and THF (50 mL). To the mixture was added phenylsilane (1.181 mL, 9.57 mmol), and the mixture was stirred, open to air, at room temperature for 5 days. To the mixture was added 1 M solution of TBAF (6.38 ml, 6.38 mmol) in THF. The mixture was stirred for 15 min. The solvents were evaporated. The resulting residue was purified by silica gel column chromatography with 0-10% MeOH in DCM as eluent, to afford ethyl (1R,3R or 1S,3S)-3-hydroxy-3-(1-(2-hydroxy-2-methylpropyl)-1H-pyrazol-4-yl)cyclohexane-1-carboxylate (Int-B11-4A). LC/MS (ES, m/z)=311 [M+H]$^+$.

Step E—Synthesis of Intermediate B11. (1R,3R or 1S,3S)-3-hydroxy-3-(1-(2-hydroxy-2-methylpropyl)-1H-pyrazol-4-yl)cyclohexane-1-carbohydrazide To a 20 mL vial was added ethyl (1R,3R or 1S,3S)-3-hydroxy-3-(1-(2-hydroxy-2-methylpropyl)-1H-pyrazol-4-yl)cyclohexane-1-carboxylate (Int-B11-4A) (190 mg, 0.612 mmol), EtOH (1.5 mL), and hydrazine hydrate (0.210 ml, 3.67 mmol). The mixture was heated at 90° C. for 24 h. The solvents were evaporated to afford the title Intermediate B11. LC/MS (ES, m/z)=297 [M+H]$^+$.

Intermediate B12

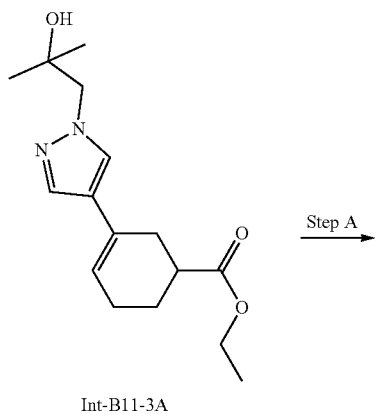

Step A—Synthesis of Intermediate B12. 3-(1-(2-hydroxy-2-methylpropyl)-1H-pyrazol-4-yl)cyclohexane-1-carbohydrazide To a 100 mL flask was added ethyl (R or S)-3-(1-(2-hydroxy-2-methylpropyl)-1H-pyrazol-4-yl)cyclohex-3-ene-1-carboxylate (Int-B11-3A) (444 mg, 1.519 mmol), 10% Pd on carbon (162 mg, 0.152 mmol) and EtOAc (30 mL). The mixture was degassed with vacuum and refilled with hydrogen from a balloon three times. The mixture was stirred under a hydrogen atmosphere for 1 h. The mixture was filtered through Celite® (diatomaceous earth), and the solvents of the filtrate were evaporated. To the residue was added EtOH (2.5 ml) and hydrazine hydrate (0.511 ml, 8.96 mmol). The mixture was heated at 90° C. for 24 h. The solvents were evaporated, to afford 3-(1-(2-hydroxy-2-methylpropyl)-1H-pyrazol-4-yl)cyclohexane-1-carbohydrazide (Intermediate B12) as a mixture of enantiopure diastereomers. LC/MS (ES, m/z)=281 [M+H]+.

Intermediate B13 in Table 1) was prepared using a procedure similar to that described for the preparation of Intermediate B12 but starting with Int-B11-3B.

TABLE D

| Intermediate | Structure Name | Observed m/z [M + H]+ |
|---|---|---|
| B13 | ethyl 3-(1-(2-hydroxy-2-methylpropyl)-1H-pyrazol-4-yl)cyclohexane-1-carboxylate | 281 |

Intermediate B14

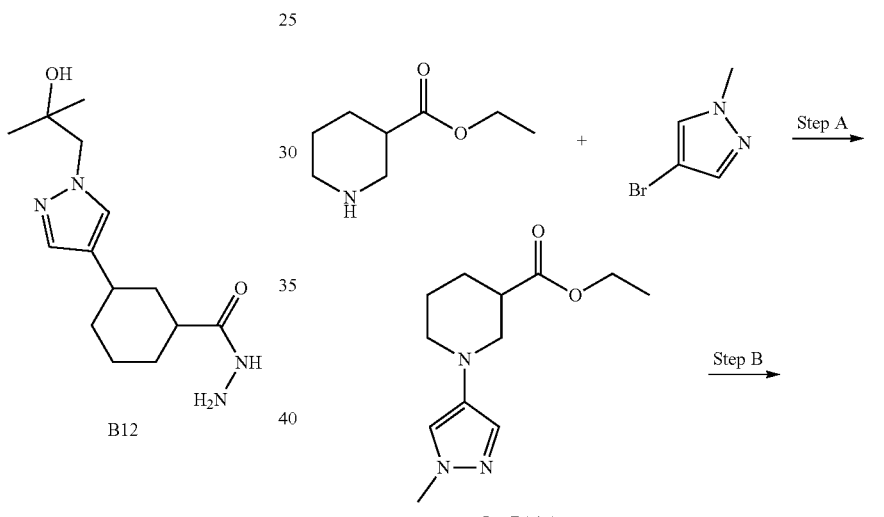

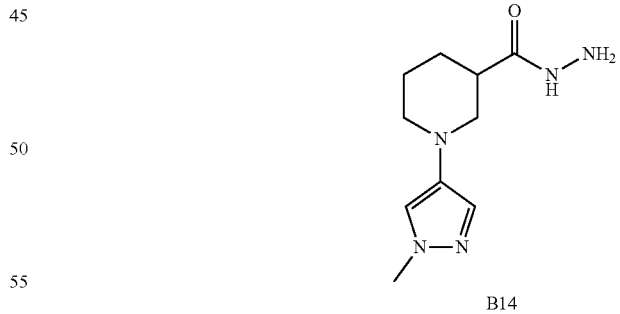

Step A—Synthesis of Compound Int-B14-1. rac-ethyl 1-(1-methyl-1H-pyrazol-4-yl)piperidine-3-carboxylate A 40 mL reaction vial was charged with rac-ethyl 1-(1-methyl-1H-pyrazol-4-yl)piperidine-3-carboxylate (1.00 g, 6.36 mmol) and THF (15 mL). To the mixture was added 4-bromo-1-methyl-1H-pyrazole (4.96 mL, 48.0 mmol), followed by t-BuXPhos Pd G3 (2.02 g, 2.54 mmol) and sodium tert-butoxide (4.61 g, 48.0 mmol). The mixture was bubbled through N₂ for 10 minutes. The vial was sealed and heated at 65° C. for 24 hours. The mixture was cooled to room temperature, diluted to EtOAc (40 mL), and filtered through Celite® (diatomaceous earth). The solvents of the filtrate were evaporated. The resulting residue was purified by silica gel column chromatography with 0-10% MeOH in DCM as eluent to afford the title compound Int-B14-1. LC/MS (ES, m/z)=238 [M+H]⁺.

Step B—Synthesis of Intermediate B14. (R)-1-(1-methyl-1H-pyrazol-4-yl)piperidine-3-carbohydrazide A round bottom flask was charged with Int-B14-1 (7.72 g, 32.5 mmol) and EtOH (77 mL). To the mixture was added hydrazine hydrate (31.7 mL, 651 mmol). The round bottom flask was fitted with a reflux condenser and then heated at 80° C. for 16 hours. Upon completion, the mixture was cooled to room temperature, and the solvents were evaporated to afford (RS)-1-(1-methyl-1H-pyrazol-4-yl)piperidine-3-carbohydrazide. The racemic mixture was resolved by chiral SFC separation using AD-H column and 40% MeOH (0.25% DEA modifier) as co-solvent to afford the title compound (R or S)-1-(1-methyl-1H-pyrazol-4-yl)piperidine-3-carbohydrazide (Intermediate B14, second eluting, peak). LC/MS (ES, m/z)=224 [M+H]⁺.

Intermediate B15

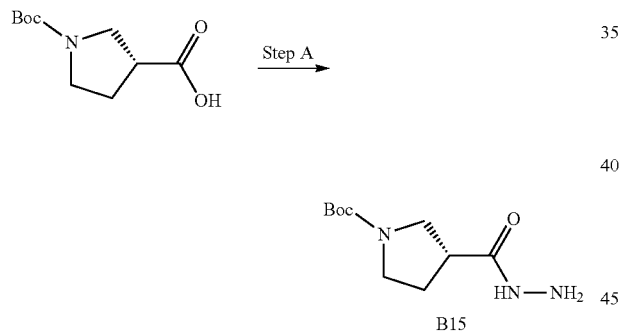

Step A—Synthesis of Compound B15. tert-butyl (R)-3-(hydrazinecarbonyl)pyrrolidine-1-carboxylate To a 100 mL round bottom flask was added (R)-1-(tert-butoxycarbonyl)pyrrolidine-3-carboxylic acid (2.00 g, 9.29 mmol), 1,1'-carbonyldiimidazole (1.96 g, 12.1 mmol) and THF (18.6 mL). The mixture was heated at 60° C. for 30 minutes. Upon completion, the mixture was cooled to room temperature and transferred to a stirring mixture of hydrazine hydrate (0.447 g, 13.9 mmol) in THF (10 mL) dropwise over 25 min. The resulting mixture was stirred at room temperature for 2 hours. The reaction mixture was quenched with water (50 mL) and extracted with EtOAc (2×60 mL). The combined organic layers were dried over anhydrous MgSO₄, filtered, and the solvents of the filtrate were evaporated to afford the title compound Intermediate B15. LC/MS (ES, m/z)=230 [M+H]⁺.

Intermediate C1

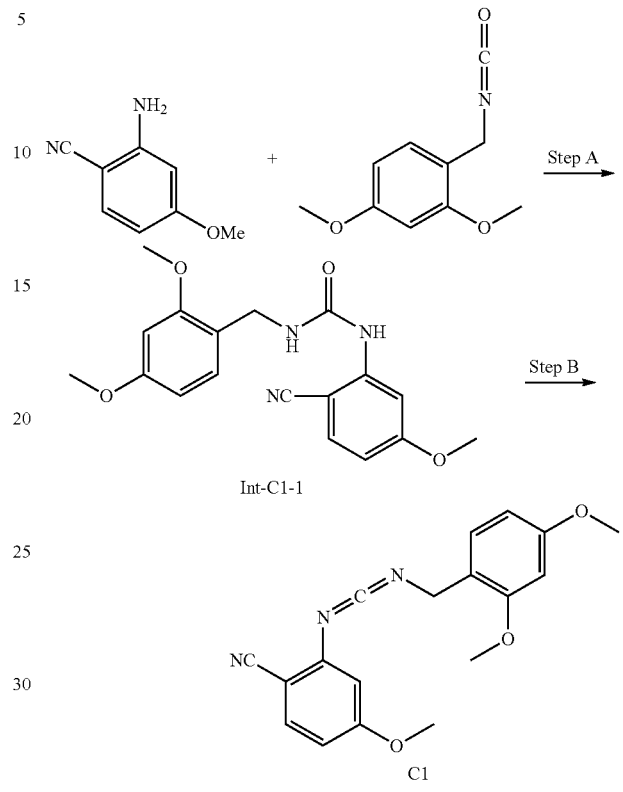

Step A—Synthesis of Compound Int-C1-. 1-(2-cyano-5-methoxyphenyl)-3-(2,4-dimethoxybenzyl) urea To a stirred solution of 2-amino-4-methoxybenzonitrile (6.0 g, 40.5 mmol) in pyridine (12 mL) and dichloromethane (12 mL) was added 1-(isocyanatomethyl)-2,4-dimethoxybenzene (6.75 ml, 40.5 mmol). The resulting reaction mixture was sealed and then heated at 40° C. overnight. Upon completion, the reaction was cooled and diluted with DCM (100 mL) to give a thick suspension. The suspension was filtered and washed with a minimal amount of DCM. The collected material was resuspended in 100 mL DCM and sonicated for 20 min. The suspension was filtered to provide the title compound Int-C1-1. LC/MS (ES, m/z)=342 [M+H]⁺.

Step B—Synthesis of Intermediate C1. 2-((((2,4-dimethoxybenzyl)imino)methylene amino)-4-methoxybenzonitrile To a solution of Int-C1-1 (1.0 g, 2.93 mmol), triphenylphosphine (1.537 g, 5.86 mmol) and triethylamine (1.633 mL, 11.72 mmol) in DCII (26.4 mL) was added a solution of carbon tetrabromide (1.943 g, 5.86 mmol) in DCM (2.93 mL) at 0° C. The reaction mixture was stirred for 30 min at room temperature, then concentrated to dryness. The resulting residue was re-dissolved in a minimal amount of DCM, filtered, and the filtrate was purified by silica gel chromatography with 5-50% ethyl acetate in hexanes as eluent to provide Intermediate C1. LC/MS (ES, m/z)=346 [M+Na]⁺.

123

Intermediate C4

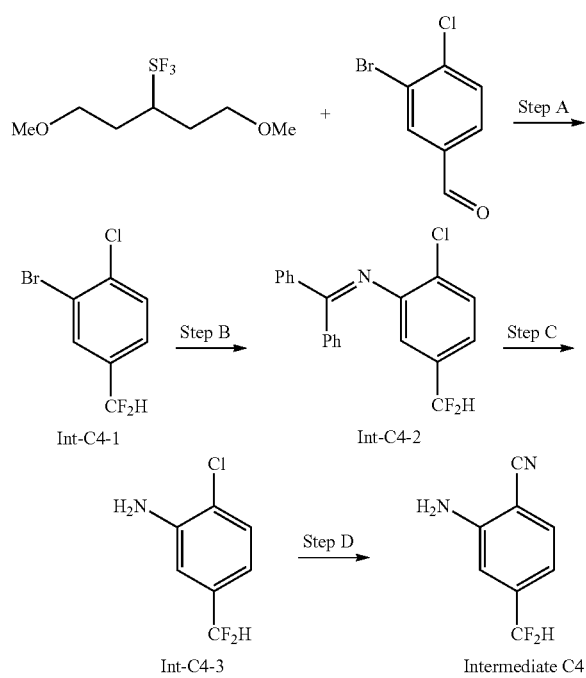

Step A—Synthesis of Compound Int-C4-1. 2-bromo-1-chloro-4-(difluoromethyl)benzene To a solution of 3-promo-4-chlorobenzaldehyde (1.9 g, 8.66 mmol) in DCM (15 mL) at 0° C. was added bis(2-methoxyethyl)aminosulfur trifluoride (6.41 mL, 17.32 mmol, 2.7 M in toluene). The mixture was stirred at room temperature for 24 hours. Upon completion, the mixture was cooled at 0° C., and then saturated sodium bicarbonate (30 mL) was added dropwise over 5 minutes. The mixture was diluted in EtOAc (30 mL) and water (30 mL). The organic layer was separated, washed with water (2×30 mL), dried over sodium sulfate, and filtered. The solvents of the filtrate were evaporated, yielding Int-C4-1.

Step B—Synthesis of Compound Int-C4-2. N-(2-chloro-5-(difluoromethyl)phenyl)-1,1-diphenyl-methanimine To a 20 mL microwave vial was added Pd-BINAP G3 (216 mg, 0.217 mmol), cesium carbonate (2834 mg, 8.70 mmol), Int-C4-1 (0.467 ml, 2.90 mmol), diphenylmethanimine (0.535 ml 3.19 mmol) and dioxane (14 ml). The mixture was stirred and heated at 170° C. in a microwave for 35 minutes. Upon completion, to the mixture was added EtOAc (10 mL) and filtered. The solvents were evaporated to provide Int-C4-2. The material was used in the next step without further purification. LC/MS (ES, m/z)=342 [M+H]$^+$.

Step C—Synthesis of Compound Int-C4-3. 2-chloro-5-(difluoromethyl)aniline

To the solution of Int-C4-2 (991 mg, 2.9 mmol) in MeOH (1.5 mL) obtained above was added concentrated aqueous HCl (4.76 mL, 58.0 mmol). The mixture was stirred and heated at for 30 minutes. Upon completion, the mixture was diluted in water (30 mL) and then extracted with DCM (3×30 mL). The organic layer was dried over sodium sulfate, filtered, and the solvents of the filtrate were evaporated. The residue was purified by silica gel column chromatography with 0-50% EtOAc in hexanes as eluent to provide Int-C4-3. LC/MS (ES, m/z)=178 [M+H]$^+$.

Step D—Synthesis of Compound Intermediate C4. 2-amino-4-(difluoromethyl)benzonitrile To a 20 mL vial was added zinc (10.93 mg, 0.167 mmol), zinc cyanide (196 mg, 1.672 mmol), 2-chloro-5-(difluoromethyl)aniline (297 mg, 1.672 mmol) and t-BuXPhos Pd G3 (66.4 mg, 0.084 mmol). The vial was sealed, evacuated, and refilled with N$_2$ three times. To the mixture was added DMA (3 mL). The resulting mixture was stirred and heated at 110° C. for 2 hours. Upon completion, the reaction mixture was cooled to room temperature. To the mixture was added diethyl ether (50 mL), then the mixture was filtered through Celite® (diatomaceous earth). The filtrate was washed with water (3×50 mL). The organic layer was dried over magnesium sulfate, filtered, and the solvents of the filtrate were evaporated. The residue was purified by silica gel column chromatography with 0-65% EtOAc in hexanes as eluent, yielding Intermediate C4. LC/MS (ES, m/z)=169 [M+H]$^+$.

Intermediate C5

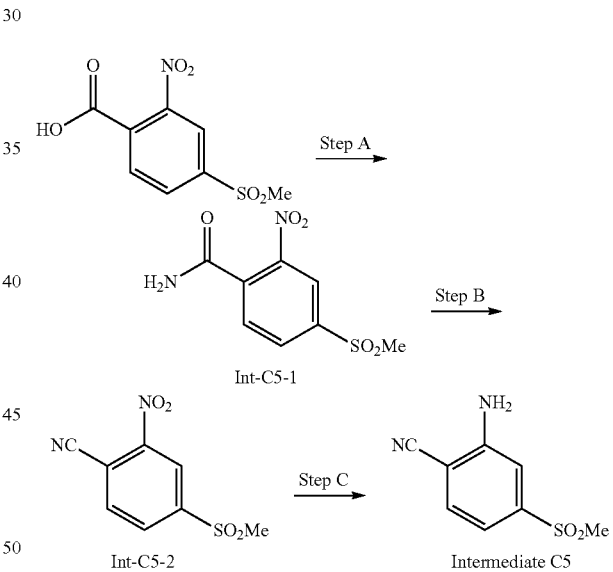

Step A—Synthesis of Compound Int-C5-1. 4-(methylsulfonyl)-2-nitrobenzamide

To a mixture of 4-(methylsulfonyl)-2-nitrobenzoic acid (1.5 g, 6.12 mmol) in DCM (35 mL) and DMF (0.024 mL, 0.306 mmol) was added oxalyl chloride (0.803 mL, 9.18 mmol) dropwise over 30 seconds. The resulting mixture was stirred for 30 minutes, at which point the mixture became a solution. To another 250 mL flask was added a 0.5 M solution of ammonia (61.2 mL, 30.6 mmol) in dioxane. The flask was fitted with an addition funnel, to which the solution of the acid chloride was added. The flask containing the ammonia was cooled at 0° C. and then the acid chloride was added drop wise over 10 minutes. Upon completion, the reaction mixture was diluted with 1:1 DCM:MeOH (100 mL) and filtered. The filter cake was washed with 1:1 DCM:MeOH (5×50 mL). The filtrate was concentrated to provide Int-C5-1.

Step B—Synthesis of Compound Int-C5-2. 4-(methylsulfonyl)-2-nitrobenzonitrile To a 40 mL vial was added Int-C5-1 (1.02 g, 3.13 mmol) and POCl$_3$ (2.88 mL, 30.9 mmol). The vial was sealed and then fined with an N$_2$ inlet and heated at 90° C. for 35 minutes. Upon completion, the mixture was cooled to room temperature. The mixture was triturated with anhydrous diethyl ether (10 mL), and the solid was collected by filtration, washing with anhydrous diethyl ether (3×5 mL) to yield Int-E5-2. LC/MS (ES, m/z)=227 [M+H]$^+$.

Step C—Synthesis of intermediate C5. 2-amino-4-(methylsulfonyl)benzonitrile

To a 100 mL round bottom flask was added Pd on carbon (119 mg, 0.112 mmol), 4-(methylsulfonyl)-2-nitrobenzonitrile (507 mg, 2.241 mmol) and EtOAc (20 mL). The mixture was degassed, then stirred under a balloon of hydrogen for 60 hours. Upon completion, the reaction mixture was filtered through Celite® (diatomaceous earth) and washed with MeOH. The solvents of the filtrate were evaporated to provide the title compound Intermediate C5. LC/MS (ES, m/z)=197 [M+H]$^+$.

Intermediate C6

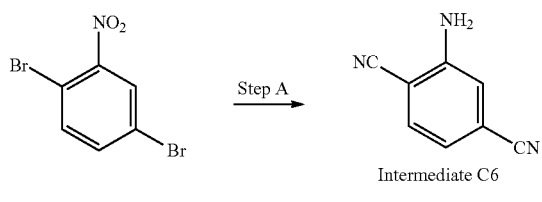 [SMILES: O=[N+]([O-])c1cc(Br)ccc1Br ; N#Cc1ccc(C#N)c(N)c1]

Intermediate C6

Step A—Synthesis of Compound Intermediate C6. 2-aminoterephthalonitrile

To a 4 mL vial was added XPhos (0.113 g, 0.237 mmol), palladium (II) acetate (0.027 g, 0.119 mmol), potassium hydrogen sulfate (0.032 g, 0.237 mmol) and DMA (2 mL). The mixture was heated at 65° C. for 15 minutes. To a 20 mL microwave vial was added zinc (0.016 g, 0.237 mmol), dicyanozinc (1.114 g, 9.49 mmol), 2,5-dibromoaniline (1.19 g, 4.74 mmol) and DMA (8 ml). To the microwave vial was added the catalyst mixture from the 4 mL vial. The resulting mixture was stirred and heated at 130° C. for 1 hour. Upon completion, the mixture was diluted in diethyl ether (70 mL) and washed with water (3×70 mL). The organic layer was dried over magnesium sulfate, filtered, and the solvents were evaporated, yielding Intermediate C6.

The intermediates in the following Table E were prepared using a procedure similar to Intermediate C1, substituting the appropriate intermediates and starting materials.

TABLE E

| Intermediate | Structure Name | Observed m/z [M + Na]$^+$ |
|---|---|---|
| C2 | 2-((((2,4-dimethoxybenzyl)imino)methylene)amino)-4-methylbenzonitrile | 330 |
| C3 | 4-chloro-2-((((2,4-dimethoxybenzyl)imino)methylene)amino)benzonitrile | 350 |
| C7 | 2-((((2,4-dimethoxybenzyl)imino)methylene)amino)-3-methoxybenzonitrile | 346 |
| C8 | 4-(difluoromethyl)-2-((((2,4-dimethoxybenzyl)imino)methylene)amino)benzonitrile | 366 |

TABLE E-continued

| Intermediate | Structure Name | Observed m/z [M + Na]+ |
|---|---|---|
| C9 | 2-((((2,4-dimethoxybenzyl)imino)methylene)amino)-4-(methylsulfonyl)benzonitrile | 394 |
| C10 | 2-((((2,4-dimethoxybenzyl)imino)methylene)amino)terephthalonitrile | 341 |

Intermediate D1

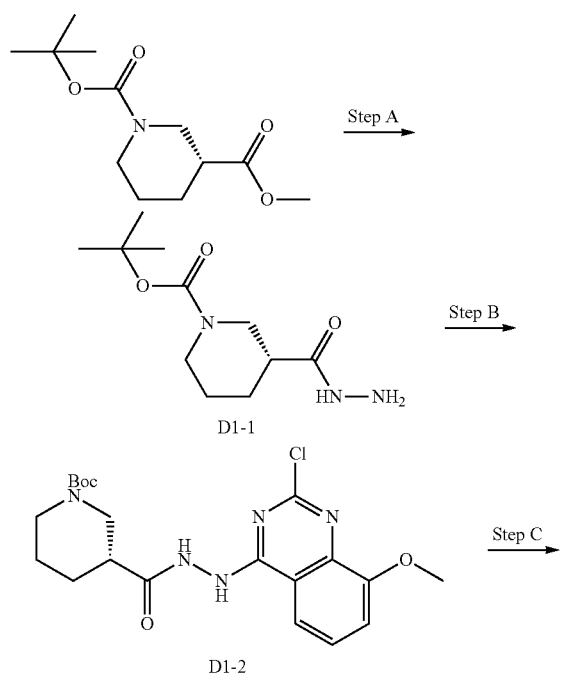

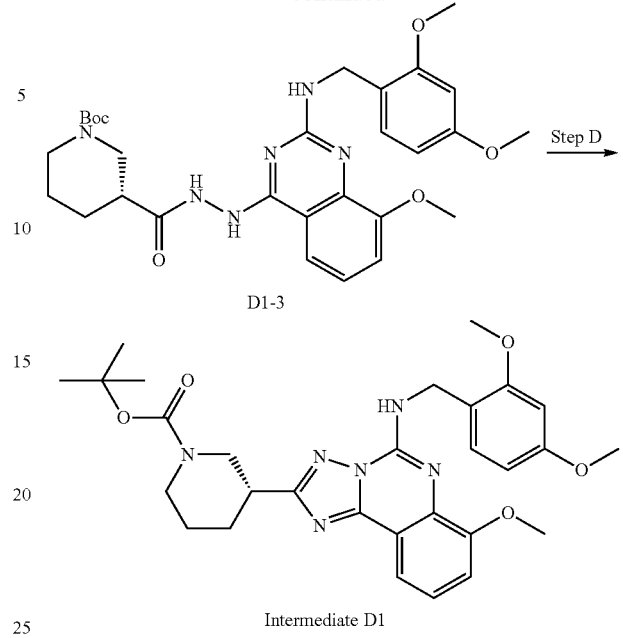

Intermediate D1

Step A—Synthesis of Compound D1-1. tert-butyl (R)-3-(hydrazinecarbonyl)piperidine-1-carboxylate A methanol solution (50 mL) of 1-(tert-butyl) 3-methyl (R)-piperidine-1,3-dicarboxylate (13.3 g, 51.7 mmol) and hydrazine hydrate (13.0 g, 259 mmol) was stirred at 80° C. for 12 hours. The solvent was removed under reduced pressure. The residue was purified by silica gel chromatography with 0-10% methanol in dichloromethane as eluent to afford the title compound D1-1. LC/MS (ES, m/z)=244 [M+H]+.

Step B—Synthesis of Compound D1-2. tert-butyl (R)-3-(2-(2-chloro-8-methoxyquinazolin-4-yl)hydrazine-1-carbonyl)piperidine-1-carboxylate To a tetrahydrofuran solution (200 mL) of D1-1 (11.2 g, 46.1 mmol) and N,N-diisopropylethylamine (12.0 g, 92 mmol) at 70° C. was added dropwise a tetrahydrofuran solution (150 mL) of 2,4-dichloro-8-methoxyquinazoline (10.4 g, 35 mmol) over 20 minutes. The resulting reaction mixture was stirred at 70° C. for 12 hours. Upon completion, the reaction mixture was concentrated under reduced pressure, diluted with dichloromethane (100 mL), and then washed with water (50 mL×2). The organic layer was dried over anhydrous magnesium sulfate and concentrated under reduced pressure to afford the title compound D1-2. LC/MS (ES, m/z)=436 [M+H]+.

Step C—Synthesis of Compound D1-3. tert-butyl (R)-3-(2-(2-((2,4-dimethoxybenzyl)amino)-8-methoxyquinazolin-4-yl)hydrazine-1-carbonyl)piperidine-1-carboxylate A solution of D1-2 (16 g, 37 mmol), 2,4-dimethoxybenzylamine (7.4 g, 44.4 mmol) and N,N-diisopropylethylamine (9.5 g, 74 mmol) in 1,4-dioxane (300 mL) was stirred at 80° C. for 12 hours. Upon completion, the solution was concentrated under reduced pressure. The resulting residue was diluted with dichloromethane (100 mL) and washed with water (50 mL×2). The organic layer was dried over anhydrous magnesium sulfate and concentrated to afford the title compound D1-3. LC/MS (ES, m/z)=567 [M+H]$^+$.

Step D—Synthesis of Intermediate D1. tert-butyl (R)-3-(5-((2,4-dimethoxybenzyl)amino)-7-methoxy-[1,2,4]triazolo[1,5-e]quinazolin-2-yl)piperidine-1-carboxylate A solution of N,O-bis(trimethylsilyl)acetamide (100 mL) and D1-3 (21 g, 37 mmol) was stirred at 140° C. for 12 hours. Upon completion, the reaction mixture was concentrated under reduced pressure. The resulting residue was purified by silica gel column chromatography with 20% EtOAc in petroleum ether as eluent to afford the title compound Intermediate D1. LC/MS (ES, m/z)=549 [M+H]$^+$.

The following intermediates in Table F were prepared using a procedure similar to that described for the preparation of INTERMEDIATE D1, substituting the appropriate ester and the appropriately substituted 2,4-dichloroquinazoline in Step A.

TABLE F

| Intermediate | Structure Name | Observed m/z [M + H]$^+$ |
|---|---|---|
| D2 | tert-butyl 5-(5-((2,4-dimethoxybenzyl)amino)-7-methoxy-[1,2,4]triazolo[1,5-c]quinazolin-2-yl)-2-methylpiperidine-1-carboxylate | 563 |
| D3 | tert-butyl 3-(5-((2,4-dimethoxybenzyl)amino)-7-methoxy-[1,2,4]triazolo[1,5-c]quinazolin-2-yl)-5-fluoropiperidine-1-carboxylate | 567 |
| D4 | rac-tert-butyl 5-(5-((2,4-dimethoxybenzyl)amino)-7-methoxy-[1,2,4]triazolo[1,5-c]quinazolin-2-yl)-3,3-difluoropiperidine-1-carboxylate | 585 |

TABLE F-continued

| Intermediate | Structure Name | Observed m/z [M + H]+ |
|---|---|---|
| D5 | tert-butyl 3-(5-((2,4-dimethoxybenzyl)amino)-7-methoxy-[1,2,4]triazolo[1,5-c]quinazolin-2-yl)pyrrolidine-1-carboxylate | 535 |

Intermediate E1

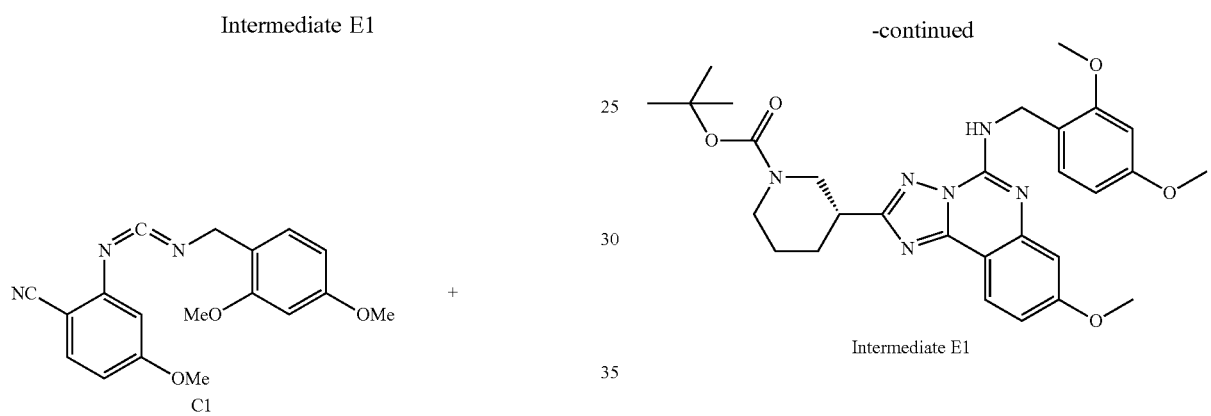

Step A—Synthesis of Intermediate E1. tert-butyl (R)-3-(5-((2,4-dimethoxybenzyl)amino)-8-methoxy-[1,2,4]triazolo[1,5-c]quinazolin-2-yl)piperidine-1-carboxylate A solution of (R)-tert-butyl 3-(hydrazinecarbonyl)piperidine-1-carboxylate (1.66 g, 6.82 mmol) in toluene (20 mL) was added to C1 (2.1 g, 6.49 mmol) in toluene (20 mL) dropwise at room temperature. The resulting mixture was heated at 100° C. for 3 hours. Upon completion, the reaction mixture was cooled to room temperature and the toluene was removed. The resulting residue was purified by silica gel chromatography with 20-60% ethyl acetate in hexanes as eluent to afford Intermediate E1. LC/MS (ES, m/z)=549 [M+H]+.

The following intermediates in Table G were prepared similarly to that described for the preparation of INTERMEDIATE E1 with the appropriate hydrazide in Step A and the appropriately substituted benzonitrile.

TABLE G

| Intermediate | Structure Name | Observed m/z [M + H]+ |
|---|---|---|
| E2 | 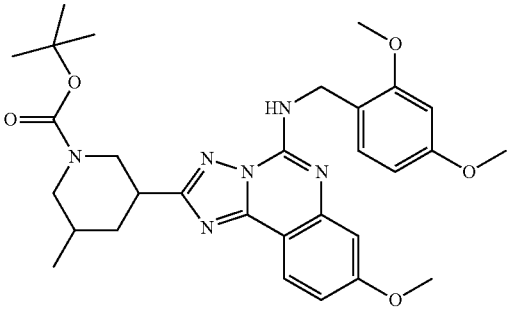<br>tert-butyl 3-(5-((2,4-dimethoxybenzyl)amino)-8-methoxy-[1,2,4]triazolo[1,5-c]quinazolin-2-yl)-5-methylpiperidine-1-carboxylate | 563 |
| E3 | 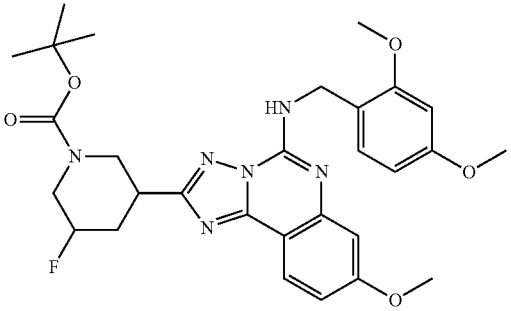 [SMILES: COc1ccc(CNc2nc3cc(OC)ccc3c3nc(C4CC(F)CN(C(=O)OC(C)(C)C)C4)nn23)c(OC)c1]<br>tert-butyl 3-(5-((2,4-dimethoxybenzyl)amino)-8-methoxy-[1,2,4]triazolo[1,5-c]quinazolin-2-yl)-5-fluoropiperidine-1-carboxylate | 567 |
| E4 | 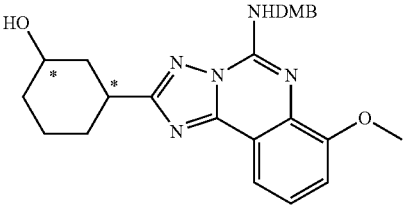<br>3-(5-((3,4-dimethylbenzyl)amino)-7-methoxy-[1,2,4]triazolo[1,5-c]quinazolin-2-yl)cyclohexan-1-ol | 432 |
| E5 | 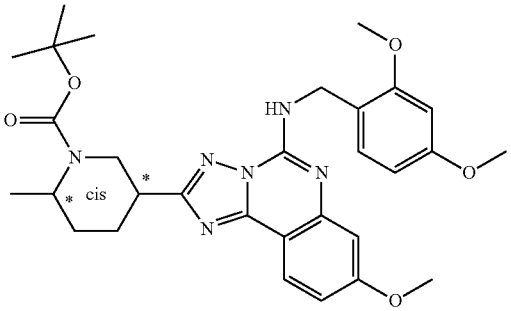 [SMILES: COc1ccc(CNc2nc3cc(OC)ccc3c3nc(C4CCC(C)N(C(=O)OC(C)(C)C)C4)nn23)c(OC)c1]<br>tert-butyl (2S,5R and 2R,5S)-5-(5-((2,4-dimethoxybenzyl)amino)-8-methoxy-[1,2,4]triazolo[1,5-c]quinazolin-2-yl)-2-methylpiperidine-1-carboxylate | 563 |

TABLE G-continued

| Intermediate | Structure<br>Name | Observed m/z [M + H]+ |
|---|---|---|
| E6 | tert-butyl 2-(5-((2,4-dimethoxybenzyl)amino)-7-methoxy-[1,2,4]triazolo[1,5-c]quinazolin-2-yl)-8-azabicyclo[3.2.1]octane-8-carboxylate | 575 |
| E7 | rac-tert-butyl 3-(5-((2,4-dimethoxybenzyl)amino)-7-methoxy-[1,2,4]triazolo[1,5-c]quinazolin-2-yl)azepane-1-carboxylate | 563 |

Intermediate F1

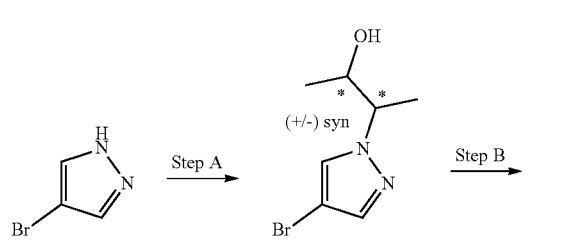

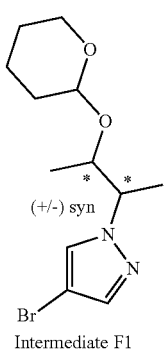

Intermediate F1

Step A—rac, syn-3-(4-bromo-1H-pyrazol-1-yl)butan-2-ol

To a mixture of 4-bromo-1H-pyrazole (2.00 g, 13.6 mmol) and cesium carbonate (13.3 g, 40.8 mmol) in MeCN (20 mL) was added cis-2,3-dimethyloxirane (2.38 ml, 27.2 mmol). The mixture was stirred and heated at 80° C. for 16 h. The mixture was cooled to room temperature and the solids were removed by filtration. The filtrate was concentrated, and the residue was diluted with DCM and washed with water and brine solution. The organic layer was dried over sodium sulfate. The residue was purified by silica gel chromatography with 0-100% EtOAc in hexanes as eluent to afford rac, syn-3-(4-bromo-1H-pyrazol-1-yl)butan-2-ol. LCMS ($C_7H_{11}BrN_2O$) (ES, m/z) [M+H]+: 219, 221.

Step B—Synthesis of Compound F1 rac-4-bromo-1-((2R,3R)-3-((tetrahydro-2H-pyran-2-yl)oxy)butan-2-yl)-1H-pyrazole To a solution of rac, syn-3-(4-bromo-1H-pyrazol-1-yl)butan-2-ol (1.10 g, 5.02 mmol) in DCM (21 mL) was added 3,4-dihydro-2H-pyran (2.290 ml, 25.1 mmol) and PPTS (1.26 g, 5.02 mmol). The mixture was stirred at room temperature for 16 hours. The mixture was diluted with DCM (5 mL), washed with sat. NaHCO₃, and brine solution. The organic layer was dried over sodium sulfate, filtered, and the solvents of the filtrate were evaporated. The residue was purified by silica gel chromatography with 0-30% of EtOAc in hexanes to afford Intermediate F1. LCMS ($C_{12}H_{19}BrN_2O_2$) (ES, m/z) [M+H]+: 304, 306.

The intermediates in the following Table H were prepared from the appropriate starting materials in a manner similar to that described for the preparation of Intermediate F1.

TABLE H

| Intermediate | Structure Name | Observed m/z [M + H]+ |
|---|---|---|
| F2 | (+/−) syn<br><br>rac, syn-3-(4-bromo-3-methyl-1H-pyrazol-1-yl)butan-2-ol | 318, 320 |
| F3 | (+/−) anti<br><br>rac, anti-3-(4-bromo-3-methyl-1H-pyrazol-1-yl)butan-2-ol | 304, 306 |

Intermediate F4

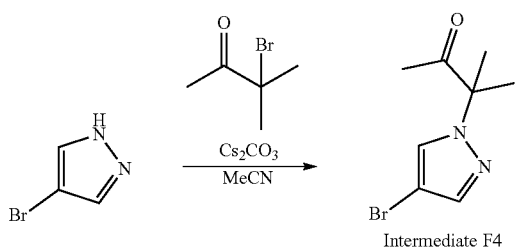

Intermediate F4

To a mixture of 4-bromo-1H-pyrazole (2.00 g, 13.6 mmol) and 3-bromo-3-methylbutan-2-one (3.37 g. 20.4 mmol) in MeCN (20 mL) was added cesium carbonate (6.65 g, 20.4 mmol). The mixture was heated at 65° C. for 16 h. The solids were removed by filtration and washed with ethyl acetate (30 mL). The solvents of the filtrate were evaporated. The resulting residue was purified by silica gel chromatography with 3-30% EtOAc in hexanes to afford Intermediate F4. LCMS ($C_8H_{11}BrN_2O$) (ES, m/z) [M+H]+: 231, 233.

Example 1

Preparation of the compound of Example 1

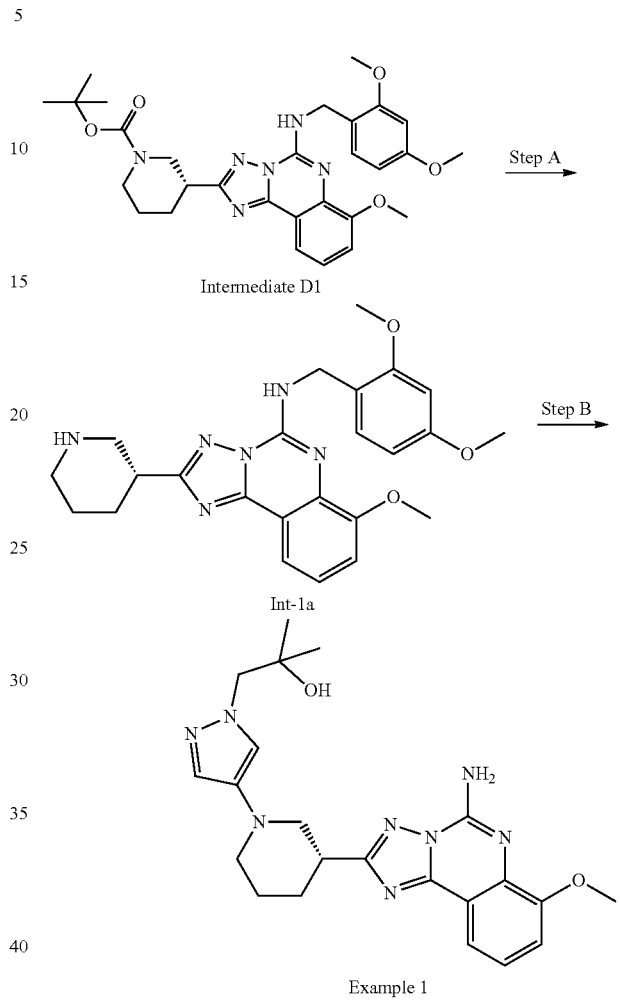

Step A—Synthesis of Compound Int-1a (R)—N-(2,4-dimethoxybenzyl)-7-methoxy-2-(piperidin-3-yl)-[1,2,4]triazolo[1,5-c]quinazolin-5-amine To a solution of Intermediate D1 (8.2 g, 15 mmol) in 1,4-dioxane (20 mL) was added 4M hydrochloric acid in dioxane (18 mL, 75 mmol). The mixture was stirred at room temperature for 3 hours. Upon completion, the reaction mixture was concentrated under reduced pressure. The resulting residue was purified by silica gel column chromatography with a 6% solution of 7-N ammonia in methanol/dichloromethane as eluent to afford Int-1a LC/MS (ES, m/z)=449 [M+H]+.

Step B—Synthesis of Example 1. (R)-7-methoxy-2-(1-(1-methyl-1H-pyrazol-4-yl)piperidin-3-yl)-[1,2,4]triazolo[1,5-c] quinazolin-5-amine A 5 mL microwave vial equipped with a stir bar was charged with Int-1a (100 mg, 0.214 mmol), t-BuXPhos Pd G3 (68.1 mg, 0.086 mmol) and sodium tert-butoxide (82 mg, 0.86 mmol) under nitrogen. To this mixture was added 1-(3-bromo-1H-1,2,4-triazol-1-yl)-2-methylpropan-2-ol (94 mg, 0.429 mmol) in THF (4 mL). The resulting mixture was bubbled with nitrogen for 10 minutes. The vial was then sealed with a cap and stirred at 90° C. for 16 hours. Upon completion, the reaction was cooled to room temperature, and then filtered to remove the solid precipitates. The filtrate was concentrated. To the resulting residue was added TFA (0.5 mL) and the residue was stirred at 50° C. for 2 hours. The mixture was cooled to room temperature and concentrated. The resulting residue was purified by reversed phase HPLC (Sunfire prep C18 OBD, 10 uM, 30×150 mm column) with 0-100% MeCN/H$_2$O with 0.1% TFA as eluent, yielding the title compound Example 1 of the invention. LC/MS (ES, m/z)=437 [M+H]$^+$. $^1$H NMR (500 MHz, Methanol-d$^4$) δ 7.85 (d, J=8.0 Hz, 1H), 7.48-7.27 (m, 3H), 7.24 (d, J=7.9 Hz, 1H), 4.00 (d, J=4.1 Hz, 2H), 3.76 (dd, J=11.6, 3.3 Hz, 1H), 3.48-3.35 (m, 2H), 2.98 (t, J=11.2 Hz, 1H), 2.76-2.54 (m, 1H), 2.40-2.19 (m, 1H), 2.06-1.75 (m, 3H), 1.17 (s, 6H).

The example compounds of the invention shown in Table 1 were prepared using a procedure similar to the procedure used to prepare Example 1, substituting the appropriate starting aryl halide.

TABLE 1

| Example | Structure Name | Observed m/z [M + H]$^+$ |
|---|---|---|
| 2 | (R)-7-methoxy-2-(1-(1-methyl-5-(trifluoromethyl)-1H-pyrazol-4-yl)piperidin-3-yl)-[1,2,4]triazolo[1,5-c]quinazolin-5-amine | 447 |
| 3 | (R)-2-(1-(1-(difluoromethyl)-1H-pyrazol-4-yl)piperidin-3-yl)-7-methoxy-[1,2,4]triazolo[1,5-c]quinazolin-5-amine | 415 |
| 4 | (R)-2-(1-(1-ethyl-1H-pyrazol-4-yl)piperidin-3-yl)-7-methoxy-[1,2,4]triazolo[1,5-c]quinazolin-5-amine | 393 |

TABLE 1-continued

| Example | Structure Name | Observed m/z [M + H]+ |
|---|---|---|
| 5 | (R)-2-(1-(1-isopropyl-1H-pyrazol-4-yl)piperidin-3-yl)-7-methoxy-[1,2,4]triazolo[1,5-c]quinazolin-5-amine | 407 |
| 6 | (R)-2-(1-(1-(tert-butyl)-1H-pyrazol-4-yl)piperidin-3-yl)-7-methoxy-[1,2,4]triazolo[1,5-c]quinazolin-5-amine | 421 |
| 7 | (R)-2-(1-(1-cyclopropyl-1H-pyrazol-4-yl)piperidin-3-yl)-7-methoxy-[1,2,4]triazolo[1,5-c]quinazolin-5-amine | 405 |
| 8 | (R)-2-(1-(1-(cyclobutylmethyl)-1H-pyrazol-4-yl)piperidin-3-yl)-7-methoxy-[1,2,4]triazolo[1,5-c]quinazolin-5-amine | 433 |

TABLE 1-continued

| Example | Structure Name | Observed m/z [M + H]+ |
|---|---|---|
| 9 | (R)-7-methoxy-2-(1-(1-(2,2,2-trifluoroethyl)-1H-pyrazol-4-yl)piperidin-3-yl)-[1,2,4]triazolo[1,5-c]quinazolin-5-amine | 447 |
| 10 | (R)-2-(1-(1,5-dimethyl-1H-pyrazol-4-yl)pipiperidin-3-yl)-7-methoxy-[1,2,4]triazolo[1,5-c]quinazolin-5-amine | 393 |
| 11 | (R)-7-methoxy-2-(1-(1,3,5-trimethyl-1H-pyrazol-4-yl)piperidin-3-yl)-[1,2,4]triazolo[1,5-c]quinazolin-5-amine | 407 |
| 12 | (R)-7-methoxy-2-(1-(pyrazolo[1,5-b]pyridazin-3-yl)-piperidin-3-yl)-[1,2,4]triazolo[1,5-c]quinazolin-5-amine | 416 |

TABLE 1-continued
| Example | Structure Name | Observed m/z [M + H]⁺ |
|---|---|---|
| 13 | 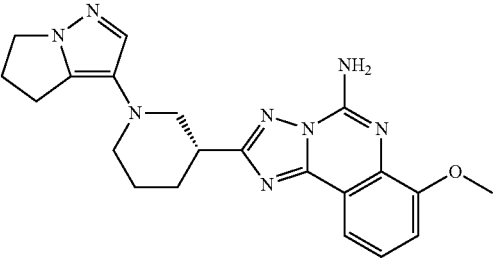 [SMILES: COc1cccc2c1nc(N)n1nc([C@@H]3CCCN(c4cnn5c4CCC5)C3)nc21]<br>(R)-2-(1-(5,6-dihydro-4H-pyrrolo[1,2-b]pyrazol-3-yl)piperidin-3-yl)-7-methoxy-[1,2,4]triazolo[1,5-c]quinazolin-5-amine | 405 |
| 14 | 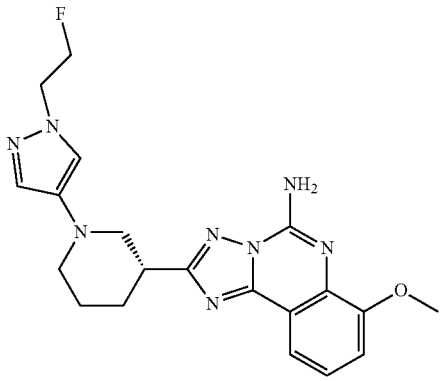 [SMILES: COc1cccc2c1nc(N)n1nc([C@@H]3CCCN(c4cnn(CCF)c4)C3)nc21]<br>(R)-2-(1-(1-(2-fluoroethyl)-1H-pyrazol-4-yl)piperidin-3-yl)-7-methoxy-[1,2,4]triazolo[1,5-c]quinazolin-5-amine | 411 |
| 15 | 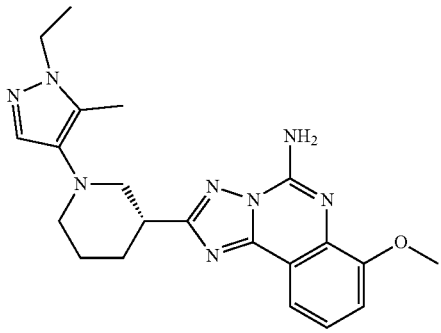 [SMILES: CCn1ncc(N2CCC[C@@H](c3nc4c5cccc(OC)c5nc(N)n4n3)C2)c1C]<br>(R)-2-(1-(1-ethyl-5-methyl-1H-pyrazol-4-yl)piperidin-3-yl)-7-methoxy-[1,2,4]triazolo[1,5-c]quinazolin-5-amine | 407 |

TABLE 1-continued

| Example | Structure Name | Observed m/z [M + H]+ |
|---|---|---|
| 16 | 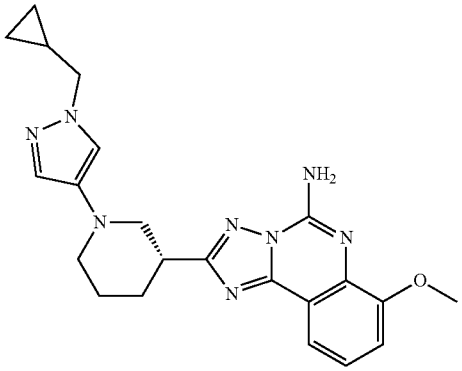 [SMILES: COc1cccc2c1nc(N)n1nc([C@@H]3CCCN(c4cnn(CC5CC5)c4)C3)nc21]<br>(R)-2-(1-(1-(cyclopropylmethyl)-1H-pyrazol-4-yl)piperidin-3-yl)-7-methoxy-[1,2,4]triazolo[1,5-c]quinazolin-5-amine | 419 |
| 17 | 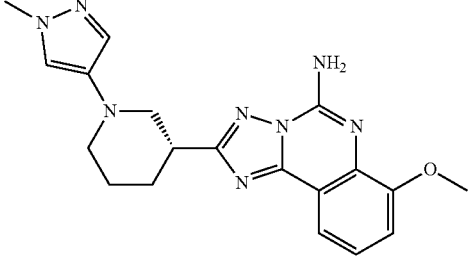<br>(R)-7-methoxy-2-(1-(1-methyl-1H-pyrazol-4-yl)piperidin-3-yl)-[1,2,4]triazolo[1,5-c]quinazolin-5-amine | 379 |
| 18 | 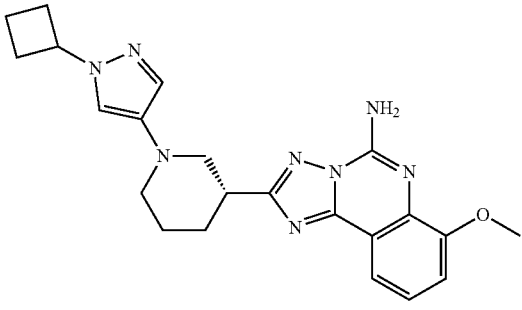 [SMILES: COc1cccc2c1nc(N)n1nc([C@@H]3CCCN(c4cnn(C5CCC5)c4)C3)nc21]<br>(R)-2-(1-(1-cyclobutyl-1H-pyrazol-4-yl)piperidin-3-yl)-7-methoxy-[1,2,4]triazolo[1,5-c]quinazolin-5-amine | 419 |
| 19 | 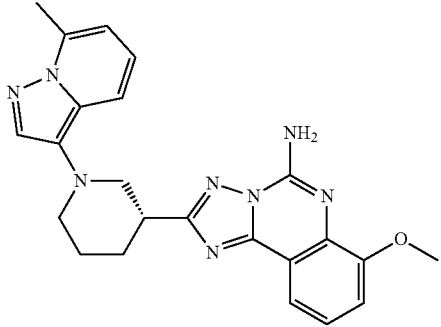 [SMILES: COc1cccc2c1nc(N)n1nc([C@@H]3CCCN(c4cnn5c(C)cccc45)C3)nc21]<br>(R)-7-methoxy-2-(1-(7-methylpyrazolo[1,5-a]pyridin-3-yl)piperidin-3-yl)-[1,2,4]triazolo[1,5-c]quinazolin-5-amine | 429 |

TABLE 1-continued
| Example | Structure Name | Observed m/z [M + H]+ |
|---|---|---|
| 20 | 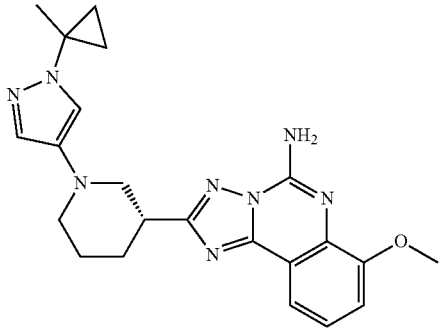 [SMILES: COc1cccc2c1nc(N)n1nc([C@@H]3CCCN(c4cnn(C5(C)CC5)c4)C3)nc21]<br>(R)-7-methoxy-2-(1-(1-(1-methylcyclopropyl)-1H-pyrazol-4-yl)piperidin-3-yl)-[1,2,4]triazolo[1,5-c]quinazolin-5-amine | 419 |
| 21 | 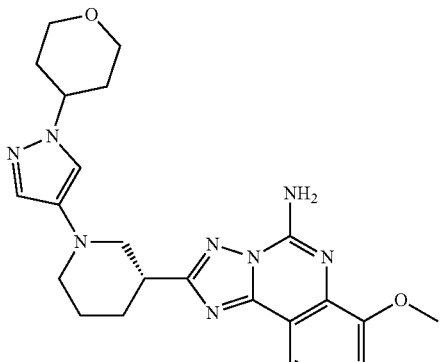<br>(R)-7-methoxy-2-(1-(1-(tetrahydro-2H-pyran-4-yl)-1H-pyrazol-4-yl)piperidin-3-yl)-[1,2,4]triazolo[1,5-c]quinazolin-5-amine | 449 |
| 22 | 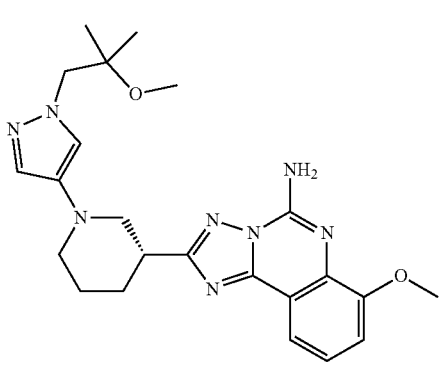 [SMILES: COc1cccc2c1nc(N)n1nc([C@@H]3CCCN(c4cnn(CC(C)(C)OC)c4)C3)nc21]<br>(R)-7-methoxy-2-(1-(1-(2-methoxy-2-methylpropyl)-1H-pyrazol-4-yl)piperidin-3-yl)-[1,2,4]triazolo[1,5-c]quinazolin-5-amine | 451 |

TABLE 1-continued
| Example | Structure Name | Observed m/z [M + H]+ |
|---|---|---|
| 23 | 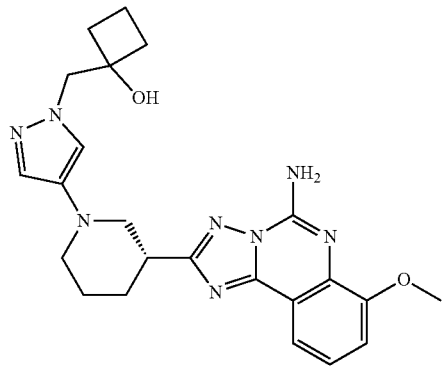 [SMILES: COc1cccc2c1nc(N)n1nc([C@@H]3CCCN(c4cnn(CC5(O)CCC5)c4)C3)nc21]<br>(R)-1-((4-(3-(5-amino-7-methoxy-[1,2,4]-triazolo[1,5-c]quinazolin-2-yl)piperidin-1-yl)-1H-pyrazol-1-yl)methyl)cyclobutan-1-ol | 449 |
| 24 | 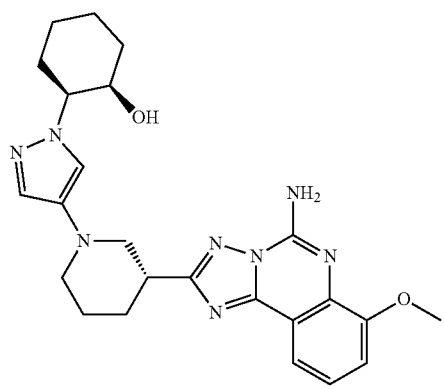 [SMILES: COc1cccc2c1nc(N)n1nc([C@@H]3CCCN(c4cnn([C@H]5CCCC[C@H]5O)c4)C3)nc21]<br>(1R,2S)-2-(4-((R)-3-(5-amino-7-methoxy-[1,2,4]triazolo[1,5-c]quinazolin-2-yl)piperidin-1-yl)-1H-pyrazol-1-yl)cyclohexan-1-ol | 463 |
| 25 | 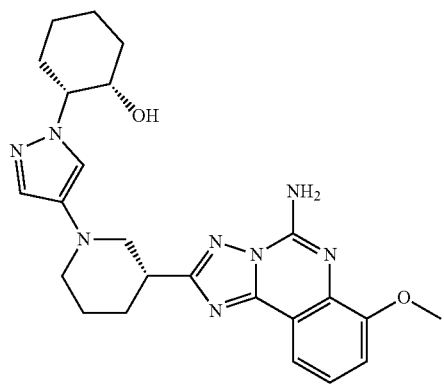 [SMILES: COc1cccc2c1nc(N)n1nc([C@@H]3CCCN(c4cnn([C@@H]5CCCC[C@@H]5O)c4)C3)nc21]<br>(1S,2R)-2-(4-((R)-3-(5-amino-7-methoxy-[1,2,4]triazolo[1,5-c]quinazolin-2-yl)piperidin-1-yl-1H-pyrazol-1-yl)cyclohexan-1-ol | 463 |

TABLE 1-continued
| Example | Structure Name | Observed m/z [M + H]+ |
|---|---|---|
| 26 | 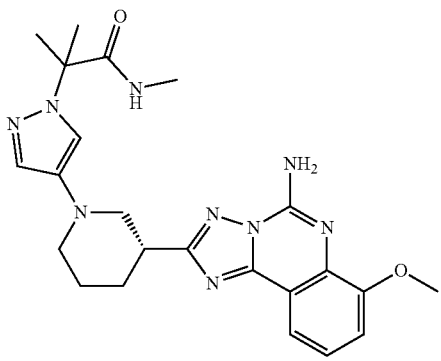 [SMILES: CNC(=O)C(C)(C)n1cc(N2CCC[C@@H](c3nc4c5cccc(OC)c5nc(N)n4n3)C2)cn1]<br>(R)-2-(4-(3-(5-amino-7-methoxy-[1,2,4]triazolo[1,5-c]quinazolin-2-yl)piperidin-1-yl)-1H-pyrazol-1-yl)-N,2-dimethylpropanamide | 464 |
| 27 | 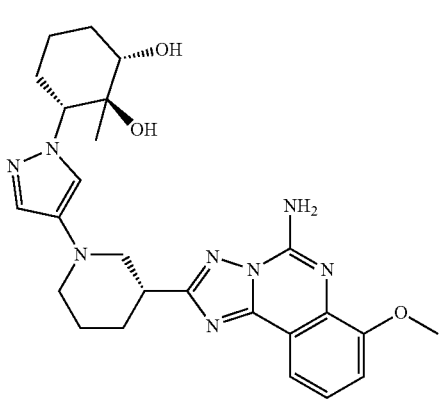 [SMILES: COc1cccc2c1nc(N)n1nc([C@@H]3CCCN(c4cnn([C@@H]5CCC[C@H](O)[C@@]5(C)O)c4)C3)nc21]<br>(1S,2S,6R)-6-(4-((R)-3-(5-amino-7-methoxy-[1,2,4]triazolo[1,5-c]quinazolin-2-yl)piperidin-1-yl)-1H-pyrazol-1-yl)-1-methylcyclohexane-1,2-diol | 493 |
| 28 | 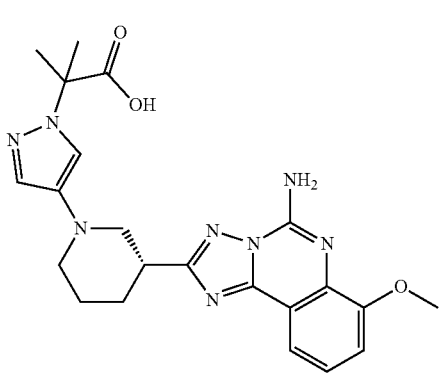 [SMILES: COc1cccc2c1nc(N)n1nc([C@@H]3CCCN(c4cnn(C(C)(C)C(=O)O)c4)C3)nc21]<br>(R)-2-(4-(3-(5-amino-7-methoxy-[1,2,4]triazolo[1,5-c]quinazolin-2-yl)piperidin-1-yl)-1H-pyrazol-1-yl)-2-methylpropanoic acid | 451 |

TABLE 1-continued
| Example | Structure Name | Observed m/z [M + H]+ |
|---|---|---|
| 29 | 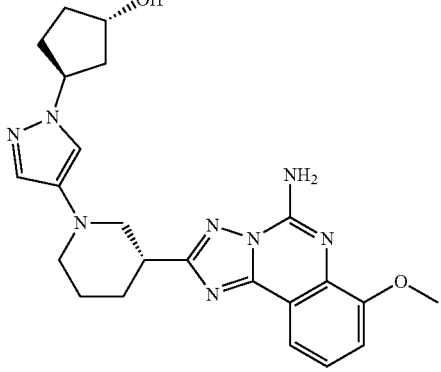<br>(1S,3S)-3-(4-((R)-3-(5-amino-7-methoxy-[1,2,4]triazolo[1,5-c]quinazolin-2-yl)piperidin-1-yl)-1H-pyrazol-1-yl)cyclopentan-1-ol | 449 |
| 30 | 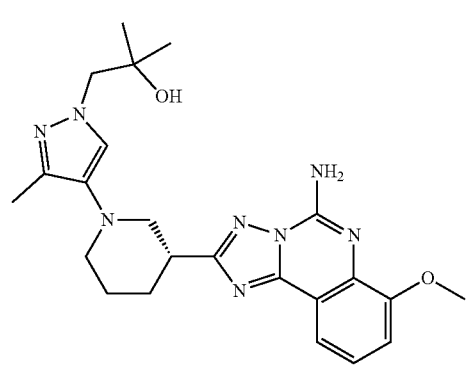<br>(R)-1-(4-(3-(5-amino-7-methoxy-[1,2,4]triazolo[1,5-c]quinazolin-2-yl)piperidin-1-yl)-3-methyl-1H-pyrazol-1-yl)-2-methylpropan-2-ol | 451 |
| 31 | 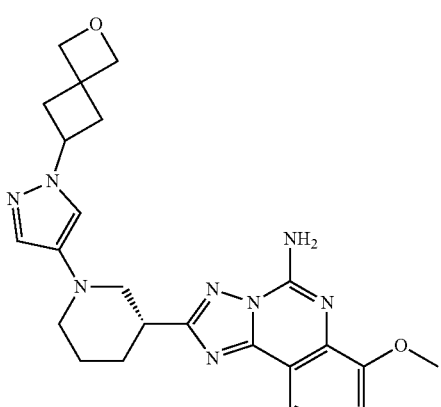<br>(R)-2-(1-(1-(2-oxaspiro[3.3]heptan-6-yl)-1H-pyrazol-4-yl)piperidin-3-yl)-7-methoxy-[1,2,4]triazolo[1,5-c]quinazolin-5-amine | 461 |

TABLE 1-continued

| Example | Structure Name | Observed m/z [M + H]+ |
|---|---|---|
| 32 | (R)-1-((4-(3-(5-amino-7-methoxy-[1,2,4]triazolo[1,5-c]quinazolin-2-yl)piperidin-1-yl)-3-methyl-1H-pyrazol-1-yl)methyl)cyclobutan-1-ol | 463 |
| 33 | (R)-1-(4-(3-(5-amino-7-methoxy-[1,2,4]triazolo[1,5-c]quinazolin-2-yl)piperidin-1-yl)-5-methyl-1H-pyrazol-1-yl)-2-methylpropan-2-ol | 451 |
| 34 | (R)-1-((4-(3-(5-amino-7-methoxy-[1,2,4]triazolo[1,5-c]quinazolin-2-yl)piperidin-1-yl)-5-methyl-1H-pyrazol-1-yl)methyl)cyclobutan-1-ol | 463 |

TABLE 1-continued
| Example | Structure Name | Observed m/z [M + H]+ |
|---|---|---|
| 35 | 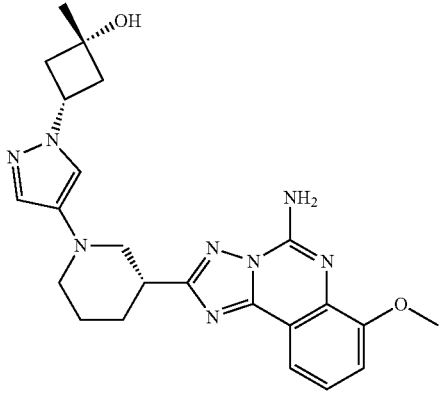 [SMILES: COc1cccc2c1nc(N)n1nc([C@@H]3CCCN(c4cnn([C@H]5C[C@@](C)(O)C5)c4)C3)nc21]<br>(R)-3-(4-(3-(5-amino-7-methoxy-[1,2,4]triazolo[1,5-c]quinazolin-2-yl)piperidin-1-yl)-1H-pyrazol-1-yl)-1-methylcyclobutan-1-ol | 449 |
| 36 | 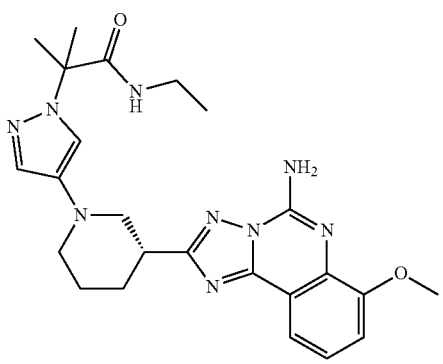 [SMILES: CCNC(=O)C(C)(C)n1cc(N2CCC[C@@H](c3nc4c5cccc(OC)c5nc(N)n4n3)C2)cn1]<br>(R)-2-(4-(3-(5-amino-7-methoxy-[1,2,4]triazolo[1,5-c]quinazolin-2-yl)piperidin-1-yl)-1H-pyrazol-1-yl)-N-ethyl-2-methylpropanamide | 478 |
| 37 | 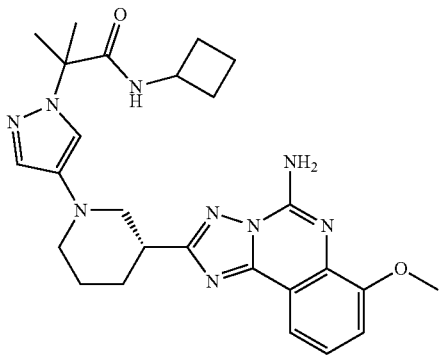 [SMILES: COc1cccc2c1nc(N)n1nc([C@@H]3CCCN(c4cnn(C(C)(C)C(=O)NC5CCC5)c4)C3)nc21]<br>(R)-2-(4-(3-(5-amino-7-methoxy-[1,2,4]triazolo[1,5-c]quinazolin-2-yl)piperidin-1-yl)-1H-pyrazol-1-yl)-N-cyclobutyl-2-methylpropanamide | 504 |

TABLE 1-continued

| Example | Structure Name | Observed m/z [M + H]+ |
|---|---|---|
| 38 | (R)-2-(4-(3-(5-amino-7-methoxy-[1,2,4]triazolo[1,5-c]quinazolin-2-yl)piperidin-1-yl)-1H-pyrazol-1-yl)-N-isopropyl-2-methylpropanamide | 492 |
| 39 | (R)-7-methoxy-2-(1-(1-(oxetan-3-yl)-1H-pyrazol-4-yl)piperidin-3-yl)-[1,2,4]triazolo[1,5-c]quinazolin-5-amine | 421 |
| 40 | (R)-3-((4-(3-(5-amino-7-methoxy-[1,2,4]triazolo[1,5-c]quinazolin-2-ylpiperidin-1-yl)-1H-pyrazol-1-yl)methyl)pentan-3-ol | 465 |

TABLE 1-continued

| Example | Structure Name | Observed m/z [M + H]+ |
|---|---|---|
| 41 | (R)-1-((4-(3-(5-amino-7-methoxy-[1,2,4]triazolo[1,5-c]quinazolin-2-yl)piperidin-1-yl)-1H-pyrazol-1-yl)methyl)cyclopentan-1-ol | 463 |
| 42 | (1S,2R)-2-(4-((R)-3-(5-amino-7-methoxy-[1,2,4]triazolo[1,5-c]quinazolin-2-yl)piperidin-1-yl)-1H-pyrazol-1-yl)-1-methylcyclohexan-1-ol | 477 |
| 43 | (1S,2S)-2-(4-((R)-3-(5-amino-7-methoxy-[1,2,4]triazolo[1,5-c]quinazolin-2-yl)piperidin-1-yl)-1H-pyrazol-1-yl)-1-methylcyclohexan-1-ol | 477 |

TABLE 1-continued

| Example | Structure Name | Observed m/z [M + H]+ |
|---|---|---|
| 44 | (R)-1-((4-(3-(5-amino-7-methoxy-[1,2,4]triazolo[1,5-c]quinazolin-2-yl)piperidin-1-yl)-1H-pyrazol-1-yl)methyl)cyclohexan-1-ol | 477 |
| 45 | 7-methoxy-2-((R)-1-(1-((R)-pyrrolidin-3-yl)-1H-pyrazol-4-yl)piperidin-3-yl)-[1,2,4]triazolo[1,5-c]quinazolin-5-amine | 434 |
| 46 | (R)-7-methoxy-2-(1-(3-methyl-1-(tetrahydro-2H-pyran-4-yl)-1H-pyrazol-4-yl)piperidin-3-yl)-[1,2,4]triazolo[1,5-c]quinazolin-5-amine | 463 |

TABLE 1-continued

| Example | Structure Name | Observed m/z [M + H]+ |
|---|---|---|
| 47 | (R)-7-methoxy-2-(1-(5-methyl-1-(tetrahydro-2H-pyran-4-yl)-1H-pyrazol-4-yl)piperidin-3-yl)-[1,2,4]triazolo[1,5-c]quinazolin-5-amine | 463 |
| 48 | (R)-2-(3-(difluoromethyl)-1-tetrahydro-2H-pyran-4-yl)-1H-pyrazol-4-yl)piperidin-3-yl)-7-methoxy-[1,2,4]triazolo[1,5-c]quinazolin-5-amine | 499 |
| 49 | (R)-2-(1-(5-(difluoromethyl)-1-(tetrahydro-2H-pyran-4-yl)-1H-pyrazol-4-yl)piperidin-3-yl)-7-methoxy-[1,2,4]triazolo[1,5-c]quinazolin-5-amine | 499 |

TABLE 1-continued

| Example | Structure Name | Observed m/z [M + H]+ |
|---|---|---|
| 50 | 7-methoxy-2-((R)-1-(1-(((S)-1-methylpyrrolidin-3-yl)-1H-pyrazol-4-yl)piperidin-3-yl)-[1,2,4]triazolo[1,5-c]quinazolin-5-amine | 448 |
| 51 | (R)-7-methoxy-2-(1-(1-methyl-3-(trifluoromethyl)-1H-pyrazol-4-yl)piperidin-3-yl)-[1,2,4]triazolo[1,5-c]quinazolin-5-amine | 447 |
| 52 | (R)-1-(4-(3-(5-amino-7-methoxy-[1,2,4]triazolo[1,5-c]quinazolin-2-yl)piperidin-1-yl)-3-(trifluoromethyl)-1H-pyrazol-1-yl)-2-methylpropan-2-ol | 505 |

TABLE 1-continued
| Example | Structure Name | Observed m/z [M + H]+ |
|---|---|---|
| 53 | 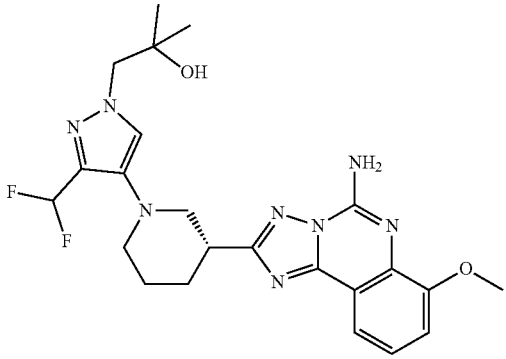 [SMILES: COc1cccc2c1nc(N)n1nc([C@@H]3CCCN(c4cn(CC(C)(C)O)nc4C(F)F)C3)nc21]<br>(R)-1-(4-(3-(5-amino-7-methoxy-[1,2,4]triazolo[1,5-c]quinazolin-2-yl)piperidin-1-yl)-3-(difluoromethyl)-1H-pyrazol-1-yl)-2-methylpropan-2-ol | 487 |
| 54 | 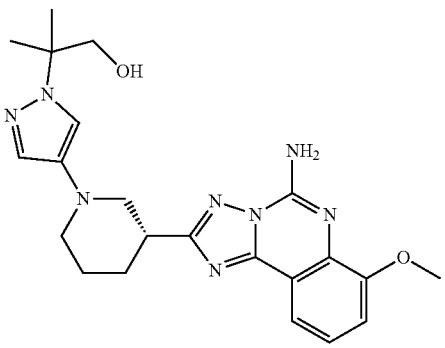 [SMILES: COc1cccc2c1nc(N)n1nc([C@@H]3CCCN(c4cnn(C(C)(C)CO)c4)C3)nc21]<br>(R)-2-(4-(3-(5-amino-7-methoxy-[1,2,4]triazolo[1,5-c]quinazolin-2-yl)piperidin-1-yl)-1H-pyrazol-1-yl)-2-methylpropan-1-ol | 437 |
| 55 | 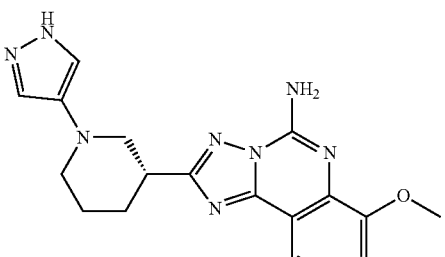<br>(R)-2-(1-(1H-pyrazol-4-yl)piperidin-3-yl-7-methoxy-[1,2,4]triazolo[1,5-c]quinazolin-5-amine | 365 |

TABLE 1-continued

| Example | Structure Name | Observed m/z [M + H]+ |
|---|---|---|
| 56 | 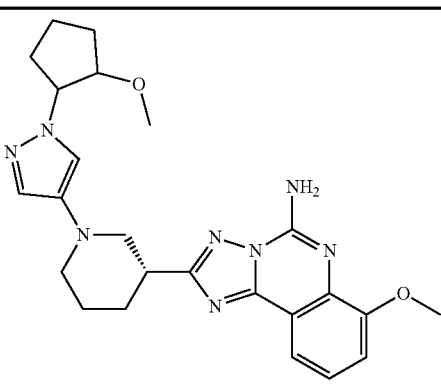7-methoxy-2-((3R)-1-(1-(2-methoxycyclopentyl)-1H-pyrazol-4-yl)piperidin-3-yl)-[1,2,4]triazolo[1,5-c]quinazolin-5-amine | 463 |
| 57A, 57B | 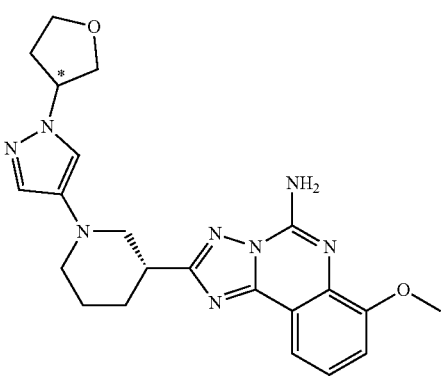 [SMILES: COc1cccc2c1nc(N)n1nc([C@@H]3CCCN(c4cnn(C5CCOC5)c4)C3)nc21]7-methoxy-2-((R)-1-(1-((S)-tetrahydrofuran-3-yl)-1H-pyrazol-4-yl)piperidin-3-yl)-[1,2,4]triazolo[1,5-c]quinazolin-5-amine, 7-methoxy-2-((R)-1-(1-((R)-tetrahydrofuran-3-yl)-1H-pyrazol-4-yl)piperidin-3-yl)-[1,2,4]triazolo[1,5-c]quinazolin-5-amine Precursor was resolved by AD-H 21 × 250 mm column with 55% EtOH (0.2% DIPA) as co-solvent | 435 |
| 58A, 58B | 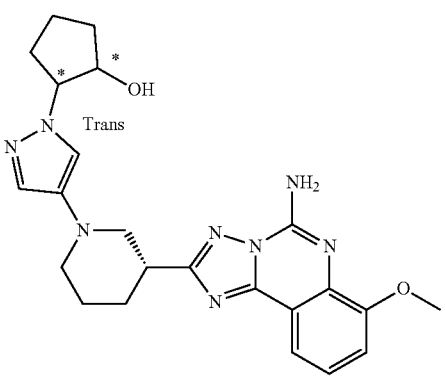 [SMILES: COc1cccc2c1nc(N)n1nc([C@@H]3CCCN(c4cnn(C5CCCC5O)c4)C3)nc21](1R,2R)-2-_4-((R)-3-(5-amino-7-methoxy-[1,2,4]triazolo[1,5-c]quinazolin-2-yl)piperidin-1-yl)-1H-pyrazol-1-yl)cyclopentan-1-ol, (1S,2S)-2-(4-((R)-3-(5-amino-7-methoxy-[1,2,4]triazolo[1,5-c]quinazolin-2-yl)piperidin-1-yl)-1H-pyrazol-1-yl)cyclopentan-1-ol Precursor was resolved by Whelko-1, 21 × 250 mm column with 50% 1:1 MeOH/ACN (0.2% DIPA) as co-solvent | 449 |

TABLE 1-continued

| Example | Structure Name | Observed m/z [M + H]+ |
|---|---|---|
| 59A, 59B | (1S,2S)-2-(4-((R)-3-(5-amino-7-methoxy-[1,2,4]triazolo[1,5-c]quinazolin-2-yl)piperidin-1-yl)-1H-pyrazol-1-yl)-1-methylcyclopentan-1-ol, (1R,2R)-2-(4-((R)-3-(5-amino-7-methoxy-[1,2,4]triazolo[1,5-c]quinazolin-2-yl)piperidin-1-yl)-1H-pyrazol-1-yl)-1-methylcyclopentan-1-ol Precursor was resolved by Chiral AD-3, 21 × 250 mm column with 40% EtOH (0.2% DEA) as co-solvent | 463 |
| 60A, 60B | (1R,2R)-2-(4-((R)-3-(5-amino-7-methoxy-[1,2,4]triazolo[1,5-c]quinazolin-2-yl)piperidin-1-yl)-1H-pyrazol-1-yl)cyclobutan-1-ol, (1S,2S)-2-(4-((R)-3-(5-amino-7-methoxy-[1,2,4]triazolo[1,5-c]quinazolin-2-yl)piperidin-1-yl)-1H-pyrazol-1-yl)cyclobutan-1-ol Precursor was resolved by Chiral AD-3, 21 × 250 mm column with 40% EtOH (0.2% DEA) as co-solvent | 435 |
| 61A, 61B | 2-((R)-1-(1-((S)-3,3-dimethylbutan-2-yl)-1H-pyrazol-4-yl)piperidin-3-yl)-7-methoxy-[1,2,4]triazolo[1,5-c]quinazolin-5-amine, 2-((R)-1-(1-((R)-3,3-dimethylbutan-2-yl)-1H-pyrazol-4- | 451 |

TABLE 1-continued

| Example | Structure Name | Observed m/z [M + H]+ |
|---|---|---|
| | yl)piperidin-3-yl)-7-methoxy-[1,2,4]triazolo[1,5-c]quinazolin-5-amine Precursor was resolved by AD-H, 21 × 250 mm column with 45% IPA (0.2% DIPA) as co-solvent | |
| 62 | 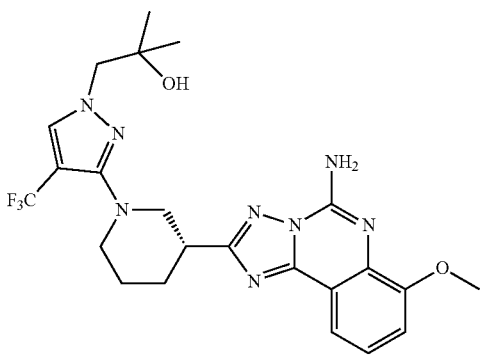 [SMILES: COc1cccc2c1nc(N)n1nc([C@@H]3CCCN(c4nn(CC(C)(C)O)cc4C(F)(F)F)C3)nc21]<br>(R)-1-(3-(3-(5-amino-7-methoxy-[1,2,4]triazolo[1,5-c]quinazolin-2-yl)piperidin-1-yl)-4-(trifluoromethyl)-1H-pyrazol-1-yl)-2-methylpropan-2-ol | 505 |
| 63 | 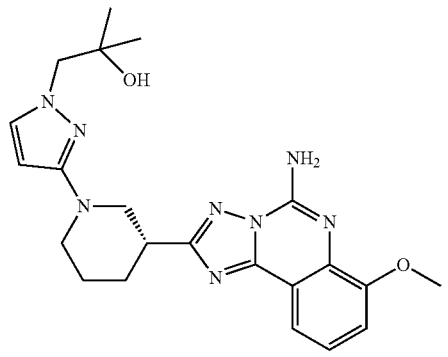 [SMILES: COc1cccc2c1nc(N)n1nc([C@@H]3CCCN(c4ccn(CC(C)(C)O)n4)C3)nc21]<br>(R)-1-(3-(3-(5-amino-7-methoxy-[1,2,4]triazolo[1,5-c]quinazolin-2-yl)piperidin-1-yl)-1H-pyrazol-1-yl)-2-methylpropan-2-ol | 437 |
| 64 | 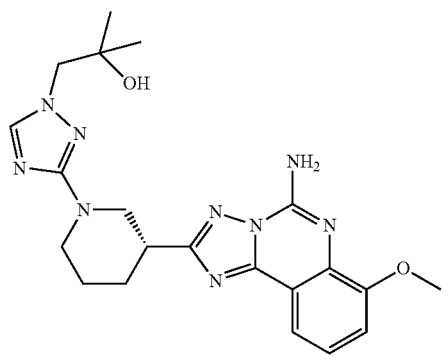 [SMILES: COc1cccc2c1nc(N)n1nc([C@@H]3CCCN(c4ncn(CC(C)(C)O)n4)C3)nc21]<br>(R)-1-(3-(3-(5-amino-7-methoxy[1,2,4]triazolo[1,5-c]quinazolin-2-yl)piperidin-1-yl)-1H-1,2,4-triazol-1-yl)-2-methylpropan-2-ol | 438 |

TABLE 1-continued

| Example | Structure Name | Observed m/z [M + H]⁺ |
|---|---|---|
| 65 | (R)-1-(4-(3-(5-amino-7-methoxy-[1,2,4]triazolo[1,5-c]quinazolin-2-yl)piperidin-1-yl)-2H-1,2,3-triazol-2-yl)-2-methylpropan-2-ol | 438 |
| 66 | (R)-7-methoxy-2-(1-(1-methyl-1H-pyrazol-3-yl)piperidin-3-yl)-[1,2,4]triazolo[1,5-c]quinazolin-5-amine | 379 |
| 67 | (R)-7-methoxy-2-(1-(1-methyl-1H-1,2,3-triazol-4-yl)piperidin-3-yl)-[1,2,4]triazolo[1,5-c]quinazolin-5-amine | 380 |
| 68 | (R)-7-methoxy-2-(1-(1-(tetrahydro-2H-pyran-4-yl)-1H-1,2,4-triazol-3-yl)piperidin-3-yl)-[1,2,4]triazolo[1,5-c]quinazolin-5-amine | 450 |

TABLE 1-continued

| Example | Structure Name | Observed m/z [M + H]+ |
|---|---|---|
| 69 | (R)-7-methoxy-2-(1-(1-(2,2,2-trifluoroethyl)-1H-1,2,4-triazol-3-yl)piperidin-3-yl)-[1,2,4]triazolo[1,5-c]quinazolin-5-amine | 448 |
| 70 | (R)-2-(1-(2,5-dimethyl-2H-1,2,3-triazol-4-yl)piperidin-3-yl)-7-methoxy-[1,2,4]triazolo[1,5-c]quinazolin-5-amine | 394 |
| 71 | (R)-7-methoxy-2-(1-(5,6,7,8-tetrahydro-[1,2,4]triazolo[4,3-a]pyrazin-3-yl)piperidin-3-yl)-[1,2,4]triazolo[1,5-c]quinazolin-5-amine | 421 |

TABLE 1-continued

| Example | Structure Name | Observed m/z [M + H]+ |
|---|---|---|
| 72 | (R)-7-methoxy-2-(1-(2-(tetrahydro-2H-pyran-4-yl)-2H-1,2,3-triazol-4-yl)piperidin-3-yl)-[1,2,4]triazolo[1,5-c]quinazolin-5-amine | 450 |
| 73 | (R)-7-methoxy-2-(1-(1-(2,2,2-trifluoroethyl)-1H-1,2,3-triazol-4-yl)piperidin-3-yl)-[1,2,4]triazolo[1,5-c]quinazolin-5-amine | 448 |
| 74 | (R)-2-(1-(1,5-dimethyl-1H-pyrazol-3-yl)piperidin-3-yl)-7-methoxy-[1,2,4]triazolol[1,5-c]quinazolin-5-amine | 393 |
| 75 | (R)-7-methoxy-2-(1-(2-methyl-2H-1,2,3-triazol-4-yl)piperidin-3-yl)-[1,2,4]triazolo[1,5-c]quinazolin-5-amine | 380 |

TABLE 1-continued

| Example | Structure Name | Observed m/z [M + H]+ |
|---|---|---|
| 76 | (R)-7-methoxy-2-(1-(1-methyl-1H-imidazol-4-yl)piperidin-3-yl)-[1,2,4]triazolo[1,5-c]quinazolin-5-amine | 379 |
| 77 | (R)-7-methoxy-2-(1-(1-methyl-3-(trifluoromethyl)-1H-pyrazol-5-yl)piperidin-3-yl)-[1,2,4]triazolo[1,5-c]quinazolin-5-amine | 447 |
| 78 | (R)-7-methoxy-2-(1-(1-methyl-5-(trifluoromethyl)-1H-pyrazol-3-yl)piperidin-3-yl)-[1,2,4]triazolo[1,5-c]quinazolin-5-amine | 447 |
| 79 | (R)-2-(1-(1,5-dimethyl-1H-1,2,3-triazol-4-yl)piperidin-3-yl)-7-methoxy-[1,2,4]triazolo[1,5-c]quinazolin-5-amine | 394 |

TABLE 1-continued
| Example | Structure Name | Observed m/z [M + H]+ |
|---|---|---|
| 80 | 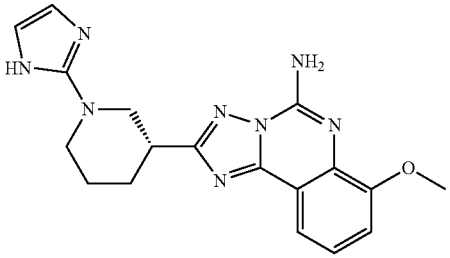 [SMILES: COc1cccc2c1nc(N)n1nc([C@@H]3CCCN(c4ncc[nH]4)C3)nc21]<br>(R)-2-(1-(1H-imidazol-2-yl)piperidin-3-yl)-7-methoxy-[1,2,4]triazolo[1,5-c]quinazolin-5-amine | 365 |
| 81 | 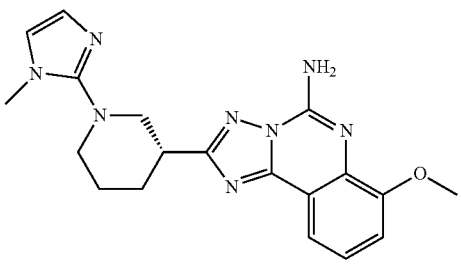<br>(R)-7-methoxy-2-(1-(1-methyl-1H-imidazol-2-yl)piperidin-3-yl)-[1,2,4]triazolo[1,5-c]quinazolin-5-amine | 379 |
| 82 | 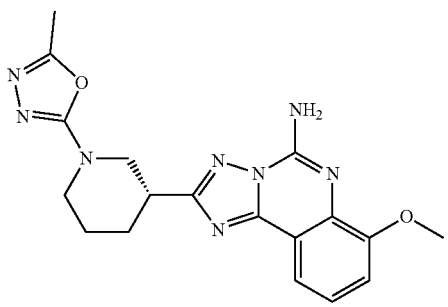 [SMILES: COc1cccc2c1nc(N)n1nc([C@@H]3CCCN(c4nnc(C)o4)C3)nc21]<br>(R)-7-methoxy-2-(1-(5-methyl-1,3,4-oxadiazol-2-yl)piperidin-3-yl)-[1,2,4]triazolo[1,5-c]quinazolin-5-amine | 381 |
| 83 | 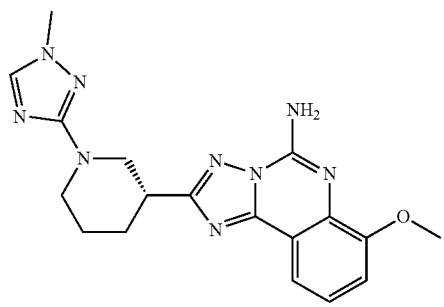 [SMILES: COc1cccc2c1nc(N)n1nc([C@@H]3CCCN(c4ncn(C)n4)C3)nc21]<br>(R)-7-methoxy-2-(1-(1-methyl-1H-1,2,4-triazol-3-yl)piperidin-3-yl)-[1,2,4]triazolo[1,5-c]quinazolin-5-amine | 380 |

TABLE 1-continued

| Example | Structure Name | Observed m/z [M + H]+ |
|---|---|---|
| 84 | 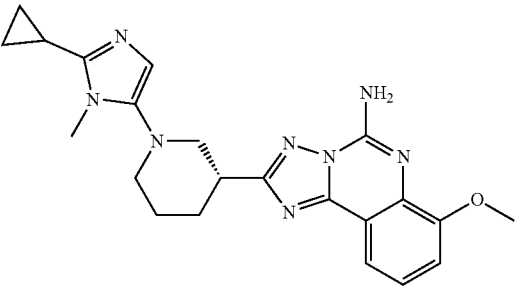 [SMILES: COc1cccc2c1nc(N)n1nc([C@@H]3CCCN(c4cnc(C5CC5)n4C)C3)nc21]<br>(R)-2-(1-(2-cyclopropyl-1-methyl-1H-imidazol-5-yl)piperidin-3-yl)-7-methoxy-[1,2,4]triazolo[1,5-c]quinazolin-5-amine | 419 |
| 85 | 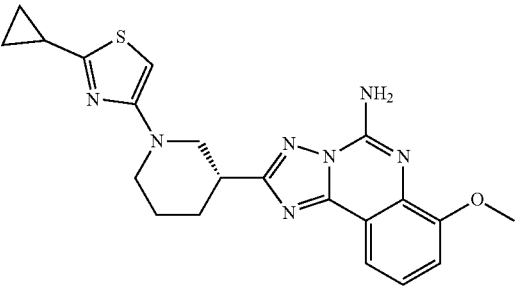 [SMILES: COc1cccc2c1nc(N)n1nc([C@@H]3CCCN(c4csc(C5CC5)n4)C3)nc21]<br>(R)-2-(1-(2-cyclopropylthiazol-4-yl)piperidin-3-yl)-7-methoxy-[1,2,4]triazolo[1,5-c]quinazolin-5-amine | 422 |
| 86 | 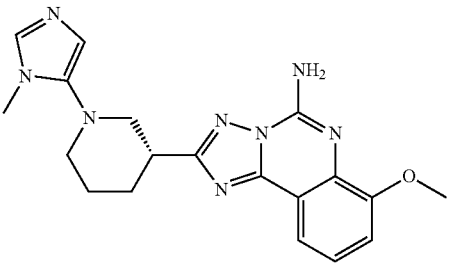<br>(R)-7-methoxy-2-(1-(1-methyl-1H-imidazol-5-yl)piperidin-3-yl)-[1,2,4]triazolo[1,5-c]quinazolin-5-amine | 379 |
| 87 | 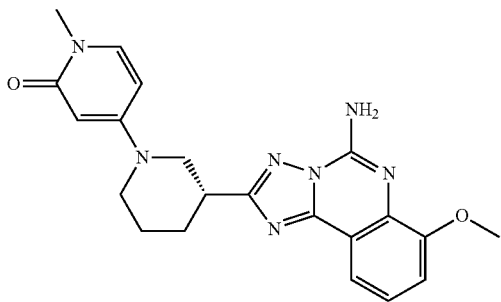 [SMILES: COc1cccc2c1nc(N)n1nc([C@@H]3CCCN(c4ccn(C)c(=O)c4)C3)nc21]<br>(R)-4-(3-(5-amino-7-methoxy-[1,2,4]triazolo[1,5-c]quinazolin-2-yl)piperidin-1-yl)-1-methylpyridin-2(1H)-one | 406 |

TABLE 1-continued
| Example | Structure Name | Observed m/z [M + H]+ |
|---|---|---|
| 88 | 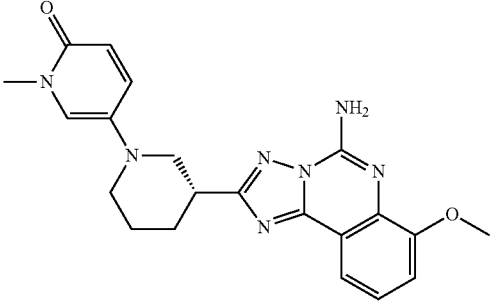<br>(R)-5-(3-(5-amino-7-methoxy-[1,2,4]triazolo[1,5-c]quinazolin-2-yl)piperidin-1-yl)-1-methylpyridin-2(1H)-one | 406 |
| 89 | 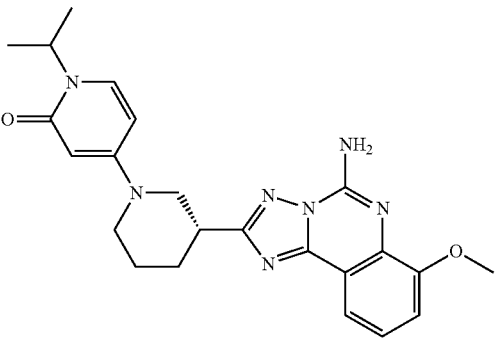<br>(R)-4-(3-(5-amino-7-methoxy-[1,2,4]triazolo[1,5-c]quinazolin-2-yl)piperidin-1-yl)-1-isopropylpyridin-2(1H)-one | 434 |
| 90 | 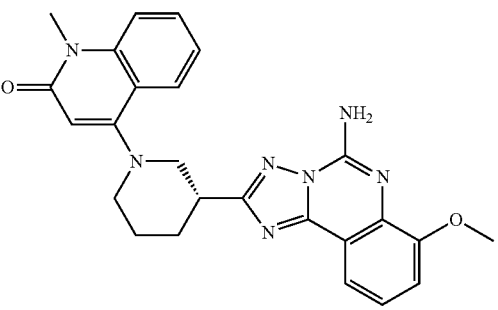 [SMILES: COc1cccc2c1nc(N)n1nc([C@@H]3CCCN(c4cc(=O)n(C)c5ccccc45)C3)nc21]<br>(R)-4-(3-(5-amino-7-methoxy-[1,2,4]triazolo[1,5-c]quinazolin-2-yl)piperidin-1-yl)-1-methylquinolin-2(1H)-one | 456 |

TABLE 1-continued

| Example | Structure Name | Observed m/z [M + H]+ |
|---|---|---|
| 91 | (R)-4-(3-(5-amino-7-methoxy-[1,2,4]triazolo[1,5-c]quinazolin-2-yl)piperidin-1-yl)-1-ethylpyridin-2(1H)-one | 420 |
| 92 | (R)-5-(3-(5-amino-7-methoxy-[1,2,4]triazolo[1,5-c]quinazolin-2-yl)piperidin-1-yl)-1-(difluoromethyl)pyridin-2(1H)-one | 442 |
| 93 | (R)-5-(3-(5-amino-7-methoxy-[1,2,4]thiazolo[1,5-c]quinazolin-2-yl)piperidin-1-yl)-1,3-dimethylpyridin-2(1H)-one | 420 |
| 94 | (R)-5-(3-(5-amino-7-methoxy-[1,2,4]triazolo[1,5-c]quinazolin-2-yl)piperidin-1-yl)-6-methyl-1-(2,2,2-trifluoroethyl)pyridin-2(1H)-one | 488 |

TABLE 1-continued
| Example | Structure Name | Observed m/z [M + H]+ |
|---|---|---|
| 95 | 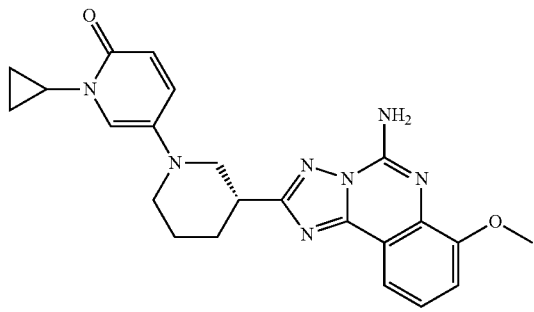 [SMILES: COc1cccc2c1nc(N)n1nc([C@@H]3CCCN(c4ccc(=O)n(C5CC5)c4)C3)nc21]<br>(R)-5-(3-(5-amino-7-methoxy-[1,2,4]triazolo[1,5-c]quinazolin-2-yl)piperidin-1-yl)-1-cyclopropylpyridin-2(1H)-one | 432 |
| 96 | 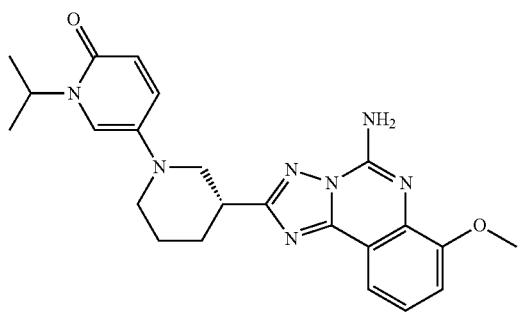 [SMILES: COc1cccc2c1nc(N)n1nc([C@@H]3CCCN(c4ccc(=O)n(C(C)C)c4)C3)nc21]<br>(R)-5-(3-(5-amino-7-methoxy-[1,2,4]triazolo[1,5-c]quinazolin-2-yl)piperidin-1-yl)-1-isopropylpyridin-2(1H)-one | 434 |
| 97 | 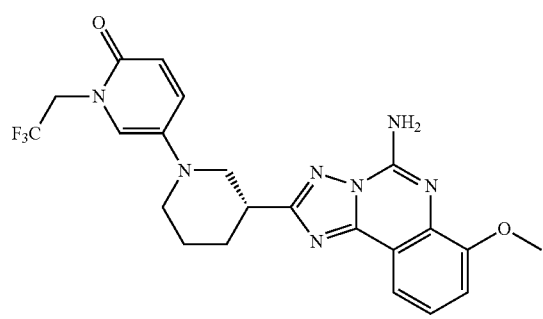 [SMILES: COc1cccc2c1nc(N)n1nc([C@@H]3CCCN(c4ccc(=O)n(CC(F)(F)F)c4)C3)nc21]<br>(R)-5-(3-(5-amino-7-methoxy-[1,2,4]triazolo[1,5-c]quinazolin-2-yl)piperidin-1-yl)-1-(2,2,2-trifluoroethyl)pyridin-2(1H)-one | 474 |

TABLE 1-continued

| Example | Structure Name | Observed m/z [M + H]+ |
|---|---|---|
| 98 | (R)-6-(3-(5-amino-7-methoxy-[1,2,4]triazolo[1,5-c]quinazolin-2-yl)piperidin-1-yl)-2-methylpyridazin-3(2H)-one | 407 |
| 99 | (R)-5-(3-(5-amino-7-methoxy-[1,2,4]triazolo[1,5-c]quinazolin-2-yl)piperidin-1-yl)-1-methyl-3-(trifluoromethyl)pyridin-2(1H)-one | 474 |
| 100 | (R)-2-(1-(6-(difluoromethoxy)-5-methylpyridin-3-yl)piperidin-3-yl)-7-methoxy-[1,2,4]-triazolo[1,5-c]quinazolin-5-amine | 456 |
| 101 | (R)-7-methox-2-(1-(3-methylpyrazin-2-yl)piperidin-3-yl)-[1,2,4]triazolo[1,5-c]quinazolin-5-amine | 391 |

TABLE 1-continued

| Example | Structure Name | Observed m/z [M + H]+ |
|---|---|---|
| 102 | 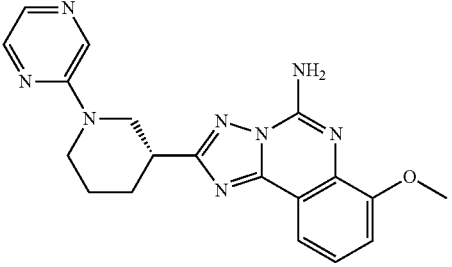 [SMILES: COc1cccc2c1nc(N)n1nc([C@@H]3CCCN(c4cnccn4)C3)nc21]<br>(R)-7-methoxy-2-(1-(pyrazin-2-yl)piperidin-3-yl)-[1,2,4]triazolo[1,5-c]quinazolin-5-amine | 377 |
| 103 | 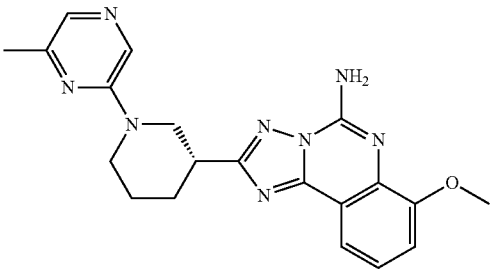<br>(R)-7-methoxy-2-(1-(6-methylpyrazin-2-yl)piperidin-3-yl)-[1,2,4]triazolo[1,5-c]quinazolin-5-amine | 391 |
| 104 | 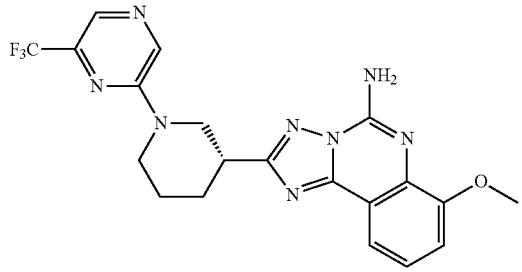 [SMILES: COc1cccc2c1nc(N)n1nc([C@@H]3CCCN(c4cncc(C(F)(F)F)n4)C3)nc21]<br>(R)-7-methoxy-2-(1-(6-(trifluoromethyl)pyrazin-2-yl)piperidin-3-yl)-[1,2,4]triazolo[1,5-c]quinazolin-5-amine | 445 |
| 105 | 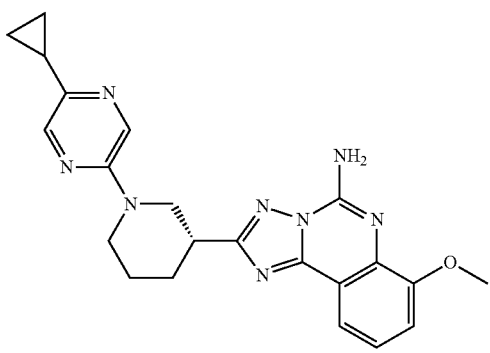 [SMILES: COc1cccc2c1nc(N)n1nc([C@@H]3CCCN(c4cnc(C5CC5)cn4)C3)nc21]<br>(R)-2-(1-(5-cyclopropylpyrazin-2-yl)piperidin-3-yl)-7-methoxy-[1,2,4]triazolo[1,5-c]quinazolin-5-amine | 417 |

TABLE 1-continued

| Example | Structure Name | Observed m/z [M + H]+ |
|---|---|---|
| 106 | (R)-7-methoxy-2-(1-(5-methylpyrazin-2-yl)piperidin-3-yl)-[1,2,4]triazolo[1,5-c]quinazolin-5-amine | 391 |
| 107 | (R)-2-(1-(6-isopropylpyridazin-3-yl)piperidin-3-yl)-7-methoxy-[1,2,4]triazolo[1,5-c]quinazolin-5-amine | 419 |
| 108 | (R)-7-methoxy-2-(1-(4-(trifluoromethyl)pyridin-3-yl)piperidin-3-yl)-[1,2,4]triazolo[1,5-c]quinazolin-5-amine | 444 |
| 109 | (R)-7-methoxy-2-(1-(5-(trifluoromethyl)pyrimidin-2-yl)piperidin-3-yl)-[1,2,4]triazolo[1,5-c]quinazolin-5-amine | 445 |

TABLE 1-continued

| Example | Structure Name | Observed m/z [M + H]+ |
|---|---|---|
| 110 | 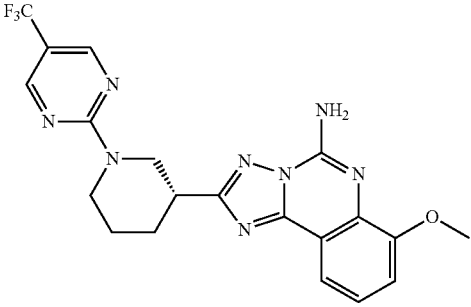<br>(R)-2-(1-(5-fluoropyrimidin-2-yl)piperidin-3-yl)-7-methoxy-[1,2,4]triazolo[1,5-c]quinazolin-5-amine | 395 |
| 111 | 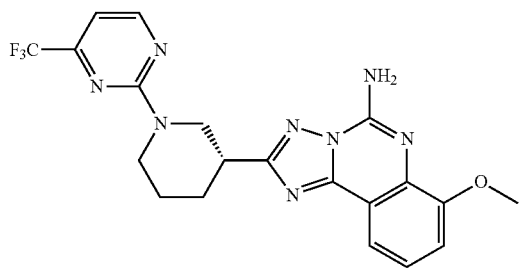 [SMILES: COc1cccc2c1nc(N)n1nc([C@@H]3CCCN(c4nccc(C(F)(F)F)n4)C3)nc21]<br>(R)-7-methoxy-2-(1-(4-(trifluoromethyl)pyrimidin-2-yl)piperidin-3-yl)-[1,2,4]triazolo[1,5-c]quinazolin-5-amine | 445 |
| 112 | 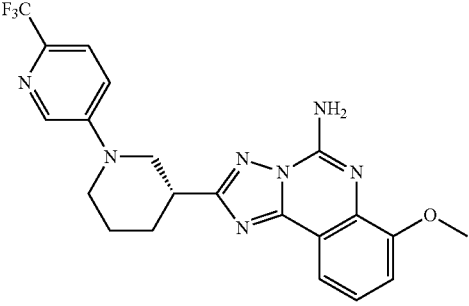 [SMILES: COc1cccc2c1nc(N)n1nc([C@@H]3CCCN(c4ccc(C(F)(F)F)nc4)C3)nc21]<br>(R)-7-methoxy-2-(1-(6-(trifluoromethyl)pyridin-3-yl)piperidin-3-yl)-[1,2,4]triazolo[1,5-c]quinazolin-5-amine | 444 |
| 113 | 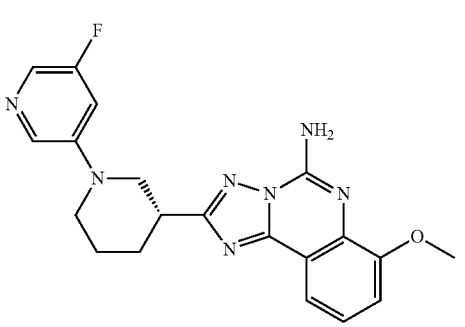 [SMILES: COc1cccc2c1nc(N)n1nc([C@@H]3CCCN(c4cncc(F)c4)C3)nc21]<br>(R)-2-(1-(5-fluoropyridin-3-yl)piperidin-3-yl)-7-methoxy-[1,2,4]triazolo[1,5-c]quinazolin-5-amine | 394 |

TABLE 1-continued

| Example | Structure Name | Observed m/z [M + H]+ |
|---|---|---|
| 114 | (R)-7-methoxy-2-(1-(3-(trifluoromethyl)phenyl)piperidin-3-yl)-[1,2,4]triazolo[1,5-c]quinazolin-5-amine | 443 |
| 115 | (R)-2-(1-(5-fluoropyridin-2-yl)piperidin-3-yl)-7-methoxy-[1,2,4]triazolo[1,5-c]quinazolin-5-amine | 394 |
| 116 | (R)-7-methoxy-2-(1-(4-(trifluoromethyl)pyridin-2-yl)piperidin-3-yl)-[1,2,4]triazolo[1,5-c]quinazolin-5-amine | 444 |
| 117 | (R)-7-methoxy-2-(1-(pyrimidin-2-yl)piperidin-3-yl)-[1,2,4]triazolo[1,5-c]quinazolin-5-amine | 377 |

TABLE 1-continued
| Example | Structure Name | Observed m/z [M + H]+ |
|---|---|---|
| 118 | 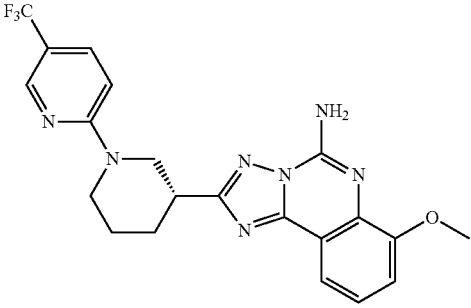 [SMILES: COc1cccc2c1nc(N)n1nc([C@@H]3CCCN(c4ccc(C(F)(F)F)cn4)C3)nc21]
(R)-7-methoxy-2-(1-(5-(trifluoromethyl)pyridin-2-yl)piperidin-3-yl)-[1,2,4]triazolo[1,5-c]quinazolin-5-amine | 444 |
| 119 | 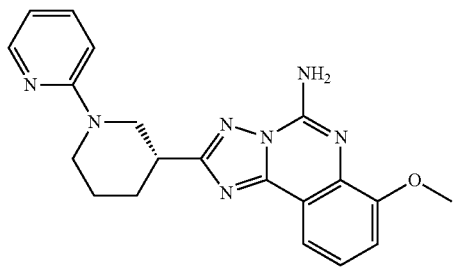 [SMILES: COc1cccc2c1nc(N)n1nc([C@@H]3CCCN(c4ccccn4)C3)nc21]
(R)-7-methoxy-2-(1-(pyridin-2-yl)piperidin-3-yl-[1,2,4]triazolo[1,5-c]quinazolin-5-amine | 376 |
Example 120
Preparation of the Compound of Example 120
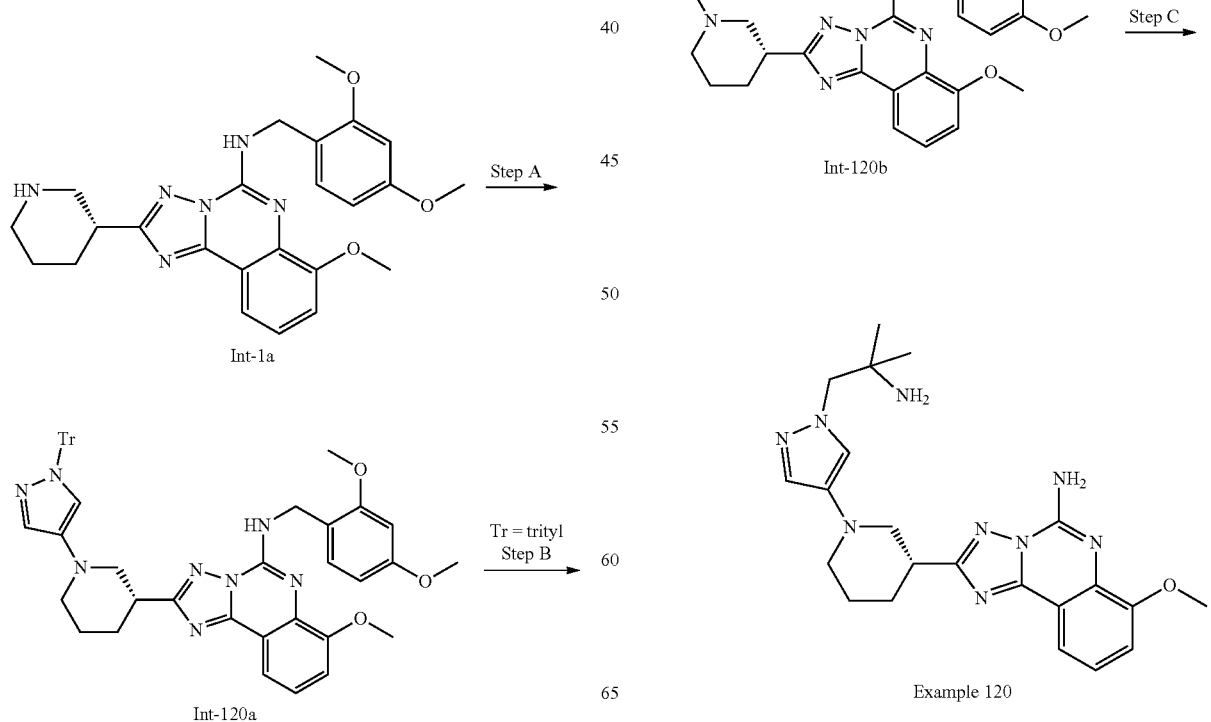

Step A—Synthesis of Compound Int-120a (R)—N-(2,4-dimethoxybenzyl)-7-methoxy-2-(1-(1-trityl-1H-pyrazol-4-yl)piperidin-3-yl)-[1,2,4]triazolo[1,5-c]quinazolin-5-amine To a reaction vial containing of (R)—N-(2,4-dimethoxybenzyl)-7-methoxy-2-(piperidin-3-yl)-[1,2,4]triazolo[1,5-c]quinazolin-5-amine (100 mg, 0.223 mmol) in THF (2 mL) was added 4-bromo-1-trityl-1H-pyrazole (217 mg, 0.557 mmol), methanesulfonato (2-di-t-butylphosphino-2',4',6'-tri-i-propyl-1,1'-biphenyl)(2'-amino-1,1'-biphenyl-2-yl)palladium(II (t-BuXPhos Pd G3 53.1 mg, 0.067 mmol) and sodium tert-butoxide (64.3 mg, 0.669 mmol). The resulting reaction mixture was purged with $N_2$ for 10 minutes, then sealed and heated at 90° C. for 10 hours. Upon completion, the reaction mixture was purified by preparative silica gel TLC plates with 4% MeOH in DCM as eluent to afford the title compound Int-120a LC/MS (ES, m/z)=757 [M+H]$^+$.

Step B—Synthesis of Compound Int-120b. (R)-2-(1-(1H-pyrazol-4-yl)piperidin-3-yl)-N-(2,4-dimethoxybenzyl)-7-methoxy-[1,2,4]triazolo[1,5-c]quinazolin-5-amine To a stirred solution of Int-120a (122 mg, 0.161 mmol) in MeOH (2 mL) was added hydrogen chloride in dioxane (403 μL, 1.61 mmol), then stirred at room temperature for 1 hour. Upon completion, the reaction was concentrated to provide Int-120b. The crude was used in the next step without further purification. LC/MIS (ES, m/z)=515 [M+H]$^+$.

Step C—Synthesis of Example 120. (R)-2-(1-(1-(2-amino-2-methylpropyl)-1H-pyrazol-4-yl)piperidin-3-yl)-7-methoxy-[1,2,4]triazolo[1,5-c]quinazolin-5-amine A mixture of Int-120b (23 mg, 0.045 mmol), tert-butyl 4,4-dimethyl-1,2,3-oxathiazolidine-3-carboxylate 2,2-dioxide (22.46 mg, 0.089 mmol) and 2,3,4,6,7,8,9,10-octahydropyrimido[1,2-a]azepine (13.61 mg, 0.089 mmol) in acetonitrile (1 mL) was heated on microwave reactor at 130° C. for 6 hours. The reaction was concentrated and the resulting residue was purified by preparative reverse phase HPLC using C18 column (Sunfire prep C18 OBD 10 uM 30×150 mm column) and 10%-100% acetonitrile/water with 0.1% TFA as eluent to provide the crude intermediate.

The above intermediate was then added to 1 mL TFA and heated at 60° C. for 1 hour. Upon completion, the reaction mixture was cooled and then concentrated. The residue was purified by preparative reverse phase HPLC using C18 column (Sunfire prep C18 OBD 10 uM 30×150 mm column) and 10%-100% acetonitrile/water with 0.1% TFA as eluent to provide 120. LC/MS (ES, m/z)=436 [M+H]$^+$. $^1$H NMR (500 MHz, Methanol-d$^4$) δ 7.91 (d, J=7.1 Hz, 1H), 7.51 (s, 1H), 7.49-7.44 (m, 2H), 7.38 (d, J=7.7 Hz, 1H), 4.22 (s, 2H), 4.07 (s, 3H), 3.80 (d, J=11.4 Hz, 1H), 3.52-3.40 (m, 2H), 3.09 (t, J=11.2 Hz, 1H), 2.84-2.78 (m, 1H), 2.32 (s, 1H), 2.11-1.88 (m, 2H), 1.85-1.62 (m, 2H), 1.31 (s, 6H).

The example compounds of the invention shown in Table 2 were prepared using a procedure similar to the procedure used to prepare Example 120, using the appropriate alkyl halide instead of tert-butyl 4,4-dimethyl-1,2,3-oxathiazolidine-3-carboxylate 2,2-dioxide in Step C.

TABLE 2

| Example | Structure Name | Observed m/z [M + H]$^+$ |
|---|---|---|
| 121 | (R)-3-(4-(3-(5-amino-7-methoxy-[1,2,4]triazolo[1,5-c]quinazolin-2-yl)piperidin-1-yl)-1H-pyrazol-1-yl)thietane 1,1-dioxide | 469 |
| 122 | (R)-4-(4-(3-(5-amino-7-methoxy-[1,2,4]triazolo[1,5-c]quinazolin-2-yl)piperidin-1-yl)-1H-pyrazol-1-yl)tetrahydro-2H-thiopyran 1,1-dioxide | 497 |

Example 123

The Preparation of the Compound of Example 123

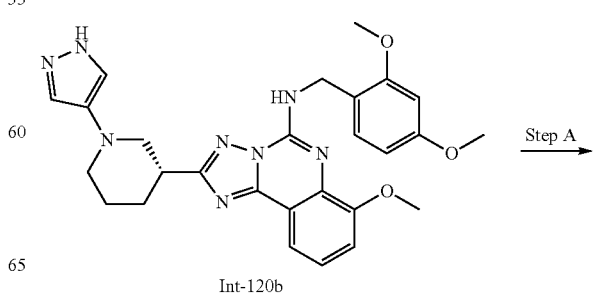

Int-120b

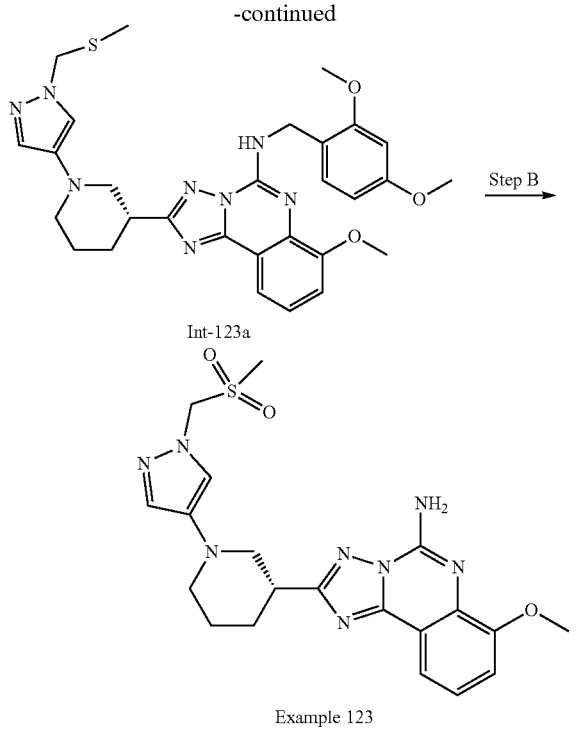

Int-123a

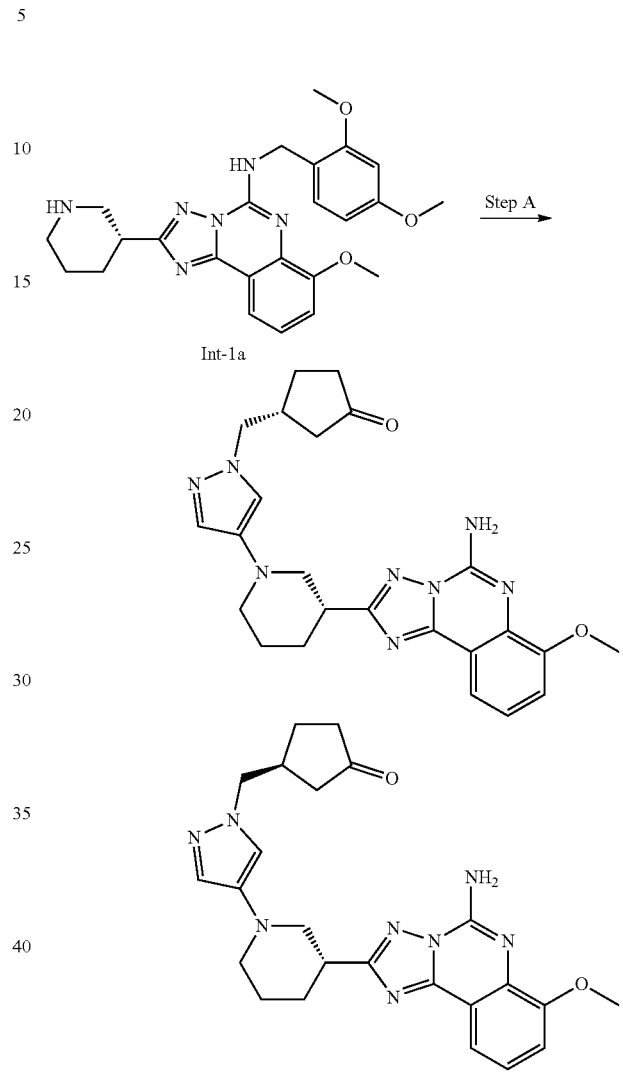

Example 123

Examples 124A and 124B

The Preparation of the Compounds of Examples 124A and 124B

Step A—Synthesis of Compound Int-123a (R)—N-(2,4-dimethoxybenzyl)-7-methoxy-2-(1-(1-((methylthio)methyl)-1H-pyrazol-4-yl)piperidin-3-yl)-[1,2,4]triazolo[1,5-c]quinazolin-5-amine A mixture of Int-120b (269 mg, 0.488 mmol) and (chloromethyl)(methyl)sulfane (49.2 µL, 0.586 mmol) in dioxane (5 mL) was added to cesium carbonate (318 mg, 0.976 mmol). The resulting mixture was stirred at 75° C. overnight, and then cooled to room temperature and diluted with water and DCM. The DCM layer was separated, dried over anhydrous $Na_2SO_4$, filtered, and concentrated. The resulting residue was purified by silica gel column chromatography with 5% MeOH in DCM as eluent to provide the title compound Int-123a LC/MS (ES, m/z)=575 $[M+H]^+$.

Step B—Synthesis of Example 123. (R)-7-methoxy-2-(1-(1-((methylsulfonyl)methyl)-1H-pyrazol-4-yl)piperidin-3-yl)-[1,2,4]triazolo[1,5-c]quinazolin-5-amine To a solution of Int-123a (95 mg, 0.165 mmol) in MeOH (551 µL) and water (551 µL) was added OXONE® (potassium peroxymonosulfate, 203 mg, 0.331 mmol). The mixture was stirred for 10 minutes at room temperature. Upon completion, the reaction mixture was then concentrated. The resulting residue was then diluted with water and DCM. The DCM layer was separated, dried over anhydrous $Na_2SO_4$, filtered, and concentrated. The resulting residue was purified by silica gel column chromatography with 10% MeOH/DCM as eluent to provide the title compound Example 123. LC/MS (ES, m/z)=457 $[M+H]^+$. $^1H$ NMR (499 MHz, DMSO-$d^6$) δ 7.80 (s, 2H), 7.75 (d, J=6.7 Hz, 1H), 7.50 (s, 1H), 7.43 (s, 1H), 7.31 (t, J=8.0 Hz, 1H), 7.23 (d, J=7.0 Hz, 1H), 5.56 (s, 2H), 3.91 (s, 3H), 3.75-3.63 (m, 1H), 3.42-3.26 (m, 2H), 2.96 (s, 3H), 2.93-2.89 (m, 1H), 2.21-2.14 (hr. s, 1H), 1.87-1.76 (m, 2H), 1.24 (s, 1H).

Step A—Synthesis of Compound 124A, 124B. (R)-3-((4-((R)-3-(5-amino-7-methoxy-[1,2,4]triazolo[1,5-c]quinazolin-2-yl)piperidin-1-yl)-1H-pyrazol-1-yl)methyl)cyclopentan-1-one, (S)-3-((4-((R)-3-(5-amino-7-methoxy-[1,2,4]triazolo[1,5-c]quinazolin-2-yl)piperidin-1-yl)-1H-pyrazol-1-yl)methyl)cyclopentan-1-one To a reaction vial containing Int-1a (100 mg, 0.223 mmol) in THF (2 mL) was added (1S,2S)-4-((4-bromo-1H-pyrazol-1-yl)methyl)-2-fluorocyclopentanol (35.2 mg, 0.134 mmol), methanesulfonato (2-di-t-butylphosphino-2',4',6'-tri-i-propyl-1,1'-biphenyl)(2'-amino-1,1'-biphenyl-2-yl)palladium (II) (t-BuXPhos Pd G3, 31.9 mg, 0.040 mmol), and sodium text-butoxide (77 mg, 0.803 mmol). The resulting reaction mixture was bubbled through $N_2$ for 10 minutes, then the vial was sealed and heated at 90° C. for 10 hours. Upon completion, the reaction mixture was purified by preparative silica gel TLC plates with 4% MeOH in DCM as eluent to afford 22 mg more polar isomer and 21 mg less polar isomer.

To above 21 mg less polar isomer was added 1 mL TFA, and the mixture was heated at 60° C. for 1 h. The resulting mixtures were then purified by preparative reverse phase HPLC using C18 column (SunFire prep C18 OBD 10 uM 30×150 mm column) and 10%-100% acetonitrile in water with 0.1% TFA as eluent to provide Example 124A.

124A: LC/MS (ES, m/z)=461 [M+H]+, 1H NMR (500 MHz, Methanol-d4) δ 8.07 (s, 1H), 8.02 (s, 1H), 7.92 (dd, J=8.0, 1.1 Hz, 1H), 7.49 (t, J=8.0 Hz, 1H), 7.46-7.34 (m, 1H), 4.81 (s, 1H), 4.45 (dd, J=12.7, 3.3 Hz, 1H), 4.36 (d, J=12.6 Hz, 1H), 4.20 (d, J=5.0 Hz, 1H), 4.09 (s, 2H), 3.86-3.73 (m, 1H), 3.48 (d, J=12.2 Hz, 1H), 3.40 (d, J=8.2 Hz, 1H), 3.27-3.15 (m, 1H), 3.02 (s, 1H), 2.97-2.81 (m, 1H), 2.46 (d, J=11.4 Hz, 1H), 2.33 (s, 1H), 2.29-2.17 (m, 2H), 2.11-1.84 (m, 4H).

To above 22 mg more polar isomer was added 1 mL TFA, and the mixture was heated at 60° C. for 1 h. The resulting mixtures were then purified by preparative reverse phase HPLC using C18 column (SunFire prep C18 OBD 10 uM 30×150 mm column) and 10%-100% acetonitrile in water with 0.1% TFA as eluent to provide Example 124B.

124B: LC/MS (ES, m/z) 461 [M+H]+. 1H NMR (500 MHz, Methanol-d4) δ 8.07 (s, 1H), 8.02 (s, 1H), 7.93 (dd, J=8.0, 1.1 Hz, 1H), 7.52 (t, J=8.0 Hz, 1H), 7.43 (d, J=7.1 Hz, 1H), 4.81 (s, 1H), 4.52-4.40 (m, 1H), 4.36 (d, J=12.0 Hz, 1H), 4.20 (d, J=5.0 Hz, 1H), 4.10 (s, 3H), 3.82 (d, J=12.5 Hz, 1H), 3.48 (d, J=11.5 Hz, 1H), 3.42 (d, J=2.0 Hz, 1H), 3.24-3.14 (m, 1H), 3.02 (s, 1H), 2.97-2.81 (m, 1H), 2.46 (d, J=14.4 Hz, 1H), 2.33 (s, 1H), 2.25 (d, J=13.8 Hz, 2H), 2.13-1.84 (m, 41H).

Example 125

The Preparation of the Compound of Example 125

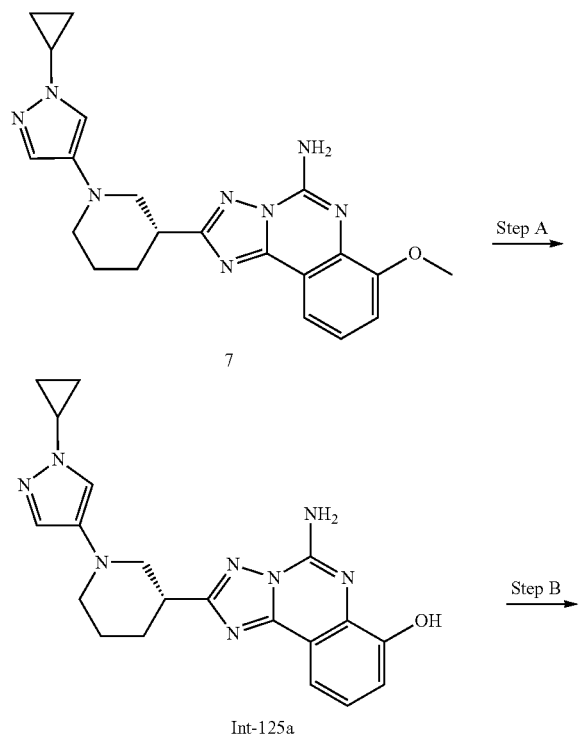

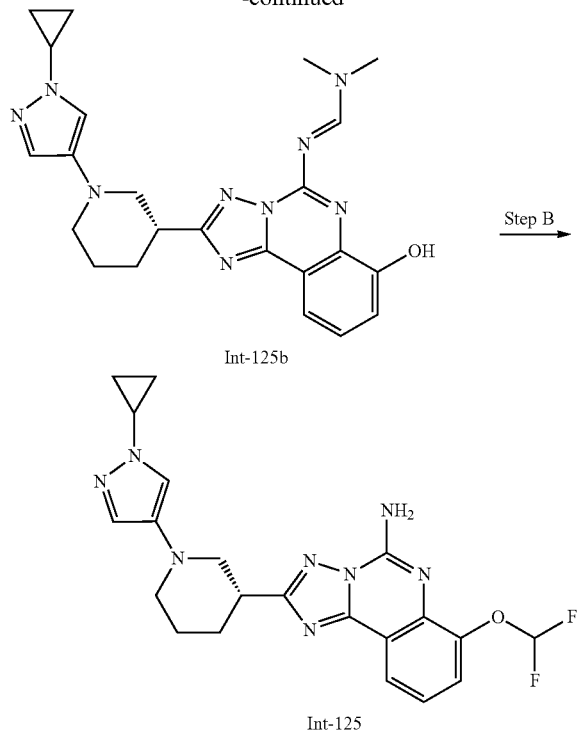

Step A—Synthesis of Compound Int-125a (R)-5-amino-2-(1-(1-cyclopropyl-1H-pyrazol-4-yl)piperidin-3-yl)-[1,2,4]triazolo[1,5-c]quinazolin-7-ol To a solution of 7 (30 mg, 0.074 mmol) in 1,2-dichloroethane (2 mL) was added BBr3 (0.056 mL, 0.593 mmol) at 25° C. The resulting mixture was stirred at 100 for 1 hour. Upon completion, the reaction mixture was cooled and 5 mL water was added. The mixture was then basified to pH 8~9 and extracted with DCM (3×5 mL). The combined organic layers were washed with brine, dried over anhydrous sodium sulfate, filtered, and concentrated to afford Int-125a LC/MS (ES, m/z)=391 [M+H]+.

Step B—Synthesis of Compound Int-125b. (R,E)-N'-(2-(1-(1-cyclopropyl-1H-pyrazol-4-yl)piperidin-3-yl)-7-hydroxy-[1,2,4]triazolo[1,5-c]quinazolin-5-yl)-N,N-dimethylformimidamide To a solution of Int-125a (20 mg, 0.051 mmol) EtOH (1 mL) was added N,N-dimethylformamide (22.46 mg, 0.307 mmol) at 25° C. The resulting mixture was stirred at 40° C. for 18 hours. Upon completion, the reaction mixture was cooled, diluted with DCM (15 mL), and then washed with brine, dried over anhydrous sodium sulfate, filtered, and concentrated. The residue was purified by preparative silica gel TLC plate with 10% MeOH in DCM as eluent to provide Int-125b. LC/MS (ES, m/z)=446 [M+H]+.

Step C—Synthesis of Example 125. (R)-2-(1-(1-cyclopropyl-1H-pyrazol-4-yl)piperidin-3-yl)-7-(difluoromethoxy)-[1,2,4]triazolo[1,5-c]quinazolin-5-amine To a stirred mixture of Int-125b (20 mg, 0.045 mmol) in 1:1 ACN:H2O (1.0 mL) at −78° C. was added 2-chloro-2, 2-difluoro-1-phenylethanone (42.8 mg, 0.224 mmol) and KOH (52.9 mg, 0.943 mmol). The resulting mixture was stirred at 80° C. for 18 hours. Upon completion, the mixture was cooled, diluted with DCM (20 mL), and then washed with brine, dried over anhydrous sodium sulfate, filtered, and concentrated. The resulting residue was purified by preparative silica gel TLC plate with 10% MeOH in DCM as eluent to afford Example 125. LC/MS (ES, m/z)=441 [M+H]+. 1H NMR (400 MHz, Methanol-d4) δ 8.18 (d, J=8.33 Hz, 1H), 7.50 (d, J=7.45 Hz, 1H), 7.34-7.41 (m, 2H), 7.30 (s, 1H), 7.19 (s, 1H), 3.74 (br d, J=10.96 Hz, 1H), 3.54 (tt, J=7.13, 3.62 Hz, 1H), 3.34-3.41 (m, 2H), 2.96 (t, J=11.18 Hz, 1H), 2.61-2.70 (m, 1H), 2.24-2.36 (m, 2H), 1.81-1.98 (m, 4H), 0.96-1.01 (m, 2H), 0.81-0.96 (m, 2H).

The example compound of the invention shown in Table 3 was prepared using a procedure similar to the procedure used to prepare the Example 125, substituting the appropriate starting materials.

TABLE 3

| Example | Structure Name | Observed m/z [M + H]+ |
|---|---|---|
| 126 | 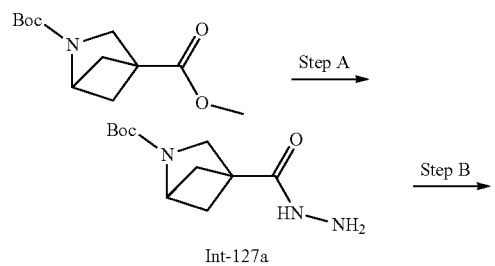<br>(R)-7-(difluoromethoxy)-2-(1-(1-methyl-1H-pyrazol-4-yl)piperidin-3-yl)-[1,2,4]triazolo[1,5-c]quinazolin-5-amine | 415 |

Example 127

The Preparation of the Compound of Example 127

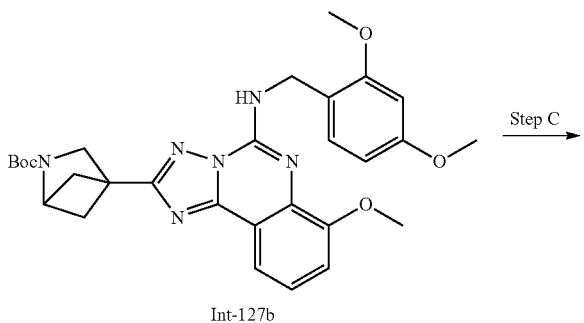

Int-127b

Step C

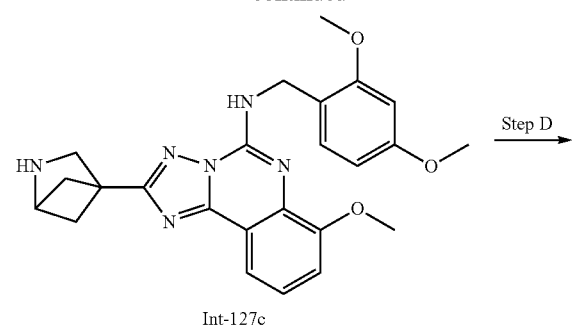

Int-127c

Step D

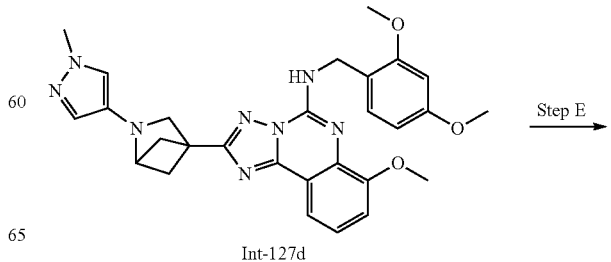

Int-127d

Step E

-continued

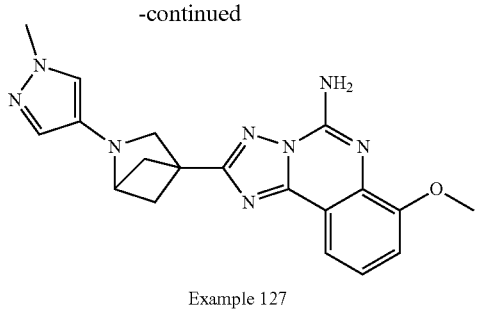

Example 127

Step A—Synthesis of Compound Int-127a tert-butyl 4-(hydrazinecarbonyl)-2-azabicyclo[2.1.1]hexane-2-carboxylate To a stirred solution of 2-tert-butyl 4-methyl 2-azabicyclo[2.1.1]hexane-2,4-dicarboxylate (1 g, 4.14 mmol) in ethanol (10 mL) was added hydrazine hydrate (4.15 g, 83 mmol). The mixture was stirred at 90° C. for 5 hours. Upon completion, the mixture was concentrated to give the crude Int-127a. It was used to next step without purification. LC/MS (ES, m/z)=242 [M+H]$^+$.

Step B—Synthesis of Compound Int-127b tert-butyl4-(5-((2,4-dimethoxybenzyl)amino)-7-methoxy-[1,2,4]triazolo[1,5-c]quinazolin-2-yl)-2-azabicyclo[2.1.1]hexane-2-carboxylate To a stirred solution of Int-127a (210 mg, 0.870 mmol) in NMP (2 mL) was added 2-((((2,4-dimethoxybenzyl)imino)methylene)amino)-3-methoxybenzonitrile (C7, 298 mg, 0.923 mmol). The mixture was stirred at 170° C. under microwave heating for 1.5 hours. Upon completion, the mixture was diluted with water (20 mL), and then extracted with DCM (20 mL×2). The combined organic layers were concentrated under reduced pressure. The resulting residue was purified by silica gel column chromatography with 0~30% ethyl acetate in petroleum ether as eluent to afford Int-127b. LC/MS (ES, m/z)=547 [M+H]$^+$.

Step C—Synthesis of Compound Int-127c. 2-(2-azabicyclo[2.1.1]hexan-4-yl)-N-(2,4-dimethoxy benzyl)-7-methoxy-[1,2,4]triazolo[1,5-c]quinazolin-5-amine A solution of Int-127b (200 mg, 0.366 mmol) in formic acid (2 mL) was stirred at 15° C. for 5 h. Upon completion, the mixture was concentrated under reduced pressure. The residue was diluted with DCM (20 mL), washed with aqueous NaHCO$_3$ solution (20 mL) and brine (10 mL), and then dried over anhydrous Na$_2$SO$_4$, filtered, and concentrated to afford the crude Int-127c, which was used in the next step without further purification. LC/MS (ES, m/z)=447 [M+H]$^+$.

Step D—Synthesis of Compound Int-127d. N-(2,4-dimethoxybenzyl)-7-methoxy-2-(2-(1-methyl-1H-pyrazol-4-yl)-2-azabicyclo[2.1.1]hexan-4-yl)-[1,2,4]triazolo[1,5-c]quinazolin-5-amine To a solution of Int-127c (20 mg, 0.045 mmol), 4-bromo-1-methyl-1H-pyrazole (22 mg, 0.137 mmol) and t-Bu X-Phos Pd G3 (11 mg, 0.014 mmol) in THF (0.5 mL) was added sodium ter t-butoxide (18 mg, 0.187 mmol) under N$_2$. The resulting mixture was then stirred at 100° C. for 16 hours. Upon completion, the reaction mixture was cooled and then concentrated. The resulting residue was purified by preparative silica gel TLC plate with 50% EtOAc in hexanes as eluent to afford Int-127d. LC/MS (ES, m/z)=527 [M+H]$^+$.

Step E—Synthesis of Example 127. 7-methoxy-2-(2-(1-methyl-1H-pyrazol-4-yl)-2-azabicyclo[2.1.1]hexan-4-yl)-[1,2,4]triazolo[1,5-e]quinazolin-5-amine To a solution of Int-127d (18 mg, 0.034 mmol) in DCM (1 mL) was added TFA (2 mL). The reaction mixture was stirred at 45° C. for 16 hours. Upon completion, the reaction mixture was cooled and then concentrated. The resulting residue was purified by reversed phase HPLC using C18 column (Sunfire prep C18 OBD 10 uM 30×150 mm column) and 0-100% ACN/H$_2$O (0.1% TFA) as eluent to afford the title compound 127. LC/MS (ES, m/z)=[M+H]$^+$. $^1$H NMR (400 MHz, Methanol-d$^4$) δ 8.09 (s, 1H), 7.88 (dd, J=0.88, 7.89 Hz, 1H), 7.79 (s, 1H), 7.45 (t, J=7.89 Hz, 1H), 7.32-7.39 (m, 1H), 4.61 (s, 1H), 4.25 (s, 2H), 4.05 (s, 3H), 3.94-3.97 (m, 1H), 3.95 (s, 2H), 2.79-2.87 (m, 2H), 2.29-2.36 (m, 2H).

Examples 128A and 128B

The Preparation of the Compounds of Examples 128A and 128B

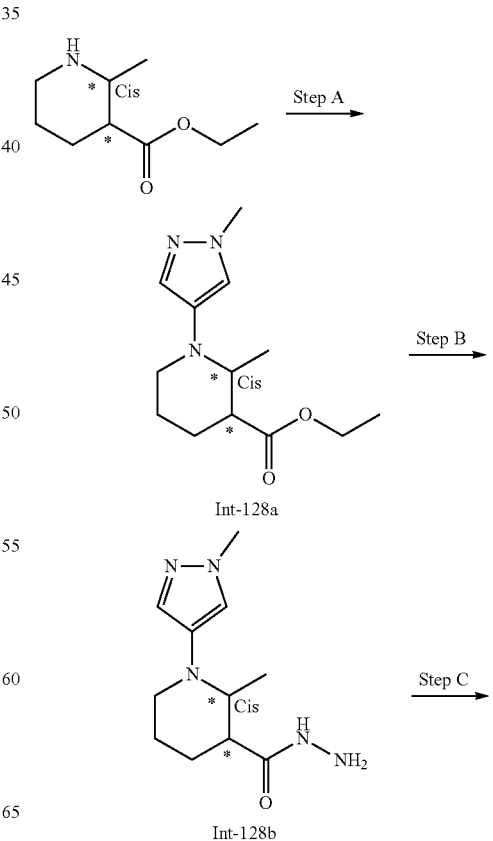

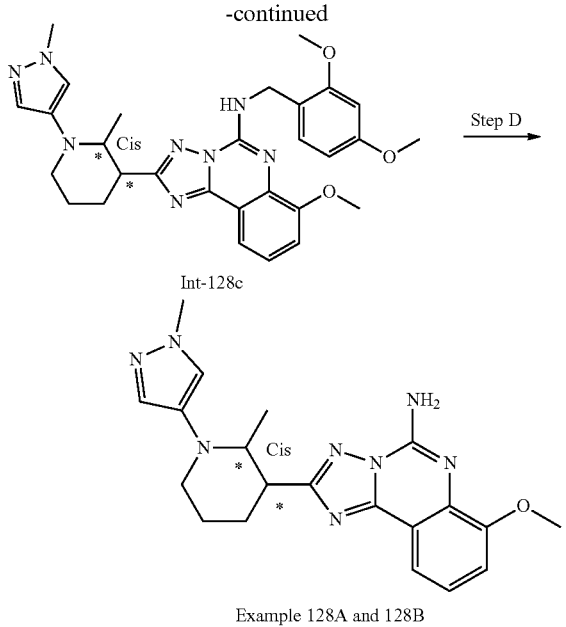

Int-128c

-continued

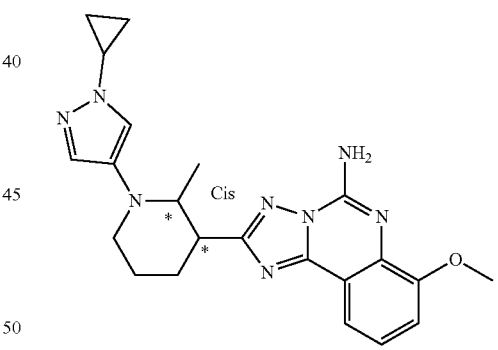

Example 128A and 128B

Step A—Synthesis of Compound Int-128a rac, cis-ethyl 2-methyl-1-(1-methyl-1H-pyrazol-4-yl)piperidine-3-carboxylate To a solution of rac, cis-ethyl 2-methylpiperidine-3-carboxylate (40 mg, 0.234 mmol) and 4-bromo-1-methyl-1H-pyrazole (113 mg, 0.701 mmol) in THF (1 mL) was added methanesulfonato(2-di-t-butylphosphino-2',4',6'-tri-i-propyl-1,1'-biphenyl)(2'-amino-1,1'-biphenyl-2-yl)palladium (II) (55.7 mg, 0.070 mmol) and sodium tert-butoxide (90 mg, 0.934 mmol) under $N_2$ in glove box. The resulting mixture was then stirred at 100° C. for 16 hours. Upon completion, the reaction mixture was cooled and concentrated. The resulting residue was purified by reversed phase C18 column with 0-100% ACN/water (0.1% TFA) as eluent to provide the title compound Int-128a LC/MS (ES, m/z)=252 [M+H]$^+$.

Step B—Synthesis of Compound Int-128b, rac, cis-2-methyl-1-(1-methyl-1H-pyrazol-4-yl)piperidine-3-carbohydrazide To a stirred solution of Int-128a (30 mg, 0.119 mmol) in ethanol (5 mL) was added hydrazine hydrate (120 mg, 2.387 mmol). The mixture was stirred at 90° C. for 16 hours. Upon completion, the reaction mixture was cooled and then concentrated. The resulting residue was purified by reverse phase C18 column with 0-100% ACN/water (0.1%0 TFA) as eluent to provide the title compound Int-128b. LC/MS (ES, m/z)=238 [M+H]$^+$.

Step C—Synthesis of Compound Int-128c

To a stirred solution of Int-128b (20 mg, 0.084 mmol) in NMP (0.5 mL) was added 2-((((2,4-dimethoxybenzyl)imino)methylene)amino)-3-methoxybenzonitrile (C7, 30 mg, 0.093 mmol). The resulting mixture was stirred at 170° C. under microwave heating for 1.5 hours. Upon completion, the reaction mixture was purified by reverse phase C18 column with 0-100% ACN/water (0.1% TEA) as eluent to provide Int-128c. LC/MS (ES, m/z)=544 [M+H]$^+$.

Step C—Synthesis of Examples 128A and 128B

To a solution of Int-128c (15 mg, 0.028 mmol) in DCM (2 ml) was added TFA (1 mL). The reaction mixture was stirred at 45° C. for 16 h. Upon completion, the reaction mixture was cooled, concentrated, and then purified by reversed phase C18 column with 0-100% ACN/water (0.1% TFA) as eluent to provide racemic compound 128. The product was then resolved by SFC (Chiralpak AD-3 column with 40% EtOH as cosolvent) to afford title compounds Example 128A (peak 1) and Example 1288 (peak 2).

128A: LC/MS (ES, m/z)=393 [M+H]$^+$. $^1$H NMR (400 MHz, Methanol-d$^4$) δ 7.84-7.91 (m, 1H), 7.48 (s, 1H), 7.35-7.41 (m, 2H), 7.27 (d, J=7.34 Hz, 1H), 4.01 (s, 3H), 3.83 (s, 3H), 3.45-3.54 (m, 1H), 3.05-3.18 (m, 2H), 2.95-3.04 (m, 1H), 2.04-2.05 (m, 1H), 2.03-2.16 (m, 2H), 1.91-1.96 (m, 1H), 0.94-0.96 (m, 3H).

128B: LC/MS (ES, m/z)=393 [M+H]$^+$. $^1$H NMR (400 MHz, Methanol-d$^4$) δ 7.88 (d, J=7.89 Hz, 1H), 7.68 (br s, 1H), 7.52 (br s, 1H), 7.39 (t, J=8.11 Hz, 1H), 7.29 (d, J=8.33 Hz, 1H), 4.02 (s, 3H), 3.87 (s, 3H), 3.61 (q, J=7.31 Hz, 1H), 3.08-3.29 (m, 3H), 2.16 (br d, J=4.38 Hz, 2H), 1.99 (br s, 2H), 1.01 (d, J=6.14 Hz, 3H).

Example 129

The Preparation of the Compound of Example 129

Example 129

Example 129 was prepared using a procedure similar to the procedure used to prepare the compounds of Examples 128A and 128B except without chiral resolution, substituting the appropriate starting aryl halide.

129: LC/MS (ES, m/z)=419 [M+H]$^+$. $^1$H NMR (400 MHz, Methanol-d$^4$) δ 8.08-8.14 (m, 1H), 7.91 (d, J=8.31 Hz, 1H), 7.51-7.63 (m, 1H), 7.39-7.49 (m, 2H), 7.33 (d, J=7.34 Hz, 1H), 4.22-4.32 (m, 1H), 4.00-4.08 (m, 3H), 3.58-3.70 (m, 2H), 2.48-2.61 (m, 2H), 2.20-2.27 (m, 2H), 1.92-2.06 (m, 2H), 1.05-1.12 (m, 2H), 0.98-1.05 (m, 2H), 0.87-0.97 (m, 3H).

Examples 130A and 130B

The Preparation of the Compounds of Examples 130A and 130B

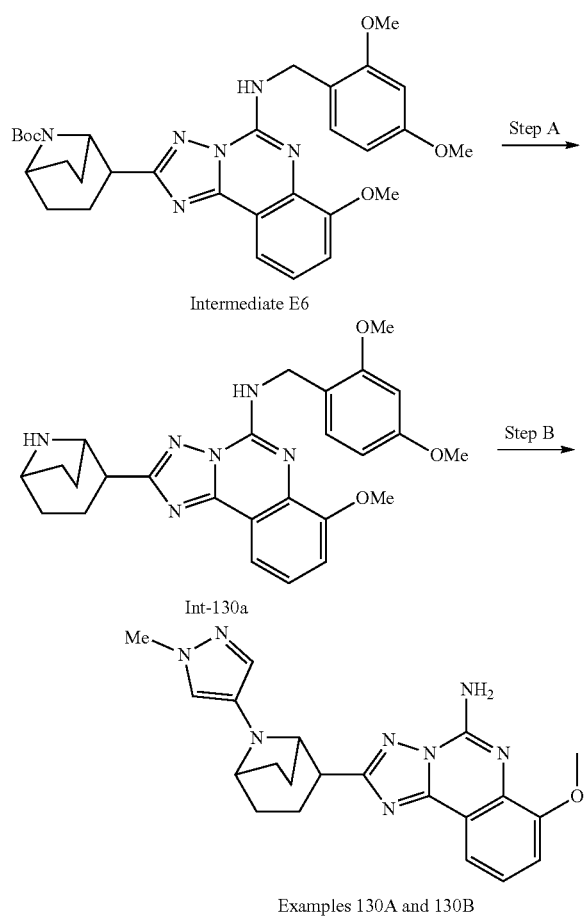

Step A—Synthesis of Compound Int-130a 2-(8-azabicyclo[3.2.1]octan-2-yl)-N-(2,4-dimethoxybenzyl)-7-methoxy-[1,2,4]triazolo[1,5-c]quinazolin-5-amine A solution of Intermediate E6 (141 mg, 0.245 mmol) in formic acid (3 was stirred at room temperature for 3 hours. Upon completion, the mixture was concentrated under reduced pressure. The resulting residue was diluted with DCM (20 mL), washed with aqueous NaHCO₃ solution (20 mL), brine (10 mL), dried over anhydrous Na₂SO, filtered, and concentrated to afford the crude Int-130a which was used for next step without purification. LC/MS (ES, m/z)=475 [M+H]⁺.

Step B—Synthesis of Examples 130A and 130B

A 5 mL microwave vial equipped with a stir bar was charged with Int-130a (68 mg, 0.143 mmol) and THF (896 µL). To the mixture was added 4-bromo-1-methyl-1H-pyrazole (46 mg, 0.287 mmol), followed by t-BuXPhos Pd G3 (45.5 mg, 0.057 mmol) and sodium tert-butoxide (55.1 mg, 0.573 mmol). The mixture was purged with N₂ for 10 minutes. The vial was then sealed with a cap and the mixture was heated at 90° C. for 12 hours. Upon completion, the reaction mixture was cooled, filtered, washed with DCM, and the combined filtrates concentrated. Next, the resulting residue was dissolved in TFA (552 µL, 7.16 mmol) and heated to 50° C. for 3 hours. The reaction mixture was then cooled to room temperature and the reaction quenched with saturated NaHCO₃ aqueous solution and diluted with DCM. The DCVI layer was collected using a phase separator and then concentrated. The resulting residue was purified by reversed phase C18 column (Surefire prep C18 OBD 10 uM 30×150 mm column) with 0-100% ACN/water (0.1% TEA) as eluent to provide the title compounds Example 130A (Peak 1) and Example 130B (Peak 2) as racemic diastereomers.

130A (peak 1): LC/MS (ES, m/z)=405 [M+H]⁺. ¹H NMR (500 MHz, DMSO-d⁶) δ 7.84 (s, 1H), 7.72 (d, J=7.9 Hz, 1H), 7.32 (t, J=7.9 Hz, 1H), 7.24 (d, J=7.3 Hz, 1H), 4.21 (d, J=149.4 Hz, 2H), 3.91 (s, 3H), 3.84 (s, 3H), 3.58 (s, 1H), 2.44 (m, 3H), 2.02 (m, 5H).

130B (peak 2): LC/MS (ES, m/z)=405 [M+H]⁺. ¹H NMR (499 MHz, DMSO-d⁶) δ 7.94 (d, J=33.8 Hz, 2H), 7.76 (dd, J=7.9, 1.2 Hz, 1H), 7.32 (t, J=7.9 Hz, 1H), 7.25 (dd, J=8.0, 1.1 Hz, 1H), 4.37 (br. s, 2H), 3.92 (s, 3H), 3.85 (s, 3H), 3.48 (s, 1H), 2.92 (s, 1H), 2.64 (s, 2H), 1.79 (d, J=35.3 Hz, 5H).

Examples 1314 and 131B

The Preparation of the Compounds of Examples 131A and 131B

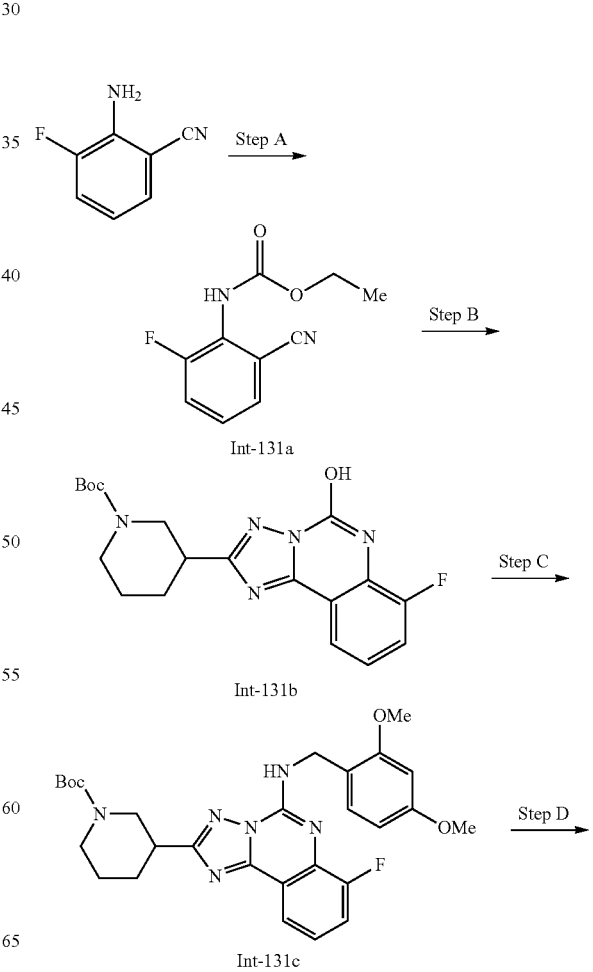

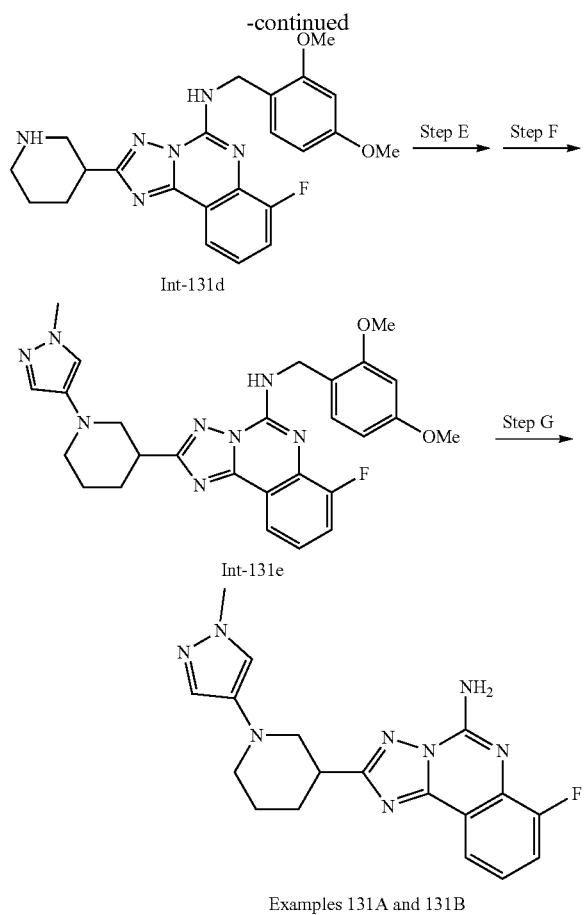

Examples 131A and 131B

Step A—Synthesis of Compound Int-131a ethyl (2-cyano-6-fluorophenyl)carbarmate A 500 mL round bottom flask equipped with a stir bar was charged with 2-amino-3-fluorobenzonitrile (25.016 g, 184 mmol) and ethyl chloroformate (225 mL, 2339 mmol). The reaction flask was equipped with a super air-cooled reflux condenser and heated to reflux for 6 hours. Upon completion, the reaction mixture was cooled to room temperature. Hexanes (150 mL) were added and the mixture was stirred briefly. The solid was filtered with vacuum suction under the flow of nitrogen to yield the title compound Int-131a LC/MS (ES, m/z)=209 [M+H]$^+$.

Step B—Synthesis of Compound Int-131b rac-tert-butyl 3-(7-fluoro-5-hydroxy-[1,2,4]triazolo[1,5-c]quinazolin-2-yl)piperidine-1-carboxylate A 100 mL round bottom flask equipped with a stir bar was charged with Int-131a (5.4 g, 25.9 mmol) and tert-butyl 3-(hydrazinecarbonyl)piperidine-1-carboxylate (6.94 g, 28.5 mmol). The material was suspended in NMP (27.0 mL), and the reaction mixture was heated at 160° C. under an atmosphere of nitrogen. Upon completion, the reaction mixture was cooled to room temperature, and then diluted with 25 mL water to cause a gummy residue to separate. The mixture was sonicated for 30 min to give a suspension. The suspension was filtered to yield the title compound Int-131b. LC/MS (ES, m/z)=410 [M+Na]$^+$.

Step C—Synthesis of Compound Int-131c rac-tert-butyl 3-(5-((2,4-dimethoxybenzyl)amino)-7-fluoro-[1,2,4]triazolo[1,5-c]quinazolin-2-yl)piperidine-1-carboxylate To a stirred mixture of Int-131b (2.0 g, 5.16 mmol), BOP (5.94 g, 13.42 mmol) in acetonitrile (30.4 mL) was added DBU (2.412 ml 16.00 mmol) dropwise and the reaction mixture was then stirred for 30 minutes. Then, (2,4-dimethoxyphenyl)methanamine (2.404 mL, 16.00 mmol) was added. The resulting reaction mixture was stirred at room temperature for 48 hours. Upon completion, the crude reaction was suspended in EtOAc and washed with water. The organic layer was washed sequentially with 1M HCl (10 mL), 1M NaOH (10 mL), and brine (20 mL), and then dried over anhydrous MgSO$_4$, filtered, and concentrated. The resulting residue was purified by silica gel column chromatography with 0-50% EtOAc in hexanes as eluent to yield the title compound Int-131c. LC/MS (ES, m/z)=537 [M+H]$^+$.

Step D—Synthesis of Compound Int-131d rac-N-(2,4-dimethoxybenzyl)-7-fluoro-2-(piperidin-3-yl)-[1,2,4]triazolo[1,5-c]quinazolin-5-amine A 20 ml scintillation vial equipped with a stirbar was charged with Int-131c (356 mg, 0.663 mmol) and formic acid (1.908 mL, 49.8 mmol). The reaction mixture was stirred at room temperature for 2 hours. Upon completion, the reaction mixture was concentrated, diluted with 50 mL DCM and washed with 50 mL saturated NaHCO$_3$ solution. The DCM layer was dried over anhydrous MgSO$_4$, filtered, and concentrated. The resulting residue was purified by silica gel column chromatography with 10-20% MeOH in DCM as eluent to yield the title compound Int-131d. LC/MS (ES, m/z)=437 [M+H]$^+$.

Step E—Synthesis of Compound Int-131e rac-N-(3,5-dimethoxylbenzyl)-7-fluoro-2-(1-(1-methyl-1H-pyrazol-4-yl)piperidin-3-yl)-[1,2,4]triazolo[1,5-c]quinazolin-5-amine A 20 mL microwave vial equipped with a stir bar was charged with Int-131d (0.235 g, 0.524 mmol) and THF (5.88 mL). To the mixture was added 4-bromo-1-methyl-1H-pyrazole (0.217 mL, 2.096 mmol), followed by t-BuXPhos Pd G3 (0.166 g, 0.210 mmol) and sodium tert-butoxide (0.201 g, 2.096 mmol). The mixture was purged with N$_2$ for 10 minutes. The vial was then sealed with a fresh cap and the mixture heated at 90° C. overnight. The reaction mixture was then cooled, filtered, washed with DCM, and the combined filtrates concentrated. The resulting residue was purified by silica gel column chromatography with 0-10% MeOH in DCM as eluent, yielding the title compound Int-131e. LC/MS (ES, m/z)=517 [M+H]$^+$.

Step F—Synthesis of Examples 131A and 131B. (R or S)-7-fluoro-2-(1-(1-methyl-1H-pyrazol-4-yl)piperidin-3-yl)-[1,2,4]triazolo[1,5-c]quinazolin-5-amine and (S or R)-7-fluoro-2-(1-(1-methyl-1H-pyrazol-4-yl)piperidin-3-yl)-[1,2,4]triazolo[1,5-c]quinazolin-5-amine TFA (477 µL, 6.19 mmol) was added to Int-131e (64 mg, 0.124 mmol) in a 20 mL scintillation vial equipped with a stir bar and heated at 50° C. for 3 hours. The slurry was then concentrated, quenched with 1 mL 7N NH$_3$ in MeOH, and concentrated. The resulting residue was triturated with MeCN and filtered, then the filter cake was resolved by SFC with CCC column (ChromegaChiral™) and 40% MeOH with 0.25% DMEA as co-solvent to provide the title compounds Examples 131A (peak 1) and 131B (peak 2).

131A (peak 1): LC/MS (ES, m/z)=367 [M+H]$^+$. $^1$H NMR (600 MHz, DMSO-d$^6$) δ 8.00 (d, J=8.0 Hz, 1H), 7.61-7.44 (m, 1H), 7.33 (m, 1H), 7.30 (s, 1H), 7.18 (s, 1H), 3.73 (s, 3H), 3.61 (m, 1H), 3.30-3.22 (m, 1H), 2.85 (m, 1H), 2.16 (br. s, 1H), 1.92-1.62 (m, 3H).

131B (peak 2): LC/MS (ES, m/z)=367 [M+H]$^1$H NMR (600 MHz, DMSO-d$^6$) δ 8.00 (d, J=8.0 Hz, 1H), 7.54 (dd, J=10.2, 8.0 Hz, 1H), 7.18 (s, 1H), 3.73 (s, 3H), 3.61 (dd, J=11.4, 3.7 Hz, 1H), 3.30-3.22 (m, 1H), 2.85 (t, J=11.1 Hz, 1H), 2.16 (s, 1H), 1.93-1.60 (m, 3H).

The compounds of the invention shown in Table 4 were prepared using a procedure similar to the procedure used to prepare Examples 131A and 131B, substituting the appropriate starting aryl halide and benzonitrile.

TABLE 4

| Example | Structure Name | Observed m/z [M + H]$^+$ |
|---|---|---|
| 132A (Peak 1) and 132B (Peak 2) | ((R)-7-chloro-2-(1-(1-methyl-1H-pyrazol-4-yl)piperidin-3-yl)-[1,2,4]triazolo[1,5-c]quinazolin-5-amine, ((S)-7-chloro-2-(1-(1-methyl-1H-pyrazol-4-yl)piperidin-3-yl)-[1,2,4]triazolo[1,5-c]quinazolin-5-amine, The intermediate prepared in the step analogous to that of Step E in the preparation of Examples 131A and 131B was resolved by via chiral SFC with a Chiral Technologies AS-H 21 × 250 mm column with 1:1 MeOH:ACN (0.2% DMEA) as co-solvent | 383 |
| 133 | rac-7-chloro-2-(1-(1-cyclopropyl-1H-pyrazol-4-yl)piperidin-3-yl)-[1,2,4]triazolo[1,5-c]pyquinazolin-5-amine (Enantiomers were not separated in last step) | 409 |

Examples 134A and 134B

The Preparation of the Compounds of Examples 134A and 134B

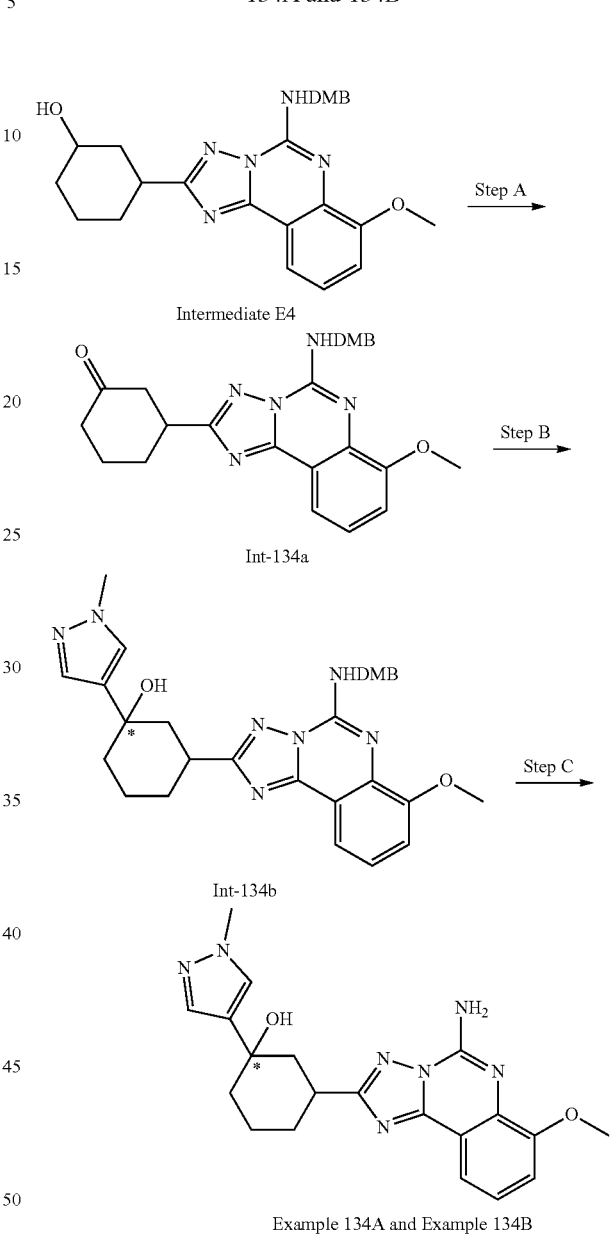

Example 134A and Example 134B

Step A Synthesis of Compound Int-134a 3-(5-((3,4-dimethylbenzyl)amino)-7-methoxy-[1,2,4]triazolo[1,5-c]quinazolin-2-yl)cyclohexan-1-one To a stirred solution of Intermediate E4 (1 g, 2.157 mmol) in DCM (5 mL) was added Dess-Martin Periodinane (1.830 g, 4.31 mmol) at 0° C. The resulting mixture was stirred at 0° C. for 1 hour. Upon completion, the reaction mixture was filtered, and the filtrate was concentrated under reduced pressure. The resulting residue was purified by silica gel column chromatography with 0~65% EtOAc/hexane as eluent to provide Int-134a LC/MS (ES, m/z)=430 [M+H]$^+$.

Step B—Synthesis of Compound Int-134b. 3-(5-((3, 4-dimethylbenzyl)amino)-7-methoxy-[1,2,4]triazole [1,5-c]quinazolin-2-yl)-1-(1-methyl-1H-pyrazol-4-yl)cyclohexan-1-ol To a stirred solution of 4-bromo-1-methyl-1H-pyrazole (209 mg, 1.300 mmol) in THF (3 mL) was added n-butyllithium in hexanes (0.7 mL, 1.750 mmol) at −78° C. The mixture was stirred at −78° C. for 20 min, and then Int-134a (150 mg, 0.325 mmol) in THF (3 mL) was added at −78° C. The resulting mixture was slowly warmed to 15° C. for 4 hours, Upon completion, the reaction was then quenched with aqueous NH$_4$Cl solution (40 mL), and then extracted with DCM (40 mL×2). The combined organic layers were concentrated. The resulting residue was purified by silica gel column chromatography with 5% MeOH in DCM as eluent to provide Int-134b. LC/MS (ES, m/z)=544 [M+H]$^+$.

Step C—Synthesis of Compounds 134A and 134B

To a stirred solution of Int-134b (70 mg, 0.129 mmol) in DCM (2 mL)/Water (1 mL) was added 2,3-dichloro-5,6-dicyano-1,4-benzoquinone (58 mg, 0.256 mmol) at 15° C. The resulting reaction was stirred at 15° C. for 2 hours, and upon completion, diluted with 10 mL DCM and then washed with aqueous Na$_2$SO$_3$ solution (2 mL). The organic layer was concentrated and the resulting residue was purified by reversed phase HPLC using Prep OBD C18 column and 0-100% ACN/water (0.04% NH$_4$OH) as eluent to provide the title compounds Example 134A (peak 1) and Example 134B (Peak 2).

134A: LC/MS (ES, m/z)=394 [M+H]$^+$. $^1$H NMR (400 MHz, CD$_3$CN) δ 7.78 (dd, J=0.9, 8.07 Hz, 1H), 7.54 (s, 1H), 7.48 (s, 1H), 7.34 (t, J=8.1 Hz, 1H), 7.21 (d, J=7.4 Hz, 1H), 6.34 (s, 2H), 3.96 (s, 3H), 3.84 (s, 3H), 3.36 (s, 1H), 3.00 (tt, J=3.6, 11.28 Hz, 1H), 2.59 (d, J=13.2 Hz, 1H), 2.25 (d, J=12.5 Hz, 1H), 2.04 (s, 1H), 1.87 (td, J=3.9, 13.21 Hz, 1H), 1.62-1.76 (m, 2H), 1.46-1.59 (m, 1H).

134B: LC/MS (ES, m/z)=394 [M+H]$^+$. $^1$H NMR (400 MHz, CD$_3$CN) δ 7.79 (d, J=7.6 Hz, 1H), 7.44 (s, 1H), 7.41 (s, 1H), 7.35 (t, J=8.1 Hz, 1H), 7.21 (d, J=7.6 Hz, 1H), 6.32 (s, 2H), 3.97 (s, 3H), 3.81 (s, 3H), 3.46 (t, J=12.4 Hz, 1H), 2.95 (s, 1H), 2.31 (d, J=13.5 Hz, 1H), 2.21 (br s, 1H), 2.10-2.15 (m, 1H), 2.01 (br s, 1H) 1.62-1.80 (m, 3H).

Example 135

The Preparation of the Compound of Example 135

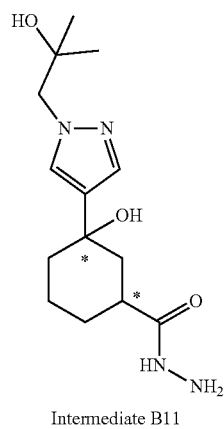

Intermediate B11

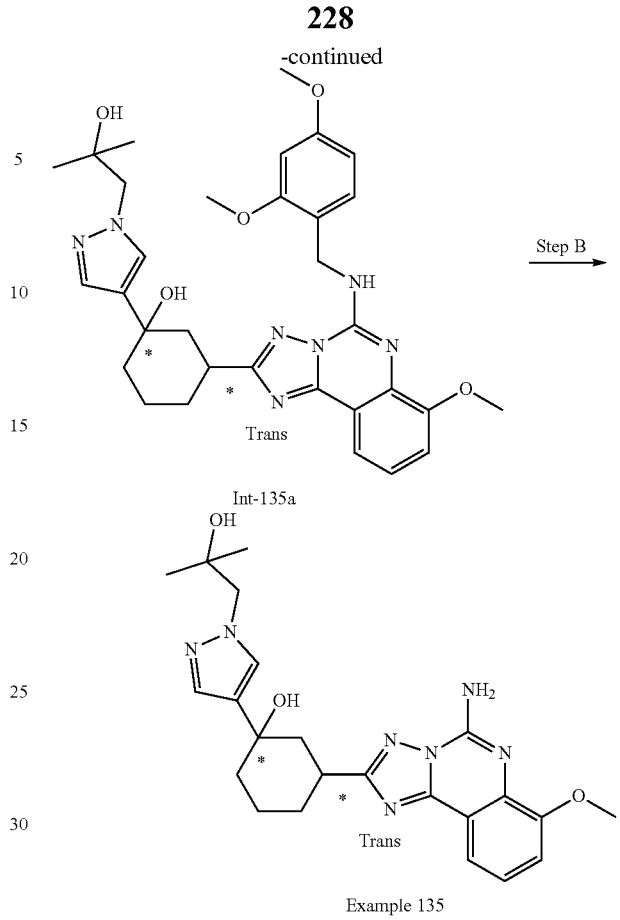

Step A—Synthesis of Compound Int-135a (1R,3R or 1S,3S)-3-(5-((2,4-dimethoxybenzyl)amino)-7-methoxy-[1,2,4]triazolo[1,5-c]quinazolin-2-yl)-1-(1-(2-hydroxy-2-methylpropyl)-1H-pyrazol-4-yl(cyclohexan-1-ol To a 20 mL vial was added (1R,3R or 1S,3S)-3-hydroxy-3-(1-(2-hydroxy-2-methylpropyl)-1H-pyrazol-4-yl)cyclohexane-1-carbohydrazide (35.0 mg, 0.118 mmol), 2-((((2,4-dimethoxybenzyl)imino)methylene amino)-3-methoxybenzonitrile (Intermediate C7, 49.6 mg, 0.154 mmol), dioxane (0.5 mL) and AcOH (3 μL, 0.06 mmol). The mixture was stirred and heated at 65° C. for 2 hours. The solvents were evaporated. The resulting residue was purified by silica gel column chromatography with 0-100% EtOAc: EtOH (3:1) in hexanes as eluent to afford the title compound Int-135a LC/MS (ES, m/z)=602 [M+H]$^+$.

Step B—Synthesis of Compound 135. (1R, 3R or 1S,3S)-3-(5-amino-7-methoxy-[1,2,4]triazolo[1,5-c] quinazolin-2-yl)-1-(1-(2-hydroxy-2-methylpropyl)-1H-pyrazol-4-yl)cyclohexan-1-ol To a 20 mL vial was added DDQ (30.3 mg, 0.133 mmol), DCM (1.0 mL), and water (0.05 mL). The mixture was cooled at 0° C. To the mixture was added Int-135a (53.5 mg, 0.089 mmol) as a solution in DCM (1 mL). The mixture was stirred for 4 hours. To the mixture was added 1 M aqueous KOH (20 mL), and the mixture was then extracted with DCM (2×20 mL). The organic layers were dried over anhydrous sodium sulfate, filtered, and the solvents of the filtrate were evaporated. The residue was purified by silica gel column chromatography with 0-100% EtOAc:EtOH (3:1) in hexanes as eluent. The resulting residue was further resolved by SFC with OJ-H column and 20% MeOH (NH₄OH modifier) as cosolvent to afford the title compound Example 135. LC/MS (ES, m/z)=452 [M+H]⁺. ¹H NMR (499 MHz, DMSO-d⁶) δ 7.73 (dd, J=8.0, 1.2 Hz, 3H), 7.56 (s, 1H), 7.39 (s, 1H), 7.29 (t, J=7.9 Hz, 1H), 7.24-7.10 (m, 1H), 4.81 (s, 1H), 4.65 (s, 1H), 3.95 (s, 2H), 3.90 (s, 3H), 3.48-3.40 (m, 1H), 2.22 (d, J=13.4 Hz, 1H), 2.09 (d, J=11.9 Hz, 1H), 1.98-1.84 (m, 3H), 1.73-1.58 (m, 3H), 1.16-0.89 (m, 9H).

Examples 136A, 136B, 136C, and 136D

The Preparation of the Compounds of examples 136A, 136B, 136C and 136D

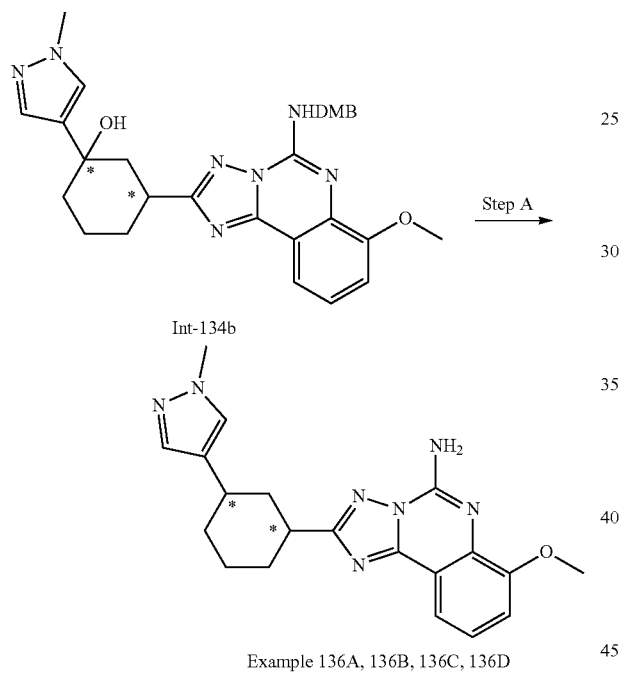

Step A—Synthesis of Examples 136A, 136B, 136C and 136D. 7-methoxy-2-((1R,3S)-3-(1-methyl-1H-pyrazol-4-yl)cyclohexyl)-[1,2,4]triazolo[1,5-c]quinazolin-5-amine, 7-methoxy-2-((1R,3R)-3-(1-methyl-1H-pyrazol-4-yl)cyclohexyl)-[1,2,4]triazolo[1,5-c]quinazolin-5-amine, and 7-methoxy-2-((1S,3R)-3-(1-methyl-1H-pyrazol-4-yl)cyclohexyl)-[1,2,4]triazolo[1,5-c]quinazolin-5-amine To a stirred solution of Int-134b (60 mg, 0.110 mmol) in DCM (1 mL) was added triethylsilane (0.03 mL, 0.188 mmol) and TFA (1 mL, 12.98 mmol) at 15° C. The resulting reaction mixture was stirred at 15° C. for 3 hours. Upon completion, the mixture was concentrated to provide crude N-(2,4-dimethoxybenzyl)-7-methoxy-2-(3-(1-methyl-1H-pyrazol-4-yl)cyclohexyl)-[1,2,4]triazolo[1,5-c]quinazolin-5-amine.

To the above crude residue (58.5 mg, 0.111 mmol) in DCM (1 mL) was added TFA (1 mL, 12.98 mmol) at 15° C.

The resulting mixture was stirred at 45° C. for 16 hours. Upon completion, the mixture was concentrated, and the resulting residue was purified by reversed phase HPLC with a Prep OBD C18 column and 0-100% ACN/water (0.1% TFA) as eluent to afford racemic 136. The racemic mixture was then further resolved by SFC with a Chiralpak AD column and 40% isopropanol (0.05% DEA) as cosolvent to provide Example 136A (Peak 1), Example 136B (Peak 2), Example 136C (Peak 3), and Example 136D (Peak 4).

136A: LC/MS (ES, m/z)=378 [M+H]⁺. ¹H NMR (400 MHz, CDCl₃) δ 7.95 (d, J=8.1 Hz, 1H), 7.34-7.41 (m, 2H), 7.13-7.22 (m, 2H), 5.93 (br s, 2H), 4.07 (s, 3H), 3.87 (s. 3H), 3.10-3.20 (m, 1H), 2.73 (t, J=12.1 Hz, 1H), 2.45 (d, J=12.7 Hz, 1H), 2.21-2.30 (m, 1H), 1.99-2.08 (m, 2H), 1.68-1.82 (m, 2H), 1.32-1.48 (m, 2H).

136B: LC/MS (ES, m/z)=378 [M+H]⁺. ¹H NMR (400 MHz, CDCl₃) δ 7.93-7.98 (m, 1H), 7.34-7.41 (m, 2H), 7.14-7.22 (m, 2H), 5.93 (s, 2H), 4.07 (s, 3H), 3.87 (s, 3H), 3.10-3.20 (m, 1H), 2.73 (t, J=12.1 Hz, 1H), 2.45 (d, J=12.9 Hz, 1H), 2.22-2.28 (m, 1H), 1.99-2.08 (m, 2H), 1.69-1.83 (m, 2H), 1.65 (d, J=14.4 Hz, 1H), 1.38-1.49 (m, 1H).

136C: LC/MS (ES, m/z)=378 [M+H]⁺. ¹H NMR (400 MHz, CDCl₃) δ 7.95 (d, J=8.1 Hz, 1H), 7.34-7.41 (m, 2H), 7.13-7.22 (m, 2H), 5.93 (br s, 2H), 4.07 (s, 3H), 3.87 (s, 3H), 3.10-320 (m, 1H), 2.73 (t, J=12.1 Hz, 1H), 2.45 (d, J=12.7 Hz, 1H), 2.21-2.30 (m, 1H), 1.99-2.08 (m, 2H), 1.68-1.82 (m, 2H), 1.32-1.48 (m, 2H).

136D: LC/MS (ES, m/z)=378 [M+H]⁺. ¹H NMR (400 MHz, CDCl₃) δ 7.93-7.98 (m, 1H), 7.34-7.41 (m, 2H), 7.14-7.22 (m, 2H), 5.93 (s, 2H), 4.07 (s, 3H), 3.87 (s, 3H), 3.10-3.20 (m, 1H), 2.73 (t, J=12.1 Hz, 1H), 2.45 (d, J=12.9 Hz, 1H), 2.22-2.28 (m, 1H), 1.99-2.08 (m, 2H), 1.69-1.83 (m, 2H), 1.65 (d, J=14.4 Hz, 1H), 1.38-1.49 (m, 1H).

Example 137

The Preparation of the Compound of Example 137

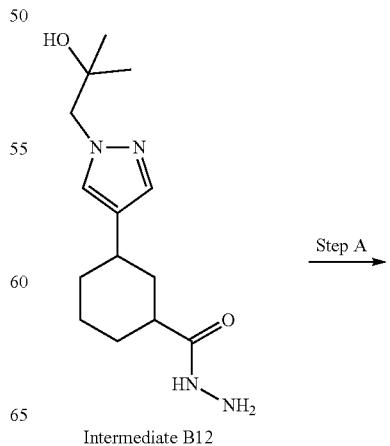

Intermediate B12

231

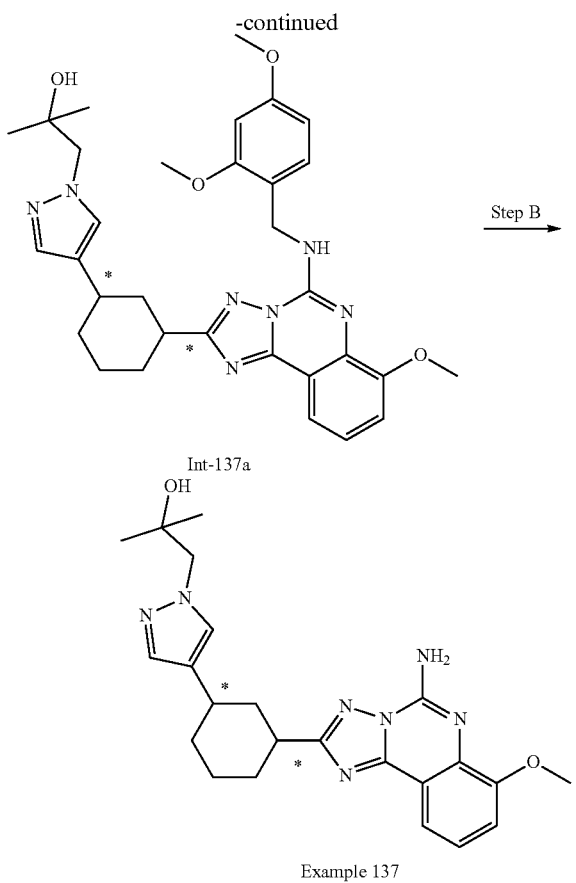

Int-137a

Example 137

Step A—Synthesis of Compound Int-137a 1-(4-4-((1S,3R or 1R,3S)-3-(5-((2,4-dimethoxybenzyl)amino)-7-methoxy-[1,2,4]triazolo[1,5-c]quinazolin-2-yl)cyclohexyl)-1H-pyrazol-1-yl)-2-methylpropan-2-ol To a 20 mL vial was added Intermediate B12 (470 mg, 1.26 mmol), 2-(((((2,4-dimethoxybenzyl)imino)methylene)amino)-3-methoxybenzonitrile (Intermediate C7, 528 mg, 1.63 mmol), dioxane (5 mL), and AcOH (0.036 mL, 0.63 mmol). The mixture was stirred and then heated at 65° C. for 2 hours. The solvents were evaporated, and the resulting residue was purified by silica gel column chromatography with 0-100% EtOAc:EtOH (1:1) in hexanes as eluent, yielding a mixture of diastereomers. The mixture was resolved by SFC with Lux-3 column and 20% MeOH (0.1% NH4OH modifier) as cosolvent to afford the enantiopure, cis-diastereomer Int-137a (second eluting peak). LC/MS (ES, m/z)=586 [M+H]+.

Step B—Synthesis of Example 137. 1-(4-((1S,3R or 1R,3S)-3-(5-amino-7-methoxy-[1,2,4]triazolo[1,5-c]quinazolin-2-yl)cyclohexyl)-1H-pyrazol-1-yl)-2-methylpropan-2-ol To a 4 mL vial was added Int-137a (10.9 mg, 0.019 mmol) and TFA (0.5 mL). The mixture was stirred and heated at 65° C. for 2 hours. The solvents were evaporated. To the resulting residue was added saturated sodium bicarbonate (3 mL), and the mixture was extracted with DCM (3×3 mL). The combined organic layers were dried over anhydrous sodium sulfate, filtered, and the solvents of the filtrate were evaporated. The resulting residue was purified by silica gel column chromatography with 0-100% EtOAc:EtOH (1:1) in hexanes as eluent to afford the title compound Example 137. LC/MS (ES, m/z)=436 [M+H]+. 1H NMR (499 MHz, DMSO-d6) δ 7.74 (dd, J=7.9, 1.1 Hz, 3H), 7.50 (s, 1H), 7.34 (s, 1H), 7.29 (t, J=7.9 Hz, 1H), 7.22 (d, J=8.0 Hz, 1H), 4.64 (s, 1H), 3.94 (s, 2H), 3.90 (s, 3H), 3.09 (t, J=11.7 Hz, 1H), 2.70 (t, J=11.9 Hz, 1H), 2.32 (d, J=13.0 Hz, 1H), 2.13 (d, J=13.3 Hz, 1H), 2.00 (d, J=8.1 Hz, 1H), 1.93 (d, J=12.7 Hz, 1H), 1.75-1.52 (m, 3H), 1.37 (d, J=12.4 Hz, 1H), 1.03 (s, 6H).

Example 138 shown in Table 5 was prepared using a procedure similar to the procedure used to prepare the compound of example 137, substituting Intermediate B13 for Intermediate B12 and the appropriate starting materials.

TABLE 5

| Example | Structure Name | Observed m/z [M + H]+ |
|---|---|---|
| 138 | 1-(4-((1R,3S or 1S,3R)-3-(5-((2,4-dimethoxybenzyl)amino)-7-methoxy-[1,2,4]triazolo[1,5-c]quinazolin-2-yl)cyclohexyl)-1H-pyrazol-1-yl)-2-methylpropan-2-ol | 436 |

Examples 139A, 139B, 1.390, and 139D

The Preparation of the Compounds of Examples 139A, 139B, 139C and 139D

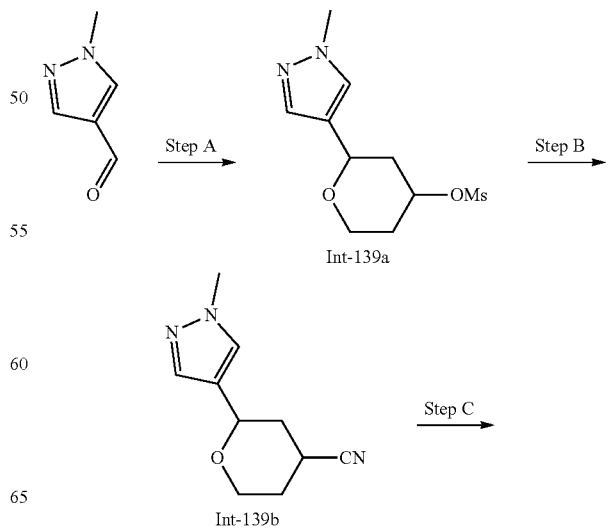

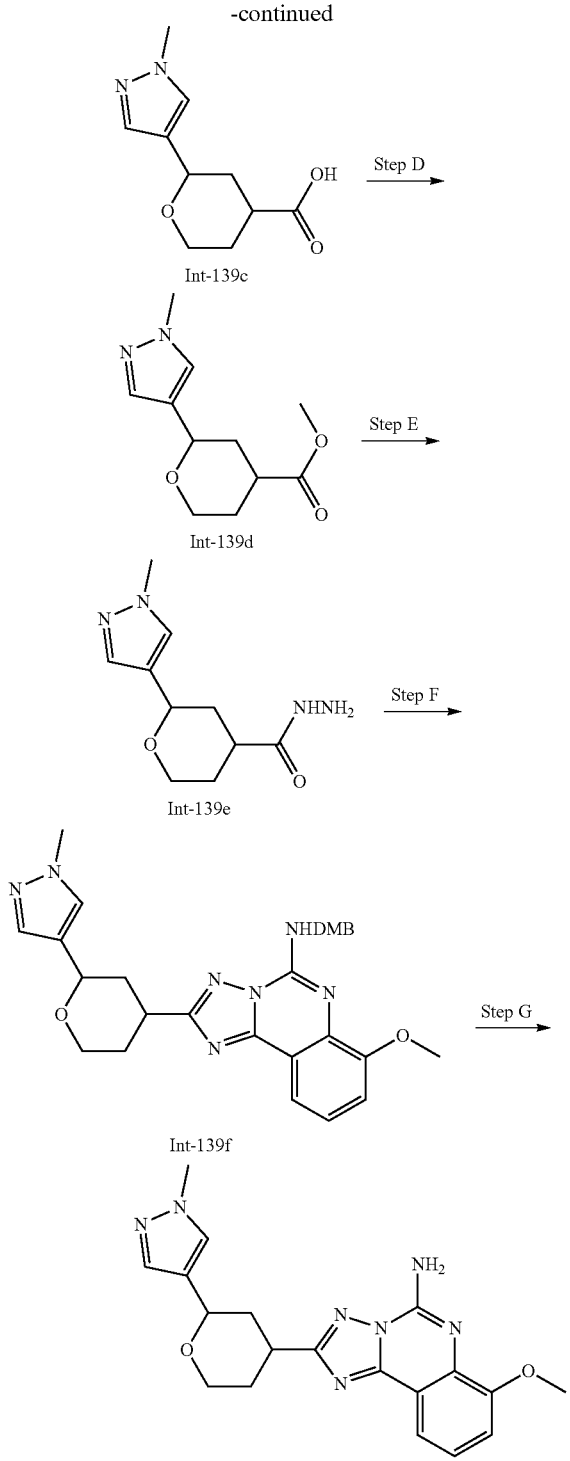

Examples 139A, 139B, 139C, 139D

Step A—Synthesis of Compound Int-139a 2-(1-methyl-1H-pyrazol-4-yl)tetrahydro-2H-pyran-4-yl methanesulfonate To a stirred solution of but-3-en-1-ol (1.964 g, 27.2 mmol) and 1-methyl-1H-pyrazole-4-carbaldehyde (2 g, 18.16 mmol) in DCM (40 mL) was added dropwise methanesulfonic acid (8.73 g. 91 mmol) at 0° C. The resulting mixture was stirred at room temperature for 12 hours. Upon completion, the reaction mixture was diluted with DCM (80 mL), washed with saturated $Na_2CO_3$ aqueous solution (30 mL), dried over anhydrous $Na_2SO_4$, and filtered. The filtrate was then concentrated and the resulting residue was purified by silica gel column chromatography with 20% EtOAc in hexane as eluent to provide Int-139a LC/MS (ES, m/z)=260 $[M+H]^+$.

Step B—Synthesis of Compound Int-139b. 2-(1-methyl-1H-pyrazol-4-yl)tetrahydro-2H-pyran-4-carbonitrile To a stirred solution of Int-139a (3 g, 11.52 mmol) in DMF (35 mL) was added NaCN (1.412 g, 28.8 mmol). The reaction mixture was stirred at 60° C. for 10 hours. Upon completion, the reaction was quenched with water (40 mL) and then extracted with EtOAc (40 mL×3). The combined organic layers were washed water (30 mL×3), dried over anhydrous $Na_2SO_4$, and filtered. The filtrate was concentrated and the resulting residue was purified by silica gel column chromatography with 15% EtOAc in hexane as eluent to provide Int-139b. LC/MS (ES, m/z)=191 $[M+H]^+$.

Step C—Synthesis of Compound Int-139c. 2-(1-methyl-1H-pyrazol-4-yl)tetrahydro-2H-pyran-4-carboxylic acid To a solution of Int-1.39b (1.5 g, 7.84 mmol) in EtOH (10 mL) and water (2 mL) was added KOH (3.52 g, 62.8 mmol). The mixture was stirred at 90° C. for 2 hours. Upon completion, the pH of the mixture was adjusted to 5 with HCl (conc.). The mixture was then concentrated to remove most of solvents. To the residue was added 20 mL DCM. The solution was dried over anhydrous $Na_2SO_4$, filtered, and concentrated to afford Int-139e. LC/MS (ES, m/z)=210 $[M+H]^+$.

Step D—Synthesis of Compound Int-139d methyl 2-(1-methyl-1H-pyrazol-4-yl)tetrahydro-2H-pyran-4-carboxylate To a solution of Int-139c (400 mg, 1.912 mmol) in DCM (20 mL) and methanol (2 mL) was added dropwise (trimethylsilyl)diazomethane (2.87 mL, 2.87 mmol) at 25° C. The mixture was stirred at 25° C. for 1 hour. Upon completion, the mixture was evaporated under reduced pressure to afford Int-139d. LC/MS (ES, m/z)=225 $[M+H]^+$.

Step E—Synthesis of Compound Int-139e. 2-(1-methyl-1H-pyrazol-4-yl)tetrahydro-2H-pyran-4-carbohydrazide To a mixture of Int-139d (230 mg, 1.026 mmol) EtOH (5 mL) was added hydrazine (164 mg, 5.13 mmol). The mixture was stirred at 90° C. for 1 hour. Upon completion, the reaction mixture was concentrated to afford Int-139e. LC/MS (ES, m/z)=225 $[M+H]^+$.

Step F—Synthesis of Compound Int-139f. N-(3,4-dimethylbenzyl)-7-methoxy-2-(2-(1-methyl-1H-pyrazol-4-yl)tetrahydro-2H-pyran-4-yl)-[1,2,4]triazolo[1,5-c]quinazolin-5-amine To a solution of Int-139e (30 mg, 0.134 mmol) in NMP (1 mL) was added 2-(((((2,4-dimethoxybenzyl)imino)methylene)amino)-3-methoxybenzonitrile (C7, 43.3 mg, 0.134 mmol). The reaction mixture was stirred at 170° C. for 1.5 hours under microwave conditions. The mixture was cooled, diluted with EtOAc (30 mL), washed with water (10 mL×2), dried over anhydrous Na$_2$SO$_4$, and filtered. The filtrate was evaporated and the resulting residue was purified by preparative silica gel TLC plate with 5% MeOH in DCM as eluent to afford Int-139f. LC/MS (ES, m/z)=530 [M+H]$^+$.

Step G—Synthesis of Examples 139A, 139B, 139C and 139D

To a solution of Int-13.9f (20 mg, 0.038 mmol) in CH$_2$Cl$_2$ (2 mL), TFA (2 mL, 26.0 mmol) was added dropwise. The mixture was stirred at 60° C. for 8 hours. Upon completion, the mixture was concentrated in vacuum. The resulting residue was purified by reversed phase HPLC using preparative OBD C18 column and 0-100% ACN/water (0.1% TFA) as eluent to afford a mixture of racemic diastereomers. The mixture was resolved by SFC using a chiral OJ column (Chiral Technologies) and 40% EtOH (0.05% DEA) as cosolvent to provide Example 139A (peak 1), Example 139B (peak 2), Example 139C (peak 3) and Example 139D (peak 4).

139A: LC/MS (ES, m/z)=380 [M+H]$^+$. $^1$H NMR (400 MHz, Methanol-d$^4$) δ 7.90 (d, J=8.1 Hz, 1H), 7.61 (s, 1H), 7.50-7.42 (m, 2H), 7.38-7.33 (m, 1H), 4.05 (s, 3H), 3.95-3.90 (m, 2H), 3.86 (s. 3H), 3.61 (t, J=4.8 Hz, 1H), 3.32-3.31 (m, 1H), 2.57 (d, J=13.7 Hz, 1H), 2.36-2.26 (m, 2H), 2.24-2.13 (m, 1H).

139B: LC/MS (ES, m/z)=380 [M+H]$^+$. $^1$H NMR (400 MHz, Methanol-d$^4$) δ 7.95-7.85 (m, 1H), 7.61 (s, 1H), 7.50-7.42 (m, 2H), 7.38-7.33 (m, 1H), 4.05 (s, 3H), 3.97-3.90 (m, 2H), 3.86 (s, 3H), 3.61 (t, J=4.6 Hz, 1H), 3.35-3.31 (m, 1H), 2.57 (d, J=13.9 Hz, 1H), 2.39-2.25 (m, 2H), 2.24-2.11 (m, 1H).

139C: LC/MS (ES, m/z)=380 [M+H]$^+$. $^1$H NMR (400 MHz, Methanol-d$^4$) δ=7.87 (d, J=7.9 Hz, 1H), 7.61 (s, 1H), 7.50 (s, 1H), 7.41-7.33 (m, 1H), 7.26 (d, J=7.9 Hz, 1H), 4.61 (d, J=11.4 Hz, 1H), 4.20 (d, J=7.9 Hz, 1H), 4.01 (s, 3H), 3.92-3.79 (m, 4H), 3.41 (s, 1H), 2.39 (d, J=10.5 Hz, 1H), 2.23-1.96 (m, 3H).

139D: LC/MS (ES, m/z)=380 [M+H]$^+$. $^1$H NMR (400 MHz, Methanol-d$^4$) δ=8.00-7.86 (m, 1H), 7.59 (s, 1H), 7.53-7.45 (m, 2H), 7.40 (d, J=7.6 Hz, 1H), 4.60 (dd, J=1.6, 11.4 Hz, 1H), 4.20 (dd, J=3.1, 11.6 Hz, 1H), 4.07 (s, 3H), 3.86 (s, 3H), 3.83-3.76 (m, 1H), 3.49-3.39 (m, 1H), 2.39 (d, J=13.2 Hz, 1H), 2.22-1.99 (m, 3H).

Examples 140A, 140B, 140C, and 140D

The Preparation of the Compounds of Examples 140A, 140B, 140C and 140D

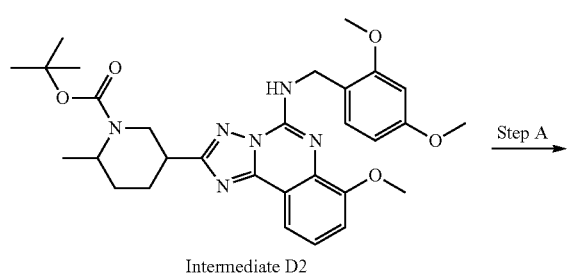

Intermediate D2

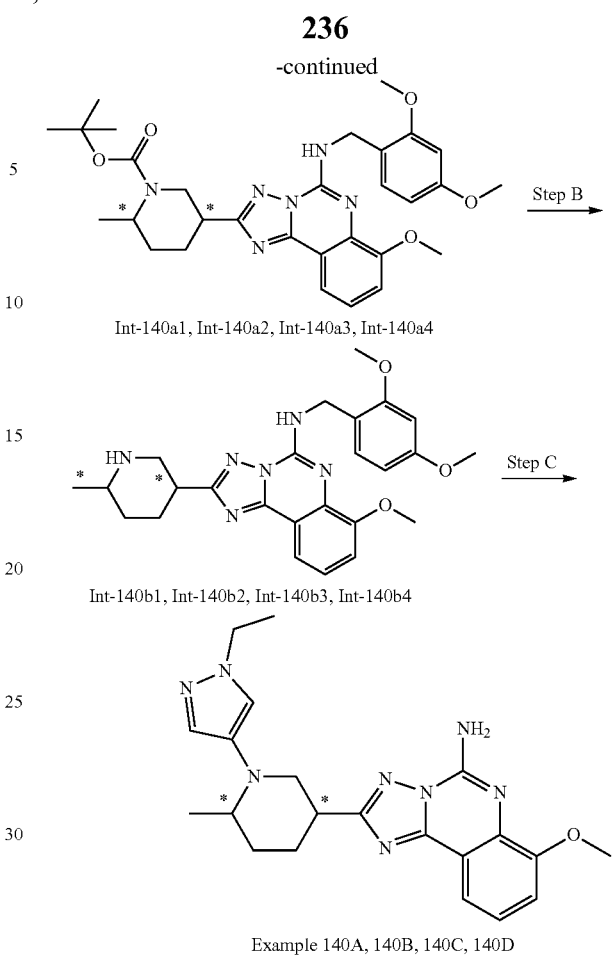

Int-140a1, Int-140a2, Int-140a3, Int-140a4

Int-140b1, Int-140b2, Int-140b3, Int-140b4

Example 140A, 140B, 140C, 140D

Step A—Synthesis of Compound Int-140a1, Int-140a2, Int-140a3 and Int-140a4

The racemic intermediate D2 (3.5 g, 20.67 mmol) was resolved by SFC with a chiral AD-H column and 50% IPA with 0.2% DTPA as cosolvent to afford the title compounds Int-140a1 (Peak 1), Int-140a2 (Peak 2), Int-140a3 (Peak 3), and Int-140a4 (Peak 9). LC/MS (ES, m/z)=563 [M+H]$^+$.

Step B—Synthesis of Compound Int-140b, Int-140b2, Int-140b3 and Int-140b4

To the solution of Int-140a1 (660 mg, 1.173 mmol) in DCM (10 mL) was added 4 M HCl in dioxane (2.053 mL, 8.21 mmol). The reaction mixture was stirred at room temperature for 2 hours. Upon completion, the reaction mixture was concentrated under reduced pressure, and the resulting residue was purified by preparative silica gel TLC plates with 6% 7 N NH$_3$ in MeOH/DCM as eluent to afford Int-140b1. LC/MS (ES, m/z)=463 [M+H]$^+$. Utilizing a method similar to that described for the preparation of Int-140b1, Int-140a2 was converted to Int-140b2, Int-140a3 was converted to Int-140b3, and Int-140a4 was converted to Int-140b4.

Step C—Synthesis of Examples 140A, 140B, 140C and 140D

To a reaction vial containing Int-140b1 (40 mg, 0.086 mmol) in THF (1 mL) was added 4-bromo-1-ethyl-1H- pyrazole (37.8 mg, 0.216 mmol), followed by methanesulfonato(2-di-t-butylphosphino-2',4',6'-tri-i-propyl-1,1'-biphenyl)(2'-amino-1,1'-biphenyl-2-yl)palladium(II) (t-BuXPhos Pd G3, 20.61 mg, 0.026 mmol) and sodium tert-butoxide (24.93 mg, 0.259 mmol). The resulting mixture was purged with $N_2$ for 10 minutes, then heated at 90 for 24 hours. Upon completion, the reaction mixture was cooled and then concentrated. The resulting residue was purified by preparative silica gel TLC plates with 4% 7N $NH_3$ in MeOH/DCM as eluent to afford DMB-protected intermediate (20 mg, 0.036 mmol).

The DMB-protected intermediate (20 mg, 0.036 mmol) was added to 2,2,2-trifluoroacetic acid (1.0 mL) and then heated at 60° C. for 1 hour. Upon completion, the reaction mixture was concentrated. The resulting residue was purified by preparative silica gel TLC plates with 60% 3:1 EtOAc:EtOH in hexane as eluent to provide Example 140A. LC/MS (ES, m/z)=407 [M+H]+. 1H NMR (400 MHz, Chloroform-d) δ 7.94 (d, J=8.0 Hz, 1H), 7.39 (s, 1H), 7.35 (t, J=8.1 Hz, 1H), 7.23 (s, 1H), 7.14 (d, J=7.8 Hz, 1H), 6.43 (s, 2H), 4.10 (q, J=7.3 Hz, 2H), 4.02 (s, 2H), 3.55 (d, J=11.7 Hz, 1H), 3.48 (d, J=4.4 Hz, 1H), 3.38 (t, J=10.8 Hz, 1H), 3.14 (t, J=11.0 Hz, 1H), 2.76 (s, 1H), 2.31 (d, J=11.8 Hz, 1H), 2.03-1.78 (m, 2H), 1.69-1.53 (m, 1H), 1.45 (t, J=7.3 Hz, 3H), 1.07 (d, J=6.1 Hz, 3H).

Utilizing a method similar to that described for the preparation of Example 140A, Int-140b2 was converted to Example 140B, Int-140b3 was converted to Example 140C, and Int-140b4 was converted to Example 140D.

140B: LC/MS (ES, m/z)=407 [M+H]+. 1H NMR (400 MHz, Chloroform-d) δ 7.93 (d, J=8.1 Hz, 1H), 7.39 (s, 1H), 7.35 (t, J=8.0 Hz, 1H), 7.24 (s, 1H), 7.14 (d, 8.0 Hz, 1H), 6.12 (s, 2H), 4.10 (q, J=7.3 Hz, 2H), 4.05 (s, 3H), 3.56 (d, J=9.9 Hz, 1H), 3.39 (s, 1H), 3.15 (t, J=11.0 Hz, 1H), 2.77 (s, 1H), 2.32 (d, J=11.6 Hz, 1H), 2.05-1.82 (m, 2H), 1.59 (d, J=12.9 Hz, 1H), 1.45 (t, J=7.3 Hz, 3H), 1.07 (d, J=6.1 Hz, 3H).

140C: LC/MS (ES, m/z)=407 [M+H]+. 1H NMR (500 MHz, Methanol-d4) δ 7.93 (d, J=8.0 Hz, 1H), 7.84 (s, 1H), 7.62 (s, 1H), 7.46 (t, J=8.0 Hz, 1H), 7.37 (d, J=7.4 Hz, 1H), 4.20 (q, J=7.1 Hz, 2H), 4.07 (s, 3H), 3.86 (m, 2H), 3.63 m, 1H), 2.46 (m, 1H), 2.35-2.14 (m, 2H), 1.97 (d, J=27.3 Hz, 1H), 1.47 (t, J=7.3 Hz, 3H), 1.21 (d, J=6.6 Hz, 3H).

140D: LC/MS (ES, m/z)=407 [M+H]1. 1H NMR (400 MHz, Methanol-d4) δ 7.91 (dd, J=8.0, 1.2 Hz, 1H), 7.84 (s, 1H), 7.61 (s, 1H), 7.45 (t, J=8.0 Hz, 1H), 7.36 (d, J=8.1 Hz, 1H), 4.19 (q, J=7.3 Hz, 2H), 4.05 (s, 3H), 3.99-3.72 (m, 2H), 3.62 (m, 1H), 2.45 (m, 1H), 2.34-2.07 (m, 2H), 1.99 (m, 1H), 1.46 (t, J=7.3 Hz, 3H), 1.20 (d, J=6.7 Hz, 3H).

The example compounds of the invention shown in Table 6 were prepared using a procedure similar to the procedure used to prepare the compounds shown above, substituting the appropriate starting aryl halide and either intermediate Int-140b1, Int-140b2, Int-140b3 or Int-140b4. The intermediate each example is derived from is noted in parentheses below the example number.

TABLE 6

| Example | Structure Name | Observed m/z [M + H]+ |
|---|---|---|
| 141A (Int-140b1) 141B (Int-140b2) 141C (Int-140b3) 141D (Int-140b4) | 2-((3R,6S)-1-(1-cyclopropyl-1H-pyrazol-4-yl)-6-methylpiperidin-3-yl)-7-methoxy-[1,2,4]triazolo[1,5-c]quinazolin-5-amine, 2-((3R,6R)-1-(1-cyclopropyl-1H-pyrazol-4-yl)-6-methylpiperidin-3-yl)-7-methoxy-[1,2,4]triazolo[1,5-c]quinazolin-5-amine, 2-((3S,6S)-1-(1-cyclopropyl-1H-pyrazol-4-yl)-6-methylpiperidin-3-yl)-7-methoxy-[1,2,4]triazolo[1,5-c]quinazolin-5-amine, 2-((3S,6R)-1-(1-cyclopropyl-1H-pyrazol-4-yl)-6-methylpiperidin-3-yl)-7-methoxy-[1,2,4]triazolo[1,5-c]quinazolin-5-amine | 419 |

TABLE 6-continued

| Example | Structure Name | Observed m/z [M + H]+ |
|---|---|---|
| 142A (Int-140b1) 142B (Int-140b2) 142D (Int-140b4) | 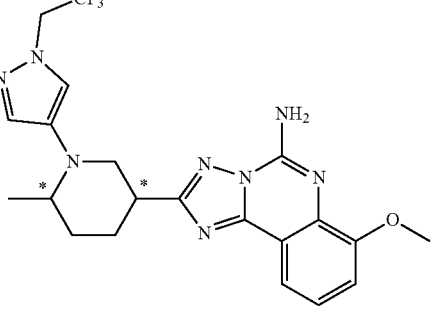7-methoxy-2-((3S,6S or 3R,6R)-6-methyl-1-(1-(2,2,2-trifluoroethyl)-1H-pyrazol-4-yl)piperidin-3-yl)-[1,2,4]triazolo[1,5-c]quinazolin-5-amine, 7-methoxy-2-((3R,6R or 3S,6S)-6-methyl-1-(1-(2,2,2-trifluoroethyl)-1H-pyrazol-4-yl)piperidin-3-yl)-[1,2,4]triazolo[1,5-c]quinazolin-5-amine, 7-methoxy-2-((3R,6S)-6-methyl-1-(1-(2,2,2-trifluoroethyl)-1H-pyrazol-4-yl)piperidin-3-yl)-[1,2,4]triazolo[1,5-c]quinazolin-5-amine, | 461 |
| 143B (Int-140b2) 143C (Int-140b3) 143D (Int-140b4) | 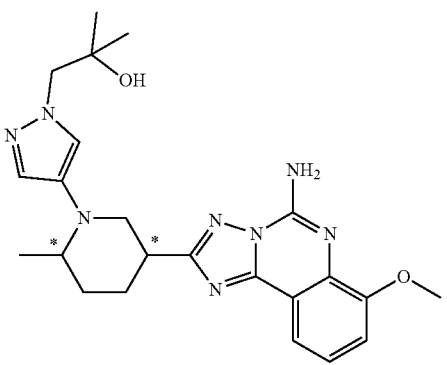 [SMILES: COc1cccc2c1nc(N)n1nc(C3CCC(C)N(c4cnn(CC(C)(C)O)c4)C3)nc21]1-(4-((2S,5S or 2R,5R)-5-(5-amino-7-methoxy-[1,2,4]triazolo[1,5-c]quinazolin-2-yl)-2-methylpiperidin-1-yl)-1H-pyrazol-1-yl)-2-methylpropan-2-ol, 1-(4-((2R,5S)-5-(5-amino-7-methoxy-[1,2,4]triazolo[1,5-c]quinazolin-2-yl)-2-methylpiperidin-1-yl)-1H-pyrazol-1-yl)-2-methylpropan-2-ol, 1-(4-((2S,5R)-5-(5-amino-7-methoxy-[1,2,4]triazolo[1,5-c]quinazolin-2-yl)-2-methylpiperidin-1-yl)-1H-pyrazol-1-yl)-2-methylpropan-2-ol | 451 |

TABLE 6-continued

| Example | Structure Name | Observed m/z [M + H]+ |
|---|---|---|
| 144C (Int-140b3) 144D (Int-140b4) | 1-((4-((2R,5S)-5-(5-amino-7-methoxy-[1,2,4]triazolo[1,5-c]quinazolin-2-yl)-2-methylpiperidin-1-yl)-1H-pyrazol-1-yl)methyl)cyclobutan-1-ol, 1-((4-((2S,5R)-5-(5-amino-7-methoxy-[1,2,4]triazolo[1,5-c]quinazolin-2-yl)-2-methylpiperidin-1-yl)-1H-pyrazol-1-yl)methyl)cyclobutan-1-ol, | 463 |
| 145C (Int-140b3) 145D (Int-140b4) | 1-(4-((2S,5R)-5-(5-amino-7-methoxy-[1,2,4]triazolo[1,5-c]quinazolin-2-yl)-2-methylpiperidin-1-yl)-3-methyl-1H-pyrazol-1-yl)-2-methylpropan-2-ol, 1-(4-((2R,5S)-5-(5-amino-7-methoxy-[1,2,4]triazolo[1,5-c]quinazolin-2-yl)-2-methylpiperidin-1-yl)-3-methyl-1H-pyrazol-1-yl)-2-methylpropan-2-ol | 465 |
| 146C (Int-140b3) 146D (Int-140b4) | 2-(4-((2S,5R)-5-(5-amino-7-methoxy-[1,2,4]triazolo[1,5-c]quinazolin-2-yl)-2-methylpiperidin-1-yl)-1H-pyrazol-1-yl)-2-methylpropan-1-ol, 2-(4-((2R,5S)-5-(5-amino-7-methoxy-[1,2,4]triazolo[1,5-c]quinazolin-2-yl)-2-methylpiperidin-1-yl)-1H-pyrazol-1-yl)-2-methylpropan-1-ol | 451 |

TABLE 6-continued
| Example | Structure Name | Observed m/z [M + H]+ |
|---|---|---|
| 147C (Int-140b4 and Intermediate A4A) | 3-(4-((2S,5R)-5-(5-amino-7-methoxy-[1,2,4]triazolo[1,5-c]quinazolin-2-yl)-2-methylpiperidin-1-yl)-1H-pyrazol-1-yl)-2-methylbutan-2-ol | 465 |
| 147D (Int-140b4 and Intermediate A4B) | 3-(4-((2S,5R)-5-(5-amino-7-methoxy-[1,2,4]triazolo[1,5-c]quinazolin-2-yl)-2-methylpiperidin-1-yl)-1H-pyrazol-1-yl)-2-methylbutan-2-ol, | 465 |
Examples 148A and 148B
The Preparation of the Compounds of Examples 148A and 148B
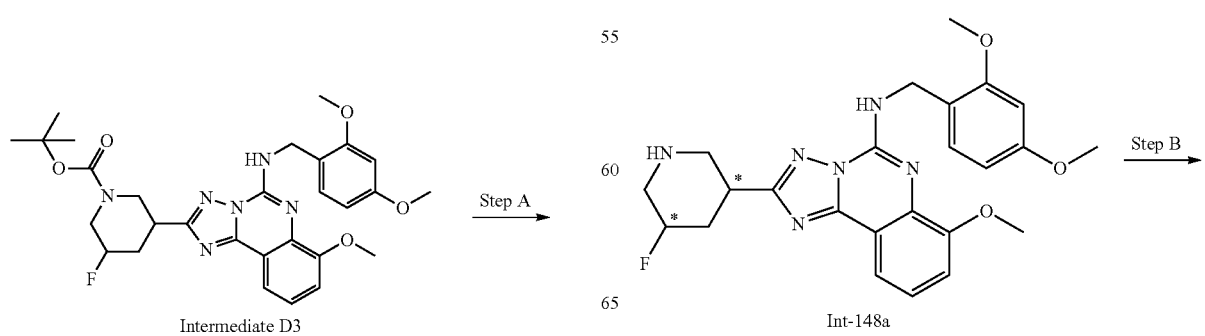

1H), 4.08 (s, 3H), 3.72 (dd, J=10.5, 3.6 Hz, 2H), 3.58-3.39 (m, 2H), 2.86 (t, J=11.5 Hz, 1H), 2.79 (dd, J=12.1, 3.9 Hz, 1H), 2.70 (td, J=10.4, 5.1 Hz, 1H), 2.03 (p, J=12.0, 11.5 Hz, 1H), 1.18-1.04 (m, 2H), 1.04-0.93 (m, 2H).

Example 149

The Preparation of the Compounds of Example 149

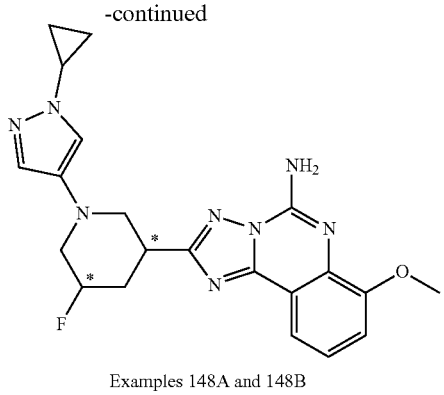

Examples 148A and 148B

Step A—Synthesis of Compound Int-148a N-(2,4-dimethoxybenzyl)-2-(5-fluoropiperidin-3-yl)-7-methoxy-[1,2,4]triazolo[1,5-c]quinazolin-5-amine To a solution of Intermediate D3 (490 mg, 0.865 mmol) in DCM (10 mL) was added 4 M HCl in dioxane (1.081 mL, 4.32 mmol). The resulting mixture was stirred at room temperature for 4 hours. Upon completion, the reaction mixture was concentrated under reduced pressure. The resulting residue was purified by preparative silica gel TLC plates with 6% 7 N $NH_3$ in MeOH/DCM as eluent to afford Int-148a LC/MS (ES, m/z)=467 [M+H]$^+$.

Step B—Synthesis of Examples 148A and 148B

To a reaction vial containing Int-148a (220 mg, 0.472 mmol) in THF (5.0 mL) was added 4-bromo-1-cyclopropyl-1H-pyrazole (221 mg, 1.179 mmol), followed by methanesulfonato(2-di-t-butylphosphino-2', 4',6'-biphenyl)(2'-amino-1,1'-biphenyl-2-yl)palladium(II) (t-BuXPhos Pd G3, 112 mg, 0.141 mmol) and sodium tert-butoxide (136 mg, 1.415 mmol). The resulting mixture was purged with $N_2$ for 10 minutes and heated at 90° C. for 24 hours. Upon completion, the reaction mixture was cooled and then concentrated. The resulting residue was purified by preparative silica gel plates with 4% 7 N $NH_3$ in MeOH/DCM as eluent to afford the DMB-protected intermediate.

The DMB-protected intermediate (210 mg, 0.367 mmol) was added to 2,2,2-trifluoroacetic acid (5.0 mL) and then heated at 60° C. for 1 hour. Upon completion, the reaction mixture was concentrated. The resulting residue was purified by preparative silica gel TLC plates with 5% 7-N ammonia in MeOH/DCM as eluent to provide racemic product. It was resolved by SFC using a chiral IA column (Chiral Technologies) with 60% MeOH as cosolvent to afford the title compounds Example 148A (Peak 1) and Example 148B (Peak 2).

148A: LC/MS (ES, m/z)=423 [M+H]$^+$. $^1$H NMR (400 MHz, Chloroform-d) δ 7.94 (dd, J=8.1, 1.2 Hz, 1H), 7.39 (t, J=8.0 Hz, 1H), 7.17 (d, J=7.1 Hz, 1H), 7.12 (d, J=0.7 Hz, 1H), 6.00 (s, 2H), 4.96 (tt, J=9.9, 4.7 Hz, 1H), 4.83 (dq, J=10.2, 5.1 Hz, 1H), 4.07 (s, 3H), 3.71 (d, J=11.0 Hz, 2H), 3.56-3.37 (m, 2H), 2.85 (t, J=11.5 Hz, 1H), 2.78 (d, J=7.3 Hz, 1H), 2.69 (td, J=10.4, 5.1 Hz, 1H), 2.02 (p, J=12.2, 1.6 Hz, 1H), 1.59 (s, 1H), 1.15-1.03 (m, 2H), 1.03-0.88 (m, 2H).

148B: LC/MS (ES, m/z)=423 [M+H]$^+$. $^1$H NMR (500 MHz. Chloroform-d) δ 7.95 (dd, J=8.1, 1.0 Hz, 1H), 7.39 (t, J=8.0 Hz, 1H), 7.18 (d, J=7.2 Hz, 1H), 7.13 (s, 1H), 6.17 (s, 2H), 4.96 (tt, J=10.1, 4.8 Hz, 1H), 4.86 (tt, J=10.0, 4.7 Hz,

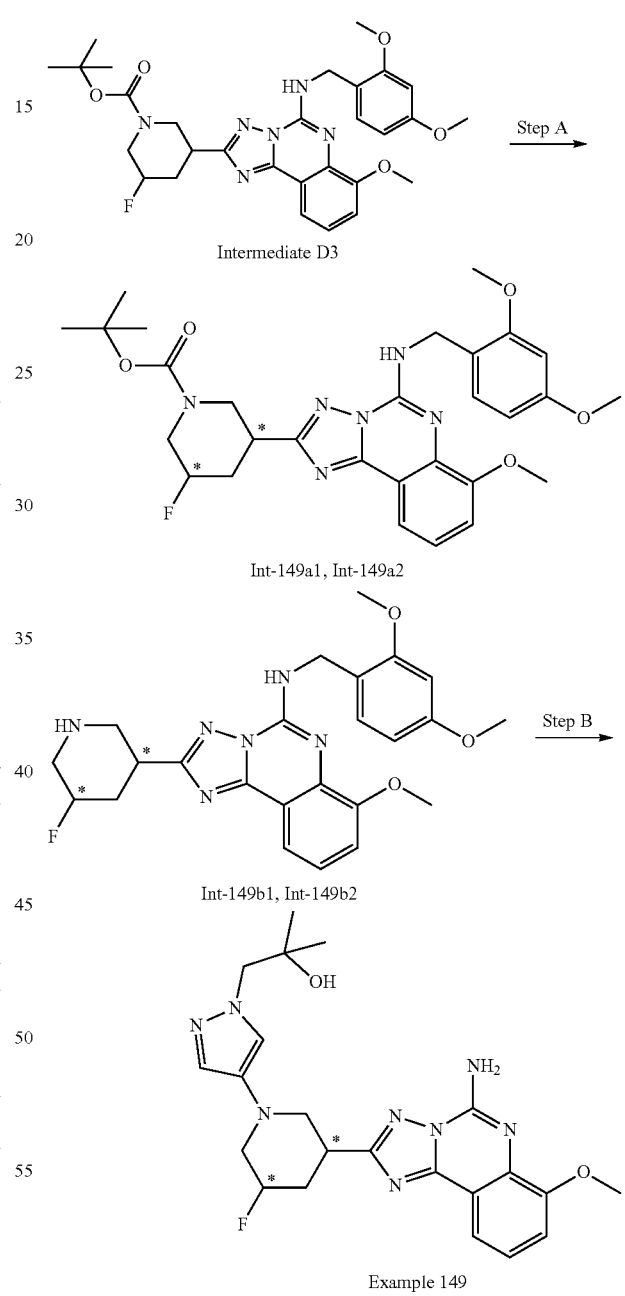

Step A—Synthesis of Compounds Int-149a1, Int-149a2

Intermediate D3 (2.0 g, 3.53 mmol) was resolved by SFC with a chiral AD-H column (Chiral Technologies) and 45%

IPA as cosolvent to afford the title compounds Int-149a1 (peak 1) and Int-149a2 (peak 2), LC/MS (ES, m/z)=567 [M+H]⁺.

Step B—Synthesis of Compounds Int-149b1

To the solution of Int-149a1 (710 mg, 1.25 mmol) in DCM (10 ml) was added 4 M HCl in dioxane (2.5 mL, 10.0 mmol). The reaction mixture was stirred at room temperature for 2 hours. Upon completion, the reaction mixture was concentrated under reduced pressure. The residue was purified by preparative silica gel TLC plates with 6% 7 N NH$_3$ in MeOH/DCM as eluent to afford Int-149b1. LC/MS (ES, m/z)=467 [M+H]⁺.

Step C—Synthesis of Example 149

To a reaction vial containing Int-149b1 (60 mg, 0.129 mmol) in THF (1 mL) was added 4-bromo-1-((1-((tetrahydro-2H-pyran-2-yl)oxy)cyclobutyl)methyl)-1H-pyrazole (64.9 mg, 0.206 mmol), followed by methanesulfonato (2-di-t-butylphosphino-2',4',6'-tri-isopropyl-1,1'-biphenyl)(2'-amino-1,1-biphenyl-2-yl)palladium(II) (t-BuXPhos Pd G3, 30.7 mg, 0.039 mmol) and sodium tert-butoxide (37.1 mg, 0.386 mmol). The resulting mixture was purged with N$_2$ for 10 minutes then heated at 90° C. for 24 hours. Upon completion, the reaction mixture was cooled down and concentrated. The resulting residue was purified by preparative silica gel TLC plates with 5% MeOH in DCM as eluent to afford the DMB-protected intermediate.

The above intermediate (89 mg, 0.127 mmol) was added to 2,2,2-trifluoroacetic acid (2.0 mL) and then heated at 60° C. for 1 hour. Upon completion, the reaction mixture was concentrated. The resulting residue was purified by preparative silica gel TLC plates with 60% 3:1 EtOAc:EtOH in hexane as eluent to provide Example 149. LC/MS (ES, m/z)=455 [M+H]⁺. ¹H NMR (400 MHz, DMSO-d⁶) δ 7.82 (s, 1H), 7.73 (d, J=8.0 Hz, 1H), 7.35 (s, 1H), 7.33-7.24 (m, 2H), 7.21 (d, J=8.0 Hz, 1H), 4.98 (s, 1H), 4.86 (s, 1H), 4.03 (s, 2H), 3.89 (s, 3H), 3.72 (s, 1H), 3.64 (d, J=12.0 Hz, 1H), 3.38 (s, 1H), 3.15 (d, J=6.7 Hz, 2H), 2.73 (t, J=11.4 Hz, 1H), 2.65 (s, 1H), 2.56 (td, J=10.7, 5.3 Hz, 1H), 1.91 (dt, J=22.6, 11.0 Hz, 1H), 1.01 (s, 6H).

The example compounds of the invention shown in Table 7 were prepared using a procedure similar to the procedure used above, substituting the appropriate starting aryl halide and Int-149b1.

TABLE 7

| Example | Structure Name | Observed m/z [M + H]⁺ |
|---|---|---|
| 150 | 1-((4-(3-(5-amino-7-methoxy-[1,2,4]triazolo[1,5-c]quinazolin-2-yl)-5-fluoropiperidin-1-yl)-1H-pyrazol-1-yl)methyl)cyclobutan-1-ol | 467 |
| 151 | 1-(4-(3-(5-amino-7-methoxy-[1,2,4]triazolo[1,5-c]quinazolin-2-yl)-5-fluoropiperidin-1-yl)-3-methyl-1H-pyrazol-1-yl)-2-methylpropan-2-ol | 469 |
| 152 | 1-(4-(3-(5-amino-7-methoxy-[1,2,4]triazolo[1,5-c]quinazolin-2-yl)-5-fluoropiperidin-1-yl)-5-methyl-1H-pyrazol-1-yl)-2-methylpropan-2-ol | 469 |

Examples 153A and 153B

The Preparation of the Compounds of Examples 153A and 153B

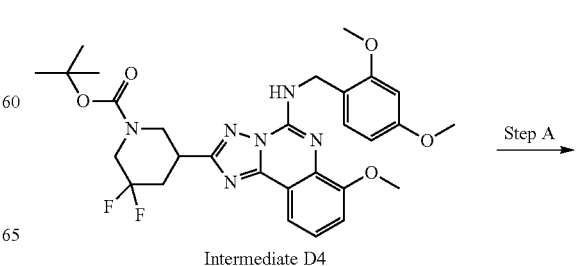

Intermediate D4

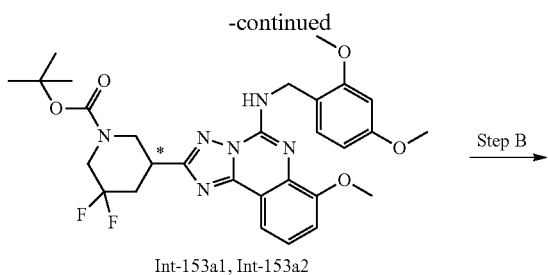

Int-153a1, Int-153a2

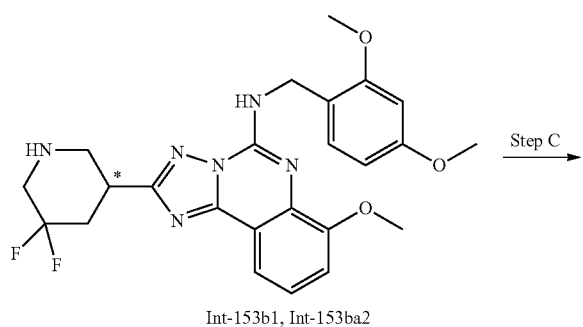

Int-153b1, Int-153ba2

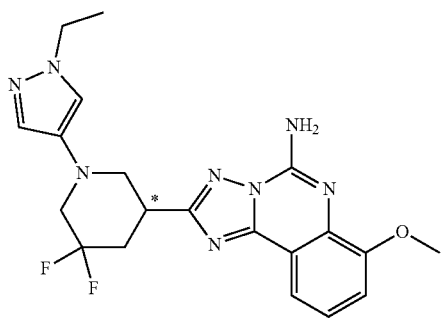

Examples 153A and 153B

Step A—Synthesis of Compounds Int-153a1, Int-153a2. tert-butyl (R)-5-(5-((2,4-dimethoxybenzyl)amino)-7-methoxy-[1,2,4]triazolo[1,5-c]quinazolin-2-yl)-3,3-difluoropiperidine-1-carboxylate and tert-butyl (S)-5-(5-((2,4-dimethoxybenzyl)amino)-7-methoxy-[1,2,4]triazolo[1,5-c]quinazolin-2-yl)-3,3-difluoropiperidine-1-carboxylate Intermediate D4 (1.2 g, 2.03 mmol) was resolved by SFC with a chiral AD-H column and 45% IPA with 0.2% DIPA as eluent to afford the title compounds Int-153a1 (Peak 1) and Int-153a2 (Peak 2). LC/MS (ES, m/z)=585 [M+H]$^+$.

Step B—Synthesis of Compound Int-153b1 and Int-153b2. (S)-2-(5,5-difluoropiperidin-3-yl)-N-(2,4-dimethoxybenzyl)-7-methoxy-[1,2,4]triazolo[1,5-c]quinazolin-5-amine and (R)-2-(5,5-difluoropiperidin-3-yl)-N-(2,4-dimethoxybenzyl)-7-methoxy-[1,2,4]triazolo[1,5-c]quinazolin-5-amine To a solution of Int-153a1 (417 mg, 0.713 mmol) in DCM (7 L) was added 4 M HCl in dioxane (1.248 mL, 4.99 mmol). The reaction mixture was stirred at room temperature under nitrogen for 2 hours. Upon completion, the reaction mixture was concentrated, and the resulting residue was purified by preparative silica gel TLC plates with 3% 7 N $NH_3$ in MeOH/DCM as eluent to afford Int-153b1. LC/MS (ES, m/z)=485 [M+H]$^+$.

Using a manner similar to that outlined for the conversion of Int-153a1 to Int-153b1, Int-153a2 was converted into Int-153b2. LC/MS (ES, m/z)=485 [M+H]$^+$.

Step C—Synthesis of Examples 153A and 153B. (S)—N-(2,4-dimethoxybenzyl)-2-(1-(1-ethyl-1H-pyrazol-4-yl)-5,5-difluoropiperidin-3-yl)-7-methoxy-[1,2,4]triazolo[1,5-c]quinazolin-5-amine and (R)—N-(2,4-dimethoxybenzyl)-2-(1-(1-ethyl-1H-pyrazol-4-yl)-5,5-difluoropiperidin-3-yl)-7-methoxy-[1,2,4]triazolo[1,5-c]quinazolin-5-amine To a reaction vial containing Int-153b1 (40 mg, 0.083 mmol) in THF (0.9 mL) was added 4-bromo-1-ethyl-1H-pyrazole (36.1 mg, 0.206 mmol), followed by methanesulfonato(2-di-t-butylphosphino-2',4',6'-tri-i-propyl-1,1'-biphenyl)(2'-amino-1,1'-biphenyl-2-yl)palladium(II) (t-BuXPhos Pd G3, 19.67 mg, 0.025 mmol) and sodium tert-butoxide (23.8 mg, 0.248 mmol). The resulting mixture was purged with $N_2$ for 10 minutes, then heated at 100° C. for 12 hours. Upon completion, the reaction mixture was concentrated and the resulting residue was purified by preparative silica gel plate with 4% MeOH in DCM as eluent to afford the DMB-protected intermediate.

The above intermediate (35 mg, 0.060 mmol) was dissolved in 2,2,2-trifluoroacetic acid (1.0 mL) and heated at 60° C. for 1 hour. Upon completion, the reaction mixture was concentrated and the resulting residue was purified by preparative silica gel TLC plates with 3% 7N ammonia in MeOH/DCM as eluent to provide Example 153A.

Using a method similar to that described for the conversion of Int-153b1 to Example 153A, Int-153b2 was converted to Example 153B.

153A: LC/MS (ES, m/z)=429 [M+H]$^+$. $^1$H NMR (400 MHz, DMSO-d$^6$) δ 7.85 (s, 2H), 7.73 (dd, J=7.9, 1.2 Hz, 1H), 7.47 (s, 1H), 7.30 (t, J=7.9 Hz, 1H), 7.21 (d, J=7.1 Hz, 1H), 3.99 (q, J=7.3 Hz, 2H), 3.89 (s, 3H), 3.73 (d, J=11.6 Hz, 1H), 3.69-3.42 (m, 2H), 3.15 (d, J=5.2 Hz, 1H), 3.06-2.79 (m, 1H), 2.65 (s, 1H), 2.46-2.21 (m, 2H), 1.31 (t, J=7.3 Hz, 3H).

153B: LC/MS (ES, m/z)=429 [M+H]$^+$. $^1$H NMR (400 MHz, Methanol-d4) δ 7.92 (dd, J=8.0, 1.2 Hz, 1H), 7.49 (t, J=8.0 Hz, 1H), 7.44 (d, J=0.8 Hz, 1H), 7.39 (d, J=7.0 Hz, 1H), 7.34 (d, J=0.9 Hz, 1H), 4.26-4.08 (m, 1H), 4.07 (s, 3H), 3.88 (d, J=12.4 Hz, 1H), 3.67 (d, J=8.3 Hz, 1H), 3.00-3.04 (m, 1H), 2.97 (t, J=11.5 Hz, 1H), 2.74 (m, 1H), 2.53-2.2.9 (m, 1H), 1.42 (t, J=7.3 Hz, 3H).

The example compounds of the invention shown in Table 8 were prepared using a procedure similar to the procedure described above for the synthesis of Examples 153A and 153B, substituting the appropriate starting aryl halide and amine coupling partner. The intermediate each example is derived from is noted in parentheses below the example number.

TABLE 8

| Example | Structure Name | Observed m/z [M + H]+ |
|---|---|---|
| 154A (Int-153b1) 154B (Int-153b2) | 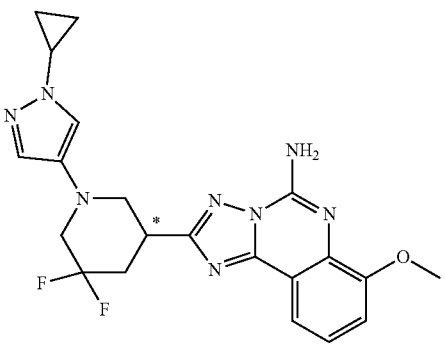 [SMILES: COc1cccc2c1nc(N)n1nc(C3CN(c4cnn(C5CC5)c4)CC(F)(F)C3)nc21]<br>(S)-2-(1-(1-cyclopropyl-1H-pyrazol-4-yl)-5,5-difluoropiperidin-3-yl)-7-methoxy-[1,2,4]triazolo[1,5-c]quinazolin-5-amine,<br>(R)-2-(1-(1-cyclopropyl-1H-pyrazol-4-yl)-5,5-difluoropiperidin-3-yl)-7-methoxy-[1,2,4]triazolo[1,5-c]quinazolin-5-amine | 441 |
| 155A (Int-153b1) 155B (Int-153b2) | 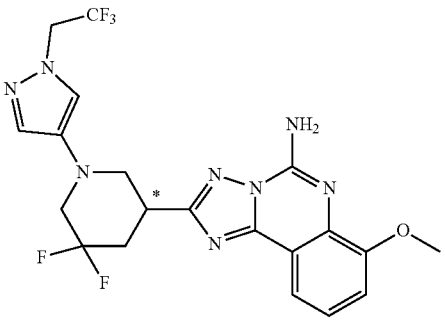 [SMILES: COc1cccc2c1nc(N)n1nc(C3CN(c4cnn(CC(F)(F)F)c4)CC(F)(F)C3)nc21]<br>(S)-2-(5,5-difluoro-1-(1-(2,2,2-trifluoroethyl)-1H-pyrazol-4-yl)piperidin-3-yl)-7-methoxy-[1,2,4]triazolo[1,5-c]quinazolin-5-amine,<br>(R)-2-(5,5-difluoro-1-(1-(2,2,2-trifluoroethyl)-1H-pyrazol-4-yl)piperidin-3-yl)-7-methoxy-[1,2,4]triazolo[1,5-c]quinazolin-5-amine, | 483 |
| 156B (Int-153b2) | 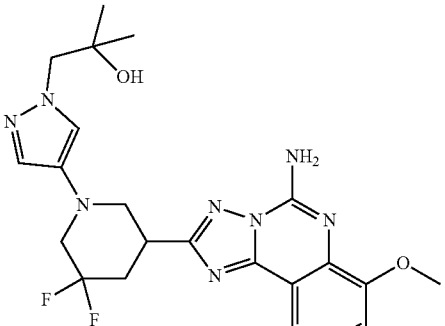<br>(R or S)-1-(4-(5-(5-amino-7-methoxy-[1,2,4]triazolo[1,5-c]quinazolin-2-yl)-3,3-difluoropiperidin-1-yl)-1H-pyrazol-1-yl)-2-methylpropan-2-ol | 473 |

TABLE 8-continued

| Example | Structure Name | Observed m/z [M + H]+ |
|---|---|---|
| 157B (Int-153b2) | (R or S)-1-((4-(5-(5-amino-7-methoxy-[1,2,4]triazolo[1,5-c]quinazolin-2-yl)-3,3-difluoropiperidin-1-yl)-1H-pyrazol-1-yl)methyl)cyclobutan-1-ol | 485 |
| 158B (Int-153b2) | (R or S)1-(4-(5-(5-amino-7-methoxy-[1,2,4]triazolo[1,5-c]quinazolin-2-yl)-3,3-difluoropiperidin-1-yl)-3-methyl-1H-pyrazol-1-yl)-2-methylpropan-2-ol | 487 |
| 159B (Int-153b2) | (R or S)-1-(4-(5-(5-amino-7-methoxy-[1,2,4]triazolo[1,5-c]quinazolin-2-yl)-3,3-difluoropiperidin-1-yl)-5-methyl-1H-pyrazol-1-yl)-2-methylpropan-2-ol | 487 |

Example 160

The Preparation of the Compound of Example 160

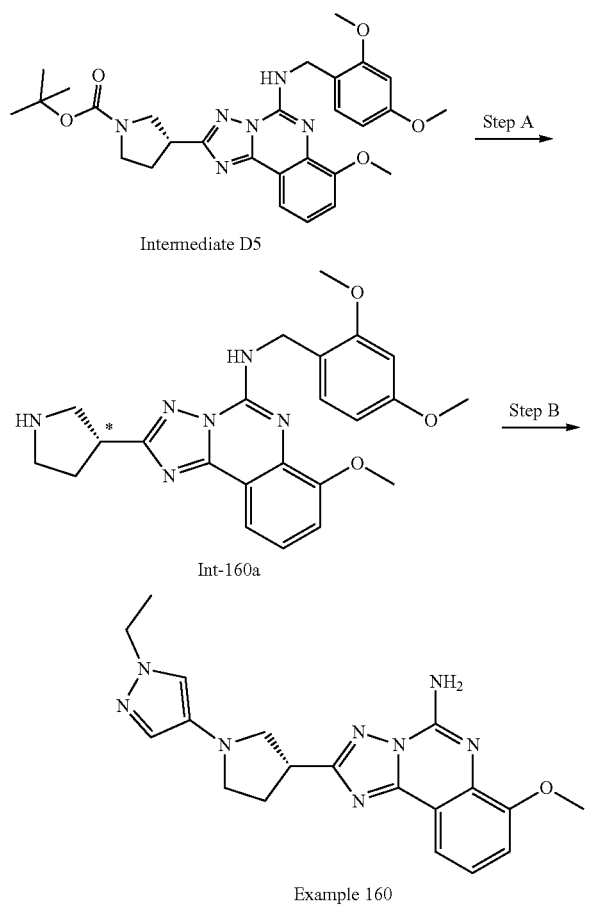

Step A—Synthesis of Compound Int-160a (R)—N-(2,4-dimethoxybenzyl)-7-methoxy-2-(pyrrolidin-3-yl)-[1,2,4]triazolo[1,5-c]quinazolin-5-amine To a solution of Intermediate D5 (2.1 g, 3.93 mmol) in DCM (40 mL) was added 4 M HCl in dioxane (5.0 mL, 20.0 mmol). The reaction mixture was stirred at room temperature under nitrogen for 2 hours. Upon completion, the mixture was concentrated. The resulting residue was purified by preparative silica gel TLC plates with 3% 7 N $NH_3$ in MeOH/DCM as eluent to afford Int-160a LC/MS (ES, m/z)=435 $[M+H]^+$.

Step B—Synthesis of Compound 160. (R)-2-(1-(1-ethyl-1H-pyrazol-4-yl)pyrrolidin-3-yl)-7-methoxy-[1,2,4]triazolo[1,5-c]quinazolin-5-amine To a reaction vial containing Int-160a (50 mg, 0.115 mmol) in THF (1 mL) was added 4-bromo-1-ethyl-1H-pyrazole (60.4 mg, 0.345 mmol), followed by methanesulfonato(2-di-t-butylphosphino-2',4',6'-tri-i-propyl-1,1'-biphenyl)(2'-amino-1,1'-biphenyl-2-yl)palladium(II) (t-BuXPhos Pd G3, 27.4 mg, 0.035 mmol) and sodium tert-butoxide (66.4 mg, 0.690 mmol). The resulting mixture was purged with $N_2$ for 10 minutes and heated at 100° C. for 12 hours. Upon completion, the reaction mixture was cooled and then concentrated. The resulting residue was purified by preparative silica gel plates with 3% MeOH in DCM as eluent to afford the DMB-protected intermediate.

The above intermediate was dissolved in 2,2,2-trifluoroacetic acid (1.0 mL) and heated at 60° C. for 1 hour. Upon completion, the reaction mixture was concentrated and the resulting residue was purified by preparative silica gel TLC plates with 3% 7 N ammonia in MeOH/DCM as eluent to provide Example 160. LC/MS (ES, m/z)=379 $[M+H]^+$. $^1$H NMR (500 MHz, Methanol-$d^4$) δ 7.93 (dd, J=8.0, 1.0 Hz, 1H), 7.61 (s, 1H), 7.51 (t, J=8.1 Hz, 1H), 7.45 (s, 1H), 7.43 (d, J=7.4 Hz, 1H), 4.16 (q, J=7.3 Hz, 2H), 4.09 (s, 3H), 3.86 (dd, J=7.4, 1.7 Hz, 2H), 3.69-3.59 (m, 1H), 3.59-3.51 (m, 1H), 2.73-2.56 (m, 3H), 1.45 (t, J=7.3 Hz, 3H).

The example compounds of the invention shown in Table 9 were prepared using a procedure similar to the procedure described for the synthesis of Example 160, substituting the appropriate starting aryl halide and Int-160a.

TABLE 9

| Example | Structure Name | Observed m/z [M + H]$^+$ |
|---|---|---|
| 161 | ![structure] (R)-2-(1-(1-cyclopropyl-1H-pyrazol-4-yl)pyrrolidin-3-yl)-7-methoxy-[1,2,4]triazolo[1,5-c]quinazolin-5-amine | 391 |

TABLE 9-continued
| Example | Structure Name | Observed m/z [M + H]+ |
|---|---|---|
| 162 | (R)-2-(1-(1-(cyclopropylmethyl)-1H-pyrazol-4-yl)pyrrolidin-3-yl)-7-methoxy[1,2,4]triazolo[1,5-c]quinazolin-5-amine | 405 |
| 163 | (R)-2-(1-(1-(tert-butyl)-1H-pyrazol-4-yl)pyrrolidin-3-yl)-7-methoxy-[1,2,4]triazolo[1,5-c]quinazolin-5-amine | 407 |
| 164 | (R)-7-methoxy-2-(1-(1-(2,2,2-trifluoroethyl)-1H-pyrazol-4-yl)pyrrolidin-3-yl)-[1,2,4]triazolo[1,5-c]quinazolin-5-amine | 433 |
Example 165
The Preparation of the Compound of Example 165
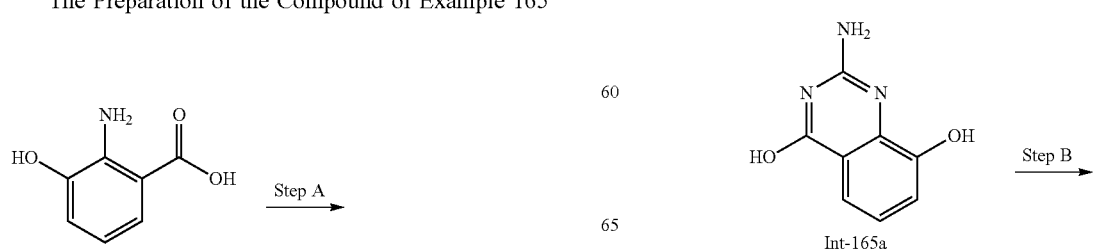

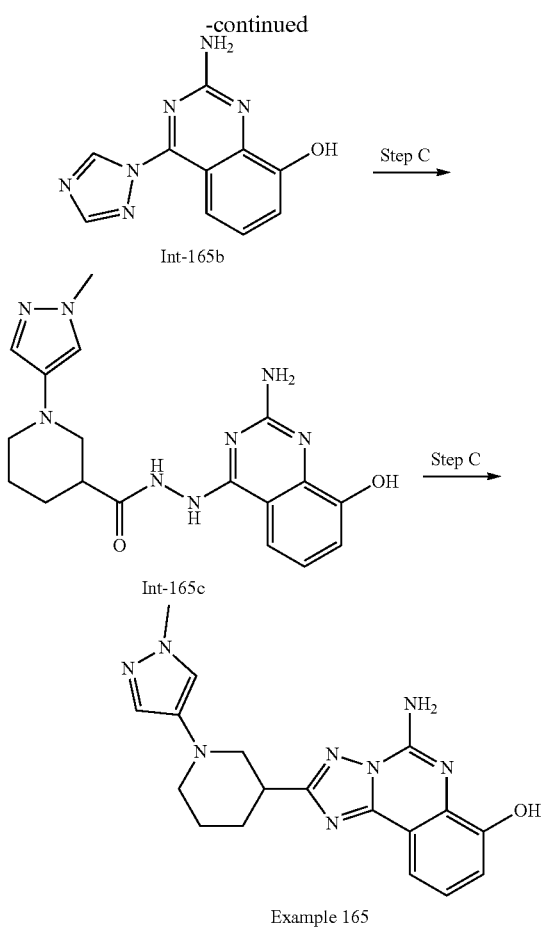

Example 165

Step A—Synthesis of Compound Int-165a 2-aminoquinazoline-4,8-diol

To a stirred suspension of 2-amino-5-fluoro-3-methoxybenzoic acid (459 mg, 3 mmol) in ethanol (3000 μL) was added cyanamide (315 mg, 7.5 mmol) and 6M aqueous hydrochloric acid (650 μL, 3.9 mmol). The reaction mixture was heated to reflux for 16 hours. The reaction mixture was cooled. The formed precipitate was collected by filtration and dried under high vacuum to afford the title compound Int-165a LC/MS (ES, m/z)=178 [M+H]$^+$.

Step B—Synthesis of Compound Int-165b. 2-amino-4-(1H-1,2,4-triazol-1-yl)quinazolin-8-ol A solution of POCl$_{23}$ (70 μL, 0.75 mmol) in acetonitrile (1.0 mL) was added to a stirred, room temperature mixture of 1,2,4-triazole (104 mg, 1.5 mmol), 2-amino-7-hydroxyquinazolin-4-ol (88 mg, 0.5 mmol) and DIEA (131 μL, 0.75 mmol) in acetonitrile (1.0 mL). The resulting mixture was stirred at 40° C. for 3 hours and then room temperature for 16 hours. The reaction mixture was filtered through Celite® (diatomaceous earth), washed through with acetonitrile and diethyl ether to afford crude product Int-165b. LC/MS (ES, m/z)=229 [M+H]$^+$.

Step C—Synthesis of Compound Int-165c. (R or S)—N'-(2-amino-8-hydroxyquinazolin-4-yl)-1-(1-methyl-1H-pyrazol-4-yl)piperidine-3-carbohydrazide A reaction vial was charged with Int-165b (61 mg, 0.267 mmol), Intermediate B14 (898 mg, 0.4 mmol), DMA (1780 μL) and DIEA (233 μL, 1.335 mmol). The vial was capped and the contents were heated at 80° C. for 4 hours. Upon completion, the mixture was evaporated under reduced pressure to afford the title compound Int-165c. LC/MS (ES, m/z)=383 [M+H]$^+$.

Step D—Synthesis of Example 165. (R or S)-5-amino-2-(1-(1-methyl-1H-pyrazol-4-yl)piperidin-3-yl)-[1,2,4]triazolo[1,5-c]quinazolin-7-ol N,O-bis(trimethylsilyl)acetamide (2 mL, 8.18 mmol) was added to Int-165c (102 mg, 0.267 mmol) and the mixture was stirred at 120° C. for 2 hours. Upon completion, the volatiles were removed by vacuum and the resulting residue taken up in DMSO (1.5 mL), filtered and purified by reverse phase HPLC with C18 column and 0-100% MeCN/water with 0.1% TPA modifier as eluent to provide the title compound Example 165. LC/MS (ES, m/z)=365 [M+H]$^+$. $^1$H NMR (600 MHz, DMSO-d$^6$) δ 8.12-7.90 (m, 2H), 7.65 (dd, J=7.9, 1.2 Hz, 1H), 7.64-7.59 (m, 1H), 7.45-7.39 (m, 1H), 7.25 (t, J=7.9 Hz, 1H), 7.16 (dd, J=7.8, 1.2 Hz, 1H), 3.78 (s, 3H), 3.77-3.73 (m, 1H), 3.50-3.44 (m, 1H), 3.43-3.36 (m, 1H), 3.24-3.13 (m, 1H), 2.98-2.80 (m, 1H), 2.25-2.17 (m, 1H), 1.96-1.92 (m, 1H), 1.91-1.79 (m, 2H).

The example compounds of the invention shown in Table 10 were prepared by a procedure similar to the procedure described above, substituting the appropriate benzoic acid in step A.

TABLE 10

| Example | Structure Name | Observed m/z [M + H]$^+$ |
|---|---|---|
| 166 | (R or S)-7-fluoro-8-methoxy-2-(1-(1-methyl-1H-pyrazol-4-yl)piperidin-3-yl)-[1,2,4]triazolo[1,5-c]quinazolin-5-amine | 397 |
| 167 | (R or S)-7,8-dimethyl-2-(1-(1-methyl-1H-pyrazol-4-yl)piperidin-3-yl)-[1,2,4]triazolo[1,5-c]quinazolin-5-amine | 377 |

TABLE 10-continued

| Example | Structure Name | Observed m/z [M + H]+ |
|---|---|---|
| 168 | (R or S)-8-fluoro-2-(1-(1-methyl-1H-pyrazol-4-yl)piperidin-3-yl)-[1,2,4]triazolo[1,5-c]quinazolin-5-amine | 367 |
| 169 | (R or S)-7, 10-dichloro-2-(1-(1-methyl-1H-pyrazol-4-yl)piperidin-3-yl)-[1,2,4]triazolo[1,5-c]quinazolin-5-amine | 417 |
| 170 | (R or S)-2-(1-(1-methyl-1H-pyrazol-4-yl)piperidin-3-yl)-10-(trifluoromethyl)-[1,2,4]triazolo[1,5-c]quinazolin-5-amine | 417 |
| 171 | (R or S)-7-methyl-2-(1-(1-methyl-1H-pyrazol-4-yl)piperidin-3-yl)-[1,2,4]triazolo[1,5-c]quinazolin-5-amine | 363 |
| 172 | (R or S)-7,10-difluoro-2-(1-(1-methyl-1H-pyrazol-4-yl)piperidin-3-yl)-[1,2,4]triazolo[1,5-c]quinazolin-5-amine | 385 |
| 173 | (R or S)-8-chloro-7-methoxy-2-(1-(1-methyl-1H-pyrazol-4-yl)piperidin-3-yl)-[1,2,4]triazolo[1,5-c]quinazolin-5-amine | 413 |
| 174 | (R or S)-2-(1-(1-methyl-1H-pyrazol-4-yl)piperidin-3-yl)-8-(trifluoromethyl)-[1,2,4]triazolo[1,5-c]quinazolin-5-amine | 417 |

Example 179

The Preparation of the Compound of Example 179

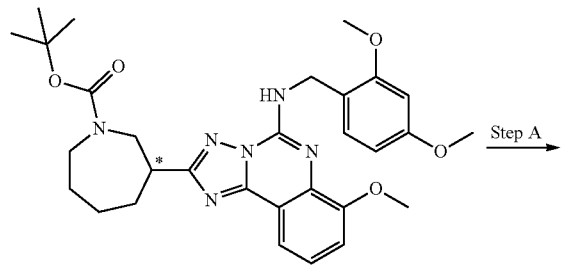

Intermediate D7

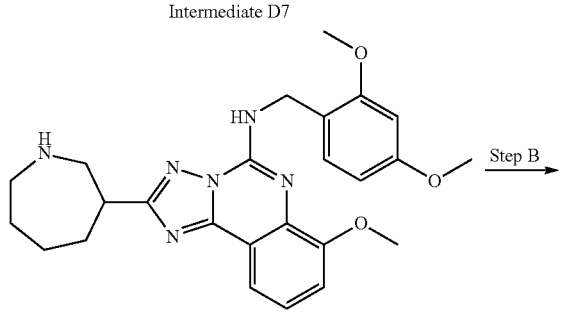

Int-175a

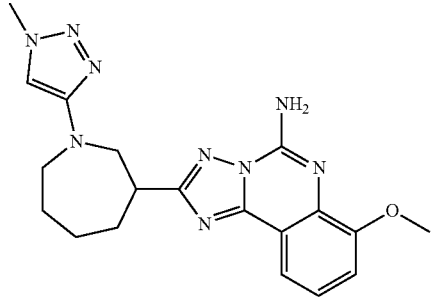

Example 175

Step A—Synthesis of Compound Int-175a 2-(azepan-3-yl)-N-(2,4-dimethoxybenzyl)-7-methoxy-[1,2,4]triazolo[1,5-c]quinazolin-5-amine A solution of Intermediate D7 (113 mg, 0.201 mmol) in formic acid (2311 μL, 60.2 mmol) was stirred at room temperature overnight. Upon completion, the reaction mixture was concentrated. The residue was purified by silica gel column chromatography with 3% 7 N ammonia in MeOH//DCM as eluent to provide Int-175a LC/MS (ES, m/z)=463 [M+H]$^+$.

Step B—Synthesis of Example 175. 7-methoxy-2-(1-(1-methyl-1-1,2,3-triazol-4-yl)azepan-3-yl-[1,2,4]triazolo[1,5-c]quinazolin-5-amine A 5 mL microwave vial equipped with a stir bar was charged with Int-180a (50 mg, 0.108 mmol), t-BuXPhos Pd G3 (38.6 mg, 0.043 mmol) and sodium tert-butoxide (41.6 mg, 0.432 mmol) under nitrogen. 4-bromo-1-methyl-1H-1,2,3-triazole (35.0 mg, 0.216 mmol) in THF (1.4 mL) was then added. The resulting mixture was sparged with nitrogen for 10 minutes. The vial was then sealed with a cap and stirred at 90° C. for 16 hours. Upon completion, the reaction was cooled to room temperature and filtered. The filtrate was concentrated. To the resulting residue was added TFA (0.5 mL). The mixture was then stirred at 50° C. for 2 hours. The mixture was then cooled to room temperature, and the solvents were evaporated. The residue was purified by reversed phase HPLC with C18 column and 0-100% MeCN/H$_2$O with 0.1% TFA as eluent, yielding title compound Example 175. LC/MS (ES, m/z): 394 [M+H]$^+$. $^1$H NMR (499 MHz, DMSO-d$^6$) δ 7.98 (s, 2H), 7.78 (d, J=7.9 Hz, 1H), 7.39-7.30 (m, 2H), 7.26 (d, J=8.0 Hz, 1H), 4.12 (dd, J=14.2, 4.0 Hz, 1H), 3.93 (s, 6H), 3.63-3.53 (m, 1H), 3.50-3.44 (m, 1H), 3.35 (dt, J=13.6, 7.0 Hz, 1H), 2.13-1.78 (m, 5H), 1.72 (m, 1H), 1.55-1.33 (m, 1H).

Example 176

The Preparation of the Compound of Example 176

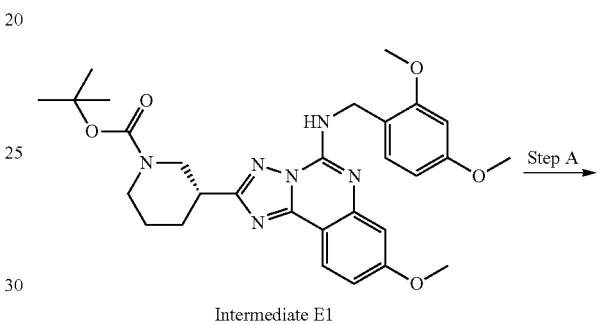

Intermediate E1

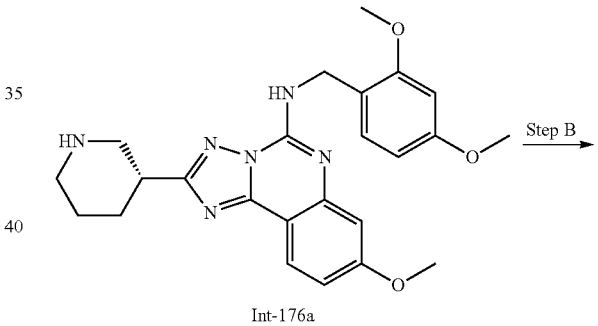

Int-176a

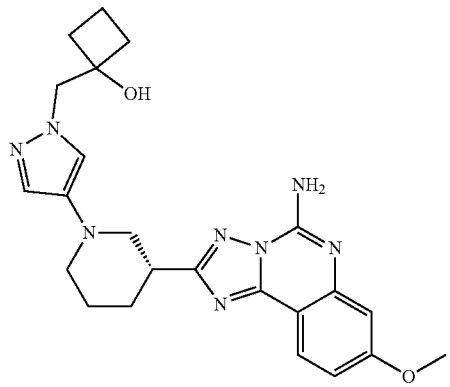

Example 176

Step A—Synthesis of Compound Int-176a (R)—N-(2,4-dimethoxybenzyl-8-methoxy-2-(piperidin-3-yl)-[1,2,4]triazolo[1,5-c]quinazolin-5-amine A solution of Intermediate E1 (2.2 g, 4.01 mmol) in DCE (4 mL) was added TFA (2.0 mL, 26.0 mmol). The resulting mixture was stirred at room temperature for 4 hours, then concentrated. The residue was then purified by silica gel chromatography with 3% 7 N ammonia in MeOH/DCM as eluent to provide Int-176a LC/MS (ES, m/z)=449 [M+H]⁺.

Step B—Synthesis of Example 176. (R)-1-((4(4-(3-(5-amino-8-methoxy-[1,2,4]triazolo[1,5-c]quinazolin-2-yl)piperidin-1-yl)-1H-pyrazol-1-yl)methyl)cyclobutan-1-ol A 5 mL microwave vial equipped with a stir bar was charged with Int-176a (80 mg, 0.178 mmol), t-BuXPhos Pd G3 (42.5 mg, 0.054 mmol) and sodium tert-butoxide (51.4 mg, 0.535 mmol) under nitrogen. 4-bromo-1-((1-((tetrahydro-2H-pyran-2)oxy)cyclobutyl)methyl)-1H-pyrazole (61.8 mg, 0.196 mmol) in THF (1.4 mL) was then added. The resulting mixture was sparged with nitrogen for 10 minutes. The vial was then sealed with a cap and stirred at 90° C. for 16 hours. Upon completion, the reaction mixture was cooled to room temperature and filtered. The filtrate was concentrated. To the resulting residue was added TFA (0.5 mL) and the mixture was then stirred at 50° C. for 2 hours. The mixture was cooled to room temperature, and the solvents were evaporated. The resulting residue was purified by reversed phase HPLC with C 18 column and 0-100% MeCN/H₂O with 0.1% TFA as eluent to provide the title compound Example 176. LC/MS (ES, m/z)=563 [M+H]⁺. ¹H NMR (500 MHz, Methanol-d⁴) δ 8.23 (d, J=9.4 Hz, 1H), 8.06 (s, 1H), 7.80 (s, 1H), 7.16 (s, 1H), 7.15 (s, 1H), 4.30 (s, 2H), 4.13 (d, J=10.3 Hz, 1H), 3.98 (s, 3H), 3.90-3.72 (m, 2H), 3.72-3.60 (m, 1H), 3.57-3.41 (m, 1H), 2.53-2.34 (m, 1H), 2.33-2.00 (m, 7H), 1.80 (q, J=10.0 Hz, 1H), 1.65 (dq, J=18.2, 9.0 Hz, 1H).

The example compounds of the invention shown in Table 11 were prepared using a procedure similar to the procedure described for the synthesis of Example 176, substituting the appropriate starting aryl halide and Int-176a.

TABLE 11

| Example | Structure Name | Observed m/z, [M + H]⁺ |
|---|---|---|
| 177 | 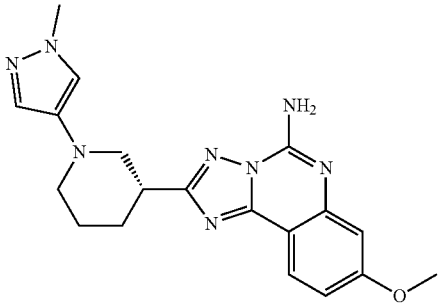 [SMILES: COc1ccc2c(c1)nc(N)n1nc([C@@H]3CCCN(c4cnn(C)c4)C3)nc21]<br>(R)-8-methoxy-2-(1-(1-methyl-1H-pyrazol-4-yl)piperidin-3-yl)-[1,2,4]triazolo[1,5-c]quinazolin-5-amine | 379 |
| 178 | 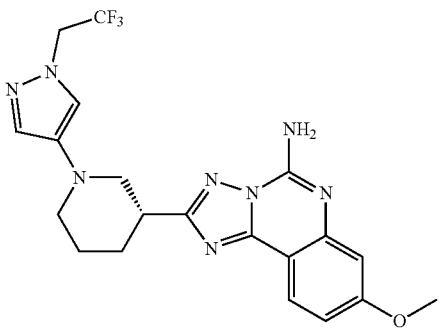 [SMILES: COc1ccc2c(c1)nc(N)n1nc([C@@H]3CCCN(c4cnn(CC(F)(F)F)c4)C3)nc21]<br>(R)-8-methoxy-2-(1-(1-(2,2,2-trifluoroethyl)-1H-pyrazol-4-yl)piperidin-3-yl)-[1,2,4]triazolo[1,5-c]quinazolin-5-amine | 447 |

TABLE 11-continued
| Example | Structure Name | Observed m/z, [M + H]+ |
|---|---|---|
| 179 | 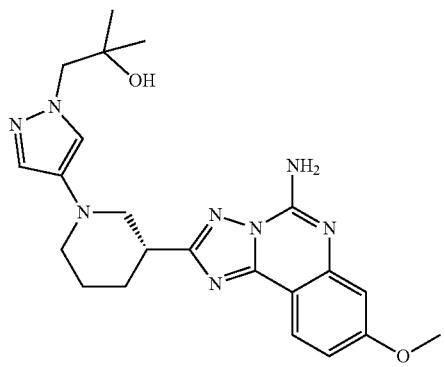 [SMILES: COc1ccc2c(c1)nc(N)n1nc([C@@H]3CCCN(c4cnn(CC(C)(C)O)c4)C3)nc21]<br>(R)-1-(4-(3-(5-amino-8-methoxy-[1,2,4]triazolo[1,5-c]quinazolin-2-yl)piperidin-1-yl)-1H-pyrazol-1-yl)-2-methylpropan-2-ol | 437 |
| 180 | 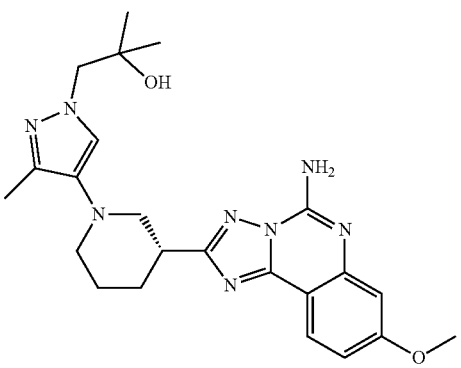<br>(R)-1-(4-(3-(5-amino-8-methoxy-[1,2,4]triazolo[1,5-c]quinazolin-2-yl)piperidin-1-yl)-3-methyl-1H-pyrazol-1-yl)-2-methylpropan-2-ol | 451 |
| 181 | 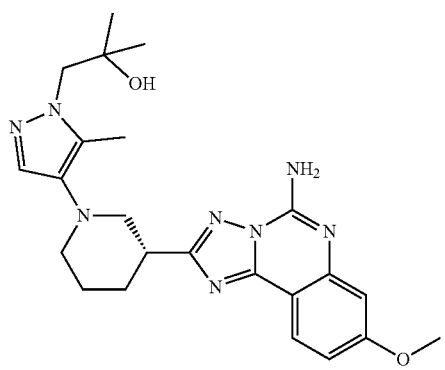 [SMILES: COc1ccc2c(c1)nc(N)n1nc([C@@H]3CCCN(c4cnn(CC(C)(C)O)c4C)C3)nc21]<br>(R)-1-(4-(3-(5-amino-8-methoxy-[1,2,4]triazolo[1,5-c]quinazolin-2-yl)piperidin-1-yl)-5-methyl-1H-pyrazol-1-yl)-2-methylpropan-2-ol | 451 |

TABLE 11-continued

| Example | Structure Name | Observed m/z, [M + H]+ |
|---|---|---|
| 182 | (1S,3s)-3-(4-((R)-3-(5-amino-8-methoxy-[1,2,4]-triazolo[1,5-c]quinazolin-2-yl)piperidin-1-yl)-1H-pyrazol-1-yl)-1-methylcyclobutan-1-ol | 449 |
| 183 | (R)-2-(1-(1-((3-(fluoromethyl)oxetan-3-yl)methyl)-1H-pyrazol-4-yl)piperidin-3-yl)-8-methoxy-[1,2,4]triazolo[1,5-c]quinazolin-5-amine | 467 |
| 184 | (R)-2-(1-(1-cyclopropyl-1H-pyrazol-4-yl)piperidin-3-yl)-8-methoxy-[1,2,4]triazolo[1,5-c]quinazolin-5-amine | 405 |

TABLE 11-continued

| Example | Structure Name | Observed m/z, [M + H]+ |
|---|---|---|
| 185A (peak 1) 185B (peak 2) | 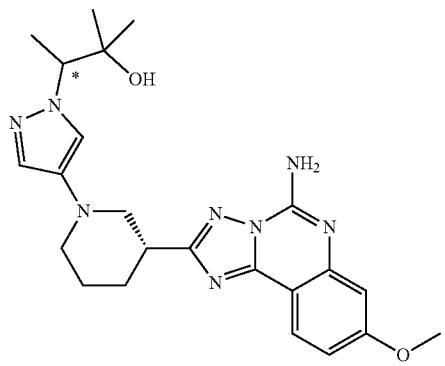 [SMILES: COc1ccc2c(c1)nc(N)n1nc([C@@H]3CCCN(c4cnn(C(C)C(C)(C)O)c4)C3)nc21]<br>(R)-3-(4-((R)-3-(5-amino-8-methoxy-[1,2,4]triazolo[1,5-c]quinazolin-2-yl)piperidin-1-yl)-1H-pyrazol-1-yl-2-methylbutan-2-ol,<br>(S)-3-(4-((R)-3-(5-amino-8-methoxy-[1,2,4]triazolo[1,5-c]quinazolin-2-yl)piperidin-1-yl)-1H-pyrazol-1-yl)-2-methylbutan-2-ol<br>DMB-protected precursor was resolved by SFC with chiral AD-H 21 × 250 column and 45% IPA with 0.2% DIPA as cosolvent | 451 |
| 186A (peak 1) 186B (peak 2) | 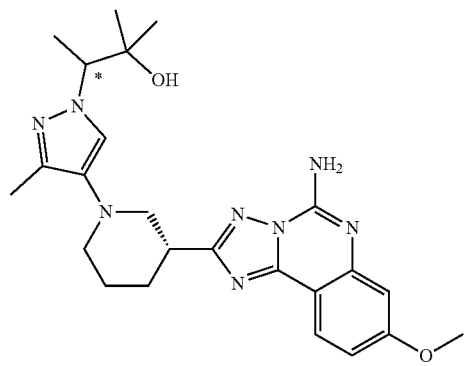<br>(R)-3-(4-((R)-3-(5-amino-8-methoxy-[1,2,4]triazolo-1,5-c]quinazolin-2-yl)piperidin-1-yl)-3-methyl-1H-pyrazo-1-yl)-2-methylbutan-2-ol,<br>(S)-3-(4-((R)-3-(5-amino-8-methoxy-[1,2,4]triazolo[1,5-c]quinazolin-2-yl)piperidin-1-yl)-3-methyl-1H-pyrazol-1-yl)-2-methylbutan-2-ol<br>The DMB-protected precursor was resolved by SFC with chiral AD-H 21 × 250 column and 50% IPA with 0.2% DIPA as cosolvent | 465 |

TABLE 11-continued

| Example | Structure Name | Observed m/z, [M + H]+ |
|---|---|---|
| 187A (peak 1) 187B (peak 2) | (1R,2R)-2-(4-((R)-3-(5-amino-8-methoxy-[1,2,4]triazolo[1,5-c]quinazolin-2-yl)piperidin-1-yl)-1H-pyrazol-1-yl)cyclopentan-1-ol<br>(1S,2S)-2-(4-((R)-3-(5-amino-8-methoxy-[1,2,4]triazolo[1,5-c]quinazolin-2-yl)piperidin-1-yl)-1H-pyrazol-1-yl)cyclopentan-1-ol<br>The DMB protected precursor was resolved by SFC with chiral AS-H 21 × 250 column and 35% EtOH with 0.2% DIPA as cosolvent | 449 |
| 188 | (R)-2-(4-(3-(5-amino-8-methoxy[1,2,4]triazolo[1,5-c]quinazolin-2-yl)piperidin-1-yl)-1H-pyrazol-1-yl)-2-methylpropan-1-ol | 437 |
| 189A (peak 1) 189B (peak 2) | (R)-3-(4-((R)-3-(5-amino-8-methoxy[1,2,4]triazolo[1,5-c]quinazolin-2-yl)piperidin-1-yl)-5-methyl-1H-pyrazol-1-yl)-2-methylbutan-2-ol,<br>(S)-3-(4-((R)-3-(5-amino-8-methoxy[1,2,4]triazolo[1,5-c]quinazolin-2-yl)piperidin-1-yl)-5-methyl-1H-pyrazol-1-yl)-2-methylbutan-2-ol<br>The DMB-protected precursor was resolved by SFC with chiral OJ-H 21 × 250 column and 15% MeOH as cosolvent | 465 |

TABLE 11-continued
| Example | Structure Name | Observed m/z, [M + H]+ |
|---|---|---|
| 190 | 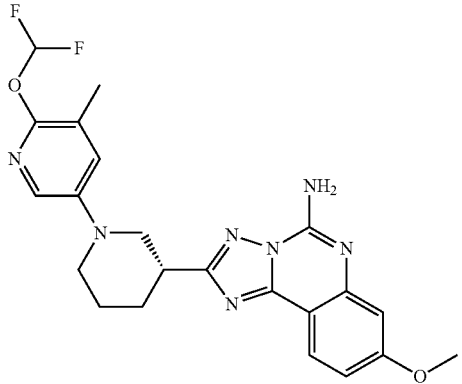 [SMILES: COc1ccc2c(c1)nc(N)n1nc([C@@H]3CCCN(c4cnc(OC(F)F)c(C)c4)C3)nc21](R)-2-(1-(6-(difluoromethoxy)-5-methylpyridin-3-yl)piperidin-3-yl)-8-methoxy-[1,2,4]triazolo[1,5-c]quinazolin-5-amine | 456 |
| 191 | 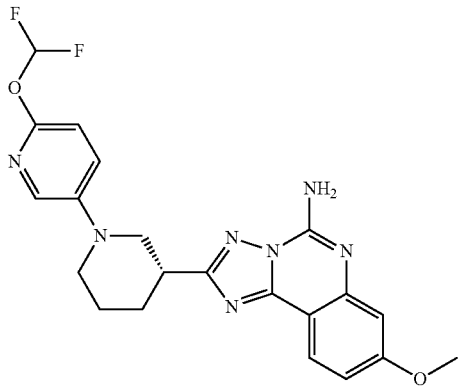 [SMILES: COc1ccc2c(c1)nc(N)n1nc([C@@H]3CCCN(c4ccc(OC(F)F)nc4)C3)nc21](R)-2-(-(6-(difluoromethoxy)pyridin-3-yl)piperidin-3-yl)-8-methoxy-[1,2,4]triazolo[1,5-c]quinazolin-5-amine | 442 |
| 192 | 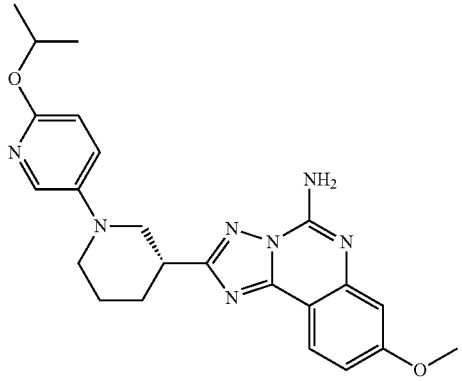 [SMILES: COc1ccc2c(c1)nc(N)n1nc([C@@H]3CCCN(c4ccc(OC(C)C)nc4)C3)nc21](R)-2-(1-(6-isopropoxypyridin-3-yl)piperidin-3-yl)-8-methoxy-[1,2,4]triazolo[1,5-c]quinazolin-5-amine | 434 |

TABLE 11-continued
| Example | Structure Name | Observed m/z, [M + H]+ |
|---|---|---|
| 193 | (R)-1-(4-(3-(5-amino-8-methoxy-[1,2,4]-triazolo[1,5-c]quinazolin-2-yl)piperidin-1-yl)phenyl)ethan-1-one | 417 |
| 194 | (R)-1-(3-(3-(5-amino-8-methoxy-[1,2,4]triazolo[1,5-c]quinazolin-2-yl)piperidin-1-yl)-1H-1,2,4-triazol-1-yl)-2-methylpropan-2-ol | 438 |
Examples 195A, 195B, 195C and 195D
The Preparation of the Compounds of Examples 195A, 195B, 195C and 195D
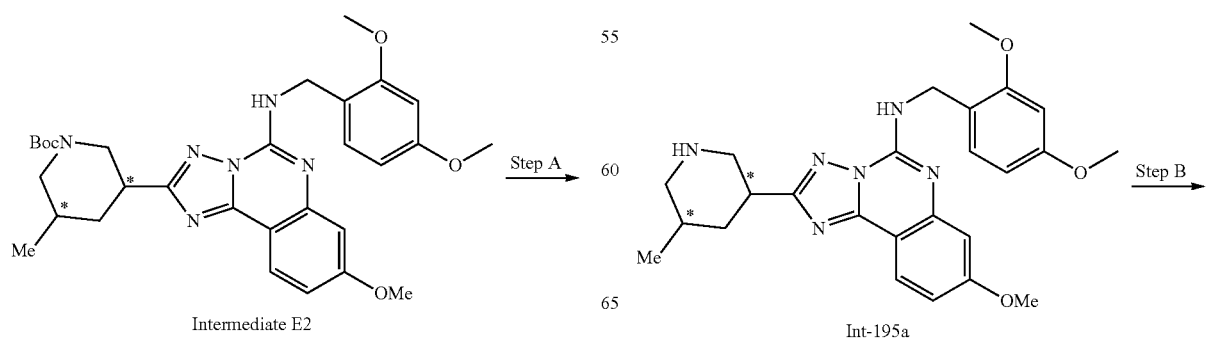

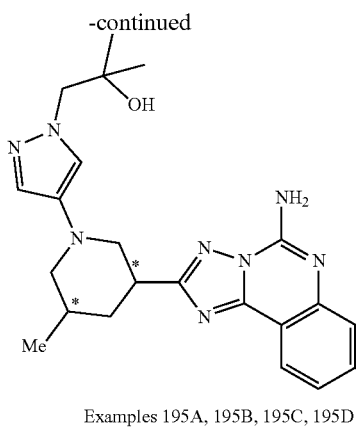

Examples 195A, 195B, 195C, 195D

Step A—Synthesis of Compound Int-195a, rac, cis- and rac, trans-N-(2,4-dimethoxybenzyl)-8-methoxy-2-(5-methylpiperidin-3-yl)-[1,2,4]triazolo[1,5-c]quinazolin-5-amine A solution of Intermediate E2 (1.2 g, 2.133 mmol) was dissolved in formic acid (10.2 mL, 266 mmol) and stirred for 3 hours at 23° C. The reaction mixture was then concentrated, diluted with 50 mL DCM, and neutralized with 50 mL saturated $NaHCO_3$ solution. The layers were separated and the basic aqueous layer was further extracted with an additional 50 mL DCM. The combined organic fractions were dried with anhydrous $MgSO_4$, filtered, and concentrated to yield Int-195a which was used in the next step without further purification. LC/MS (ES, m/z)=463 [M+H]$^+$.

Step B—Synthesis of Examples 195A, 195B, 195C and 195D

To a 20 mL microwave vial equipped with a stir bar was charged Int-195a (142 mg, 0.649 mmol), followed by t-BuXPhos Pd G3 (103 mg, 0.130 mmol) and sodium tert-butoxide (125 mg, 1.297 mmol). The mixture was purged with $N_2$ for 10 min. The vial was then sealed with a fresh cap and heated at 90° C. overnight. The reaction was cooled and filtered through Celite® (diatomaceous earth), washed with DCM, and concentrated. The resulting residue was dissolved in TFA (1.0 mL, 12.97 mmol) and stirred at 50° C. for 5 hours. The resulting mixture was concentrated. The resulting residue was purified by reversed phase HPLC with C18 column and 0-100% ACN/water with 0.05% TFA as eluent to provide the cis and trans isomers. The later-eluting racemic, trans isomer was further resolved by SFC with an OJ-H column and 20% MEOH w/0.1% $NH_4OH$ modifier as co-solvent to provide the title compounds Example 195A (Peak 1) and Example 195B (Peak 2). The earlier-eluting racemic, cis isomer was further resolved by SFC with a Lux-4 column (Phenomenex, 21 mm×250 mm) and 35% MeOH with 0.1% $NH_4OH$ modifier as co-solvent to provide the title compound Example 195C (Peak 1) and Example 195D (Peak 2).

195A: LC/MS (ES, m/z)=451 [M+H]$^+$. $^1$H NMR (499 MHz, DMSO-d$^6$) δ 8.07 (d, J=9.0 Hz, 1H), 7.67 (s, 2H), 7.24 (s, 1H), 7.19 (s, 1H), 6.99 (s, 2H), 3.88 (s, 3H), 3.87 (s, 2H), 3.47-3.39 (m, 1H), 3.22 (dd, J=11.1, 3.6 Hz, 1H), 2.92 (m, 1H), 2.62 (m, 1H), 2.22 (m, 2H), 1.73-1.61 (m, 1H), 1.10 (d, J=6.7 Hz, 3H), 1.02 (s, 6H).

195B: LC/MS (ES, m/z)=451 [M+H]$^+$. $^1$H NMR (499 MHz, DMSO-d6) δ 8.07 (d, J=9.0 Hz, 1H), 7.67 (s, 2H), 7.21 (d, J=25.6 Hz, 2H), 7.07-6.93 (m, 2H), 3.88 (s, 3H), 3.87 (s, 2H), 3.47-3.39 (m, 1H), 3.22 (dd, J=11.1, 3.7 Hz, 1H), 2.92 (dd, J=11.1, 3.3 Hz, 1H), 2.63 (dd, J=11.2, 6.0 Hz, 1H), 2.30-2.09 (m, 2H), 1.75-1.58 (m, 1H), 1.10 (d, J=6.7 Hz, 2H), 1.03 (d, J=10.6 Hz, 6H).

195C: LC/MS (ES, m/z)=451 [M+H]$^+$. $^1$H NMR (499 MHz, DMSO-d6) δ 8.06 (d, J=9.1 Hz, 1H), 7.69 (s, 2H), 7.22 (s, 1H), 7.06-6.92 (m, 2H), 4.61 (s, 1H), 3.88 (s, 3H), 3.83 (d, J=4.4 Hz, 2H), 3.50-3.43 (m, 1H), 3.19-3.10 (m, 1H), 2.64 (t, J=11.3 Hz, 1H), 2.24-2.13 (m, 2H), 2.02-1.86 (m, 1H), 1.45-1.31 (m, 1H), 1.03 (d, J=2.7 Hz, 6H), 0.97 (d, J=6.6 Hz, 3H).

195D: LC/MS (ES, m/z)=451 [M+H]$^+$. $^1$H NMR (499 MHz, DMSO-d6) δ 8.07 (d, J=9.1 Hz, 1H), 7.70 (s, 2H), 7.28 (s, 1H), 7.22 (s, 1H), 6.99 (m, 2H), 4.63 (s, 1H), 3.88 (br. S, 5H), 3.67 (d, J=7.4 Hz, 1H), 3.32-3.21 (m, 2H), 2.68 (t, J=11.5 Hz, 1H), 2.25-2.06 (m, 2H), 1.93 (br. S, 1H), 1.41 (q, J=12.4 Hz, 1H), 1.04 (s, 6H), 0.99 (d, J=6.6 Hz, 2H).

Examples 196A and 196B

The Preparation of the Compound of Example 196

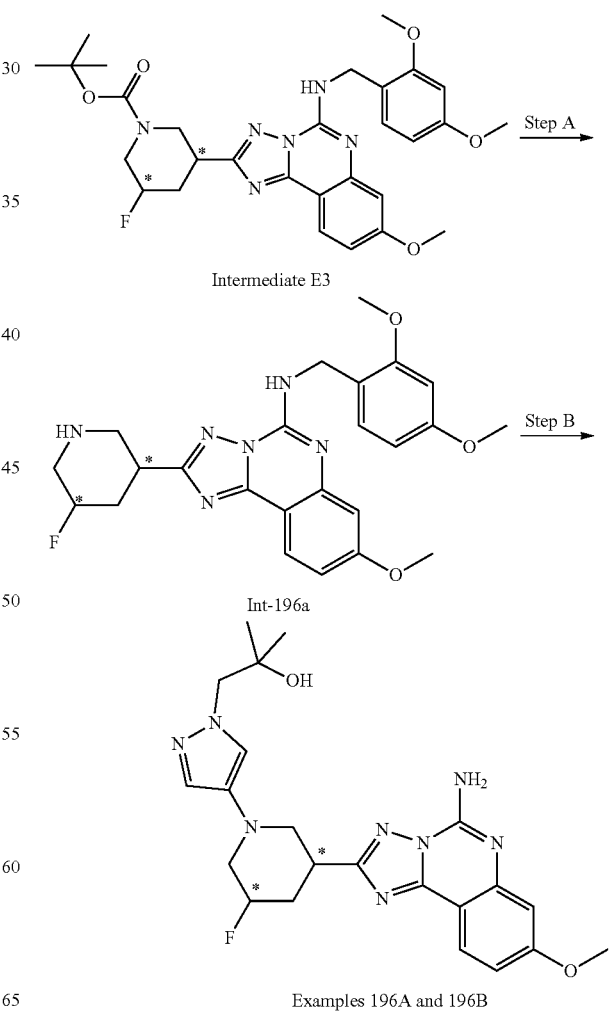

Examples 196A and 196B

Step A—Synthesis of Compound Int-196a N-(2,4-dimethoxybenzyl)-2-(5-fluoropiperidin-3-yl)-8-methoxy-[1,2,4]triazolo[1,5-c]quinazolin-5-amine A solution of Intermediate E3 (438 mg, 0.773 mmol) in formic acid (2965 μL, at 77 mmol) was stirred at room temperature overnight. Upon completion, the mixture was diluted with 10 mL DCM and neutralized with saturated NaHCO₃ solution to neutral pH. The organic layer was separated, and the aqueous layer was extracted twice with 15 mL of DCM. The combined organic layers were washed with brine, dried over anhydrous sodium sulfate, filtered, then concentrated. The residue was then purified by silica gel column chromatography with 5% MeOH in DCM as eluent to provide Int-196a LC/MS (ES, m/z)=467 [M+H]⁺.

Step B—Synthesis of Examples 196A and 196B

A 5 mL microwave vial equipped with a stir bar was charged with Int-196a (125 mg, 0.268 mmol), t-BuXPhos Pd G3 (106 mg, 0.134 mmol) and sodium tert-butoxide (103 mg, 1.072 mmol) under nitrogen. To this was added 1-(4-bromo-1H-pyrazol-1-yl)-2-methylpropan-2-ol (117 mg, 0.536 mmol) in THF (4 mL). The resulting mixture was sparged with nitrogen for 10 minutes. The vial was then sealed with a cap and stirred at 90° C. for 16 hours. Upon completion, the reaction was cooled to room temperature and filtered to remove the solid. The filtrate was concentrated. To the residue was added TFA (2 mL) and stirred at 50° C. for 3 hours. The mixture was cooled to room temperature, and the solvents were evaporated. The residue was purified by reversed phase HPLC with C18 column and 0-100% MeCN/H₂O with 0.1% TFA as eluent, providing the racemic compound, which was further resolved by SEC with chiral AS-H column (Chiral Technologies) and 1:1 MeOH (0.1% NH₃H₂O)/ACN as eluent, yielding Example 196A (Peak 1) and Example 196B (Peak 2).

196A: LC/MS (ES, m/z): 455[M+H]⁺. ¹H NMR (499 MHz, DMSO-d⁶) δ 8.12-8.05 (m, 1H), 7.75 (s, 2H), 7.37 (s, 1H), 7.28 (s, 1H), 7.00 (dd, J=6.1, 3.3 Hz, 2H), 4.94 (dd, J=53.3, 5.1 Hz, 1H), 3.89 (s, 2H), 3.89 (s, 3H), 3.78-3.63 (m, 2H), 2.74 (t, J=11.5 Hz, 1H), 2.68-2.53 (m, 3H), 1.92 (m, 1H), 1.04 (s, 6H).

196B: LC/MS (ES, m/z): 455[M+H]⁺. ¹H NMR (499 MHz, DMSO-d⁶) δ 8.11-8.05 (m, 1H), 7.73 (s, 2H), 7.37 (s, 1H), 7.28 (s, 1H), 7.02-6.96 (m, 2H), 4.94 (ddd, J=48.1, 10.3, 5.0 Hz, 1H), 4.64 (s, 1H), 3.89 (s, 2H), 3.89 (s, 3H), 3.70 (dd, J=47.3, 10.7 Hz, 2H), 2.74 (t, J=11.5 Hz, 1H), 2.68-2.54 (m, 3H), 1.92 (m, 1H), 1.04 (s, 6H).

The example compounds of the invention shown in Table 12 were prepared by a procedure similar to the procedure described for the preparation of Examples 196A and 196B, substituting the appropriate starting aryl halide and Int-196a.

TABLE 12

| Example | Structure Name | Observed m/z [M + H]⁺ |
|---|---|---|
| 197A (peak 1) 197B (peak 2) | 1-(4-((3S,5R)-3-(5-amino-8-methoxy-[1,2,4]triazolo[1,5-c]quinazolin-2-yl)-5-fluoropiperidin-1-yl)-3-methyl-1H-pyrazol-1-yl)-2-methylpropan-2-ol, 1-(4-((3R,5S)-3-(5-amino-8-methoxy-[1,2,4]triazolo[1,5-c]quinazolin-2-yl)-5-fluoropiperidin-1-yl)-3-methyl-1H-pyrazol-1-yl)-2-methylpropan-2-ol The DMB-protected precursor was resolved by SFC with chiral AS-H column and 1:1 MeOH (0.1% NH₃H₂O)/ACN as eluent | 469 |

Example 198

The Preparation of the Compound of Example 198

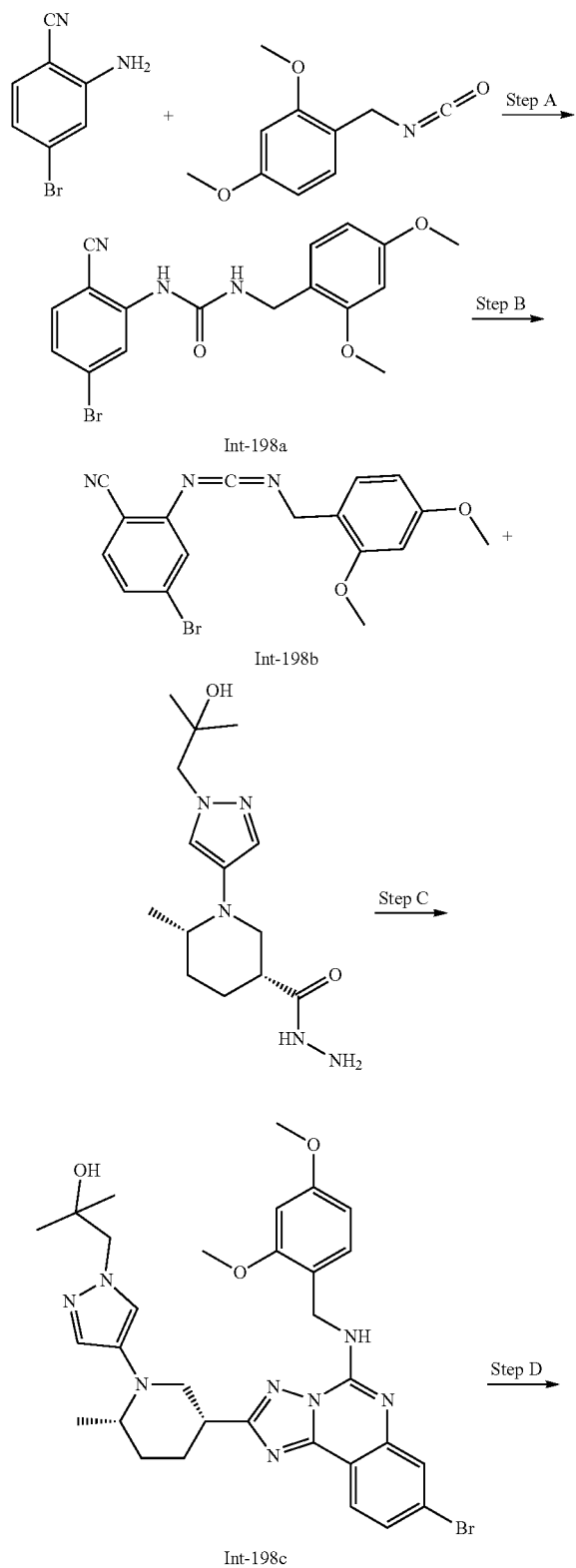

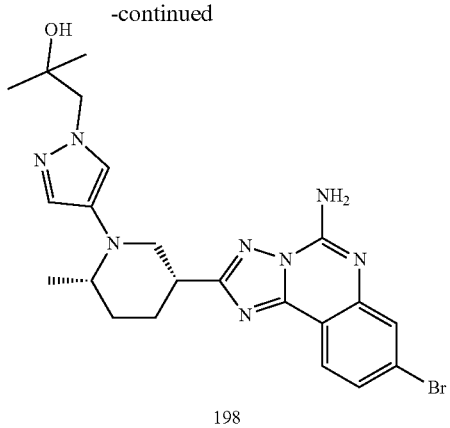

198

Step A—Synthesis of Compound Int-198a 1-(5-bromo-2-cyanophenyl)-3-(2,4-dimethoxybenzyl)urea To a 20 mL vial was added 2-amino-4-bromobenzonitrile (2.00 g, 10.1 mmol) and pyridine (3 mL). The mixture was stirred. To the mixture was added 1-(isocyanatomethyl)-2,4-dimethoxybenzene (1.96 ml, 10.1 mmol) as a solution in DCM (4.5 mL). The mixture was stirred and heated at 50° C.; for 24 hours. The mixture was cooled at room temperature for 30 minutes. The resulting solids were collected by filtration and washed with MeOH (3×3 mL), yielding Int-198a LC/MS (ES, m/z)=390, 392 [M+H]$^+$.

Step B—Synthesis of Compound Int-198b. 4-bromo-2-((((2,4-dimethoxybenzyl)imino)methylene)amino)benzonitrile To a 100 mL round bottom flask was added Int-198a (2.37 g, 6.07 mmol), triphenylphosphine (3.19 g, 12.1 mmol), triethylamine (3.39 ml, 24.3 mmol), and DCM (15 mL). The mixture was stirred and then cooled at 0° C. To the mixture was added carbon tetrabromide (4.03 g, 12.1 mmol). After 30 minutes of stirring, the mixture was concentrated and then purified by silica gel column chromatography with 0-70% EtOAc in hexanes as eluent, yielding Int-198b. LC/MS (ES, m/z)=394, 396 [M+Na]$^+$.

Step C—Synthesis of Compound Int-198c. 1-(4-((2S,5R or 2R,5S)-5-(8-bromo-5-((2,4-dimethoxybenzyl)amino)-[1,2,4]triazolo[1,5-c]quinazolin-2-yl)-2-methylpiperidin-1-yl)-1H-pyrazol-1-yl)-2-methylpropan-2-ol To a 100 mL flask was added (3R,6S)-1-(1-(2-hydroxy-2-methylpropyl)-1H-pyrazol-4-yl)-6-methylpiperidine-3-carbohydrazide (590 mg, 2.00 mmol), Int-202b (818 mg, 2.20 mmol) and 1,4-dioxane (15 mL). The mixture was stirred at room temperature for 1 hour. The solvents were evaporated. The resulting residue was purified by silica gel column chromatography with 0-100% EtOAc:EtOH (3:1) in hexanes as eluent, yielding Int-198c. LC/MS (ES, m/z)=649, 651 [M+H]$^+$.

Step D—Synthesis of Example 198. 1-(4-((2S,5R or 2R,5S)-5-(5-amino-8-bromo-[1,2,4]triazolo[1,5-c]quinazolin-2-yl)-2-methylpiperidin-1-yl)-4H-pyrazol-1-yl)-2-methylpropan-2-ol To a 4 mL vial was added Int-198e (56 mg, 0.086 mmol) and TFA (1 mL). The mixture was stirred and heated at 65°

C. for 1 h. The solvents were evaporated. To the resulting residue was added saturated aqueous sodium bicarbonate (5 mL). The layers were separated and the aqueous layer was extracted with DCM (2×5 mL). The organic layers were combined, dried over anhydrous sodium sulfate, filtered, and the solvents of the filtrate were evaporated. The resulting residue was purified by silica gel column chromatography with 0-10% MeOH in DCM as eluent, providing the title compound Example 198. LC/MS (ES, m/z)=499, 501 [M+H]+. ¹H NMR (499 MHz, DMSO-d⁶) δ 8.13 (d, J=8.5 Hz, 1H), 7.98 (s, 2H), 7.73 (d, J=1.9 Hz, 1H), 7.51 (dd, J=8.5, 1.9 Hz, 1H), 7.20 (s, 1H), 7.15 (s, 1H), 3.88 (s, 2H), 3.70 (s, 1H), 3.35 (dd, J=11.8, 4.1 Hz, 1H), 3.23 (s, 1H), 3.11 (t, J=11.5 Hz, 1H), 2.01 (d, J=6.3 Hz, 3H), 1.71 (d, J=9.5 Hz, 1H), 1.03 (t, J=3.2 Hz, 9H).

The example compounds of the invention shown in Table 13 were prepared using a procedure similar to the procedure described for the preparation of Example 198, substituting the appropriate intermediates and starting materials.

TABLE 13

| Example | Structure Name | Observed m/z [M + H]+ |
|---|---|---|
| 199 | (R or S)-8-methyl-2-(1-(1-methyl-1H-pyrazol-4-yl)piperidin-3-yl)-[1,2,4]triazolo[1,5-c]quinazolin-5-amine | 363 |
| 200 | (R or S)-8-chloro-2-(1-(1-methyl-1H-pyrazol-4-yl)piperidin-3-yl)-[1,2,4]triazolo[1,5-c]quinazolin-5-amine | 383 |
| 201 | 1-(4-((2S,5R)-5-(5-amino-8-(difluoromethyl)-[1,2,4]triazolo[1,5-c]quinazolin-2-yl)-2-methylpiperidin-1-yl)-1H-pyrazol-1-yl)-2-methylpropan-2-ol | 471 |

TABLE 13-continued
| Example | Structure Name | Observed m/z [M + H]+ |
|---|---|---|
| 202 | 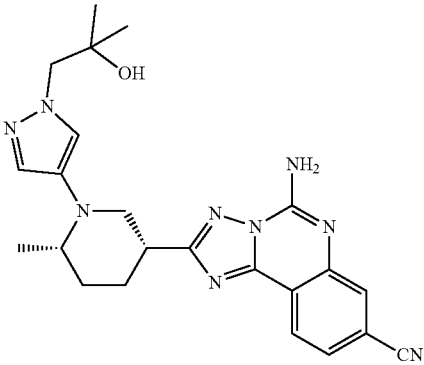 [SMILES: C[C@H]1CC[C@@H](c2nc3c4ccc(C#N)cc4nc(N)n3n2)CN1c1cnn(CC(C)(C)O)c1]<br>5-amino-2-((3R,6S)-1-(1-(2-hydroxy-2-methylpropyl)-1H-pyrazol-4-yl)-6-methylpiperidin-3-yl)-[1,2,4]triazolo[1,5-c]quinazoline-8-carbonitrile | 446 |
| 203 | 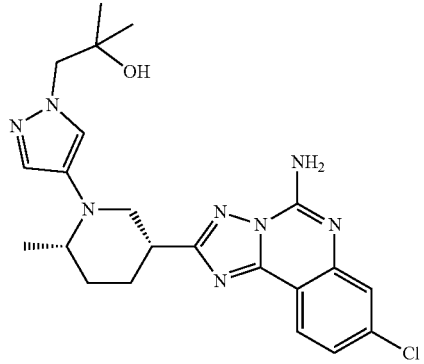 [SMILES: C[C@H]1CC[C@@H](c2nc3c4ccc(Cl)cc4nc(N)n3n2)CN1c1cnn(CC(C)(C)O)c1]<br>1-(4-((2S,5R)-5-(5-amino-8-chloro-[1,2,4]triazolo[1,5-c]quinazolin-2-yl)-2-methylpiperidin-1-yl)-1H-pyrazol-1-yl)-2-methylpropan-2-ol | 455 |
| 204 | 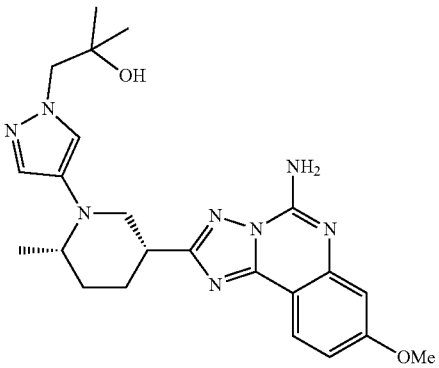 [SMILES: COc1ccc2c(c1)nc(N)n1nc([C@@H]3CC[C@H](C)N(c4cnn(CC(C)(C)O)c4)C3)nc21]<br>1-(4-((2S,5R)-5-(5-amino-8-methoxy-[1,2,4]triazolo[1,5-c]quinazolin-2-yl)-2-methylpiperidin-1-yl)-1H-pyrazol-1-yl)-2-methylpropan-2-ol | 451 |

Example 205

The Preparation of the Compound of Example 205

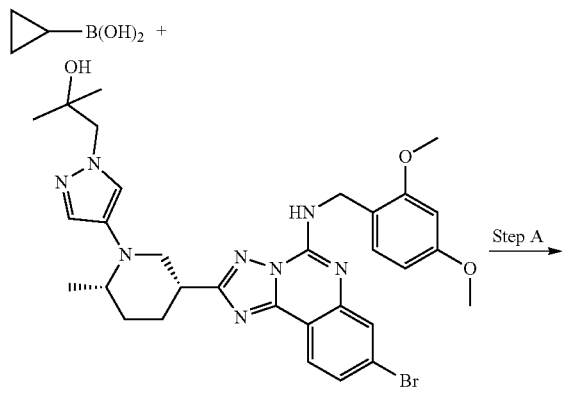

Int-198c

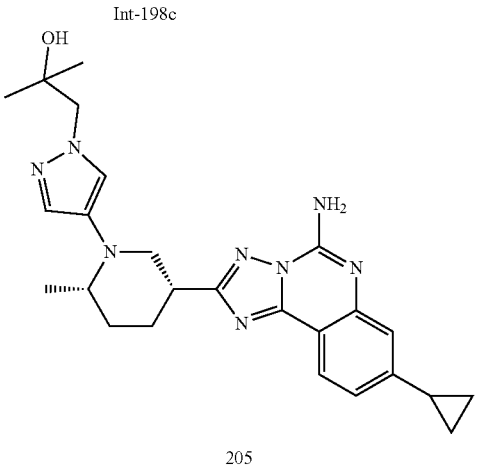

205

Step A—Synthesis of Example 205. 1-(4-((2S, 5R or 2R,5S)-5-(5-amino-8-cyclopropyl-[1,2,4]triazolo[1,5-c]quinazolin-2-yl)-2-methylpiperidin-1-yl)-1H-pyrazol-1-yl)-2-methylpropan-2-ol To a 4 mL vial was added cataCXium® A Pd G3 (Sigma Aldrich, 16.8 mg, 0.0230 mmol), potassium phosphate (49.0 mg, 0.231 mmol), cyclopropyl boronic acid (13.2 mg, 0.154 mmol) and Int-198c (50 mg, 0.077 mmol). To the vial was added 1,4-dioxane (0.5 mL) and water (0.1 mL). The mixture was degassed with nitrogen for 5 minutes. The mixture was stirred and heated at 100° C. for 2 hours. Upon completion, the mixture was diluted in EtOAc (10 mL) and filtered through Celite® (diatomaceous earth) topped with sodium sulfate. The solvents of the filtrate were evaporated. The resulting residue was purified by silica gel column chromatography with 0-10% MeOH in DCM as eluent, yielding 1-(4-((2S,5R or 2R,5S)-5-(8-cyclopropyl-5-((2,4-dimethoxybenzyl)amino)-[1,2,4]triazolo[1,5-c]quinazolin-2-yl)-2-methylpiperidin-1-yl)-1H-pyrazol-1-yl)-2-methylpropan-2-ol.

To a 4 mL vial was added 1-(4-((2S,5R or 2R,5S)-5-(8-cyclopropyl-5-((2,4-dimethoxybenzyl)amino)-[1,2,4]triazolo[1,5-c]quinazolin-2-yl)-2-methylpiperidin-1-yl)-1H-pyrazol)-1-yl)-2-methylpropan-2-ol (36 mg, 0.059 mmol) and TFA (0.5 mL). The mixture was stirred and heated at 50° C. for 3 hours. The mixture was concentrated. The resulting residue was partitioned between saturated aqueous sodium bicarbonate (5 mL) and DCM (5 mL). The layers were separated and the aqueous layer was extracted with DCM (5 mL). The combined organic layers were dried over anhydrous sodium sulfate, filtered, and the solvents were evaporated. The resulting residue was purified by silica gel column chromatography with 0-10% MeOH in DCM as eluent, yielding Example 205. LC/MS (ES, m/z)=461 [M+H]+. 1H NMR (499 MHz, DMSO-d6) δ 8.06 (d, J=8.2 Hz, 1H), 7.68 (s, 2H), 7.24 (d, J=1.5 Hz, 1H), 7.21 (s, 1H), 7.15 (s, 1H), 7.07 (dd, J=8.3, 1.6 Hz, 1H), 3.88 (s, 2H), 3.69 (s, 1H), 3.36 (d, J=4.0 Hz, 1H), 3.20 (s, 1H), 3.10 (t, J=11.5 Hz, 1H), 2.14-2.04 (m, 1H), 2.00 (d, J=6.3 Hz, 3H), 1.71 (s, 1H), 1.10-1.04 (m, 2H), 1.03 (d, J=3.7 Hz, 9H), 0.89-0.74 (m, 2H).

Example 206

The Preparation of the Compound of Example 206

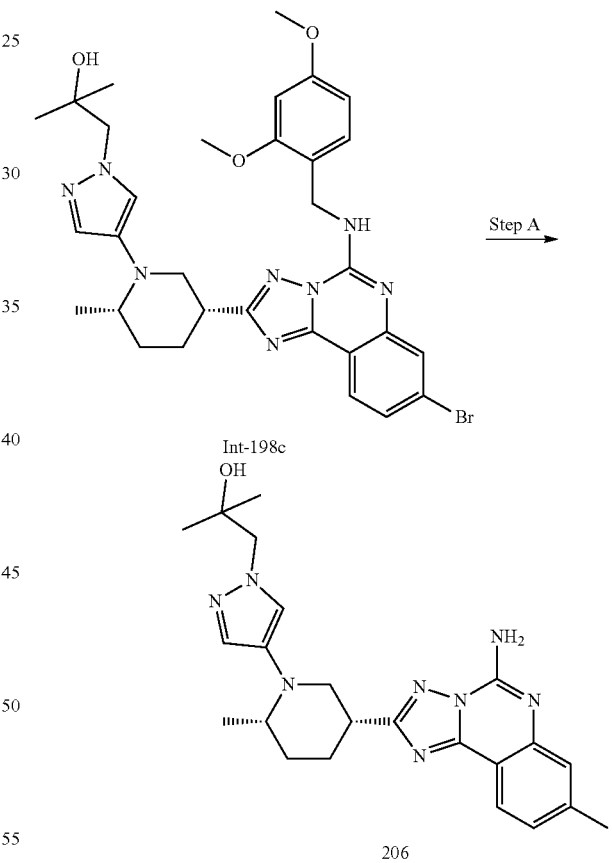

Step A—Synthesis of Example 206. 1-(4-((2S, 5R or 2R,5S)-5-5-amino-8-methyl-[1,2,4]triazolo[1,5-c]quinazolin-2-yl)-2-methylpiperidin-1-yl)-1H-pyrazol-1-yl)-2-methylpropan-2-ol To a 4 mL vial was added CPhos Pd G4 (3.2 mg, 3.8 μmol) and IM-198e (50 mg, 0.077 mmol.). The vial was evacuated and refilled with nitrogen three times. To the vial was added THF (0.3 ml). The mixture was stirred. To the mixture was added a 1 M solution of dimethylzinc (0.257 ml, 0.308 mmol) in hexanes. The resulting mixture was stirred at room temperature for 1 hour. Upon completion, saturated aqueous ammonium chloride (0.10 mL) was added dropwise to the mixture. The mixture was then diluted in dichloromethane (30 mL) and stirred vigorously for 10 minutes. The mixture was then filtered through Celite® (diatomaceous earth) topped with sodium sulfate. The solvents of the filtrate were evaporated. To the resulting residue was added TFA (0.5 ml). The mixture was stirred and heated at 65° C. for 3 h. The mixture was concentrated. The residue was partitioned between saturated aqueous sodium bicarbonate (5 mL) and DCM (5 mL). The layers were separated and the aqueous layer was extracted with DCM (5 mL). The combined organic layers were dried over anhydrous sodium sulfate, filtered, and the solvents were evaporated. The resulting residue was purified by silica gel column chromatography with 0-10% MeOH in DCM as eluent, providing the title compound Example 206. LC/MS (ES, m/z)=435 [M+H]$^+$. $^1$H NMR (499 MHz, DMSO-d$^6$) δ 8.09 (d, J=8.1 Hz, 1H), 7.71 (s, 2H), 7.37 (s, 1H), 7.21 (d, J=5.6 Hz, 2H), 7.15 (s, 1H), 3.88 (s, 2H), 3.70 (s, 1H), 3.39-3.34 (m, 1H), 3.21 (s, 1H), 3.11 (t, J=11.5 Hz, 1H), 2.46 (s, 3H), 2.01 (d, J=6.0 Hz, 3H), 1.71 (d, J=8.7 Hz, 1H), 1.04 (d, J=4.4 Hz, 9H).

The example compounds of the invention shown in Table 15 were prepared using a procedure similar to the procedure described for the preparation of Example 206, substituting the appropriate starting alkyl zincate.

TABLE 15

| Example | Structure Name | Observed m/z [M + H]$^+$ |
|---|---|---|
| 207 | ![structure] 1-(4-((2S,5R)-5-(5-amino-8-ethyl-[1,2,4]triazolo[1,5-c]quinazolin-2-yl)-2-methylpiperidin-1-yl)-1H-pyrazol-1-yl)-2-methylpropan-2-ol | 449 |

Example 208

The Preparation of the Compound of Example 208

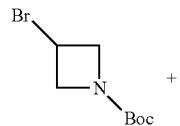

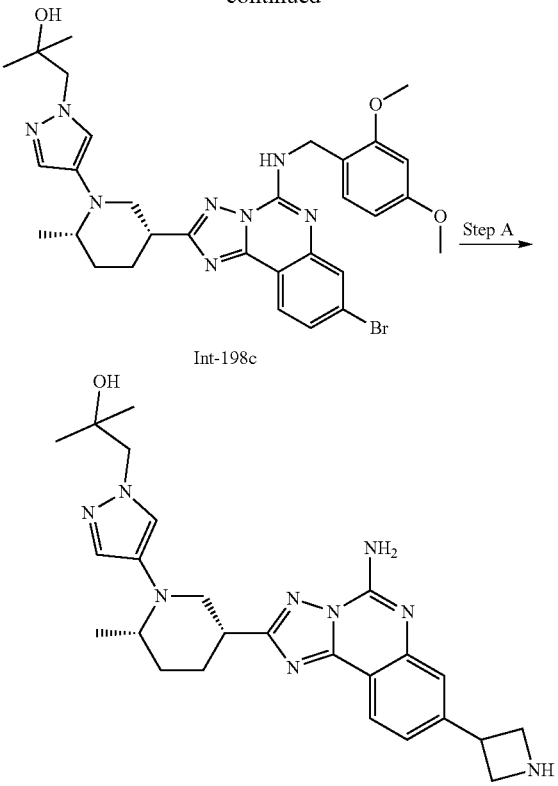

Step A—Synthesis of Example 208. 1-(4-((2S,5R or 2R,5S)-5-(5-amino-8-(azetidin-3-yl)-[1,2,4]triazolo[1,5-c]quinazolin-2-yl)-2-methylpiperidin-1-yl)-1H-pyrazol-1-yl)-2-methylpropan-2-ol To a 4 mL vial was added 4,4'-dimethoxy-2,2'-bipyridine (8.3 mg, 0.38 mmol), 1-(4-((2S,5R or 2R,5S)-5-(8-bromo-5-((2,4-dimethoxybenzyl)amino)-[1,2,4]triazolo[1,5-c]quinazolin-2-yl)-2-methylpiperidin-1-yl)-1H-pyrazol-1-yl)-2-methylpropan-2-ol (50 mg, 0.077 mmol), sodium iodide (1.1 mg. 7.7 μmol), (12.7 mg, 0.231 mmol), tert-butyl 3-bromoazetidine-1-carboxylate (0.025 mL, 0.15 mmol), and NiCl$_2$(DME) (8.5 mg, 0.38 mmol). DMPU (0.5 mL) was then added to the mixture, followed by the addition of 5% v/v solution in DMPU of pyridine (0.012 mL, 7.7 μmol). The vial was degassed with nitrogen for 5 minutes. The resulting mixture was heated at 95° C. for 3 h. Upon completion, the mixture was diluted in diethyl ether (20 mL), and filtered through Celite® (diatomaceous earth). The filtrate was washed with water (3×30 mL). The organic layer was dried over anhydrous magnesium sulfate, filtered, and the solvents were evaporated. To the resulting residue was added TFA (0.5 mL). The mixture was then stirred and heated at 50° C. for 3 hours. The mixture was concentrated. The resulting residue was purified by reversed-phase HPLC with C18 column and MeCN/water (0.1% TFA) as eluent, yielding Example 208. LC MS (ES, m/z)=476 [M+H]$^+$. $^1$H NMR (499 MHz, DMSO-d$^6$) δ 8.91 (s, 1H), 8.58 (s, 1H), 8.24 (d, J=8.2 Hz, 1H), 7.84 (s, 2H), 7.60 (s, 1H), 7.42 (d, J=8.3 Hz, 1H), 7.23 (s, 1H), 4.30 (ddd, J=32.2, 167, 8.0 Hz, 2H), 4.22-4.14 (m, 1H), 3.91 (s, 1H), 3.74 (s, 1H), 3.36 (d, J=69.2 Hz, 3H), 2.06 (d, J=28.7 Hz, 3H), 1.75 (s, 1H), 1.09-1.02 (m, 9H).

The example compounds of the invention shown in Table 16 were prepared using a procedure similar to the procedure described for the preparation of Example 208, substituting the appropriate starting alkyl bromide.

TABLE 16
| Example | Structure Name | Observed m/z [M + H]+ |
|---|---|---|
| 209 | 1-(4-((2S,5R)-5-(5-amino-8-cyclobutyl-[1,2,4]triazolo[1,5-c]quinazolin-2-yl)-2-methylpiperidin-1-yl)-1H-pyrazol-1-yl)-2-methylpropan-2-ol | 475 |
Examples 210A and 210B
The Preparation of the Compounds of Examples 210A and 210B
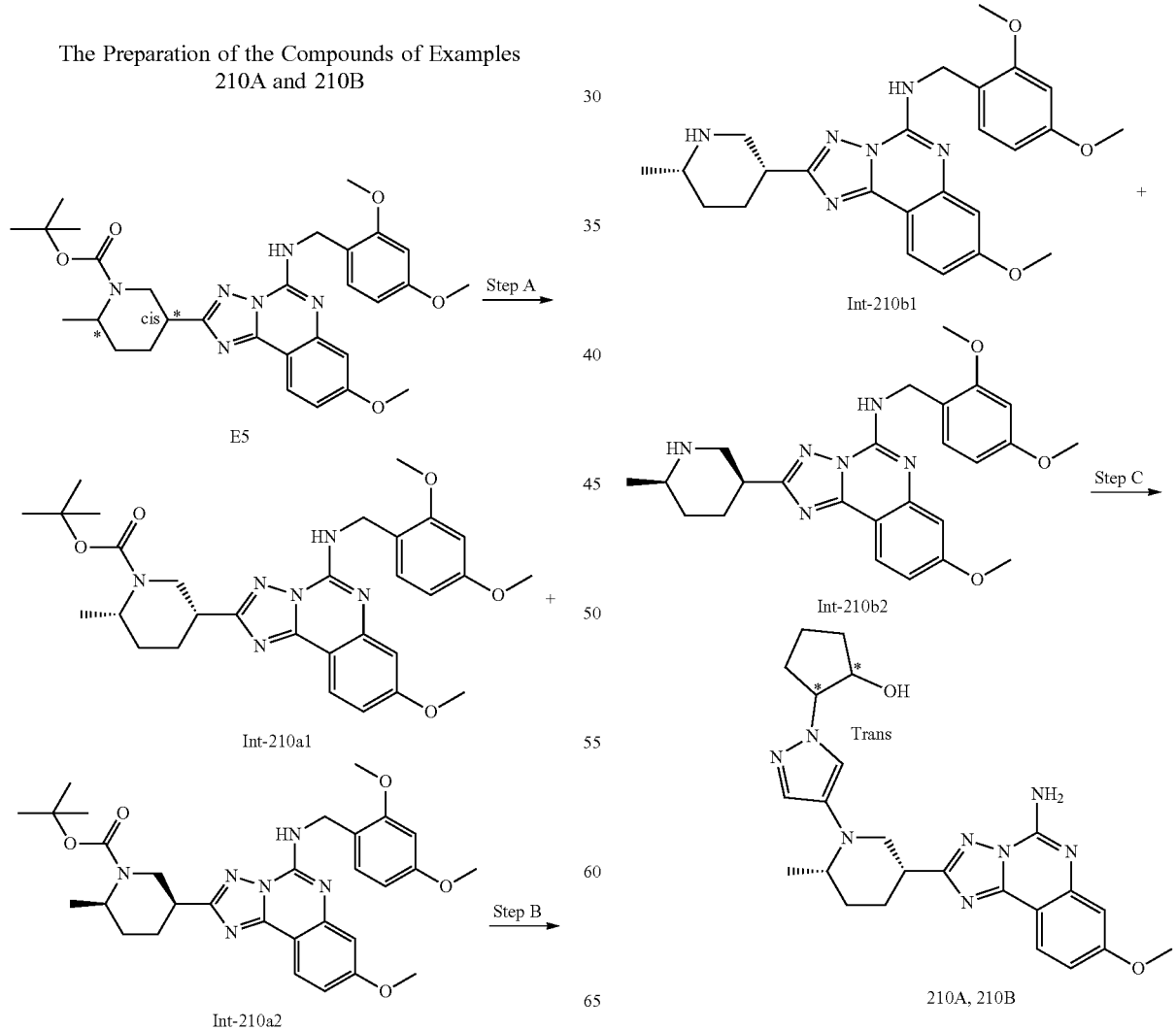

Step A—Synthesis of Compounds Int-210a1 and Int-210a2. tert-butyl (2S, 5R)-5-(5-((2,4-dimethoxybenzyl)amino)-8-methoxy-[1,2,4]triazolo[1,5-c]quinazolin-2-yl)-2-methylpiperidine-1-carboxylate and tert-butyl (2R, 5S)-5-(5-((2,4-dimethoxybenzyl) amino)-8-methoxy-[1,2,4]triazolo[1,5-c]quinazolin-2-yl)-2-methylpiperidine-1-carboxylate Intermediate E5 (2.2 g, 3.91 mmol) was resolved by SFC with a chiral AD-H column and 40% i-PrOH as co-solvent to afford the title compounds Int-210a1 (peak 1) and Int-210a2 (peak 2) LC/MS (ES, m/z)=563 [M+H]$^+$.

Step B—Synthesis of Compounds Int-210b1 and Int-210b2. N-(2,4-dimethoxybenzyl)-8-methoxy-2-((3R, 6S)-6-methylpiperidin-3-yl)-[1,2,4]triazolo[1,5-c]quinazolin-5-amine and N-(2,4-dimethoxybenzyl)-8-methoxy-2-((3S, 6R)-6-methylpiperidin-3-yl)-[1,2,4]triazolo[1,5-c]quinazolin-5-amine To the solution of Int-210a1 (680 mg, 1.209 mmol) in DCM (10 mL) was added 4 M HCl in dioxane (3 mL, 12.0 mmol). The reaction mixture was stirred at room temperature for 2 hours. Upon completion, the reaction was concentrated under reduced pressure. The resulting residue was purified by preparative silica gel TLC plates with 6% 7 N NH$_3$ in MeOH/DCM as eluent to afford Int-210b1. LC/MS (ES, m/z)=463 [M+H]$^+$.

Step C—Synthesis of Examples 210A and 210B

To a reaction vial containing Int-210b1 (135 mg, 292 mmol) in THF (3 mL,) was added 4-bromo-1-(2-((tetrahydro-2H-pyran-2-yl)oxy)cyclopentyl)-1H-pyrazole (166 mg, 0.525 mmol), followed by methanesulfonato (2-di-t-butylphosphino-2',4',6'-tri-i-propyl-1,1'-biphenyl)(2'-amino-1,1'-biphenyl-2-yl)palladium(II) (i-BuXPhos Pd G3, 69.6 mg, 0.088 mmol) and sodium tert-butoxide (84 mg, 0.876 mmol). The resulting mixture was purged with N$_2$ for 10 minutes and heated at 90° C. for 24 hours. Upon completion, the reaction mixture was cooled and then concentrated. The resulting residue was purified by preparative silica gel plates with 6% MeOH in DCM as eluent to afford the DMB-protected intermediate.

To the above intermediate (20 mg, 0.036 mmol) in DCM (1.0 mL) was added HCl (4.0 M in 1,4 dioxane, 118 uL, 0.474 mmol). The resulting mixture was stirred at room temperature for 30 minutes. Upon completion, the reaction mixture was concentrated, and the resulting residue was purified by preparative silica gel TLC plates eluting with 6% MeOH/DCM to afford 32 mg of a diastereomeric mixture, which was further resolved by SFC with a chiral AS-H column and 30% MeOH (0.2% DIPA) as eluent to afford Peak 1 (15 mg, 0.024 mmol) and Peak 2 (12 mg, 0.021 mmol).

Separate solutions of Peak 1 and Peak 2 in TFA (0.5 mL) were each heated at 50° C. for 3 hours, then concentrated. The resulting residues were purified by reversed-phase HPLC with C18 column and 0-100% MeCN/water w/0.1% TFA as eluent, providing Example 210A (derived from Peak 1) and Example 210B (derived from Peak 2).

210A: LC/MS (ES, m/z)=463 [M+H]$^1$. $^1$H NMR (400 MHz, Chloroform-d) δ 8.23 (d, J=8.7 Hz, 1H), 7.23 (s, 1H), 7.05 (d, J=2.3 Hz, 1H), 7.02 (dd, J=8.7, 2.4 Hz, 1H), 7.00 (s, 1H), 6.01 (s, 3H), 4.36 (q, J=7.5 Hz, 1H), 4.27-4.14 (m, 1H), 3.92 (s, 3H), 3.81-3.64 (m, 1H), 3.48 (s, 1H), 3.43 (dd, J=11.4, 3.7 Hz, 1H), 3.31 (d, J=11.0, 5.3 Hz, 1H), 3.20 (t, J=11.3 Hz, 1H), 2.26 (ddt, J=15.8, 7.8, 4.9 Hz, 2H), 2.06 (ddtd, J=22.2, 17.4, 12.8, 8.4 Hz, 6H), 1.86 (dtd, J=9.8, 7.8, 5.5 Hz, 2H), 1.79-1.64 (m, 2H), 1.10 (d, J=6.7 Hz, 3H).

210B: LC/MS (ES, m/z)=463 [M+H]$^+$. $^1$H NMR (400 MHz, Chloroform-d) δ 8.23 (d, J=8.7 Hz, 1H), 7.23 (s, 1H), 7.06 (d, J=2.3 Hz, 1H), 7.03 (dd, J=8.7, 2.5 Hz, 1H), 7.00 (s, 1H), 6.47-5.81 (m, 2H), 4.36 (q, J=7.5 Hz, 1H), 4.28-4.12 (m, 1H), 3.92 (s, 3H), 3.75 (dd, J=22.6, 5.9 Hz, 1H), 3.48 (s, 1H), 3.44 (dd, J=11.4, 3.8 Hz, 1H), 3.32 (d, J=11.1, 5.4 Hz, 1H), 3.20 (t, J=11.3 Hz, 1H), 2.25 (ddt, J=12.8, 7.9, 4.0 Hz, 1H), 2.06 (dddd, J=38.0, 17.3, 12.8, 8.5 Hz, 5H), 1.85 (dtt, J=10.1, 7.8, 5.3 Hz, 2H), 1.73 (dddd, J=20.1, 17.2, 10.9, 5.2 Hz, 3H), 1.11 (d, J=6.7 Hz, 3H).

The example compounds of the invention shown in Table 17 were prepared using a procedure similar to the procedure described above, substituting the appropriate starting aryl halide and Int-210b1. For Examples 210A, 210B, 211A, 211B, 212A, 212B, 213 and 214 the absolute stereochemistry of the cis-substituted piperidine was inferred based on the relative potency of the two cis-piperidine enantiomers and absolute stereochemical determination of an analogous molecule via vibrational circular dichroism.

TABLE 17

| Example | Structure Name | Observed m/z [M + H]$^+$ |
|---|---|---|
| 211A (peak 1) 211B (peak 2) | 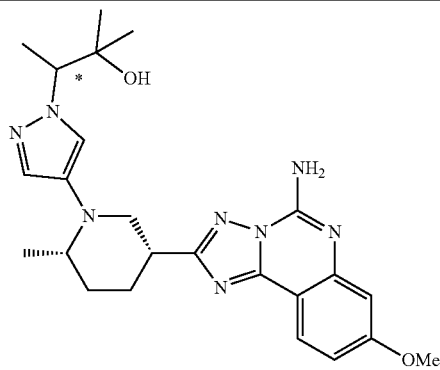 (S)-3-(4-((2S,5R)-5-(5-amino-8-methoxy-[1,2,4]triazolo[1,5-c]quinazolin-2-yl)-2-methylpiperidin-1-yl)-1H-pyrazol-1-yl)-2-methylbutan-2-ol, | 465 |

TABLE 17-continued

| Example | Structure Name | Observed m/z [M + H]+ |
|---|---|---|
| | (R)-3-(4-((2S,5R)-5-(5-amino-8-methoxy-[1,2,4]triazolo[1,5-c]quinazolin-2-yl)-2-methylpiperidin-1-yl)-1H-pyrazol-1-yl)-2-methylbutan-2-ol<br>The DMB-protected precusor was resolved by AD-H 21 × 250 min column with 1:1 MeOH:MeCN (0.2% DIPA) as co-solvent | |
| 212A (peak 1) 212B (peak2) | 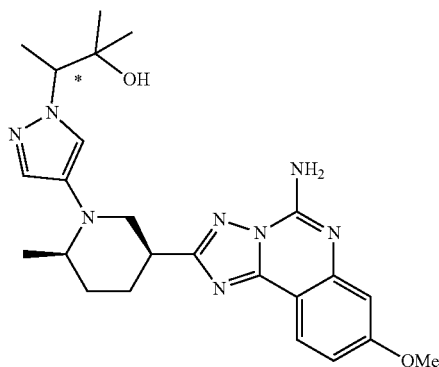 [SMILES: COc1ccc2c(c1)nc(N)n1nc([C@H]3CC[C@@H](C)N(c4cnn(C(C)C(C)(C)O)c4)C3)nc21]<br>(S)-3-4-((2R,5S)-5-(5-amino-8-methoxy-[1,2,4]triazolo[1,5-c]quinazolin-2-yl)-2-methylpiperidin-1-yl)-1H-pyrazol-1-yl)-2-methylbutan-2-ol,<br>(R)--3-(4-((2R,5S)-5-(5-amino-8-methoxy-[1,2,4]triazolo[1,5-c]quinazolin-2-yl)-2-methylpiperidin-1-yl)-1H-pyrazol-1-yl)-2-methylbutan-2-ol<br>The DMB-protected precusor was resolved by OJ-H 21 × 250 mm column with 1:1 MeOH:ACN (0.2% DIPA) as co-solvent | 465 |
| 213 | 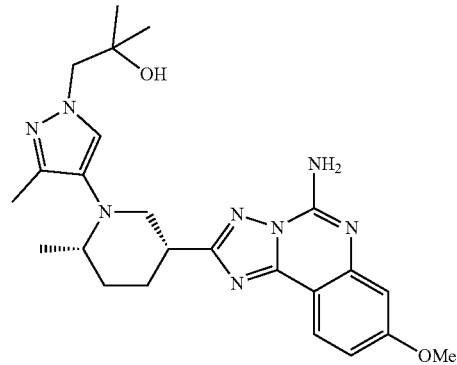 [SMILES: COc1ccc2c(c1)nc(N)n1nc([C@@H]3CC[C@H](C)N(c4cn(CC(C)(C)O)nc4C)C3)nc21]<br>1-(4-((2S,5R)-5-(5-amino-8-methoxy-[1,2,4]triazolo[1,5-c]quinazolin-2-yl)-2-methylpiperidin-1-yl)-3-methyl-1H-pyrazol-1-yl)-2-methylpropan-2-ol | 465 |

TABLE 17-continued
| Example | Structure Name | Observed m/z [M + H]+ |
|---|---|---|
| 214 | 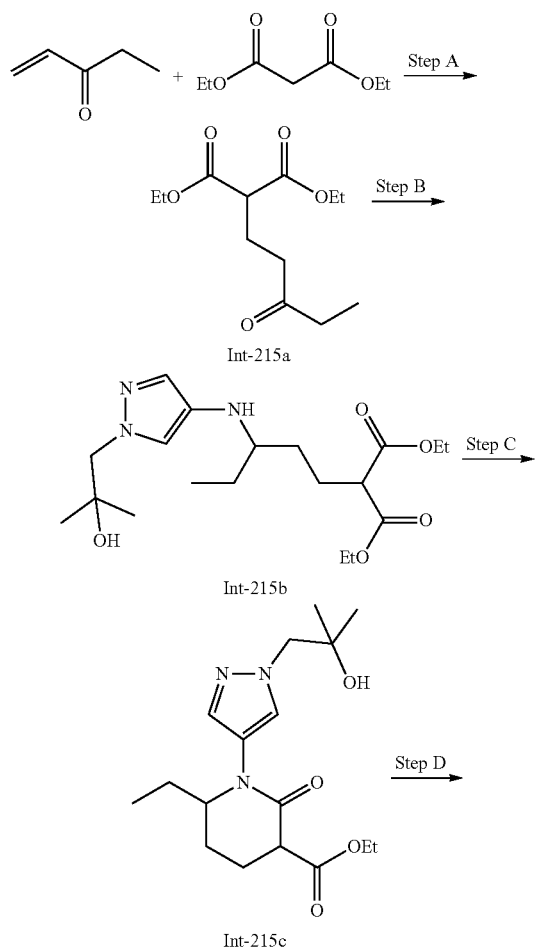 2-(4-((2S,5R)-5-(5-amino-8-methoxy-[1,2,4]triazolo[1,5-c]quinazolin-2-yl)-2-methylpiperidin-1-yl)-1H-pyrazol-1-yl)-2-methylpropan-1-ol | 451 |
Examples 215A 215B, 215C and 215D
The Preparation of the Compounds of Examples 215A, 215B, 215C and 215D
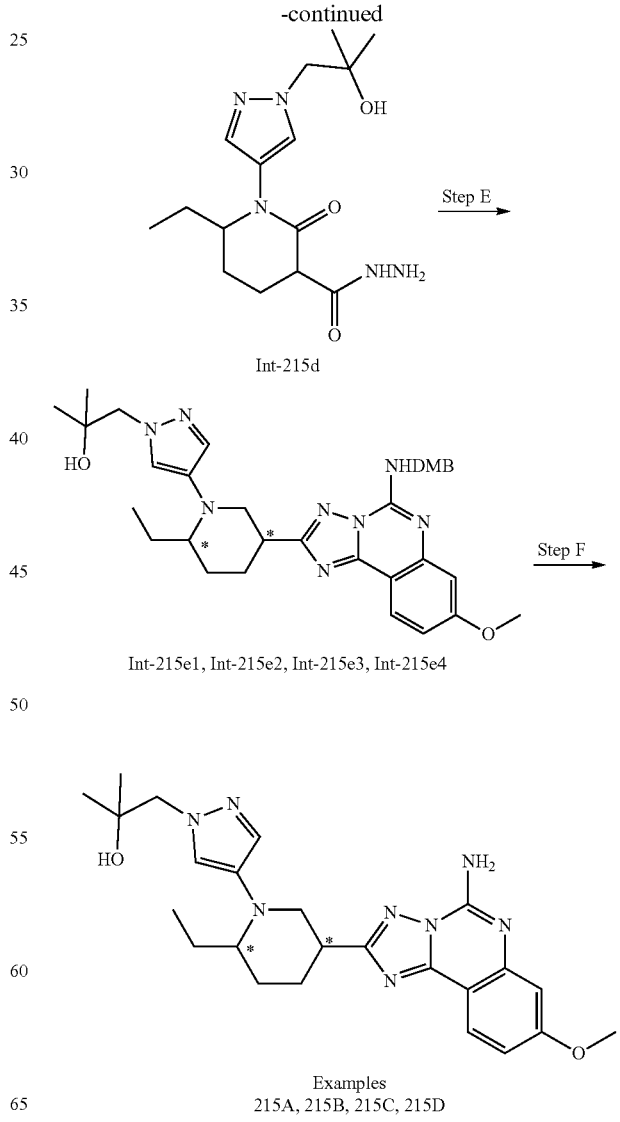

Step A—Synthesis of Compound Int-215a diethyl 2-(3-oxopentyl)malonate

A mixture of diethyl malonate (10 g, 62.4 mmol), pent-1-en-3-one (5.78 g, 68.7 mmol) and potassium carbonate (0.863 g, 6.24 mmol) in a sealed tube (Caution: exothermic) was stirred at room temperature for 3 days. The resulting mixture was filtered and purified by silica gel chromatography with 0-80% EtOAc/hexanes as eluent to provide Int-215a LC/MS (ES, m/z)=245 [M+H]$^+$.

Step B—Synthesis of Compound Int-215b diethyl 2-(3-((1-(2-hydroxy-2-methylpropyl)-1H-pyrazol-4-yl)amino)pentyl)malonate To a stirred solution of Int-215a (2.0 g, 12.89 mmol) in DCM (129 mL) was added diethyl 2-(3-oxopentyl)malonate (6.93 g, 28.4 mmol) and acetic acid (0.077 g, 1.289 mmol). The mixture was stirred at room temperature for 30 minutes, followed by the addition of sodium cyanoborohydride (1.620 g, 25.8 mmol) portionwise. The resulting mixture was then stirred at room temperature for an additional 30 minutes, and then quenched with 150 mL 1N HCl aqueous solution. The layers were separated and the aqueous layer was extracted with DCM twice. The combined organic layers were dried over anhydrous Na$_2$SO$_4$, filtered, and concentrated to afford Int-215b. LC/MS (ES, m/z)=384 [M+H]$^+$. The crude material was used in the next step without further purification.

Step C—Synthesis of Compound Int-215e ethyl 6-ethyl-1-(1-(2-hydroxy-2-methylpropyl)-1H-pyrazol-4-yl)-2-oxopiperidine-3-carboxylate To a solution of Int-215b (1.7 g, 4.43 mmol) in toluene (22 mL) was added acetic acid (0.532 g, 8.87 mmol). The mixture was then stirred at 90° C. for 2 days. Upon completion, the reaction mixture was concentrated. The resulting residue was purified by silica gel column chromatography with 0-100% EtOAc/hexane as eluent to provide Int-215e. LC/MS (ES, m/z)=339 [M+H]$^+$.

Step D—Synthesis of Compound Int-215d. 6-ethyl-1-(1-(2-hydroxy-2-methylpropyl)-1H-pyrazol-4-yl)-2-oxopiperidine-3-carbohydrazide To a solution of Int-215c (820 mg, 2.43 mmol) in MeOH (4.86 mL) was added hydrazine (312 mg, 9.72 mmol). The resulting mixture was stirred at 60° C. for 4 days, then concentrated, and the resulting residue was purified by silica gel column chromatography with 10% MeOH in DCM as eluent to provide Int-215d. LC/MS (ES, m/z)=324 [M+H]$^+$.

Step E—Synthesis of Compounds Int-215e1, Int-215e2, Int-215e3 and Int-215e4

A solution of Int-215d (500 mg, 1.546 mmol) in dioxane (7 mL) was added to acetic acid (0.044 ml, 0.773 mmol). 2-((((2,4-dimethoxybenzyl)imino)methylene)amino)-4-methoxybenzonitrile (500 mg, 1.546 mmol) was then added to the mixture. The mixture was stirred at 60° C. for 2 days. Upon completion, the resulting mixture was purified directly by silica Tel column chromatography with 0-100% 30% EtOH in EtOAc/hexanes as eluent to provide the desired intermediate. To the intermediate in THF (5 mL) was added 1M borane THF complex (6.0 mL, 6.0 mmol). The mixture was stirred at 50° C. for overnight. The resulting reaction mixture was cooled and then quenched with 50 mL 1N HCl aqueous solution. The mixture was extracted with EtOAc (2×50 mL). The combined organic layer was dried over anhydrous Na$_2$SO$_4$, filtered, and then concentrated. The resulting residue was purified by reverse phase HPLC with C18 column and 0-100% ACN/water as eluent to afford rac, cis-1-(4-(5-(5-(((3,4-dimethylbenzyl)amino-8-methoxy-[1,2,4]triazolo[1,5-c]quinazolin-2-yl)-2-ethylpiperidin-1-yl)-1H-pyrazol-1-yl)-2-methylpropan-2-ol and rac, trans-1-(4-(5-(5-(((3,4-dimethylbenzyl)amino)-8-methoxy-[1,2,4]triazolo[1,5-c]quinazolin-2-yl)-2-ethylpiperidin-1-yl)-1H-pyrazol-1-yl)-2-methylpropan-2-ol, LC/MS (ES, m/z)=583 [M+H]$^+$.

The above rac,cis-1-(4-(5-(5-(((3,4-dimethylbenzyl)amino)-8-methoxy-[1,2,4]triazolo[1,5-c]quinazolin-2-yl)-2-ethylpiperidin-1-yl)-1H-pyrazol-1-yl)-2-methylpropan-2-ol was further resolved by SFC with a chiral AS-H column (Chiral Technologies) and 50% IPA (0.2% DIPA) as co-solvent to provide Int-215e1 (peak 1) and Int-215e2 (peak 2). The rac, trans-1-(4-(5-(5-(((3,4-dimethylbenzyl)amino)-8-methoxy-[1,2,4]triazolo[1,5-c]quinazolin-2-yl)-2-ethylpiperidin-1-yl)-1H-pyrazol-1-yl)-2-methylpropan-2-ol was further resolved by SFC with a chiral AD-H column (Chiral Technologies) and 35% EtOH (0.2% DIPA) as co-solvent to provide Int-215e3 (peak 1) and Int-215e4 (peak 2).

Step F—Synthesis of Examples 215A, 215B, 215C and 215D

A solution of Int-215e1 (98 mg, 0.159 mmol) in 2,2,2-trifluoroacetic acid (4 mL) was heated at 60° C. for 1.5 hours, then concentrated. The residue was then purified by reversed-phase HPLC with C18 column and 0-100% MeCN/water w/0.1% TFA as eluent to provide Example 215A (trans peak1).

215A: LC/MS (ES, m/z)=465 [M+H]$^+$. $^1$H NMR (500 MHz, Methanol-d$^4$) δ 8.23 (d, J=8.7 Hz, 1H), 7.90 (s, 1H), 7.70 (s, 1H), 7.13 (d, J=10.7 Hz, 2H), 4.14 (s, 2H), 3.97 (s, 3H), 3.64 (s, 2H), 2.44 (s, 1H), 2.22 (d, J=14.7 Hz, 2H), 2.13-1.95 (m, 1H), 1.67 (s, 2H), 1.20 (s, 6H), 0.96 (t, J=7.5 Hz, 2H).

Using conditions similar to that described for the synthesis of Example 215A, Example 215B was prepared from Int-215e2.

215B (trans peak 2): LC/MS (ES, m/z)=465 [M+H]$^+$. $^1$H NMR (500 MHz, Methanol-d$^4$) δ 8.23 (d, J=8.7 Hz, 1H), 7.90 (s, 1H), 7.69 (s, 1H), 7.12 (d, J=11.3 Hz, 2H), 4.14 (s, 2H), 3.97 (s, 3H), 3.64 (s, 2H), 2.44 (s, 1H), 2.34-2.11 (m, 2H), 2.11-1.95 (m, 1H), 1.80-1.58 (m, 2H), 1.20 (s, 6H), 0.96 (t, J=7.5 Hz, 2H).

Using conditions similar to that described for the synthesis of Example 215A, Example 215C was prepared from Int-215e3.

215C (cis peak 1): LC MS (ES, m/z)=465 [M+H]$^+$. $^1$H NMR (500 MHz, Methanol-d$^4$) δ 8.22-8.16 (m, 1H), 8.13 (s, 1H), 7.85 (s, 1H), 7.19-7.01 (m, 2H), 4.18 (s, 2H), 4.01-3.90 (m, 3H), 3.75-3.54 (m, 2H), 2.68 (s, 2H), 2.59 (d, J=12.8 Hz, 1H), 2.48 (d, J=14.7 Hz, 1H), 2.20-2.05 (m, 1H), 1.97-1.86 (m, 1H), 1.77 (dd, J=10.7, 3.1 Hz, 1H), 1.63-1.44 (m, 1H), 1.20 (s, 5H), 1.12 (dd, J=16.5, 6.3 Hz, 1H), 0.99 (t, J=7.5 Hz, 3H).

Using conditions similar to that described for the synthesis of Example 215A, Example 215D was prepared from Int-215e4.

215D (cis peak 2): LC/MS (ES, m/z)=465 [M+H]$^+$. $^1$H NMR (500 MHz, Methanol-d$^4$) δ 8.18 (d, J=8.7 Hz, 1H), 8.15 (s, 1H), 7.87 (s, 1H), 7.18-7.06 (m, 3H), 4.19 (s, 2H), 3.96 (s, 3H), 3.76-3.58 (m, 2H), 3.33 (p, J=1.6 Hz, 9H), 2.59 (d, J=12.1 Hz, 1H), 2.51-2.42 (m, 1H), 2.25-2.09 (m, 1H), 2.05 (s, 1H), 1.98-1.87 (m, 1H), 1.86-1.71 (m, 2H), 1.53 (dt, J=14.2, 7.3 Hz, 1H), 1.20 (s, 6H), 1.12 (d, J=3.6 Hz, 1H), 0.99 (t, J=7.5 Hz, 3H).

The example compounds of the invention shown in Table 18 were prepared from the requisite starting materials, using a procedure similar to the procedure described for the preparation of Examples 215A-D.

TABLE 18

| Example | Structure Name | Observed m/z [M + H]+ |
|---|---|---|
| 216A (trans, peak 1) 216B (trans, peak 2) 216C (cis, peak 1) 216D (cis, peak 2) | 1-(4-((2S,5R)-5-(5-amino-7-methoxy-[1,2,4]triazolo[1,5-c]quinazolin-2-yl)-2-ethylpiperidin-1-yl)-1H-pyrazol-1-yl)-2-methylpropan-2-ol, 1-(4-((2R,5R)-5-(5-amino-7-methoxy-[1,2,4]triazolo[1,5-c]quinazolin-2-yl)-2-ethylpiperidin-1-yl)-1H-pyrazol-1-yl)-2-methylpropan-2-ol, 1-(4-((2S,5S)-5-(5-amino-7-methoxy-[1,2,4]triazolo[1,5-c]quinazolin-2-yl)-2-ethylpiperidin-1-yl)-1H-pyrazol-1-yl)-2-methylpropan-2-ol, 1-(4-((2R,5S)-5-(5-amino-7-methoxy-[1,2,4]-triazolo[1,5-c]quinazolin-2-yl)-2-ethylpiperidin-1-yl)-1H-pyrazol-1-yl)-2-methylpropan-2-ol | 465 |

Example 217

The Preparation of the Compound of Example 217

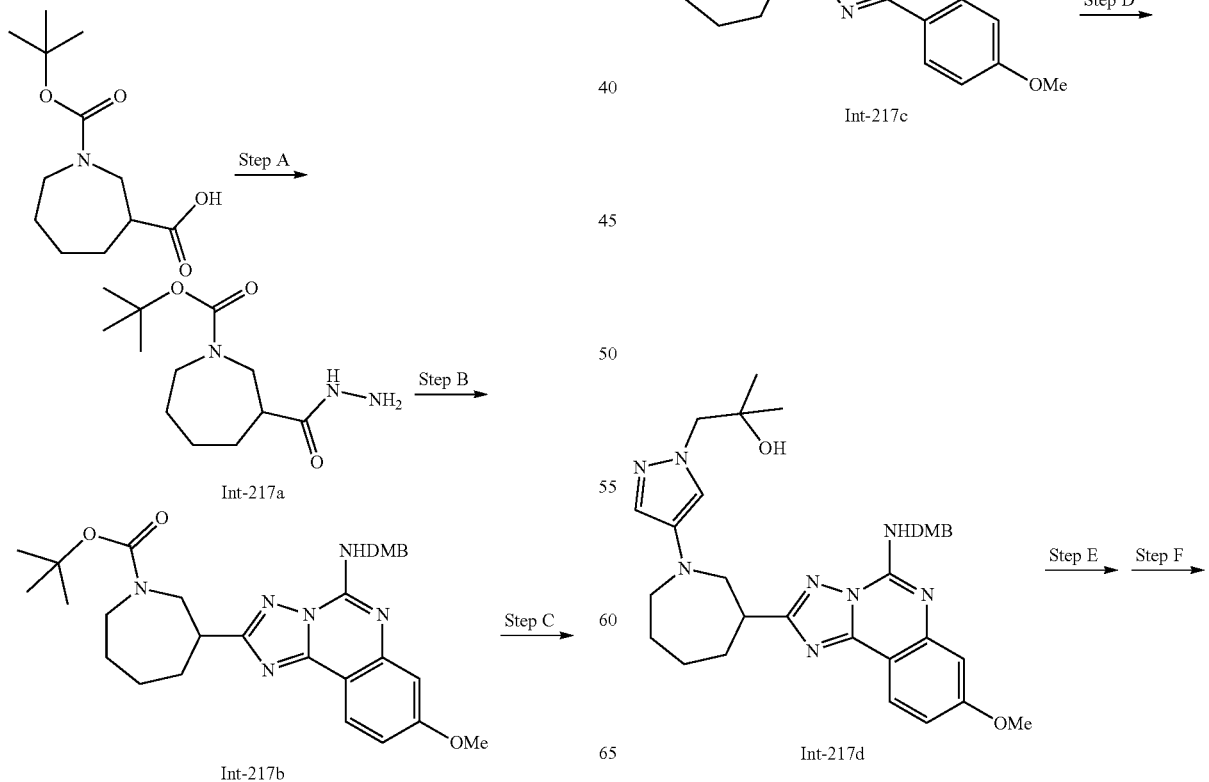

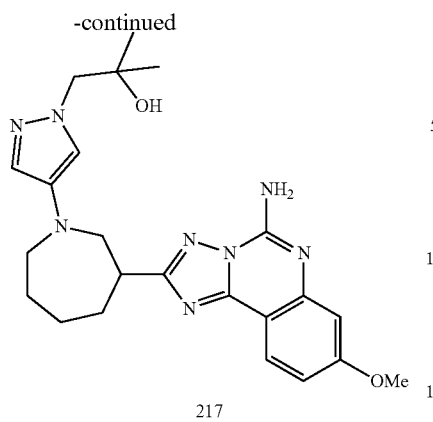

217

Step A—Synthesis of Compound Int-217a tert-butyl 3-(hydrazinecarbonyl)azepane-1-carboxylate A 20 ml scintillation vial was chanted with CDI (333 mg, 2.055 mmol) and THF (5138 μL). The resulting mixture was heated at 60° C. for 20 min. In a separate 20 mL scintillation vial was taken hydrazine hydrate (200 μL, 4.11 mmol) in THF (5138 μL) and to this was added the acyl imidazole mixture slowly for 5 minutes at room temperature. The resulting mixture was stirred for 5 minutes and concentrated under reduced pressure. The resulting residue was taken up in 20 mL of EtOAc and washed with 10 mL of saturated brine solution. The organic layer was concentrated to yield Int-217a LC/MS (ES, m/z)=258 [M+H]+.

Step B—Synthesis of Compound Int-217b tert-butyl 3-(5-((3,4-dimethylbenzyl)amino)-8-methoxy-[1,2,4]triazolo[1,5-c]quinazolin-2-yl)azepane-1-carboxylate To a solution of Int-217a (477 mg, 1.856 mmol) in 1,4-dioxane (10 mL) was added acetic acid (0.044 mL, 0.773 mmol), followed by 2-(4-((((2,4-dimethoxybenzyl)imino)methylene) amino)-4-methoxybenzonitrile (500 mg, 1.546 mmol) as solid. The resulting mixture was stirred at 60° C. for overnight. Upon completion, solvents were removed under reduced pressure to provide Int-217b. LC/MS (ES, m/z)=563 [M+H]+.

Step C—Synthesis of Compound Int-217c. 2-(azepan-3-yl)-N-(3,4-dimethylbenzyl)-8-methoxy-[1,2,4]triazolo[1,5-c]quinazolin-5-amine A 20 ml scintillation vial was charged with Int-217b (800 mg, 1.422 mmol) and formic acid (5453 μL, 142 mmol). The resulting mixture was stirred at room temperature for 2 days. Upon completion, the reaction mixture was concentrated and neutralized with 1N NaOH to neutral pH, then extracted with 20 mL of DCM. The organic phase was dried over anhydrous MgSO4, filtered, and concentrated. The crude residue was purified by silica gel column chromatography with 30% of methanol in DCM as eluent to provide the title compound Int-217c. LC/MS (ES, m/z)=463 [M+H]+.

Step D—Synthesis of Compound Int-217d. 1-(4-(3-(5-((3,4-dimethylbenzyl)amino)-8-methoxy-[1,2,4]triazolo[1,5-c]quinazolin-2-yl)azepan-1-yl)-1H-pyrazol-1-yl)-2-methylpropan-2-ol A 5 mL microwave vial equipped with a stir bar was charged with Int-217c (150 mg, 0.324 mmol), t-BuXPhos Pd G3 (129 mg, 0.162 mmol) and sodium 2-methylpropan-2-olate (125 mg, 1.297 mmol) under nitrogen. To this was added 1-(4-bromo-1H-pyrazol-1-yl)-2-methylpropan-2-ol (142 mg, 0.649 mmol) in 5 mL THF. The mixture was purged with N2 for 10 minutes. The vial was then sealed with a fresh cap and heated to 90° C. overnight. The reaction was cooled to room temperature, and then 5 mL of water and 15 ml, of DCM were added. The mixture was stirred for 5 minutes. The organic layer were separated, dried over anhydrous MgSO4, filtered, and concentrated to provide the title compound Int-217d. LC/MS (ES, m/z)=601 [M+H]+.

Step E—Synthesis of Example 217. 1-(4-(3-(5-amino-8-methoxy-[1,2,4]triazolo[1,5-c]quinazolin-2-yl)azepan-1-yl)-1H-pyrazol-1-yl)-2-methylpropan-2-ol A 20 ml scintillation vial was charged with Int-217d (150 mg, 0.250 mmol) and TFA (1250 μL, 16.23 mmol). The reaction mixture was stirred at 50° C. for 3 hours. The solvents were removed under reduced pressure and the crude residue was purified by silica gel preparative TLC to provide the title compound Example 217. LC/MS (ES, m/z)=451 [M+H]+. $^1$H NMR (499 MHz, DMSO-d$^6$) δ 8.12-8.05 (m, 1H), 7.69 (s, 2H), 7.12 (d, J=1.0 Hz, 1H), 7.07 (d, J=0.9 Hz, 1H), 6.99 (d, J=7.6 Hz, 2H), 4.63 (s, 1H), 3.88 (s, 3H), 3.87 (s, 2H), 3.75 (dd, J=14.4, 4.2 Hz, 1H), 3.55-3.50 (m, 1H), 3.45-3.40 (m, 2H), 3.23 (ddd, J=13.4, 7.7, 5.1 Hz, 1H), 2.05-1.85 (m, 4H), 1.70 (dt, J=9.9, 5.0 Hz, 1H), 1.55-1.44 (m, 1H), 1.03 (s, 6H).

Examples 218A and 218B

Preparation of the Compounds of Examples 218A and 218B

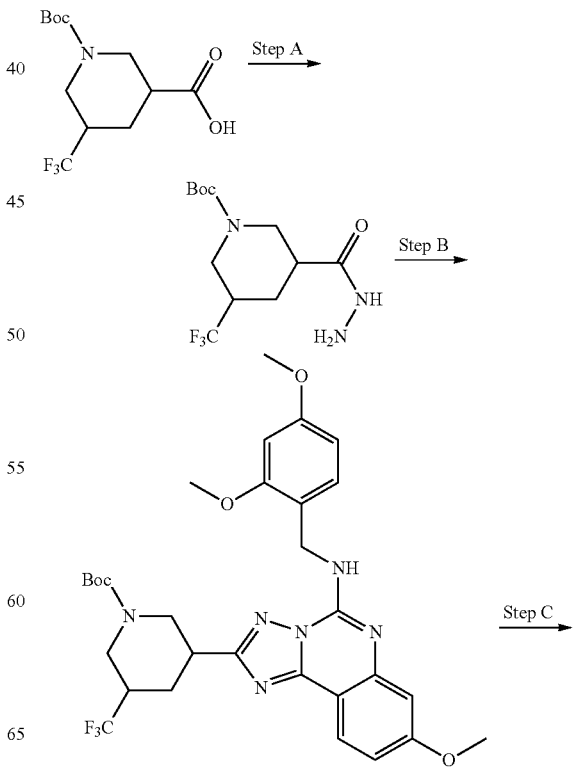

-continued

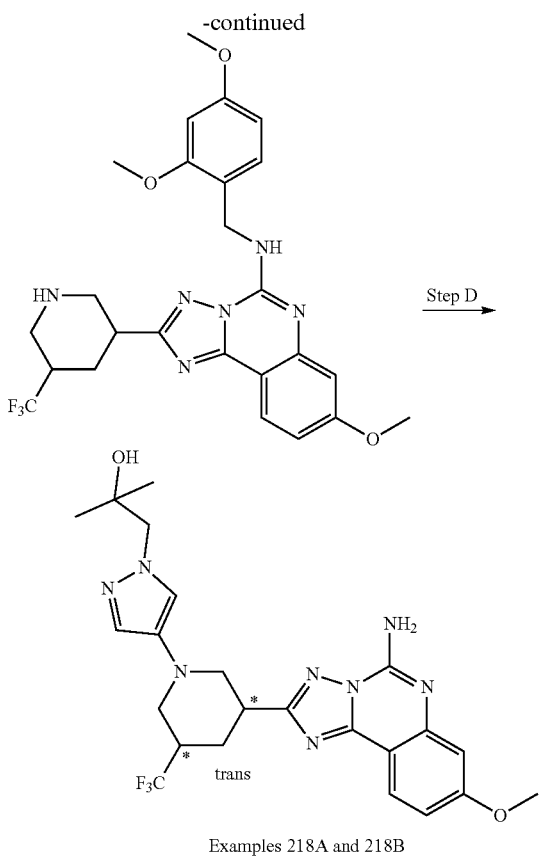

Examples 218A and 218B

Step A—tert-butyl 3-(hydrazinecarbonyl)-5-(trifluoromethyl)piperidine-1-carboxylate To a 20 ml vial was added CDI (1.36 g, 8.41 mmol), 1-(tert-butoxycarbonyl)-5-(trifluoromethyl)piperidine-3-carboxylic acid (2.50 g, 8.41 mmol) and THF (21 ml). The resulting mixture was stirred and heated at 60° C. for 20 min. To a separate vial was added hydrazine hydrate (0.817 ml, 16.8 mmol) in THF (21 ml) and to this was added the acyl imidazole mixture slowly over 5 min at room temperature. The resulting mixture was stirred for 5 min. The solvents were evaporated. The resulting residue was taken up in EtOAc and washed with brine solution. The organic layer was concentrated to afford tert-butyl 3-(hydrazinecarbonyl)-5-(trifluoromethyl)piperidine-1-carboxylate. LCMS ($C_{12}H_{20}F_3N_3O_3$) (ES, m/z) [M+Na]⁺: 334.

Step B—tert-butyl 3-(5-((2,4-dimethoxybenzyl)amino)-8-methoxy-[1,2,4]triazolo[1,5-c]quinazolin-2-yl)-5-(trifluoromethyl)piperidine-1-carboxylate To a solution of tert-butyl 3-(hydrainecarbonyl)-5-(trifluoromethyl)piperidine-1-carboxylate (1.16 g, 3.71 mmol) in 1,4-dioxane (10 mL) was added acetic acid (0.088 mL, 1.5 mmol). The mixture was stirred at room temperature. To the mixture was added 2-4-((((2,4-dimethoxybenzyl)imino)methylene)amino)-4-methoxybenzonitrile Intermediate C1 (1.00 g, 3.09 mmol). The resulting mixture was stirred at 75° C. for 16 h. The mixture was then concentrated and taken up in 20 mL of DCM. The organic layer was washed with saturated sodium bicarbonate solution and brine solution. The organic layer was dried over anhydrous sodium sulfate, filtered, and concentrated. The resulting residue was purified by silica gel chromatography with 5-30% of EtOAc in hexanes to afford tert-butyl 3-(5-((2,4-dimethoxybenzyl)amino)-8-methoxy-[1,2,4]triazolo[1,5-c]quinazolin-2-yl)-5-(trifluoromethyl)piperidine-1-carboxylate. LCMS ($C_{30}H_{35}F_3N_6O_5$) (ES, m/z) [M+H]⁺: 617.

Step C—N-(2,4-dimethoxybenzyl)-8-methoxy-2-(5-(trifluoromethyl)piperidin-3-yl)-[1,2,4]triazolo[1,5-c]quinazolin-5-amine A mixture of tert-butyl 3-(5-((2,4-dimethoxybenzyl)amino)-8-methoxy-[1,2,4]triazolo[1,5-c]quinazolin-2-yl)-5-(trifluoromethyl)piperidine-1-carboxylate (1.50 g, 2.43 mmol) and formic acid (933 ml, 243 mmol) was stirred at room temperature for 4 h. The reaction mixture was brought to neutral pH with 1 N NaOH$_{(aq.)}$. The mixture was extracted with DCM (30 mL). The organic layer was dried over anhydrous sodium sulfate, filtered, and the solvents were evaporated to afford N-(2,4-dimethoxybenzyl)-8-methoxy-2-(5-(trifluoromethyl)piperidin-3-yl)-[1,2,4]triazolo[1,5-c]quinazolin-5-amine, LCMS ($C_{25}H_{27}F_3N_6O_3$) (ES, m/z) [M+H]⁺: 517.

Step D—Synthesis of Examples 218A and 218B: 1-(4-((3S,5S or 3R,5R)-3-(5-amino-8-methoxy-[1,2,4]triazolo[1,5-c]quinazolin-2-yl)-5-(trifluoromethyl)piperidin-1-yl)-1H-pyrazol-1-yl)-2-methylpropan-2-ol and 1-(4-((3R,5R or 3S,5S)-3-(5-amino-8-methoxy-[1,2,4]triazolo[1,5-c]quinazolin-2-yl)-5-(trifluoromethyl)piperidin-1-yl)-1H-pyrazol-1-yl)-2-methylpropan-2-ol A 20 mL vial was charged with N-(2,4-dimethoxybenzyl)-8-methoxy-2-(5-(trifluoromethyl)piperidin-3-yl)-[1,2,4]triazolo[1,5-c]quinazolin-5-amine (250 mg, 0.484 mmol), 1-(4-bromo-1H-pyrazol-1-yl)-2-methylpropan-2-ol (Intermediate A1, 212 mg, 0.968 mmol), sodium 2-methylpropan-2-olate (186 mg, 1.94 mmol) and t-BuXPhos Pd G3 (192 mg, 0.242 mmol) under nitrogen. THF (3.5 mL) was added and the mixture was purged with nitrogen for 10 min. The mixture was then stirred and heated at 105° C. for 2 days. The reaction mixture was cooled to room temperature. To the mixture was added water (10 mL,) and DCM (10 mL). The mixture was stirred for 10 min and filtered. The organic layer was dried over anhydrous sodium sulfate, filtered, and concentrated. To the resulting residue was added TFA (0.037 ml, 0.48 mmol) and the mixture was heated at 50° C. for 3 h. The solvents were evaporated. To the resulting residue was added saturated aqueous NaHCO₃ solution. The mixture was extracted with DCM (30 mL) and the organic layer was dried over anhydrous sodium sulfate, filtered, and concentrated. The resulting residue was purified by silica gel chromatography with 5-30% of methanol in DCM as eluent. The resulting product was purified by SEC chiral separation (OJ-H 21×250 mm column with 20% MeOH (w/0.1% NH₄OH modifier) as cosolvent) to afford Peak 1:1-(4-((3S, 5S or 3R,5R)-3-(5-amino-8-methoxy-[1,2,4]triazol[1,5-c]quinazolin-2-yl)-5-(trifluoromethyl)piperidin-1-yl)-1H-pyrazol-1-yl)-2-methylpropan-2-ol (Example 218A) and Peak 2: 1-(4-((3R,5R or 3S,5S)-3-(5-amino-8-methoxy-[1,2,4]triazolo[1,5-c]quinazolin-2-yl)-5-(trifluoromethyl)piperidin-1-yl)-1H-pyrazol-1-yl)-2-methylpropan-2-ol (Example 218B).

218A: LCMS ($C_{23}H_{27}F_3N_8O_2$) (ES, m/z) [M+H]⁺: 505. ¹H NMR (499 MHz, DMSO-d₆) δ 8.07 (d, J=9.4 Hz, 1H), 7.72 (s, 2H), 7.31 (s, 1H), 7.22 (s, 1H), 6.99 (d, J=7.6 Hz,

2H), 4.60 (s, 1H), 3.88 (s, 3H), 3.86 (s, 2H), 3.65 (dd, J=11.6, 4.6 Hz, 1H), 3.60-3.51 (m, 1H), 3.26 (d, J=9.1 Hz, 2H), 3.12 (dd, J=11.4, 3.6 Hz, 1H), 2.79 (t, J=10.5 Hz, 1H), 1.98 (s, 1H), 1.01 (s, 6H).

218B: LCMS ($C_{23}H_{27}F_3N_8O_2$) (ES, m/z) [M+H]$^+$: 505. $^1$H NMR (499 MHz, DMSO-d$_6$) δ 8.07 (d, J=9.3 Hz, 1H), 7.74 (s, 2H), 7.31 (s, 1H), 7.22 (s, 1H), 6.99 (d, J=7.6 Hz, 2H), 3.88 (s, 3H), 3.86 (s, 2H), 3.65 (dd, J=11.5, 4.5 Hz, 1H), 3.57-3.52 (m, 1H), 3.26 (d, J 8.5 Hz, 1H), 3.12 (dd, J=11.6, 3.6 Hz, 1H), 2.79 (t, J=10.4 Hz, 1H), 2.54 (d, J=14.0 Hz, 1H), 2.04-1.95 (m, 1H), 1.01 (s, 6H).

Examples 219A, 219B, 219C, and 219D

Preparation of the compounds of examples 219A-D

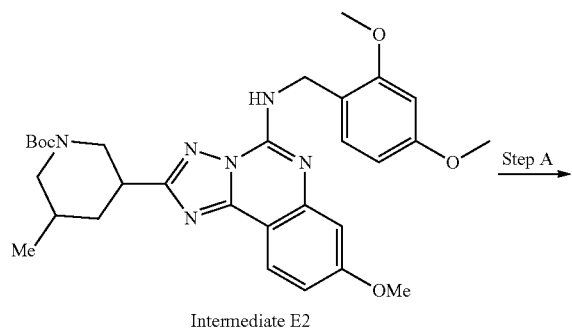

Intermediate E2

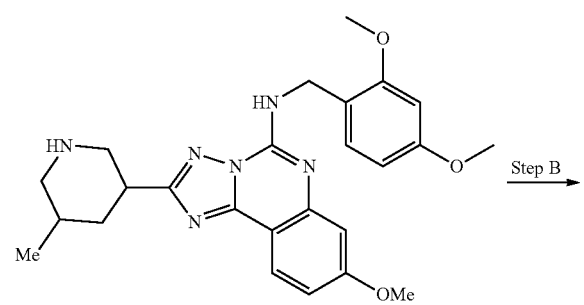

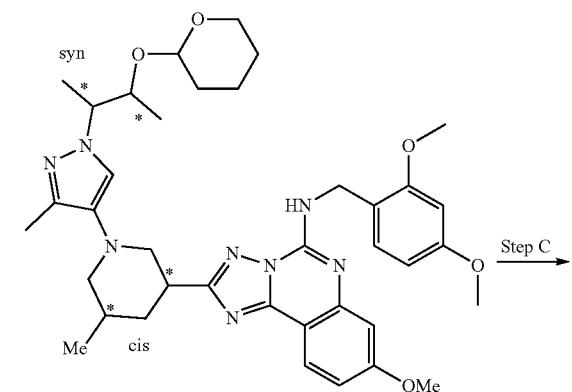

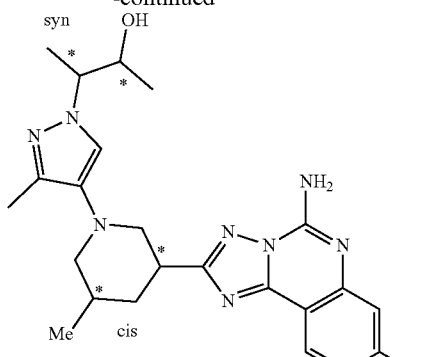

Examples 219A, 219B, 219C, 219D

Step A Synthesis of Compound (2,4-dimethoxybenzyl)-8-methoxy-2-(5-methylpiperidin-3-yl)-[1,2,4]triazolo[1,5-c]quinazolin-5-amine A solution of Intermediate E2 (1.2 g, 2.133 mmol) was dissolved in formic acid (10.2 mL, 266 mmol) and stirred for 3 hours at 23° C. The reaction mixture was then concentrated, diluted with 50 mL DCM, and neutralized with 50 mL saturated NaHCO$_3$ solution. The layers were separated and the basic aqueous layer was further extracted with an additional 50 mL DCM. The combined organic fractions were dried with anhydrous MgSO$_4$, filtered, and concentrated to yield N-(2,4-dimethoxybenzyl)-8-methoxy-2-(5-methylpiperidin-3-yl)-[1,2,4]triazolo[1,5-c]quinazolin-5-amine, which was used without further purification. LC/MS (ES, m/z)=463 [M+H]$^+$.

Step B—N-(2,4-dimethoxybenzyl)-8-methoxy-2-((3S,5R and 3R,5S)-5-methyl-1-(3-methyl-1-((2S,3S and 2R,3R)-3-(((RS)-tetrahydro-2H-pyran-2-yl)oxy)butan-2-yl)-1H-pyrazol-4-yl)piperidin-3-yl)-[1,2,4]triazolo[1,5-c]quinazolin-5-amine A 20 mL microwave vial containing a stir bar was sequentially charged with N-(2,4-dimethoxybenzyl)-8-methoxy-2-(5-methylpiperidin-3-yl)-[1,2,4]triazolo[1,5-c]quinazolin-5-amine (520 mg, 1.12 mmol), sodium tert-butoxide (432 mg, 4.50 mmol) and t-BuXPhos Pd (G3 (447 mg, 0.562 mmol). The vial was capped, flushed with nitrogen for 5 minutes, and subjected to three cycles of evacuation for 30 seconds and backfill with nitrogen for 30 seconds. To the mixture was added a degassed solution of 4-bromo-3-methyl-1-(3-(((RS)-tetrahydro-2H-pyran-2-yl)oxy)butan-2-yl)-1H-pyrazole (Intermediate F1, 713 mg, 2.25 mmol) in THF (10 mL). The reaction mixture was sparged with nitrogen for an additional 1 minute and placed in the microwave to stir at 80° C. overnight (14 hours). After cooling, 5 mL of sat. NH$_4$Cl and DCM were added to the reaction vessel. After stirring for 5 minutes, the reaction mixture was poured into a separator/funnel containing 10 mL of DCM and water. The layers were separated, and the aqueous layer was extracted with DCM (10 mL). The combined organic layers were dried with Mg$_2$SO$_4$, filtered, and concentrated under reduced pressure. The residue was purified by silica gel chromatography with 0-10% MeOH in DCM (w/1% Et$_3$N) as eluent to afford N-(2,4-dimethoxybenzyl)-8-methoxy-2-((3S,5R and 3R,5S)-5-methyl-1-(3- methyl-1-((2S,3S and 2R,3R)-3-(((RS)-tetrahydro-2H-pyran-2-yl)oxy)butan-2-yl)-1H-pyrazol-4-yl)piperidin-3-yl)-[1,2,4]triazolo[1,5-c]quinazolin-5-amine. LCMS ($C_{38}H_{50}N_8O_5$) (ES, m/z) [M+H]+: 699.

Step C—Synthesis of Examples 219A, 219B, 219C, and 219D: (2S,3S)-3-(4-((3S,5R)-3-(5-amino-8-methoxy-[1,2,4]triazolo[1,5-c]quinazolin-2-yl)-5-methylpiperidin-1-yl)-3-methyl-1H-pyrazol-1-yl)butan-2-ol, (2R,3R)-3-(4-((3R,5S)-3-(5-amino-8-methoxy-[1,2,4]triazolo[1,5-c]quinazolin-2-yl)-5-methylpiperidin-1-yl)-3-methyl-1H-pyrazol-1-yl)butan-2-ol, (2R,3R)-3-(4-((3S,5R)-3-(5-amino-8-methoxy-[1,2,4]triazolo[1,5-c]quinazolin-2-yl)-5-methylpiperidin-1-yl)-3-methyl-1H-pyrazol-1-yl)butan-2-ol, and (2S,3S)-3-(4-((3R,5S)-3-(5-amino-8-methoxy-[1,2,4]triazolo[1,5-c]quinazolin-2-yl)-5-methylpiperidin-1-yl)-3-methyl-1H-pyrazol-1-yl)butan-2-ol Water (1.471 mL) and concentrated hydrochloric acid (1.51 mL, 18.4 mmol) were sequentially added to a 40 mL scintillation vial containing N-(2,4-dimethoxybenzyl)-8-methoxy-2-((3S,5R and 3R,5S)-5-methyl-1-(3-methyl-1-((2S,3S and 2R,3R)-3-(((RS)-tetrahydro-2H-pyran-2-yl)oxy)butan-2-yl)-1H-pyrazol-4-yl)piperidin-3yl)-[1,2,4]triazolo[1,5-c]quinazolin-5-amine (514 mg, 0.735 mmol) and a stir bar. The mixture was stirred and at 45° C. After 3 hours, the resulting slurry was filtered and thoroughly rinsed with water (25 mL). The aqueous layer was poured into a separatory funnel and extracted with DCM (2×25 mL). The aqueous layer was basified with a solution of sodium hydroxide (882 mg, 22.1 mmol) in water (10 mL). To the mixture was added 3:1 $CHCl_3$/IPA (10 mL), and the mixture stirred vigorously for 16 h. The mixture was poured into a separatory funnel containing 3:1 $CHCl_3$/IPA (25 mL). The layers were separated, and the aqueous layer was extracted with 3:1 $CHCl_3$/IPA. (25 mL). The combined organic layers were dried with anhydrous $MgSO_4$, filtered, and concentrated under reduced pressure. The resulting residue was purified by silica gel chromatography with 0-10% MeOH in DCM (w/1% $Et_3N$) as eluent to afford a mixture of isomers.

The mixture was resolved by SFC chiral separation (Lux-2 21×250 mm, column with 35% MeOH (w/0.1% $NH_4OH$ modifier) as cosolvent) to afford the compounds Example 219A (Peak 1), Example 219B (Peak 2), Example 219C (Peak 3), and Example 219D (Peak 4).

219A: LCMS ($C_{24}H_{32}N_8O_2$) (ES, m/z) [M+H]+: 465. $^1$H NMR, (600 MHz, DMSO-$d_6$) δ 8.15-7:98 (m, 1H), 7.67 (s, 2H), 7.29 (s, 1H), 6.99 (dd, J=6.8, 2.4 Hz, 2H), 4.69 (d, J=5.2 Hz, 1H), 3.99 (p, J=6.9 Hz, 1H), 3.88 (s, 3H), 3.78 (dt, J=11.8, 5.9 Hz, 1H), 3.40 (d, J=3.7 Hz, 1H), 3.04 (d, J=8.6 Hz, 1H), 2.78 (d, J=8.5 Hz, 1H), 2.20 (s, 2H), 2.06 (s, 3H), 1.70 (s, 1H), 1.29 (d, J=7.0 Hz, 3H), 1.14 (d, J=6.6 Hz, 3H), 0.93 (d, J=6.3 Hz, 3H).

219B: LCMS ($C_{24}H_{32}N_8O_2$) (ES, m/z) [M+H]+: 465. $^1$H NMR (600 MHz, DMSO-$d_6$) δ 8.13-8.01 (m, 1H), 7.67 (s, 2H), 7.29 (s, 1H), 6.99 (dd, J=6.9, 2.4 Hz, 2H), 4.70 (d, J=5.1 Hz, 1H), 4.00 (p, J=6.8 Hz, 1H), 3.88 (s, 3H), 3.80 (q, J=5.5 Hz, 1H), 3.40 (d, J=4.0 Hz, 1H), 3.04 (d, J=9.0 Hz, 1H), 2.78 (d, J=8.0 Hz, 1H), 2.21 (s, 2H), 2.06 (s, 3H), 1.69 (s, 1H), 1.29 (d, J=7.0 Hz, 3H), 1.14 (d, J=6.6 Hz, 3H), 0.91 (d, J=6.3 Hz, 3H).

219C: LCMS ($C_{24}H_{32}N_8O_2$) (ES, m/z) [M+H]+: 465. $^1$H NMR (600 MHz, DMSO-$d_6$) δ 8.11-8.03 (m, 1H), 7.67 (s, 2H), 7.29 (s, 1H), 6.99 (dd, J=6.9, 2.4 Hz, 2H), 4.71 (d, J=5.2 Hz, 1H), 4.04-3.96 (m, 1H), 3.88 (s, 3H), 3.80 (dq, J=11.6, 6.2 Hz, 1H), 3.40 (d, J=3.6 Hz, 1H), 3.04 (d, J=8.8 Hz, 1H), 2.78 (d, J=7.8 Hz, 1H), 2.21 (s, 2H), 2.06 (s, 3H), 1.69 (s, 1H), 1.29 (d, J=7.0 Hz, 3H), 1.14 (d, J=6.6 Hz, 3H), 0.91 (d, J=6.3 Hz, 3H).

219D: LCMS ($C_{24}H_{32}N_8O_2$) (ES, m/z) [M+H]+: 465. $^1$H NMR (600 MHz, DMSO-$d_6$) δ 8.14-8.02 (m, 1H), 7.67 (s, 2H), 7.30 (s, 1H), 6.99 (dd, J=6.8, 2.4 Hz, 2H), 4.69 (d, J=5.2 Hz, 1H), 4.02-3.96 (m, 1H), 3.88 (s, 3H), 3.78 (dt, J=11.7, 5.8 Hz, 1H), 3.40 (d, J=3.5 Hz, 1H), 3.04 (d, J=10.3 Hz, 1H), 2.78 (d, J=8.0 Hz, 1H), 2.20 (s, 2H), 2.06 (s, 3H), 1.69 (s, 1H), 1.30 (s, 3H), 1.14 (d, J=6.6 Hz, 3H), 0.93 (d, J=6.3 Hz, 3H).

The example compounds of the invention shown in Table 19 were prepared using a procedure similar to the procedure described for the preparation of EXAMPLES 219A, 219B, 219C, and 219D, substituting the appropriate starting aryl halides and amines.

TABLE 19

| Example | Structure Name | SFC conditions | Observed m/z [M + H]+ |
|---|---|---|---|
| 220A (Peak 1) 220B (Peak 2) | <br>(2S,3S)-3-(4-((R)-3-(5-amino-8-methoxy-[1,2,4]triazolo[1,5-c]quinazolin-2-yl)piperidin-1-yl)-1H-pyrazol-1-yl)butan-2-ol, | AS-3 4.6 × 100 mm column; 5-40% EtOH w/ 0.05% DEA | 437 |

TABLE 19-continued

| Example | Structure Name | SFC conditions | Observed m/z [M + H]+ |
|---|---|---|---|
| | (2R,3R)-3-(4-((R)-3-(5-amino-8-methoxy-[1,2,4]triazolo[1,5-c]quinazolin-2-yl)piperidin-1-yl)-1H-pyrazol-1-yl)butan-2-ol | | |
| 221A (Peak 1) 221B (Peak 2) | (2R,3S)-3-(4-((R)-3-(5-amino-8-methoxy-[1,2,4]triazolo[1,5-c]quinazolin-2-yl)piperidin-1-yl)-1H-pyrazol-1-yl)butan-2-ol, (2S,3R)-3-(4-((R)-3-(5-amino-8-methoxy-[1,2,4]triazolo[1,5-c]quinazolin-2-yl)piperidin-1-yl)-1H-pyrazol-1-yl)butan-2-ol | AD-3 4.6 × 100 mm column; 5-40% EtOH w/ 0.05% DEA | 437 |
| 222A (Peak 1) 222B (Peak 2) 222C (Peak 3) 222D (Peak 4) | 2-(4-((3R,5S)-3-(5-amino-8-methoxy-[1,2,4]triazolo[1,5-c]quinazolin-2-yl)-5-methylpiperidin-1-yl)-1H-pyrazol-1-yl)-2-methylpropan-1-ol, 2-(4-((3S,5S)-3-(5-amino-8-methoxy-[1,2,4]triazolo[1,5-c]quinazolin-2-yl)-5-methylpiperidin-1-yl)-1H-pyrazol-1-yl)-2-methylpropan-1-ol, 2-(4-((3S,5R)-3-(5-amino-8-methoxy-[1,2,4]triazolo[1,5-c]quinazolin-2-yl)-5-methylpiperidin-1-yl)-1H-pyrazol-1-yl)-2-methylpropan-1-ol, 2-(4-((3R,5R)-3-(5-amino-8-methoxy-[1,2,4]triazolo[1,5-c]quinazolin-2-yl)-5-methylpiperidin-1-yl)-1H-pyrazol-1-yl)-2-methylpropan-1-ol | CCA 21 × 250 mm column; 30% MeOH w/ 0.1% NH4OH | 451 |

Example 223

Preparation of the Compound of Example 223

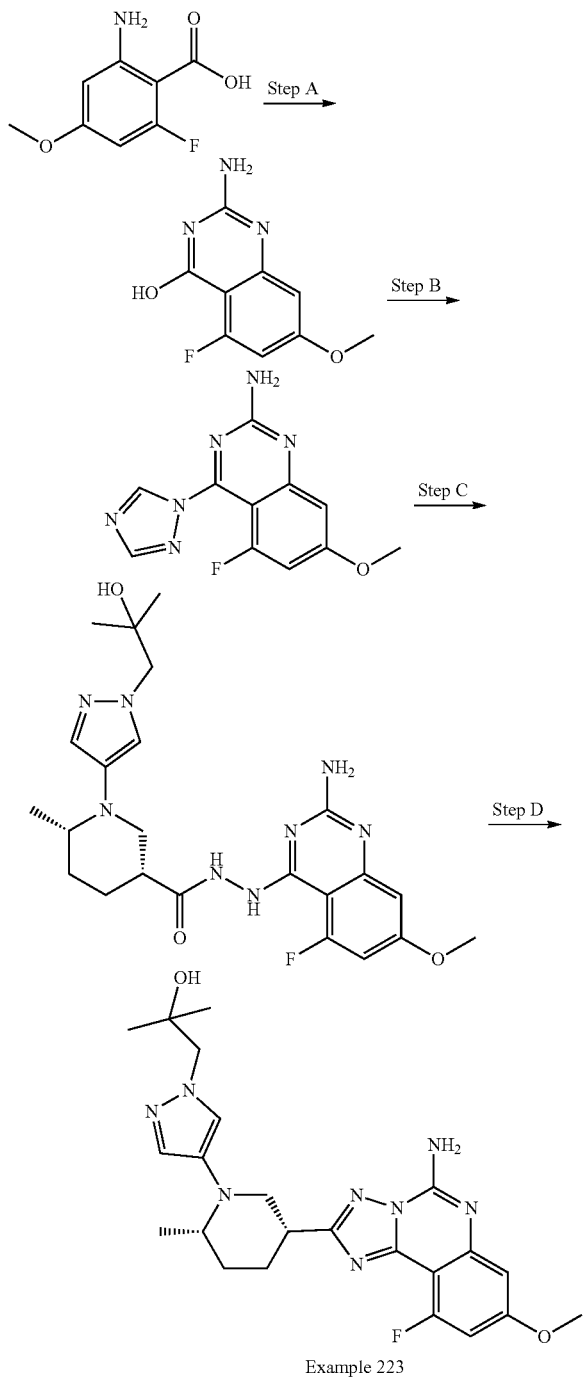

Example 223

Step A—2-amino-5-fluoro-7-methoxyquinazolin-4-ol

To a stirred suspension of 2-amino-6-fluoro-4-methoxybenzoic acid (1000 mg, 5.40 mmol) in EtOH (10.8 mL) was added cyanamide (568 mg, 13.5 mmol) and HCl (1.17 mL, 7.02 mmol) (6M, aqueous). The mixture was heated at reflux for 16 hours. The mixture was cooled to room temperature. The precipitate was collected by filtration and dried under high vacuum to afford 2-amino-5-fluoro-7-methoxyquinazolin-4-ol. LCMS ($C_9H_8FN_3O_2$) (ES, m/z) [M+H]$^+$: 210.

Step B—5-fluoro-7-methoxy-4-(1H-1,2,4-triazol-1-yl)quinazolin-2-amine

To a stirred mixture of 1,2,4-triazole (175 mg, 2.54 mmol), 2-amino-5-fluoro-7-methoxyquinazolin-4-ol (177 mg, 0.846 mmol) and DIPEA (443 μl, 2.54 mmol) in MeCN (4.2 ml) was added POCl$_3$ (237 μl, 2.54 mmol) dropwise. The mixture was stirred at 40° C. for 4 hours and then room temperature for 16 hours. The mixture was filtered through Celite®, washing with MeCN and diethyl ether to afford 5-fluoro-7-methoxy-4-(1H-1,2,4-triazol-1-yl)quinazolin-2-amine, LCMS ($C_{11}H_9FN_6O$) (ES, m/z) [M+H]$^+$: 261.

Step C—(3R,6S)—N'-(2-amino-5-fluoro-7-methoxyquinazolin-4-yl)-1-(1-(2-hydroxy-2-methylpropyl)-1H-pyrazol-4-yl)-6-methylpiperidine-3-carbohydrazide A 20 mL vial was charged with 5-fluoro-7-methoxy-4-(1H-1,2,4-triazol-1-yl)quinazolin-2-amine (50 mg, 0.192 mmol), (3R,6S)-1-(1-(2-hydroxy-2-methylpropyl)-1H-pyrazol-4-yl)-6-methylpiperidine-3-carbohydrazide (85 mg, 0.288 mmol), DMA (1.3 ml) and DIPEA (168 μl, 0.961 mmol). The vial was capped and the mixture was stirred and heated at 80° C. for 4 hours and then at room temperature for 16 hours. The mixture was concentrated to afford (3R,6S)—N'-(2-amino-5-fluoro-7-methoxyquinazolin-4-yl)-1-(1-(2-hydroxy-2-methylpropyl)-1H-pyrazol-4-yl)-6-methylpiperidine-3-carbohydrazide, which was used without further purification.

Step D—Synthesis of Example 223

(3R,6S)—N-(2-amino-5-fluoro-7-methoxyquinazolin-4-yl)-1-(1-(2-hydroxy-2-methylpropyl)-1H-pyrazol-4-yl)-6-methylpiperidine-3-carbohydrazide (93 mg, 0.192 mmol) was taken up in N, O-bis(trimethylsilyl)acetamide (2.00 mL, 0.192 mmol), and the mixture was stirred and heated at 120° C. for 2 hours. The mixture was concentrated, and the residue taken up in DCM (1 mL) and acidified with hydrochloric acid (1 mL, 4.00 mmol) (4 M solution in dioxane). The resulting solution was stirred at room temperature for 30 min. The mixture was concentrated, diluted with dichloromethane (10 mL), washed with aqueous sodium bicarbonate (saturated, 10 mL), and the organic layer collected using a phase separator and concentrated. The residue was purified by reversed phase HPLC (Waters XBridge C18 OBD Prep Column, 19×150 mm MeCN/water with 0.1% NH$_4$OH modifier) to afford 1-(4-((2S,5R)-5-(5-amino-10-fluoro-8-methoxy-[1,2,4]triazolo[1,5-c]quinazolin-2-yl)-2-methylpiperidin-1-yl)-1H-pyrazol-1-yl)-2-methylpropan-2-ol (Example 223). LCMS ($C_{23}H_{29}FN_8O_2$) (ES, m/z) [M+H]$^+$: 469. $^1$H NMR (600 MHz, DMSO-d6) δ 7.89 (s, 2H), 7.20 (s, 1H), 7.15 (s, 1H), 6.87 (dd, J=11.9, 2.2 Hz, 1H), 6.84 (d, J=2.2 Hz, 1H), 4.62 (s, 1H), 3.89 (s, 3H), 3.88 (s, 2H), 3.73-3.66 (m, 1H), 3.36-3.33 (m, 1H), 3.25-3.15 (m, 1H), 3.09 (t, J=11.5 Hz, 1H), 2.04-1.93 (m, 3H), 1.72-1.67 (m, 1H), 1.03 (s, 6H); 1.02 (d, J=5.8 Hz, 3H).

The example compounds of the invention shown in Table 20 were prepared using a procedure similar to the procedure described for the preparation of Example 223, substituting the appropriate starting materials.

317
TABLE 20
| Example | Structure Name | Observed m/z [M + H]+ |
|---|---|---|
| 224 | 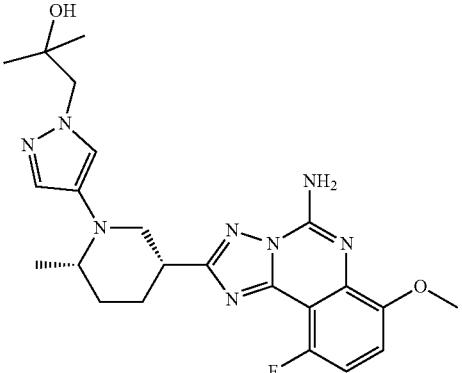
1-(4-((2S,5R)-5-(5-amino-10-fluoro-7-methoxy-[1,2,4]triazolo[1,5-c]quinazolin-2-yl)-2-methylpiperidin-1-yl)-1H-pyrazol-1-yl)-2-methylpropan-2-ol | 469 |
Examples 225A and 225B
Preparation of the Compounds of Example 225A and 225B
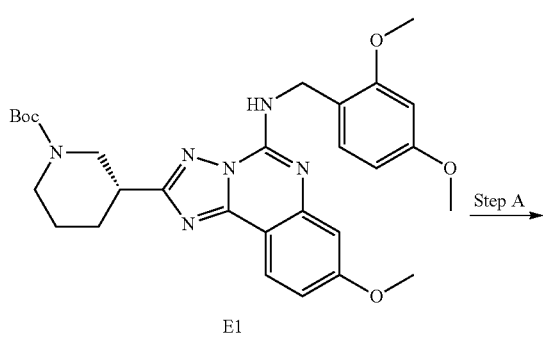
E1
Step A
-continued
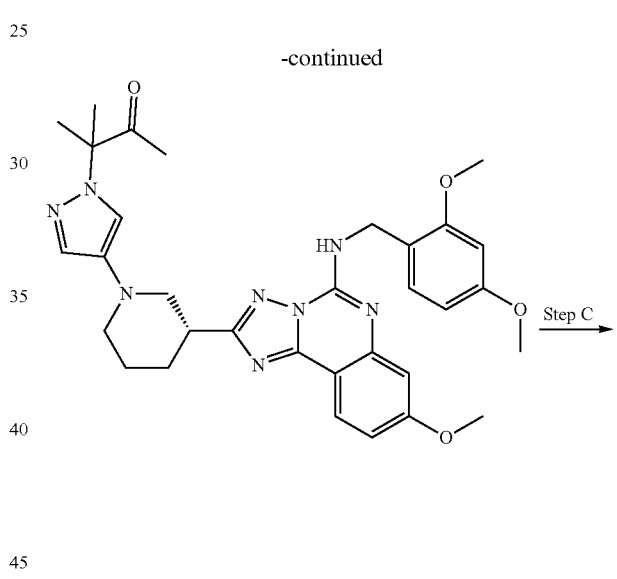
Step C
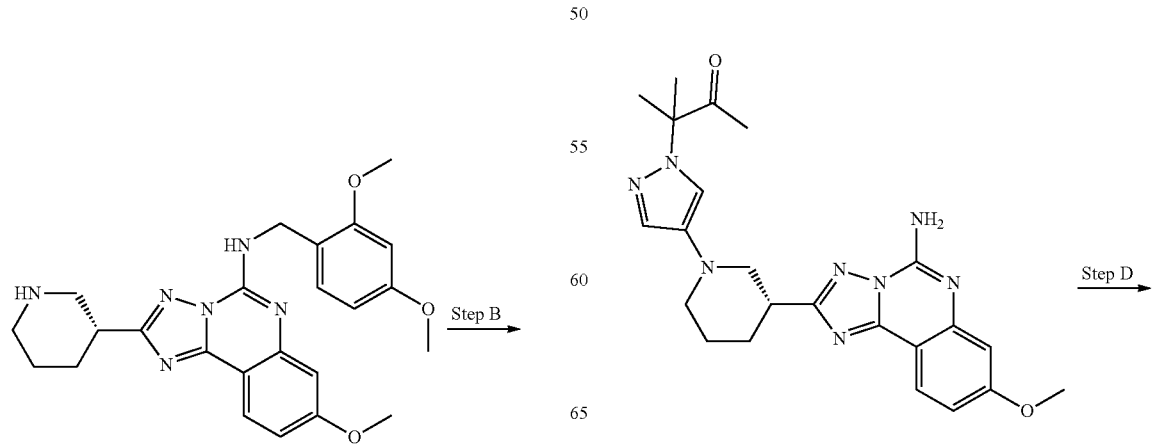
Step D
Step B

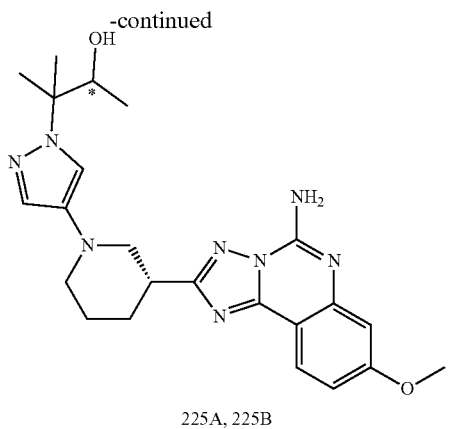

225A, 225B

Step A—(R)—N-(2,4-dimethoxybenzyl)-8-methoxy-2-(piperidin-3-yl)-[1,2,4]triazolo[1,5-c]quinazolin-5-amine A 200 mL round-bottom flask equipped with a stirbar was charged with (R)-text-butyl 3-(5-((2,4-dimethoxylbenzyl) amino)-8-methoxy-[1,2,4]triazolo[1,5-c]quinazolin-2-yl)piperidine-1-carboxylate Intermediate E1 (1.93 g, 3.52 mmol). To the flask was added formic acid (40.5 mL, 1060 mmol) and the mixture was stirred at room temperature for 2 hours. The solvents were evaporated. To the resulting residue was added saturated aqueous sodium bicarbonate (100 mL), and the mixture was extracted with DCM (2×100 mL). The organic layers were combined, dried over anhydrous magnesium sulfate, filtered, and the solvents were evaporated to afford (R)—N-(2,4-dimethoxybenzyl)-8-methoxy-2-(piperidin-3-yl)-[1,2,4]triazolo[1,5-c]quinazolin-5-amine. LCMS ($C_{24}H_{28}N_6O_3$) (ES, m/z) [M+H]$^+$: 449.

Step B—(R)-3-(4-(3-(5-((2,4-dimethoxybenzyl)amino)-8-methoxy-[1,2,4]triazolo[1,5-c]quinazolin-2-yl)piperidin-1-yl)-1H-1-pyrazol-1-yl)-3-methylbutan-2-one A 40 mL vial was charged with (R)—N-(2,4-dimethoxybenzyl)-8-methoxy-2-(piperidin-3-yl)-[1,2,4]triazolo[1,5-c]quinazolin-5-amine (1.00 g, 2.23 mmol), 3-(4-bromo-1H-pyrazol-1-yl)-3-methylbutan-2-one (1.03 g, 4.46 mmol), t-BuXPhos Pd G3 (0.886 g, 1.12 mmol) and sodium 2-methylpropan-2-olate (0.857 g, 8.92 mmol). The vial was purged with nitrogen. To the mixture was added THF (13.5 mL), and the mixture was stirred and heated at 105° C. overnight. The mixture was filtered through Celite®, rinsing with DCM, and the filtrate was concentrated. The resulting residue was purified by silica gel chromatography with 0-10% MeOH in DCM as eluent, to afford (R)-3-(4-(3-(5-((2,4-dimethoxybenzyl)amino)-8-methoxy-[1,2,4]triazolo[1,5-c]quinazolin-2-yl)piperidin-1-yl)-1H-pyrazol-1-yl)-3-methylbutan-2-one. LCMS (($C_{32}H_{38}N_8O_4$) (ES, m/z) [M+H]$^+$: 599.

Step C—(R)-3-(4-(3-(5-amino-8-methoxy-[1,2,4]triazolo[1,5-c]quinazolin-2-yl)piperidin-1-yl)-1H-pyrazol-1-yl)-3-methylbutan-2-one To a 30 mL vial containing (R)-3-(4-(3-(5-((2,4-dimethoxybenzyl)amino)-8-methoxy-[1,2,4]triazolo[1,5-c]quinazolin-2-yl)piperidin-1-yl)-1H-pyrazol-1-yl)-3-methylbutan-2-one (1.00 g, 1.670 mmol) and a stir bar, TFA (16.70 ml) was added, and the reaction mixture was stirred and heated at 50° C. for 2 h. The solvents were evaporated. The residue was dissolved in 25% IPA in Chloroform (40 mL) and sat. aq. NaHCO$_3$ (40 mL) was added. This mixture was stirred at room temperature for 2 h. The layers were separated, and the aqueous layer was extracted with 25% IPA in Chloroform (2×50 mL). The combined organic layers were dried over anhydrous MgSO$_4$, filtered and concentrated to afford (R)-3-(4-(3-(5-amino-8-methoxy-[1,2,4]triazolo[1,5-c]quinazolin-2-yl)piperidin-1-yl)-1H-pyrazol-1-yl)-3-methylbutan-2-one, which was used in the next step without further purification. LCMS ($C_{23}H_{28}N_8O_2$) (ES, m/z) [M+H]$^+$: 449.

Step D—Synthesis of Examples 225A and 225B

A sample of 3-(4-(3-(5-amino-8-methoxy-[1,2,4]triazolo[1,5-c]quinazolin-2-yl)piperidin-1-yl)-1H-pyrazol-1-yl)-3-methylbutan-2-one (1.00 g, 2.23 mmol) was suspended in EtOH (22.30 mL) in a 40 mL vial, and to this mixture was added sodium borohydride (0.253 g, 6.69 mmol). The mixture was stirred at room temperature for 3 h. The mixture was poured into a 250 mL Erlenmeyer flask and quenched with water (25 mL). The mixture was extracted with DCM (40 mL), followed by 25% IPA in Chloroform (2×50 mL). The combined organic layers were dried over anhydrous MgSO$_4$, filtered, and concentrated. The resulting residue was purified by silica gel chromatography with 0-30% MeOH in DCM as eluent, to afford a mixture of isomers. The mixture was resolved by SFC chiral separation (IC 21×250 mm column with 40% IPA (w/0.1% NH$_4$OH modifier) as cosolvent) to afford the compounds Example 225A (Peak 1) and Example 225B (Peak 2).

225A: LCMS ($C_{23}H_{30}N_8O_2$) (ES, m/z) [M+H]$^+$: 451. $^1$H NMR (600 MHz, DMSO-d$_6$) δ 8.07 (d, J=8.8 Hz, 1H), 7.72 (s, 2H), 7.38 (s, 1H), 7.21 (s, 1H), 6.99 (d, J=8.2 Hz, 2H), 4.81 (d, J=5.5 Hz, 1H), 3.88 (s, 3H), 3.81 (p, J=6.3 Hz, 1H), 3.62 (dd, J=11.3, 3.4 Hz, 1H), 3.37 (s, 1H), 3.29-3.17 (m, 1H), 2.81 (t, J=11.2 Hz, 1H), 2.55 (d, J=8.5 Hz, 1H), 2.15 (s, 1H) 1.91-1.68 (m, 3H), 1.45 (s, 3H), 1.39 (s, 3H).

225B: LCMS ($C_{23}H_{30}N_8O_2$) (ES, m/z) [M+H]$^+$: 451. $^1$H NMR (600 MHz, DMSO-d$_6$) δ 8.08 (d, J=8.8 Hz, 1H), 7.72 (s, 2H), 7.38 (s, 1H), 7.21 (s, 1H), 6.99 (d, J=8.1 Hz, 2H), 4.81 (d, J=5.5 Hz, 1H). 3.82 (p, J=6.2 Hz, 1H), 3.68-3.54 (m, 1H), 3.37 (s, 1H), 3.28-3.17 (m, 1H), 2.81 (t, J=11.2 Hz, 1H), 2.55 (s, 1H), 2.15 (s, 1H), 1.91-1.68 (m, 1H), 1.45 (s, 3H), 1.39 (s, 3H).

Biological Assays

The IC$_{50}$ values reported for each of the compounds of the invention shown in the table below were measured in accordance with the methods described below. An asterisk (*) in the table indicates that the data point was not available or not measured.

The A2a receptor affinity binding assay measured the amount of binding of a tritiated ligand with high affinity for the A2a adenosine receptor to membranes made from HEK293 or CHO cells recombinantly expressing the human A2a adenosine receptor, in the presence of varying concentrations of a compound of the invention. In each assay, the tested compounds of the invention were solubilized in 100% DMSO and further diluted in 100% DMSO to generate, typically, a 10-point titration at half-log intervals such that the final assay concentrations did not exceed 10 μM of compound or 1% DMSO.

Measurement of A2a Binding Affinity Using Radioligand Binding

148 µL, (5 µg/mL) membranes (Perkin Elmer, Cat. No. RBHA2aM4001A) and 2 µL compounds of the invention to be tested (test compound) were transferred to individual wells of a 96-well polypropylene assay plate and incubated for 15 to 30 minutes at room temperature. [$^3$H] SCH58261 ((7-(2-phenylethyl)-5-amino-2-(2-furyl)-pyrazolo-[4,3-e]-1,2,4-triazolo[1,5-c]pyrimidine)) was diluted in assay buffer (50 mM Tris pH 7.4, 10 mM $MgCl_2$, 0.005% Tween20) to a concentration of 4 nM and 50 µL transferred to each well of the assay plate. To define total and non-specific binding, wells containing 1% DMSO and 1 µZM241385 (Tocris Bioscience, Cat No. 1036) respectively, were also included. The assay plate was incubated at room temperature for 60 minutes with agitation. Using a FilterMate Harvester® (Perkin Elmer), the contents of the assay plate were filtered through a UniFilter-96® PEI coated plate (Perkin Elmer Cat. No. 6005274 or 6005277). Filtering was achieved by aspirating the contents of the assay plate for 5 seconds, then washing and aspirating the contents three times with ice-cooled wash buffer (50 mM Tris-HCl pH 7.4, 150 mM NaCl) and allowing the vacuum manifold to dry the plate for 30 seconds. The filter plate was incubated for at least 1 hour at 55° C. and allowed to dry. The bottom of the filter plate was sealed with backing tape. 40 µL Ultima Gold™ (Perkin Elmer, Cat. No. 6013329) was added to each well of the filter plate and the top of the plate was sealed with TopSeal-A PLUS® clear plate seal (Perkin Elmer, Cat. No. 6050185). The plate was incubated for at least 20 minutes, and then the amount of radioactivity remaining in each well was determined using a TopCown® (Perkin Elmer) scintillation counter. After normalization to total and non-specific binding, the percent effect at each compound concentration was calculated. The plot of percent effect versus the log of compound concentration was analyzed electronically using a 4-parameter logistic fit based on the Levenberg-Marquardt algorithm to generate $IC_{50}$ values.

Measurement of A2b Binding Affinity

The reported affinity of the compounds of the invention for the human A2b adenosine receptor was determined experimentally using a radioligand filtration binding assay. This assay measures the amount of binding of a tritiated proprietary A2b receptor antagonist, in the presence and absence of a compound of the invention, to membranes made from HEK293 cells recombinantly expressing the human A2b adenosine receptor (Perkin Elmer, Cat. No. ES-013-C).

To perform the assay, compounds of the invention to be tested were first solubilized in 100% DMSO and further diluted in 100% DMSO to generate, typically, a 10-point titration at half-log intervals such that the final assay concentrations did not exceed 10 µM of compound or 1% DMSO. 148 µL (135 µg/mL) membranes and 2 µL test compounds were transferred to individual wells of a 96-well polypropylene assay plate and incubated for 15 to 30 minutes at room temperature with agitation. Tritiated radioligand was diluted to a concentration of 14 nM in assay buffer (phosphate buffered saline without Magnesium and Calcium, pH 7.4; GE Healthcare Life Sciences, Cat. No. SH30256.01) and then 50 µL of the solution were transferred to each well of the assay plate. To define total and non-specific binding, wells containing 1% DMSO and 20 µM N-ethylcarboxamidoadenosine (Tocris Bioscience, Cat. No. 1691) respectively, were also included. The wells of the assay plate were incubated at room temperature for 60 minutes with agitation, then filtered using a FilterMate Harvester® (Perkin Elmer) or similar equipment through a Unifilter-96® PEI coated plate (Perkin Elmer Cat. No. 6005274 or 6005277). Filtering was achieved by aspirating the contents of the assay plate for 5 seconds, then washing and aspirating the contents three times with ice-cooled wash buffer (assay buffer supplemented with 0.0025% Brij58) and allowing the vacuum manifold to dry the plate for 30 seconds. The filter plate was incubated for at least 1 hour at 55° C. and allowed to dry. The bottom of the filter plate was then sealed with backing tape. 40 µL Ultima Gold™ (Perkin Elmer, Cat. No. 6013329) was added to each well of the filter plate and the top of the plate was sealed with TopSeal-A PLUS® clear plate seal (Perkin Elmer, Cat, No. 6050185). The plates were then incubated for at least 20 minutes, and then the amount of radioactivity remaining in each well was determined using a TopCount® (Perkin Elmer) scintillation counter. After normalization to total and non-specific binding, the percent effect at each compound concentration was calculated. The plot of percent effect versus the log of compound concentration was analyzed electronically using a 4-parameter logistic fit based on the Levenberg-Marquardt algorithm to generate $IC_{50}$ values.

Measurement of $A_{2A}$ and $A_{2B}$ Antagonism in cAMP Cell-Based Assay

The ability of compounds to antagonize human $A_{2A}$ and $A_{2B}$ adenosine receptors was determined using a kit to measure changes in intracellular cyclic AMP levels (LANCE cAMP 384 Kit, Perkin Elmer, Cat. No. AD0264). HEK293 cells recombinantly expressing either human $A_{2A}$ or $A_{2B}$ receptors, previously frozen in Recovery Medium (Life Technologies, Cat. No. 12648-010) were thawed and diluted into stimulation buffer (HBSS (Hyclone SR 30268.01), 5 mM HEPES (Gibco 15630-106), 200 nM rolipram (Tocris, Cat. No, 0905), and 1.5% (V/v) BSA stabilizer (kit component). The cell suspension was centrifuged at 200×g for 10 min and then resuspended in stimulation buffer, supplemented with a 1:10 000 dilution of Alexa Fluor 647 anti-cAMP antibody, to a density of $6.0 \times 10^5$ cells/mL. A Labcyte Echo 550 acoustic dispenser was used to transfer up to 25 nL of test compound dissolved in DMSO into the wells of a dry Optiplate-384 plate (Perkin Elmer, Cat. No. 6008289). All subsequent liquid additions were performed using a multichannel pipettor. Next, 5 µL of the cell suspension was added to the wells of the Optiplate-384 and incubated for 30 min. at 37° C. and 5% $CO_2$ in a humidified environment. After this time 5 µL of either 300 nM or 600 nM adenosine (Sigma Cat. No. A9251) for $A_{2A}$ and $A_{2B}$ respectively was added and incubated for 30 minutes at 37° C. and 5% $CO_2$ in a humidified environment. At this time detection mix was prepared by combining the LANCE Eu-W8044 labeled streptavidin and. Biotin-cAMP in detection buffer according to the manufacturers protocol. 10 µL of the detection mix was added to each well of the Optiplate-384 which was covered with a plate seal and incubated wider ambient conditions for 2 hours prior to reading the plate using an Envision (Perkin Elmer, Waltham, Mass.) multimode plate reader. Data was normalized by defining minimal effect as stimulation in the presence of 0.25% (v/v) DMSO and maximal effect as stimulation in the presence of 1 µM ZM241385 (Cayman, Cat. No. 1036). Curve fitting of the percent effect data versus the log of compound concentration used a 4-parameter concentration response curve fitting algorithm to calculate $IC_{50}$ values. Compound concentrations tested were 10,000, 3,333, 1,111, 370.4, 123.4, 41.2, 13.7, 4.6, 1.5 and 0.5 nM with 0.25% residual DMSO.

| Example | $A_{2A}$ IC$_{50}$ binding (nM) or *$A_{2A}$ cAMP IC$_{50}$ (nM) | $A_{2B}$ IC$_{50}$ binding (nM) or *$A_{2B}$ cAMP IC$_{50}$ (nM) |
|---|---|---|
| 1 | 0.6 | 1.2 |
| 2 | 1.0 | 763.2* |
| 3 | 1.3 | 42.6* |
| 4 | 1.4 | 49.5* |
| 5 | 2.4 | 39.5* |
| 6 | 1.3 | 30.0* |
| 7 | 1.4 | 38.5* |
| 8 | 1.4 | 210.8* |
| 9 | 0.7 | 1.0 |
| 10 | 1.5 | 251.6* |
| 11 | 0.8 | 3695.0* |
| 12 | 0.6 | 103.9* |
| 13 | 0.9 | 111.9* |
| 14 | 0.7 | 31.0* |
| 15 | 0.5 | 147.1* |
| 16 | 0.8 | 92.8* |
| 17 | 1.0 | 24.7 |
| 18 | 1.0 | 46.4* |
| 19 | 1.3 | 70.9* |
| 20 | 0.5 | 45.1 |
| 21 | 0.6 | 110.9 |
| 22 | 1.6 | 102.5* |
| 23 | 1.0 | 64.2 |
| 24 | 2.9 | 6.9 |
| 25 | 2.3 | 5.7 |
| 26 | 3.5 | 2.0 |
| 27 | 2.0 | 40.3* |
| 28 | 6.3 | 48.3* |
| 29 | 1.3 | 24.7* |
| 30 | 0.4 | 103.4 |
| 31 | 50.8 | 1698.0* |
| 32 | 1.1 | 0.7 |
| 33 | 0.1 | 320.5 |
| 34 | 1.6 | 219.2* |
| 35 | 0.7 | 41.9 |
| 36 | 1.8 | 1.7 |
| 37 | 1.5 | 10.7 |
| 38 | 4.1 | 1.4 |
| 39 | 2.5 | 29.4* |
| 40 | 3.1 | 19.7* |
| 41 | 0.8 | 22.2* |
| 42 | 1.2 | 3.5 |
| 43 | 0.5 | 1.9 |
| 44 | 1.2 | 131.5 |
| 45 | 2.6 | 350.5 |
| 46 | 0.4 | 404.3 |
| 47 | 0.1 | 222.7 |
| 48 | 0.6 | 65.5 |
| 49 | 0.2 | 36.0 |
| 50 | 0.9 | 160.2 |
| 51 | 0.1 | 85.9 |
| 52 | 0.4 | 350.1 |
| 53 | 0.7 | 150.6 |
| 54 | 0.4 | 16.3 |
| 55 | 1.5 | 4.7 |
| 56 | 0.9 | 175.0 |
| 57A | 0.4 | 70.5 |
| 57B | 0.3 | 89.3 |
| 58A | 0.2 | 64.9 |
| 58B | 0.2 | 34.9 |
| 59A | 0.4 | 6.3 |
| 59B | 0.3 | 1.7 |
| 60A | 1.8 | 281.2 |
| 60B | 2.0 | 180.6 |
| 61A | 0.2 | 45.2 |
| 61B | 0.4 | 84.0 |
| 62 | 0.3 | 630.9 |
| 63 | 2.0 | 32.7* |
| 64 | 0.1 | 374.3 |
| 65 | 2.3 | 293.6 |
| 66 | 0.7 | 143.8 |
| 67 | 1.0 | 2.0 |
| 68 | 0.3 | 340.5 |
| 69 | 0.6 | 144.1 |
| 70 | 0.8 | 151.2 |
| 71 | 0.2 | 5609.0 |
| 72 | 0.9 | 118.7 |
| 73 | 0.8 | 1.9 |
| 74 | 1.0 | 3.1 |
| 75 | 1.0 | 11.6 |
| 76 | 3.6 | 1783.0 |
| 77 | 0.8 | 539.6* |
| 78 | 3.3 | 2495.0* |
| 79 | 1.6 | 146.0* |
| 80 | 2.3 | 18.2* |
| 81 | 1.4 | 812.9 |
| 82 | 2.6 | 543.6* |
| 83 | 0.8 | 78.3* |
| 84 | 1.6 | 187.2* |
| 85 | 14.9 | 314.4* |
| 86 | 2.1 | 146.1* |
| 87 | 1.5 | 858.3 |
| 88 | 2.0 | 295.2 |
| 89 | 1.5 | 631.1* |
| 90 | 1.9 | 5932.0* |
| 91 | 1.8 | 775.2* |
| 92 | 0.7 | 196.4 |
| 93 | 1.5 | 228.8 |
| 94 | 2.4 | 210.1* |
| 95 | 2.3 | 59.1* |
| 96 | 0.6 | 290.8 |
| 97 | 4.4 | 62.4* |
| 98 | 1.4 | 690.9 |
| 99 | 0.6 | 98.4 |
| 100 | 0.7 | 56.8 |
| 101 | 0.5 | 178.5 |
| 102 | 1.0 | 151.4 |
| 103 | 1.2 | 159.1 |
| 104 | 0.1 | 3333.0 |
| 105 | 0.7 | 165.1 |
| 106 | 0.1 | 244.9 |
| 107 | 2.1 | 274.6 |
| 108 | 12.1 | 18% inh. @ 10000 nM* |
| 109 | 52.6 | 22% @ 10000 nM* |
| 110 | 2.2 | 720.6* |
| 111 | 16.4 | 10% inh. @ 10000 nM* |
| 112 | 3.5 | 213.4* |
| 113 | 0.6 | 209.3* |
| 114 | 1.7 | 370.4* |
| 115 | 1.2 | 59.1 |
| 116 | 40.5* | 18% inh. @ 10000 nM* |
| 117 | 0.9 | 430.8 |
| 118 | 10.6* | 105.2* |
| 119 | 1.2 | 18.1* |
| 120 | 3.1 | 321.0* |
| 121 | 3.6 | 284.0 |
| 122 | 0.1 | 58.4 |
| 123 | 0.8 | 13.1* |
| 124A | 26.4 | 1102.0* |
| 124B | 34.0 | 552.1* |
| 125 | 7.7 | 1282.0* |
| 126 | 13.2 | 2508.0* |
| 127 | 56.8 | 1651.0* |
| 128A | 861.5 | 18% inh. @ 10000 nM |
| 128B | 6304.0 | 14% inh. @ 10000 nM |
| 129 | 5284.0 | 30% inh. @ 10000 nM* |
| 130A | 5.8 | 7021.0 |
| 130B | 10.3 | 3523.0 |
| 131A | 34.0 | 1678.0* |
| 131B | 9.3 | 121.0* |
| 132A | 18.6 | 31% @ 10000 nM* |
| 132B | 3.9 | 204.6* |
| 133 | 1.2 | 115.7* |
| 134A | 61.8 | 7752.0 |
| 134B | 1.0 | 76.7 |
| 135 | 1.3 | 168.4 |
| 136A | 169.8 | 23% inh. @ 10000 nM* |
| 136B | 10.8 | 403.9* |
| 136C | 1.2 | 156.8 |
| 136D | 29.0 | 1979.0 |
| 137 | 119.7 | 8646.0 |
| 138 | 3.4 | 425.1 |

| Example | $A_{2A}$ IC$_{50}$ binding (nM) or *$A_{2A}$ cAMP IC$_{50}$ (nM) | $A_{2B}$ IC$_{50}$ binding (nM) or *$A_{2B}$ cAMP IC$_{50}$ (nM) |
|---|---|---|
| 139A | 166.7 | 2465.0 |
| 139B | 3.2 | 1914.0 |
| 139C | 101.3 | 1817.0 |
| 139D | 58.3 | 5294.0 |
| 140A | 66.8 | 5514.0 |
| 140B | 1.3 | 758.2 |
| 140C | 0.6 | 11.2 |
| 140D | 5.0 | 3008.0* |
| 141A | 2.2 | 712.3* |
| 141B | 28.2 | 2611.0* |
| 141C | 1.0 | 12.0 |
| 141D | 3.1 | 1648.0* |
| 142A | 53.8 | 985.4* |
| 142B | 0.8 | 1154.0* |
| 142D | 0.9 | 9.3* |
| 143B | 0.9 | 604.1* |
| 143C | 31.6 | 650.8* |
| 143D | 0.5 | 16.2 |
| 144B | 3.1 | 332.6* |
| 144D | 1.2 | 4.0* |
| 145B | 1.2 | 57.2 |
| 145D | 30.3* | 460.6* |
| 146C | 101.3* | 2199.0* |
| 146D | 0.8 | 4.6 |
| 147C | 3.9 | 778.9 |
| 147D | 0.2 | 5.6* |
| 148A | 1.0 | 234.2* |
| 148B | 27.8 | 36% inh. @ 10000 nM* |
| 149 | 200.4 | 32% inh. @ 10000 nM |
| 150 | 80.5 | 74% inh. @ 10000 nM |
| 151 | 210.0 | 27% inh. @ 10000 nM |
| 152 | 248.8 | 38% inh. @ 10000 nM |
| 153A | 20.4 | 31% inh. @ 10000 nM* |
| 153B | 1.0 | 676.6* |
| 154A | 0.8 | 385.7* |
| 154B | 17.4 | 13% inh. @ 10000 nM* |
| 155A | 12.1 | 1329.0* |
| 155B | 0.7 | 300.7* |
| 156B | 2.2 | 1391.0* |
| 157B | 0.7 | 512.5 |
| 158B | 0.4 | 525.8 |
| 159B | 0.1 | 791.9 |
| 160 | 19.0 | 394.9* |
| 161 | 13.2 | 231.3* |
| 162 | 7.8 | 17.6 |
| 163 | 14.0 | 42.1* |
| 164 | 8.9 | 29.5* |
| 165 | 19% inh. @ 10000 nM | 10% inh. @ 10000 nM |
| 166 | 18.0 | 234.2 |
| 167 | 14.1 | 117.2 |
| 168 | 17.4 | 150.0 |
| 169 | 7.7 | 4161.0 |
| 170 | 204.5 | 28% inh. @ 10000 nM |
| 171 | 34.9 | 956.2 |
| 172 | 34.2 | 374.5 |
| 173 | 3.6 | 403.3 |
| 174 | 44.3 | 479.8 |
| 175 | 0.1 | 23.2 |
| 176 | 0.7 | 189.2 |
| 177 | 4.7 | 132.5* |
| 178 | 2.1 | 2.5 |
| 179 | 3.5 | 103.1 |
| 180 | 1.0 | 249.5 |
| 181 | 0.3 | 103.7 |
| 182 | 1.3 | 188.1 |
| 183 | 157.2 | 4068.0 |
| 184 | 4.0 | 141.2* |
| 185A | 0.8 | 98.1 |
| 185B | 1.0 | 116.2 |
| 186A | 0.4 | 461.7 |
| 186B | 0.4 | 322.6 |
| 187A | 2.8 | 1294.0 |
| 187B | 406.0 | 16% inh. @ 10000 nM |
| 188 | 0.7 | 44.6 |
| 189A | 0.6 | 227.6 |
| 189B | 0.7 | 291.3 |
| 190 | 10.1 | 479.8 |
| 191 | 2.5 | 18.4 |
| 192 | 2.5 | 22.7 |
| 193 | 2.2 | 130.0 |
| 194 | 6.7 | 528.3 |
| 195A | 35.9 | 5814.0 |
| 195B | 1.7 | 9688.0 |
| 195C | 281.0 | 9445.0 |
| 195D | 0.8 | 84.9 |
| 196A | 2.9 | 801.8 |
| 196B | 124.7* | 27% inh. @ 10000 nM |
| 197A | 99.0 | 31% inh. @ 10000 nM |
| 197B | 0.4 | 1368.0 |
| 198 | 0.4 | 8.4 |
| 199 | 22.5 | 257.0 |
| 200 | 11.8 | 152.5 |
| 201 | 2.8 | 10.6 |
| 202 | 4.2 | 211.1 |
| 203 | 0.7 | 1.7 |
| 204 | 0.4 | 1.1 |
| 205 | 0.4 | 5.5 |
| 206 | 0.3 | 20.7 |
| 207 | 2.8 | 124.9 |
| 208 | 10% inh @ 10000 nM | 5% inh. @ 10000 nM |
| 209 | 28.7 | 328.1 |
| 210A | 0.2 | 4.8 |
| 210B | 0.1 | 3.2 |
| 211A | 0.5 | 3.4 |
| 211B | 0.6 | 16.1 |
| 212A | 220.9 | 5475.0 |
| 212B | 234.0 | 8282.0 |
| 213 | 0.4 | 27.6* |
| 214 | 0.2 | 2.8* |
| 215A | 68.8* | 2387.0* |
| 215B | 0.5 | 6.3* |
| 215C | 8.7 | 1330.0* |
| 215D | 20.7 | 720.8* |
| 216A | 33.9 | 651.4* |
| 216B | 0.4 | 6.6* |
| 216C | 23.5 | 292.3* |
| 216D | 2.4 | 491.0* |
| 217 | 4.6 | 206.7 |
| 218A | 50.7 | 9% inh. @ 10000 nM* |
| 218B | 635* | >10000 nM* |
| 219A | 0.5 | 1973* |
| 219B | 0.2 | 999* |
| 219C | 38.6* | 5647* |
| 219D | 44.3* | 33% inh. @ 10000 nM* |
| 220A | 1.03 | 66.2* |
| 220B | 1.393 | 52.8* |
| 221A | 1.922 | 61.0* |
| 221B | 1.499 | 86.0* |
| 222A | 1.317 | 815* |
| 222B | 63.8* | 1722* |
| 222C | 0.4 | 13.5* |
| 222D | 33.3* | 655* |
| 223 | 1.0 | 20.9* |
| 224 | 0.3 | 9.6* |
| 225A | 1.2 | 32.2* |
| 225B | 3.2 | 78.4* |

What is claimed:

1. A compound having a structural Formula (I):

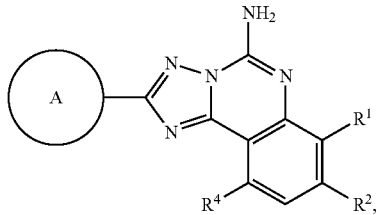

or a pharmaceutically acceptable salt thereof, wherein:
$R^1$ is selected from H, F, Cl, Br, CN, OH, $(C_1-C_6)$alkyl, $O(C_1-C_6)$alkyl, and $O(C_1-C_6)$haloalkyl;
$R^2$ is selected from H, F, Cl, Br, CN, OH, $(C_1-C_6)$alkyl, $(C_1-C_6)$haloalkyl, $O(C_1-C_6)$alkyl, $O(C_1-C_6)$haloalkyl, $(C_3-C_4)$cycloalkyl, $S(O)_2(C_1-C_6)$alkyl, $S(O)_2(C_1-C_6)$haloalkyl, and 4-5 membered monocyclic heterocycloalkyl comprising 1 or 2 ring nitrogen atoms;
$R^4$ is selected form H, F, Cl, Br, $(C_1-C_6)$alkyl, and $(C_1-C_6)$haloalkyl,
with the proviso that at least one of $R^1$, $R^2$, or $R^4$ is not H; and
ring A is a moiety selected from:

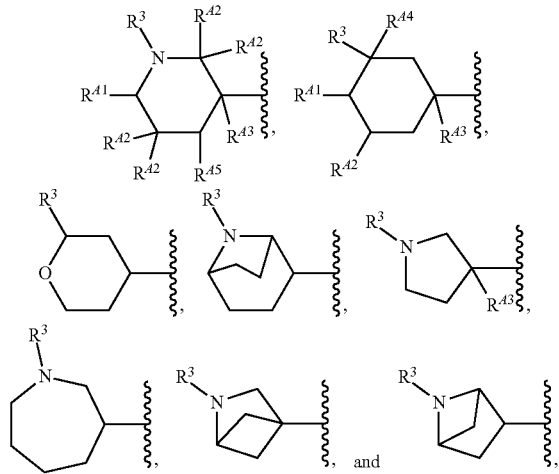

wherein:
$R^3$ is selected from:

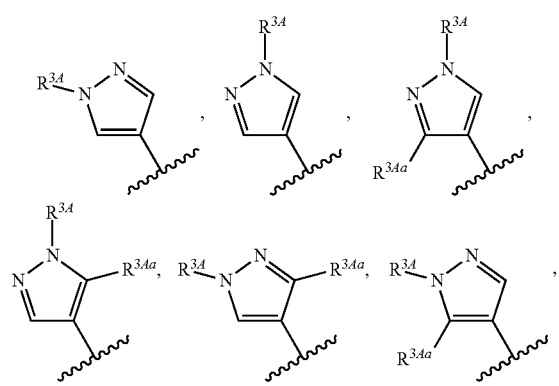

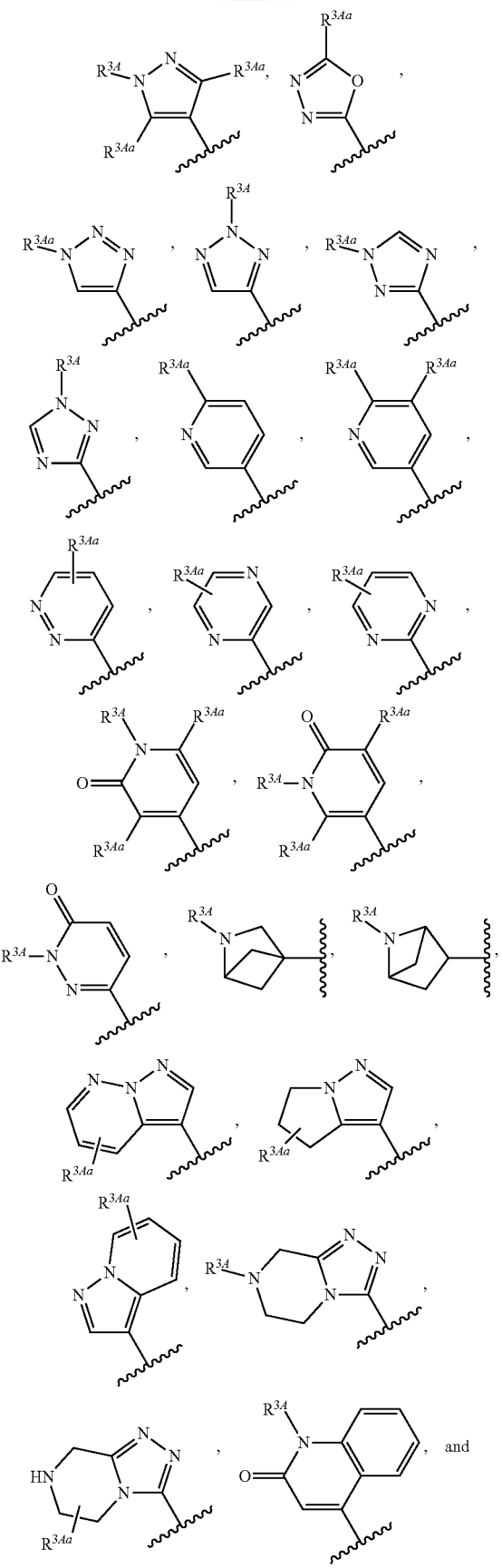

-continued

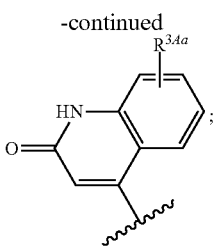

each R³ᴬ is independently selected from H, F, Cl, (C₁-C₆)alkyl, (C₁-C₆)alkyl-OH, (C₁-C₆)haloalkyl, (C₁-C₆)alkylNH₂, O(C₁-C₆)alkyl, O(C₁-C₆)haloalkyl, C(O)(C₁-C₃)alkyl, (C₁-C₄)alkylC(O)(C₁-C₃)alkyl, (C₁-C₄)alkylO(C₁-C₃)alkyl, (C₁-C₄)alkylCH(OH)(C₁-C₃)alkyl, (C₁-C₄)alkylS(O)₂(C₁-C₃)alkyl, (C₁-C₆)alkylC(O)NH(C₁-C₆)alkyl, (C₁-C₆)alkylC(O)OH, (C₁-C₆)alkylC(O)NH(C₃-C₆)cycloalkyl,

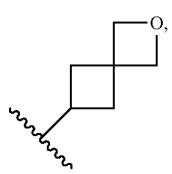 [SMILES: *C1CC2(COC2)C1]

—(CH₂)ₙ(C₃-C₇)cycloalkyl, and —(CH₂)ₙ4-7 membered monocyclic heterocycloalkyl comprising 1 or 2 ring heteroatoms selected from O, N, S, and S(O)₂,
  wherein said (C₃-C₇)cycloalkyl, and said 4-7 membered monocyclic heterocycloalkyl are each unsubstituted or substituted with 1, 2, or 3 groups independently selected from F, Cl, OH, oxo, (C₁-C₆)alkyl, O(C₁-C₆)alkyl, (C₁-C₆)haloalkyl, and O(C₁-C₆)haloalkyl;
  n is 0, 1, or 2;
  each R³ᴬᵃ is independently selected from H, (C₁-C₄)alkyl, O(C₁-C₄)alkyl, (C₁-C₄)haloalkyl, O(C₁-C₄)haloalkyl, and (C₃-C₄)cycloalkyl;
  R⁴¹ is selected from H, and (C₁-C₄)alkyl;
  each RA² is independently selected from H, F, and (C₁-C₄)alkyl;
  R⁴³ is selected from H, F, and (C₁-C₄)alkyl;
  R⁴⁴ is selected from H and OH; and
  R⁴⁵ is selected from H, F, and (C₁-C₄)alkyl.

2. The compound of claim 1, or a pharmaceutically acceptable salt thereof, wherein said compounds have the structural Formula (I.1):

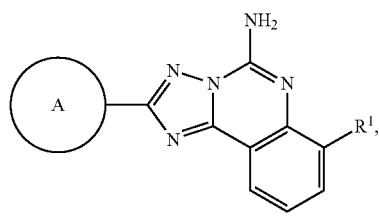

wherein R¹ is selected from F, Cl, Br, CN, OH, CH₃, CH₂CH₃, OCH₃ OCH₂CH₃ and O(C₁-C₆)haloalkyl.

3. The compound of claim 1, or a pharmaceutically acceptable salt thereof, wherein said compounds have the structural Formula (I.2):

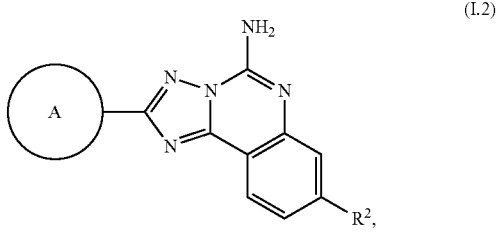

wherein R² is selected from F, Cl, Br, CN, OH, CH₃, CHF₂, CF₃, CH₂CH₃, OCH₃, OCH₂CH₃, OCHF, S(O)₂CH₃

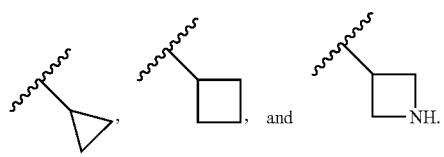

4. The compound of claim 1, or a pharmaceutically acceptable salt thereof, wherein said compounds have the structural Formula (I.3):

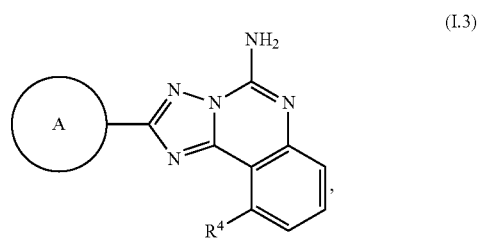

wherein R⁴ is selected from F, Cl, Br, (C₁-C₆)alkyl, and (C₁-C₆)haloalkyl.

5. The compound of claim 1, or a pharmaceutically acceptable salt thereof, wherein said compounds have the structural Formula (I.4):

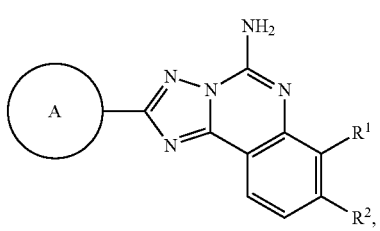

wherein R¹ is selected from F, Cl, Br, CN, OH, CH₃, OCH₃, and CF₃; and
R² is selected from F, Cl, Br, CN, OH, CH₃, OCH₃, and CF₃.

6. The compound of claim 1, or a pharmaceutically acceptable salt thereof, wherein said compounds have the structural Formula (I.5):

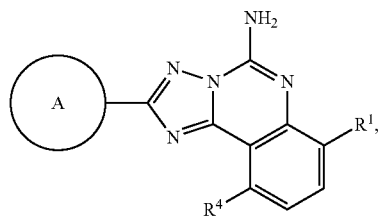

wherein R¹ is selected from F, Cl, Br, CN, OH, CH₃, OCH₃, and CF₃; and

R⁴ is selected from F, Cl, Br, CN, OH, CH₃, OCH₃, and CF₃.

7. The compound of claim 1, or a pharmaceutically acceptable salt thereof, wherein:

ring A is:

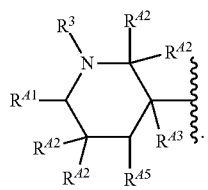

8. The compound of claim 1, or a pharmaceutically acceptable salt thereof, wherein:

ring A is:

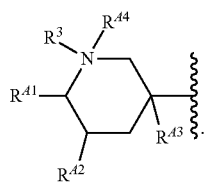

9. The compound of claim 1, or a pharmaceutically acceptable salt thereof, wherein:

ring A is:

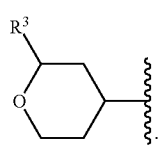

10. The compound of claim 1, or a pharmaceutically acceptable salt thereof, wherein:

ring A is:

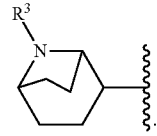

11. The compound of claim 1, or a pharmaceutically acceptable salt thereof, wherein:

ring A is a moiety selected from:

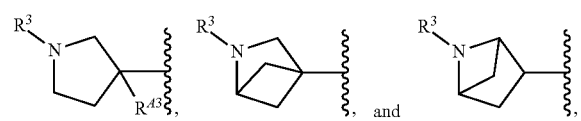

12. The compound of claim 1, or a pharmaceutically acceptable salt thereof, wherein:

ring A is:

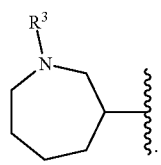

13. The compound of claim 1, or a pharmaceutically acceptable salt thereof, wherein said compound is selected from:

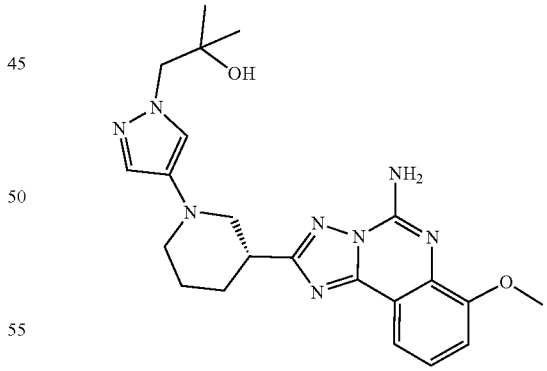

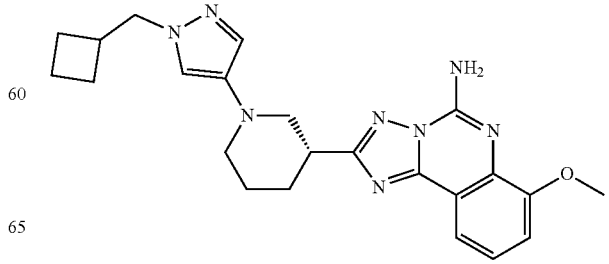

333
-continued
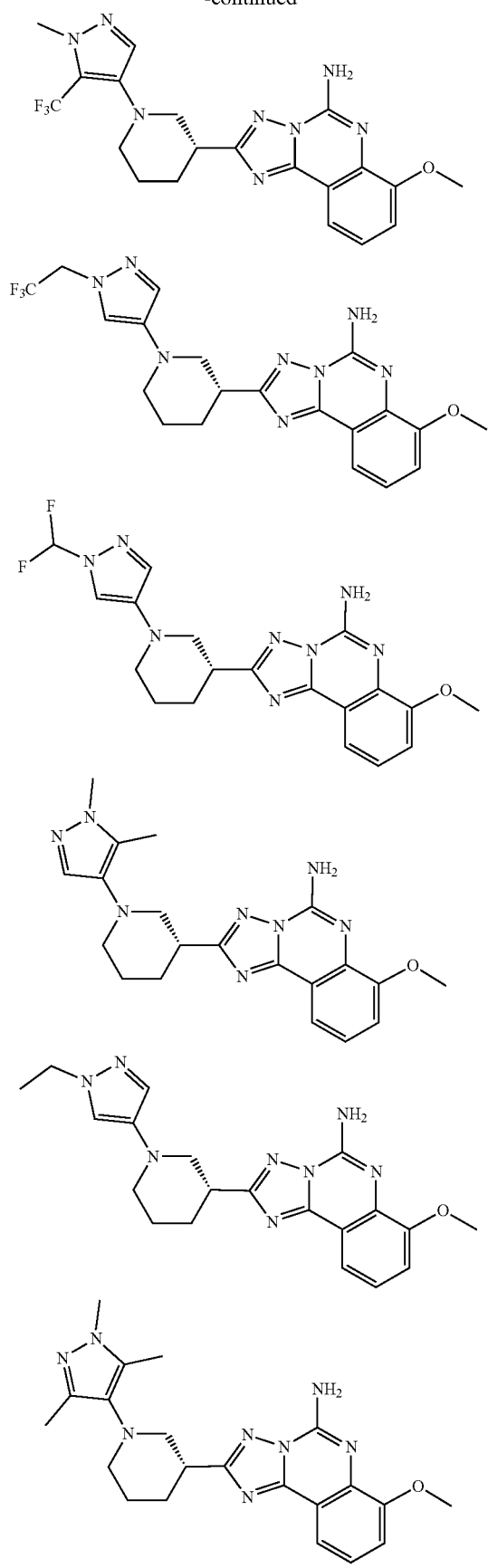
334
-continued
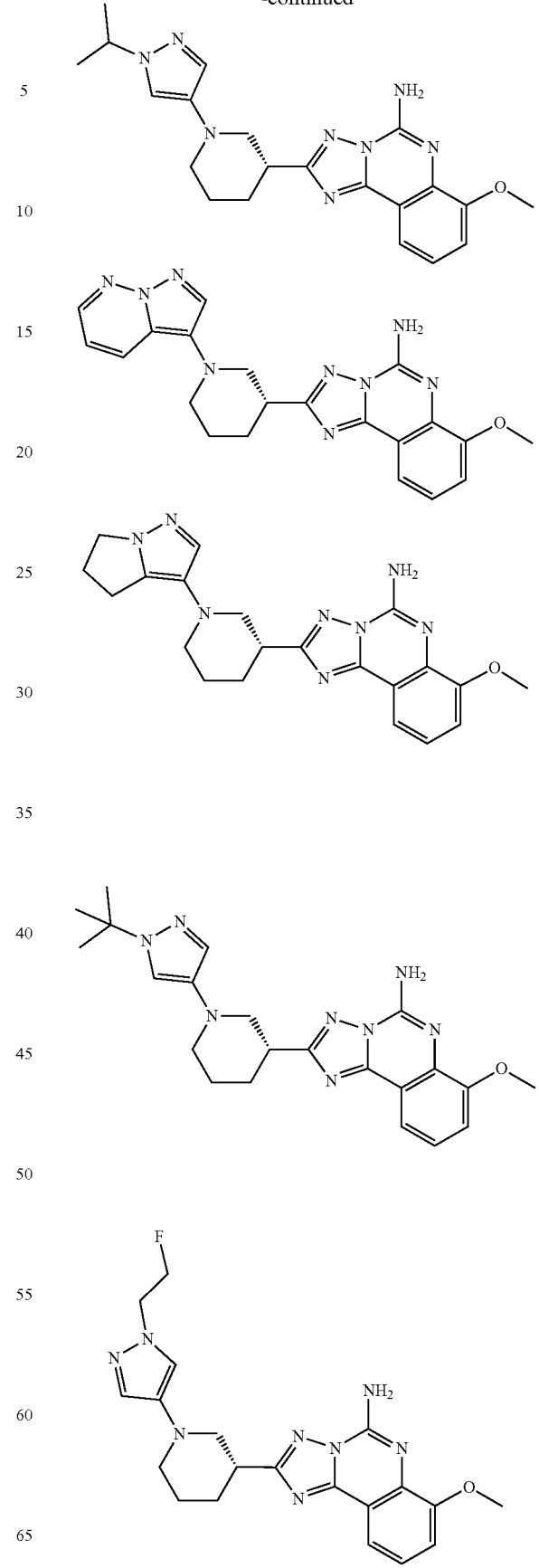

335
-continued
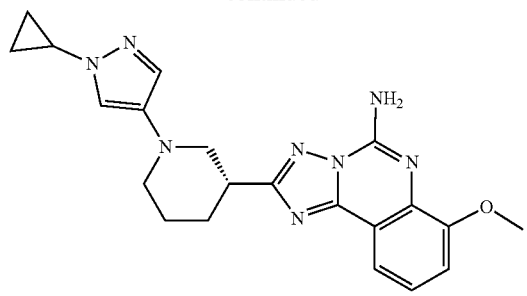
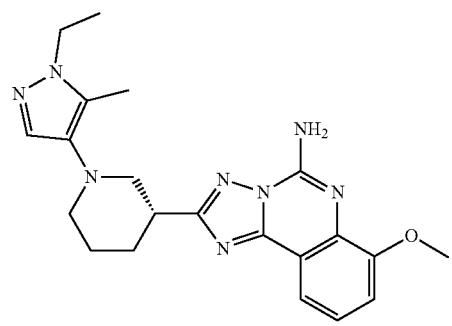
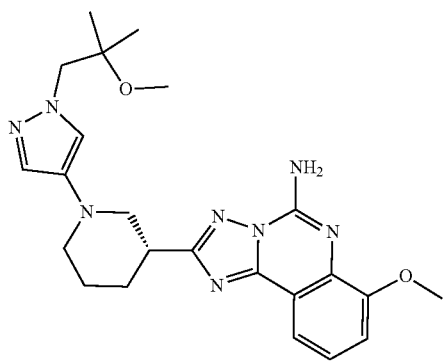
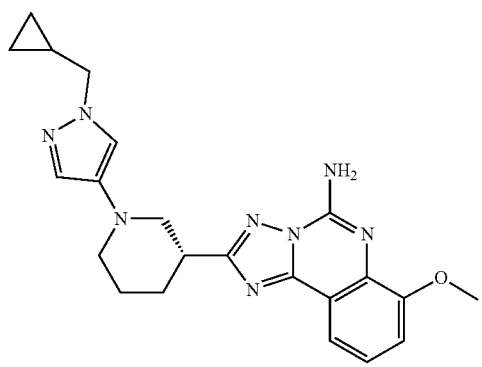
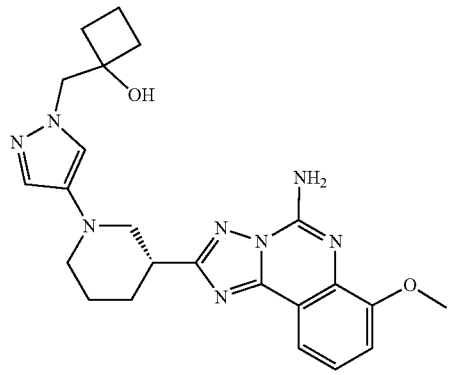
336
-continued
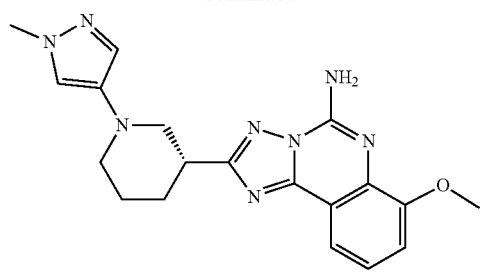
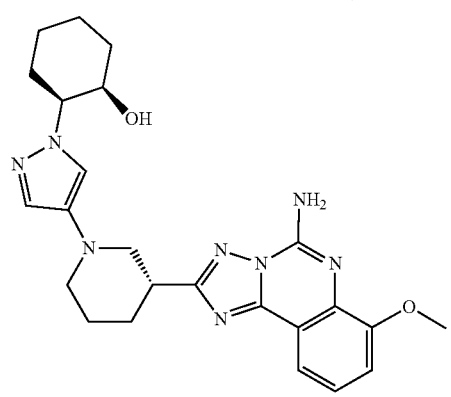
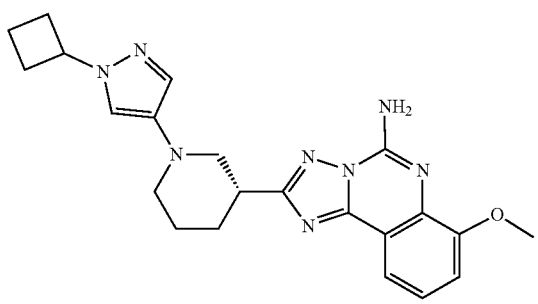
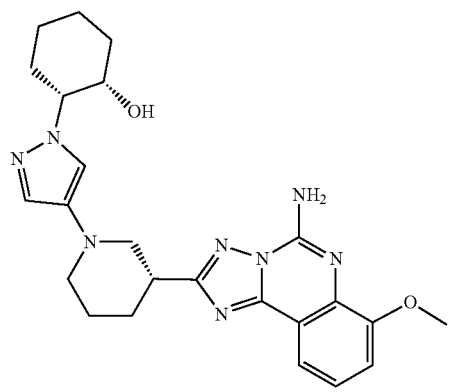
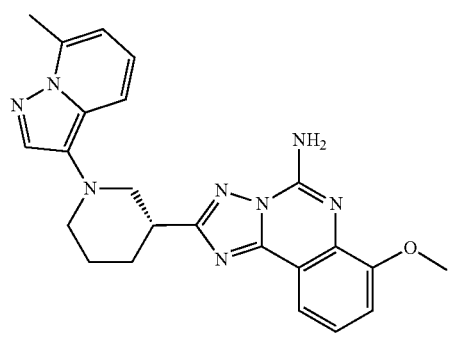

337
-continued
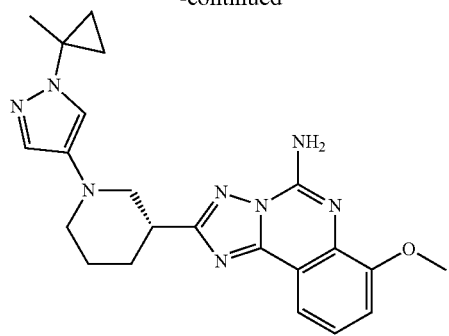
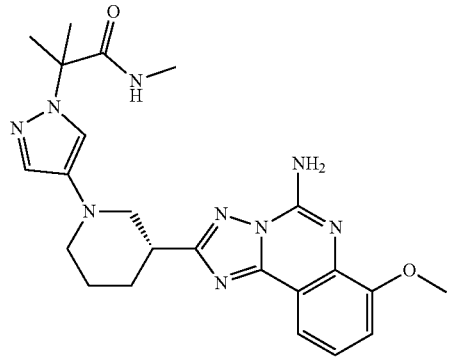
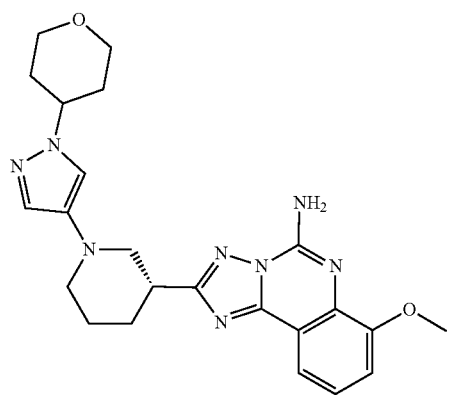
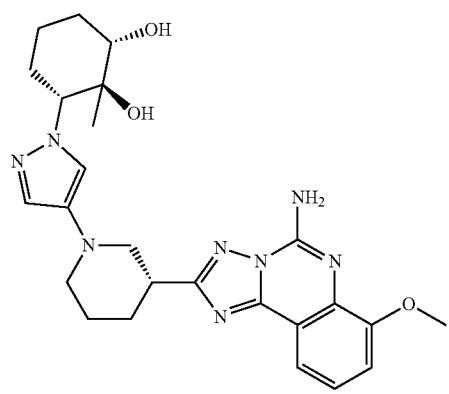
338
-continued
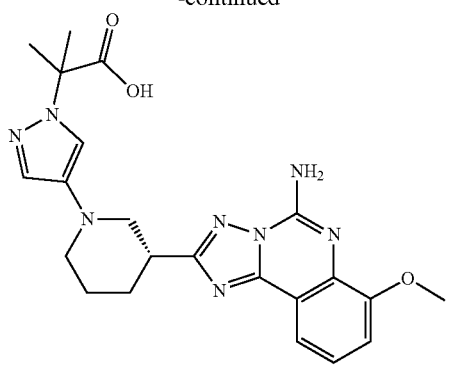
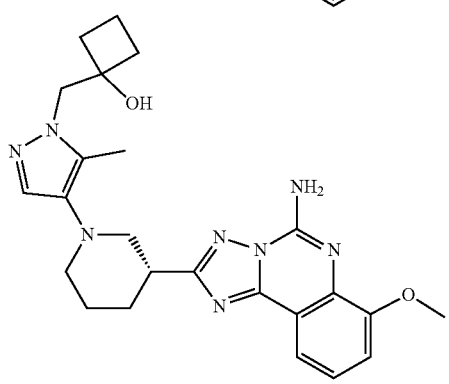
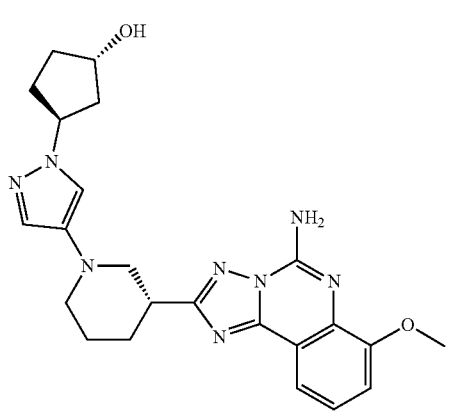
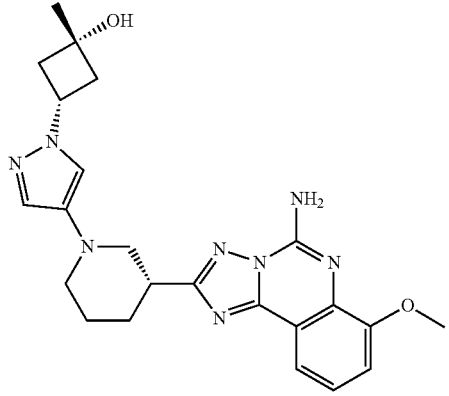

339
-continued
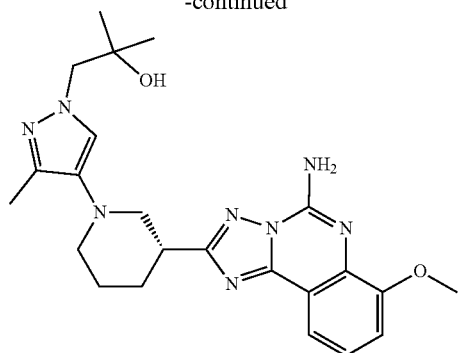
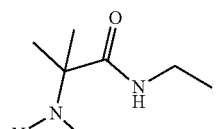
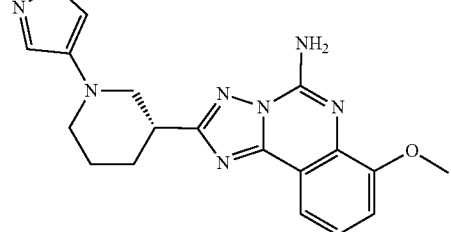
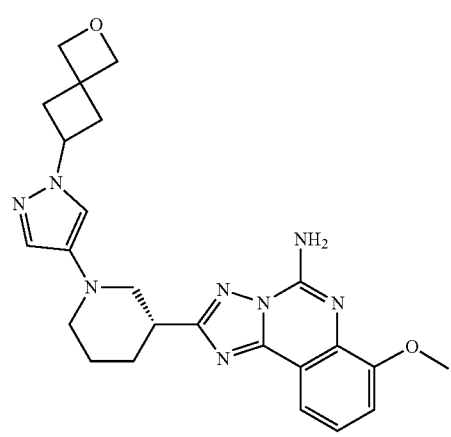
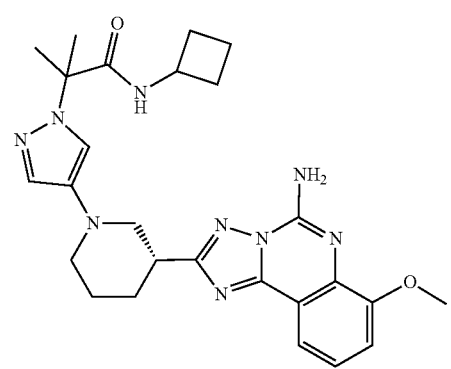
340
-continued
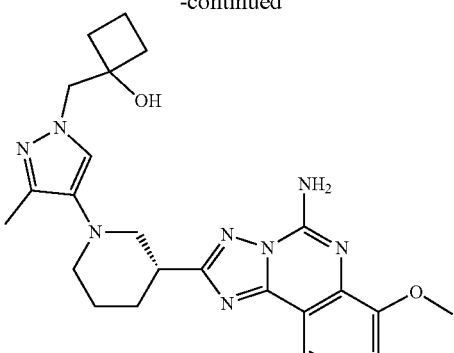
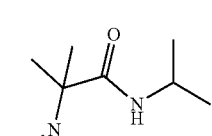
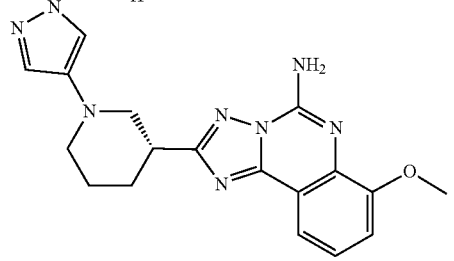
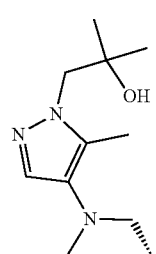
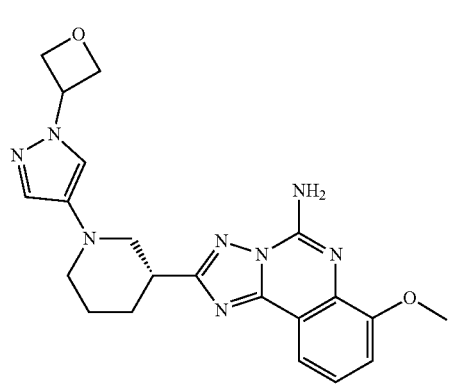

341
-continued
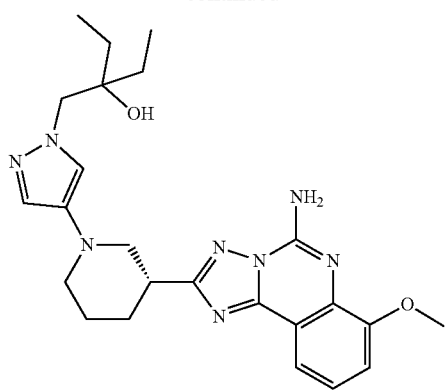
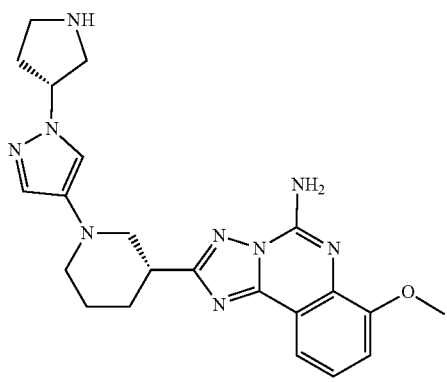
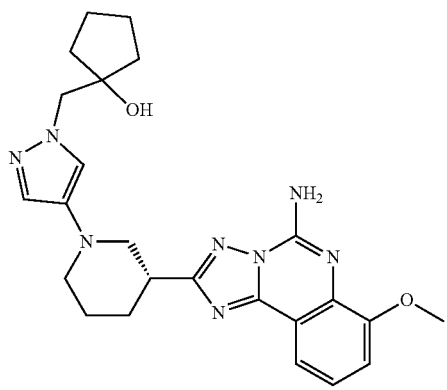
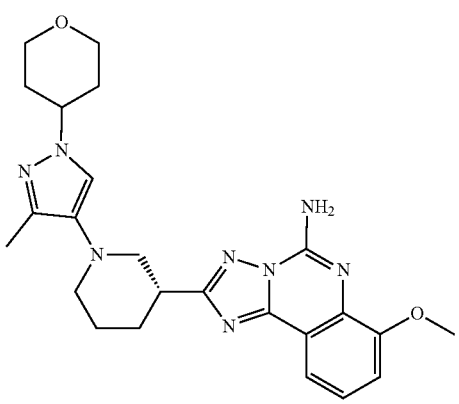
342
-continued
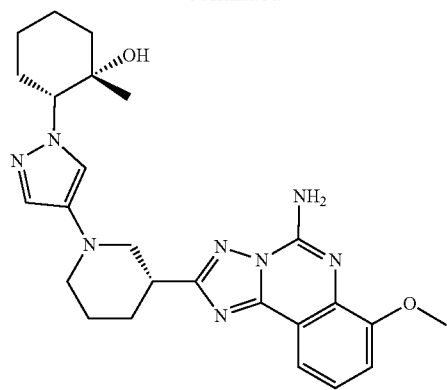
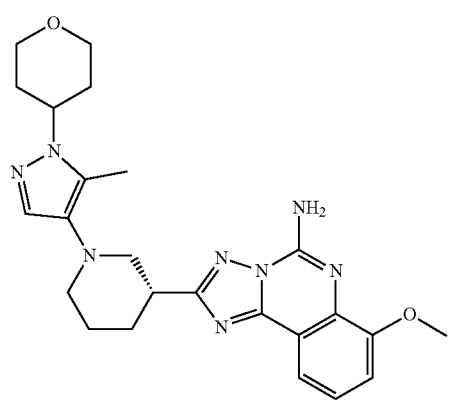
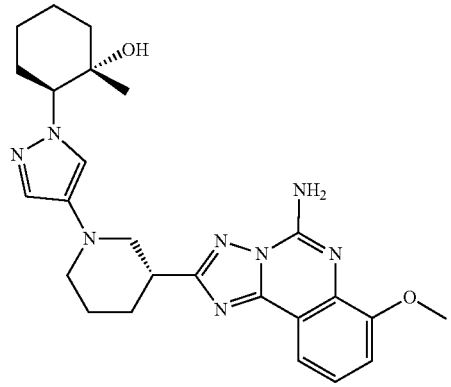
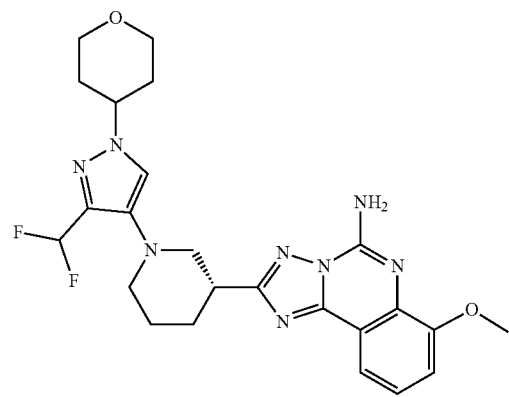

-continued
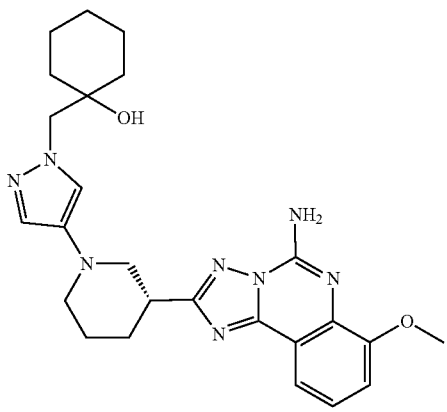
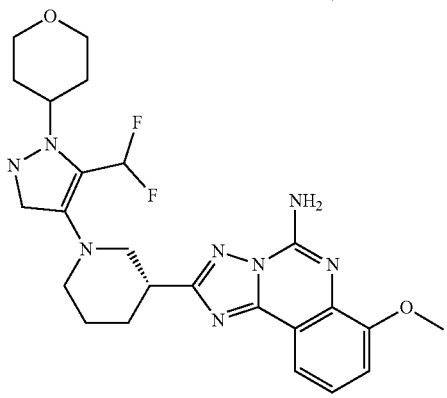
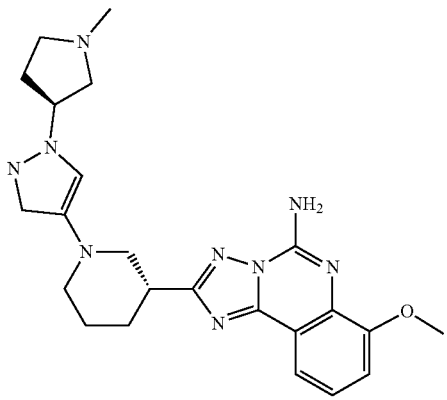
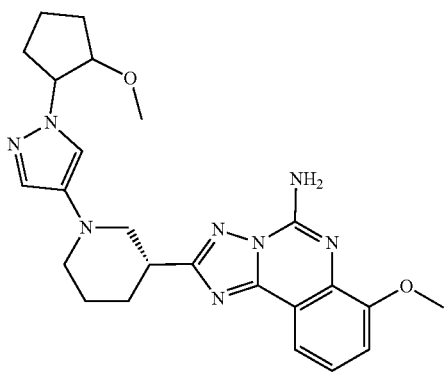
-continued
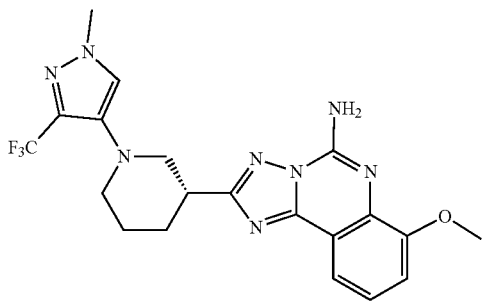
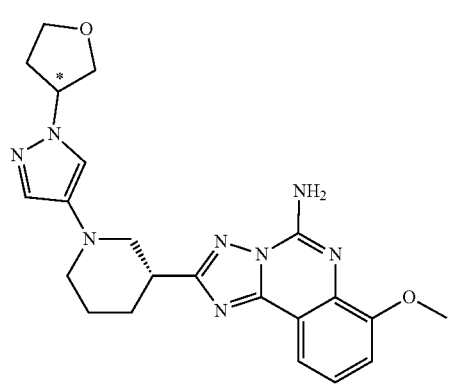
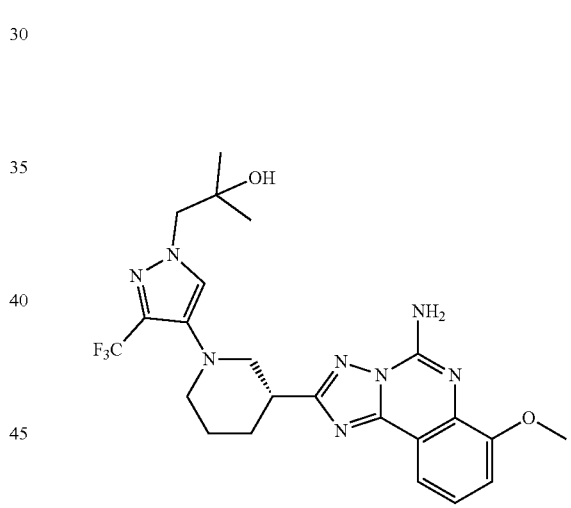
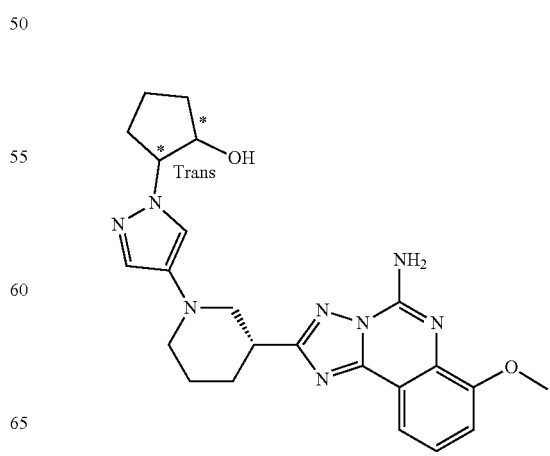

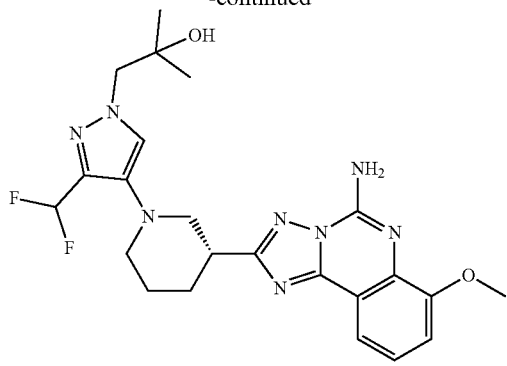
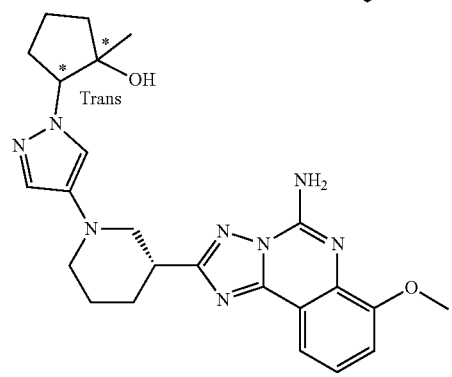
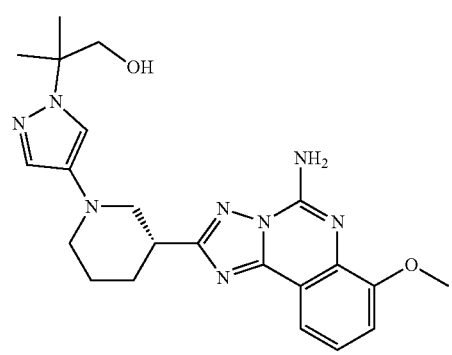
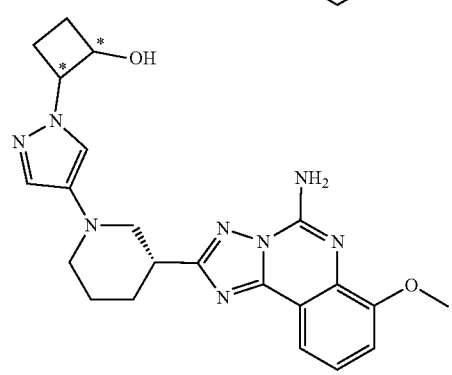
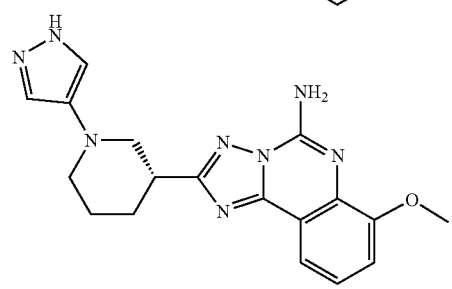
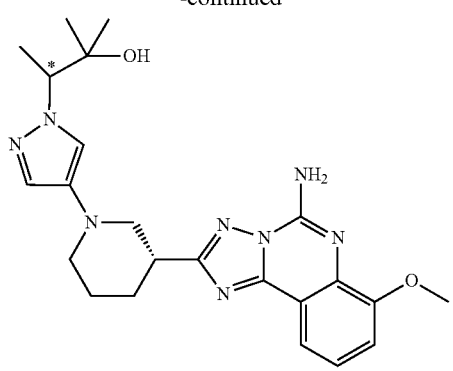
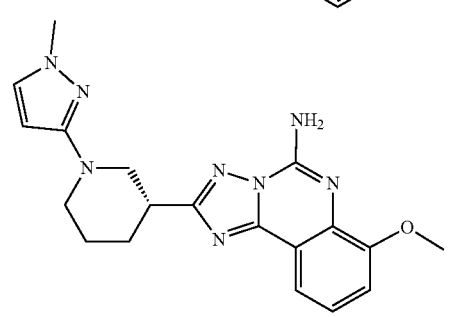
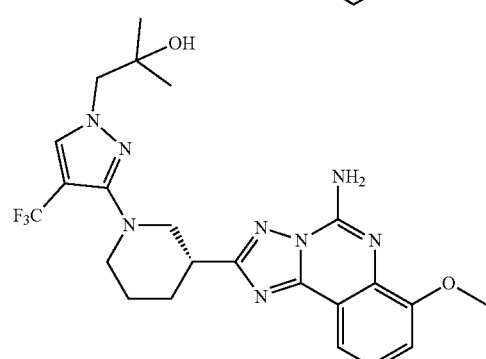
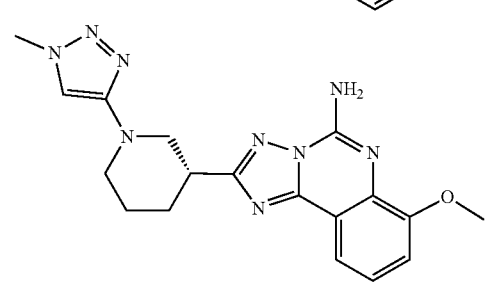
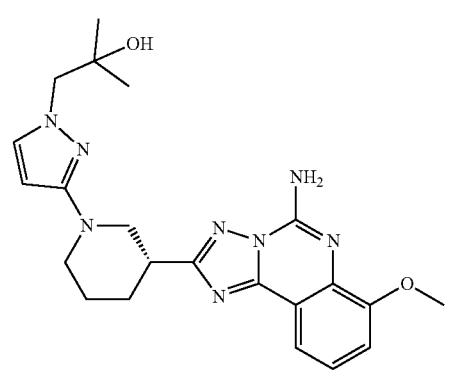

347
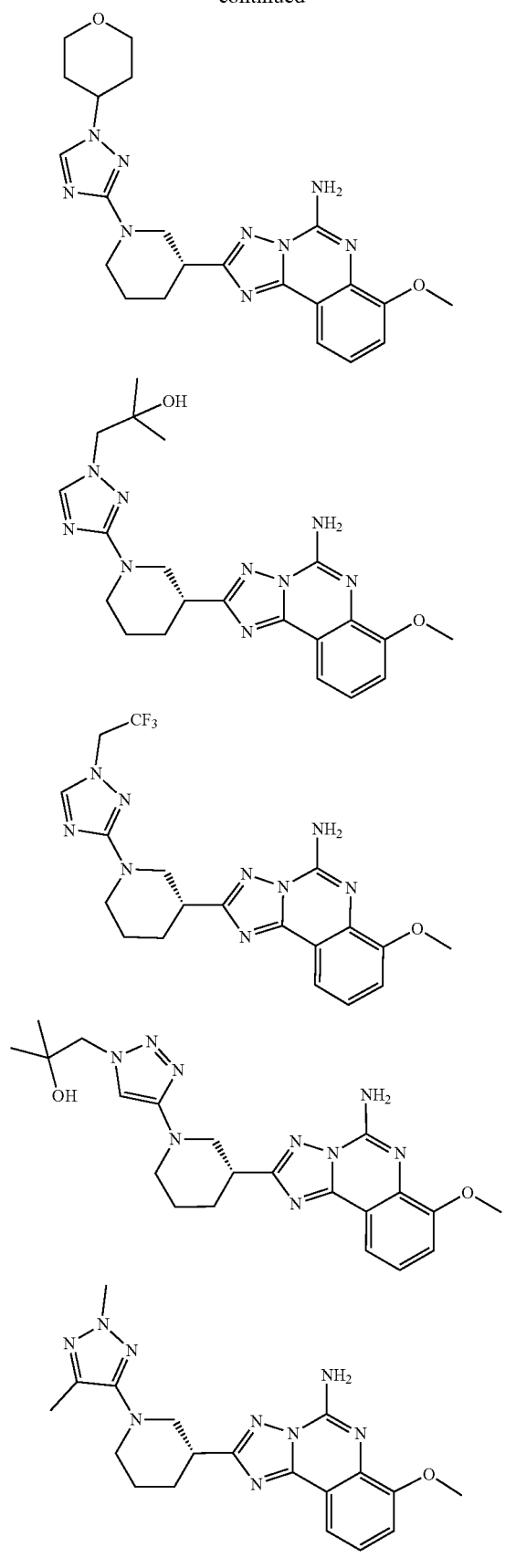
348
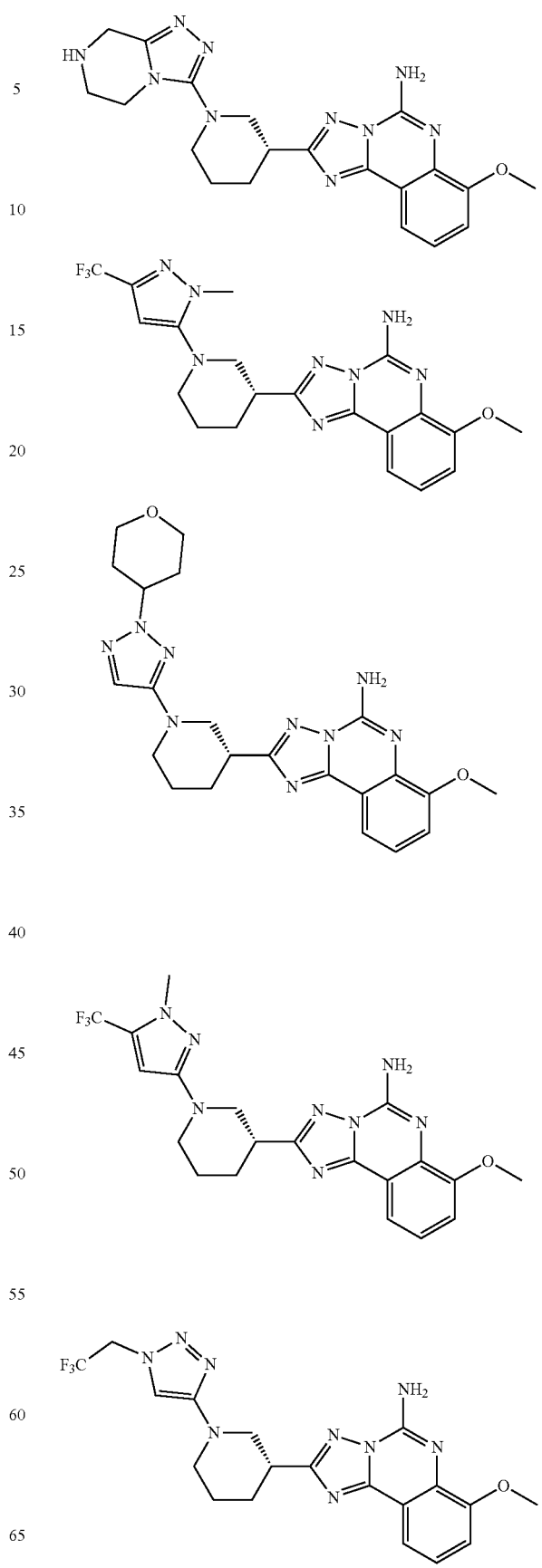

349
-continued
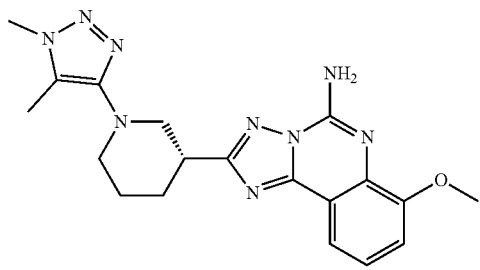
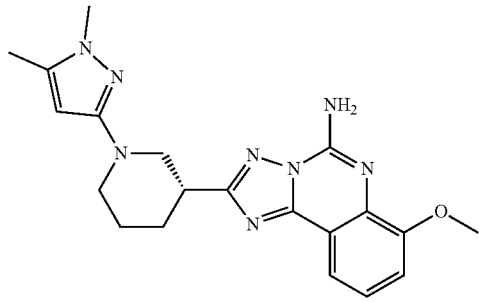
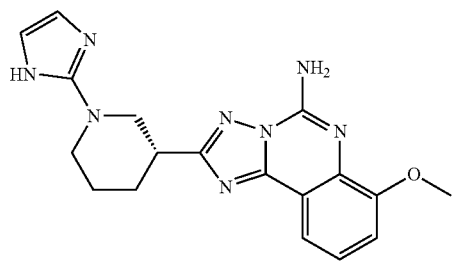
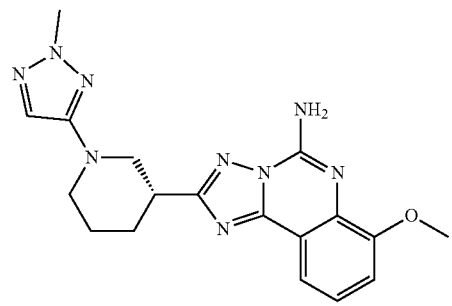
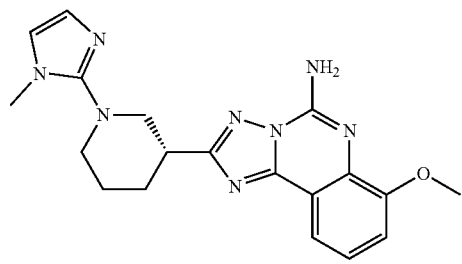
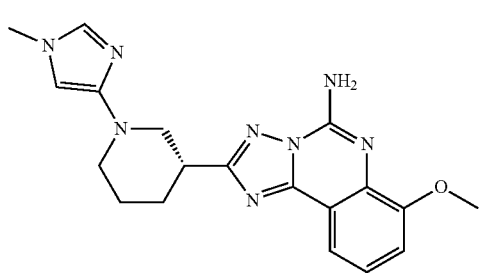
350
-continued
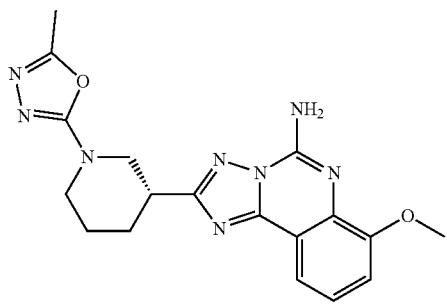
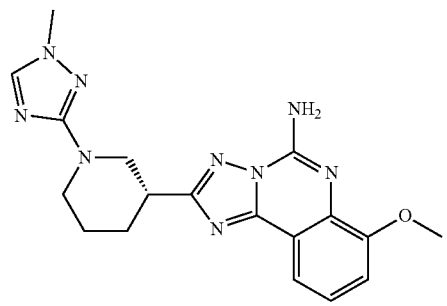
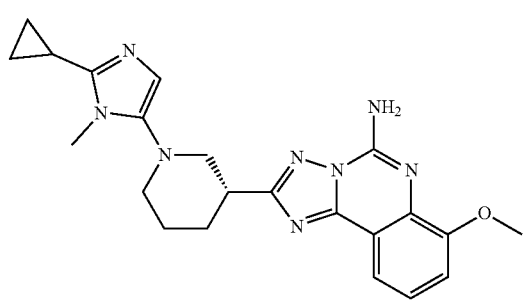
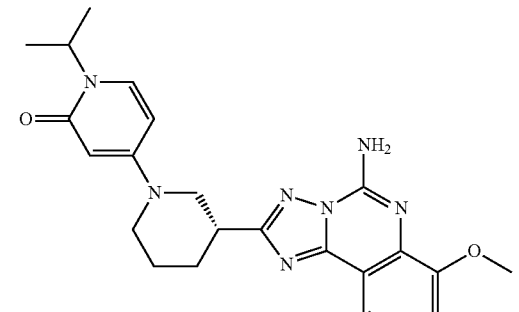
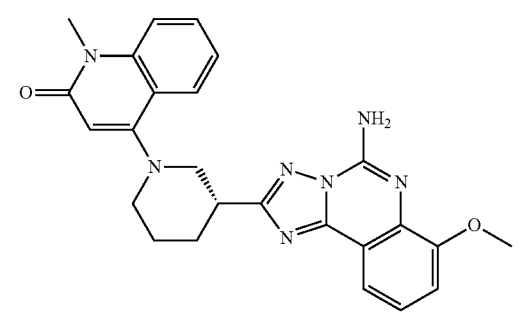

351
-continued
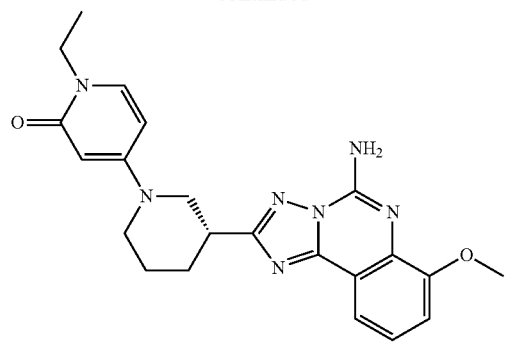
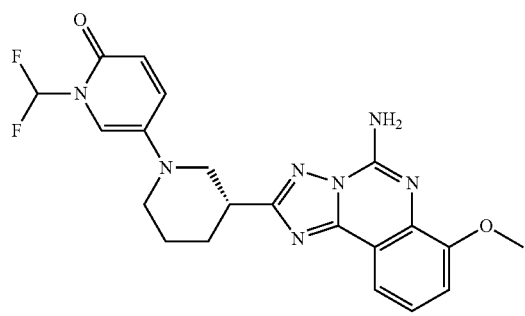
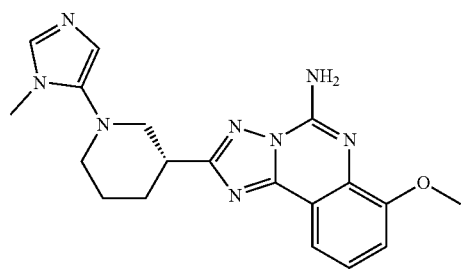
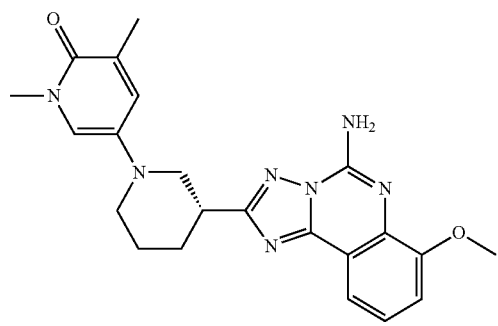
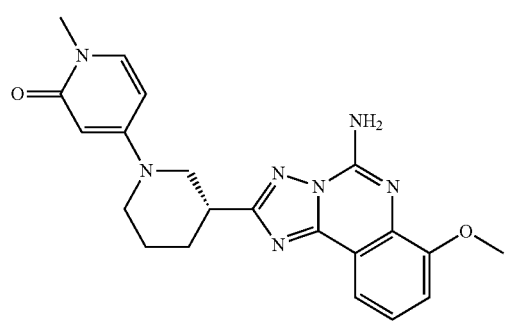
352
-continued
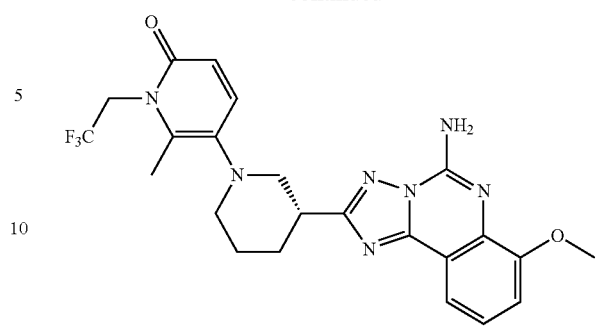
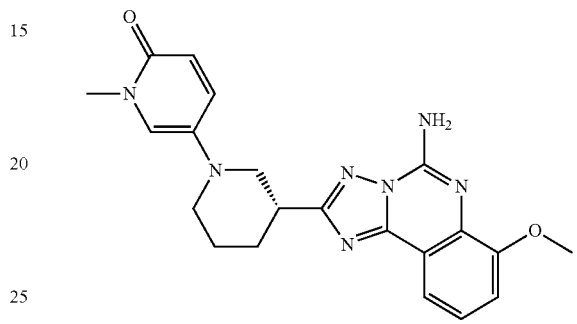
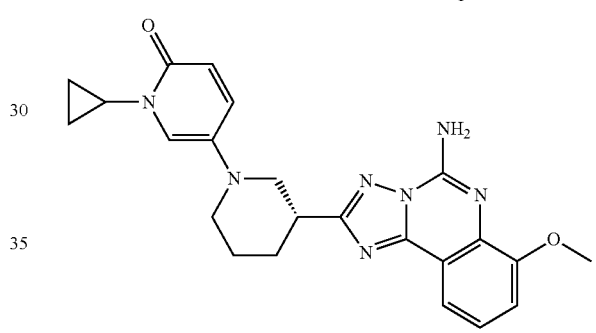
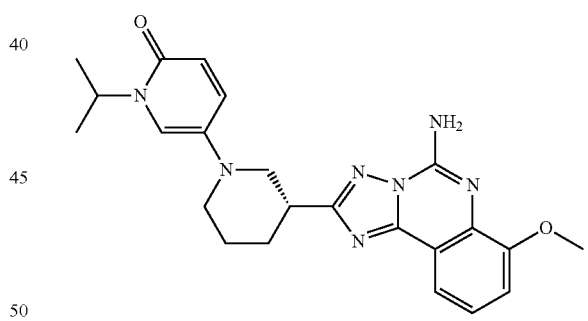
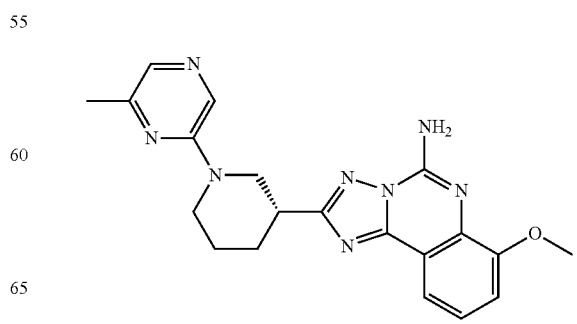

-continued
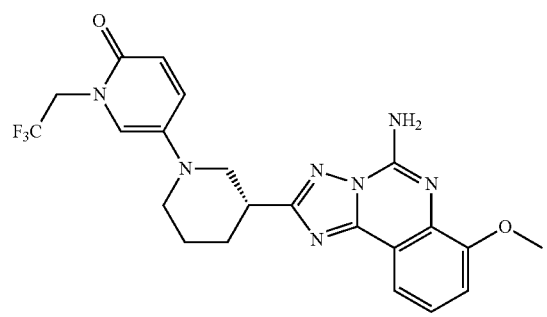
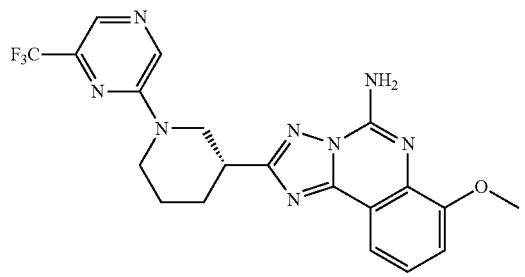
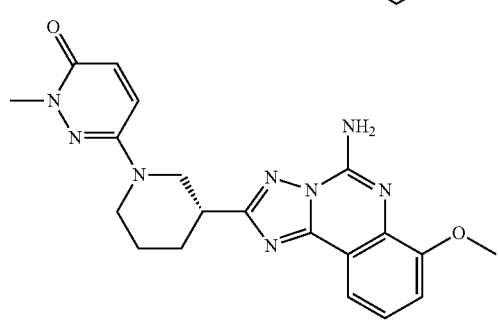
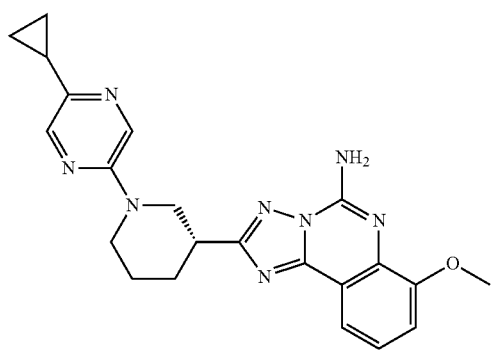
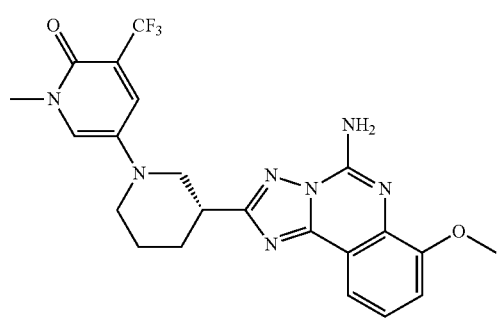
-continued
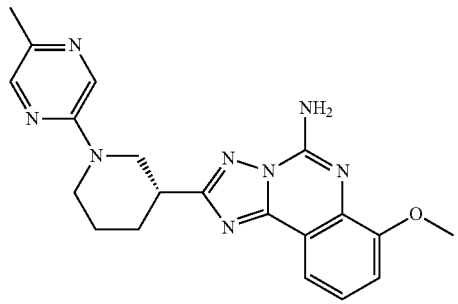
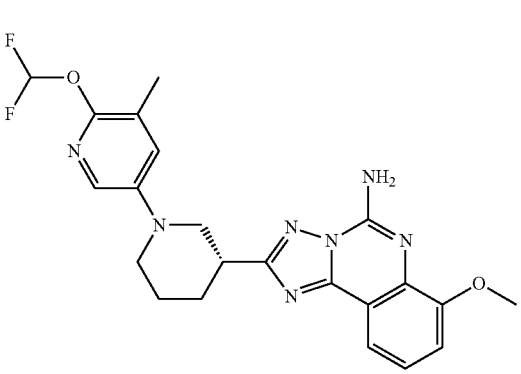
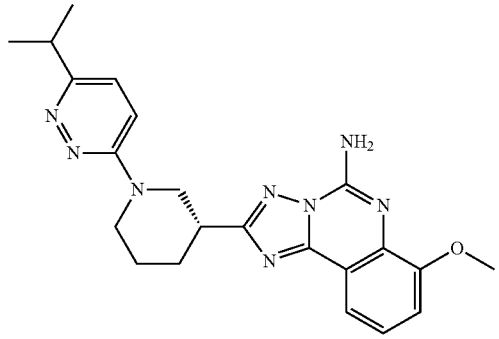
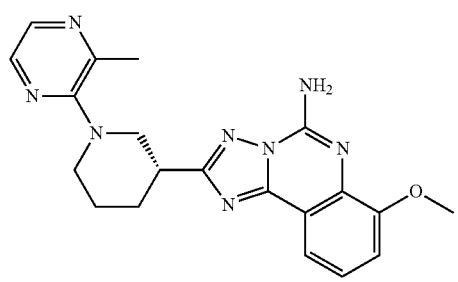
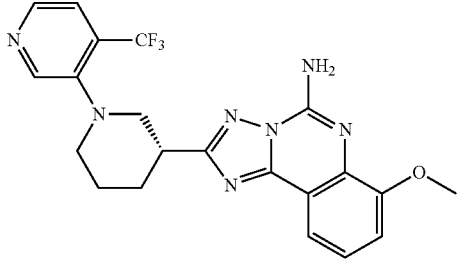

355
-continued
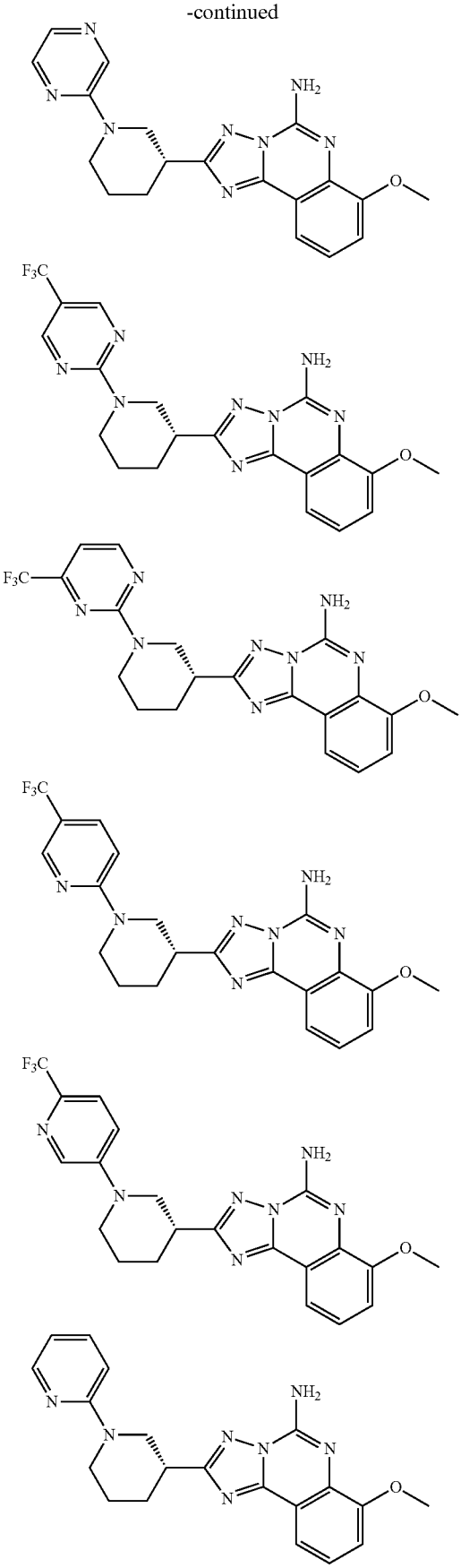
356
-continued
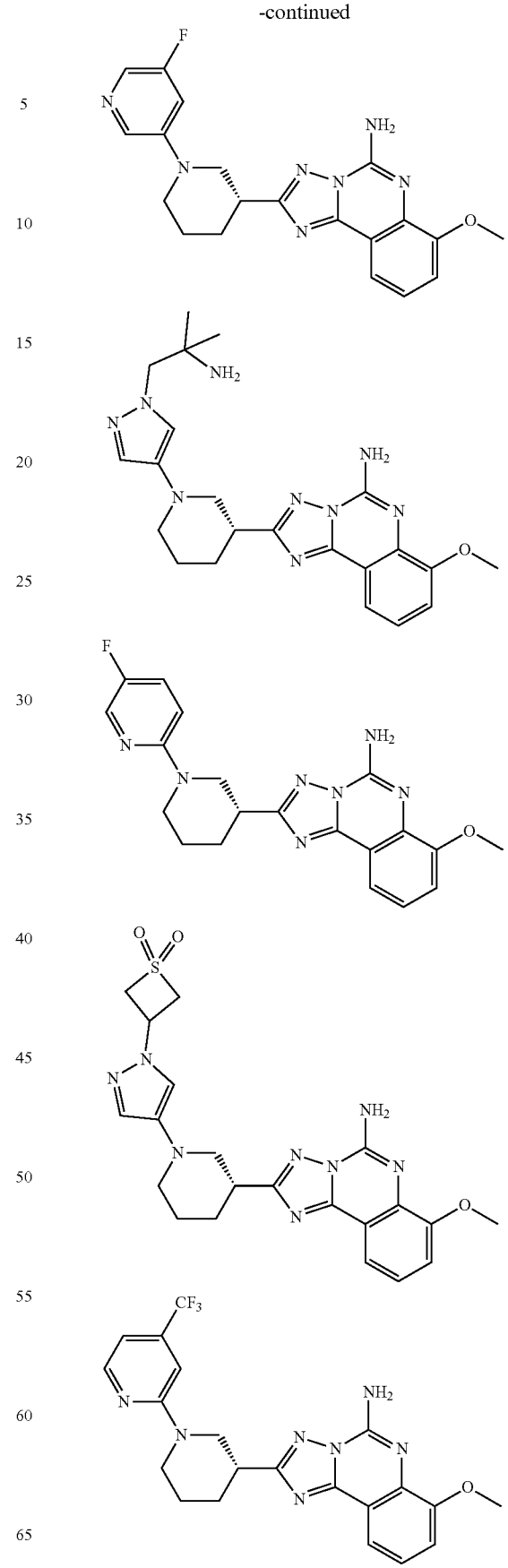

357
-continued
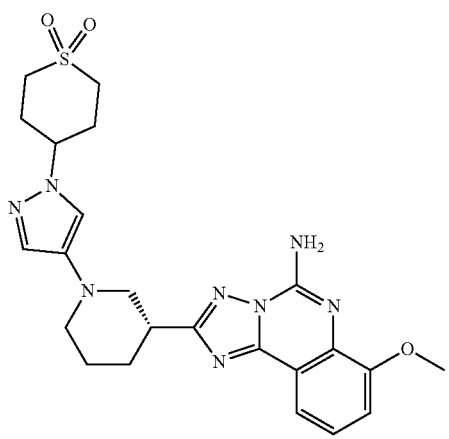
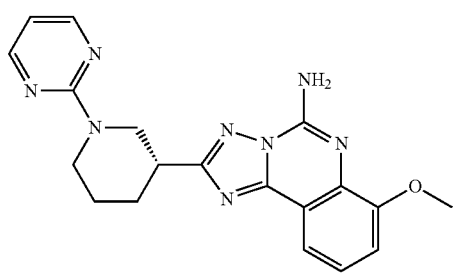
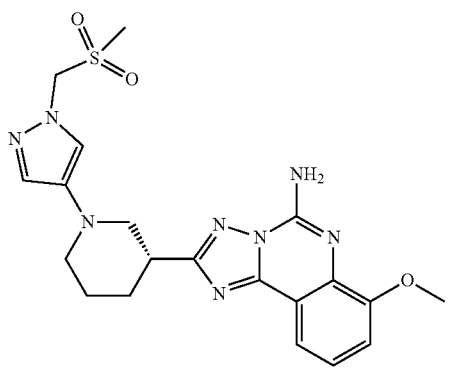
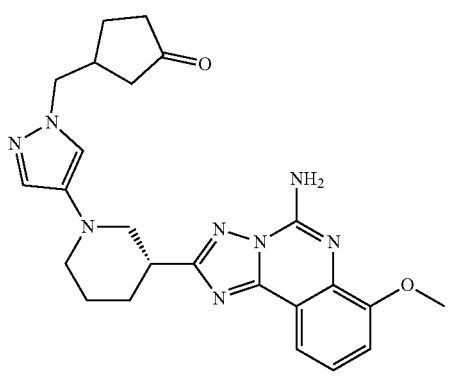
358
-continued
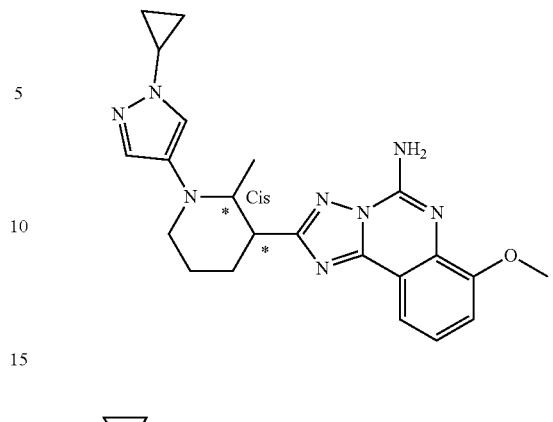
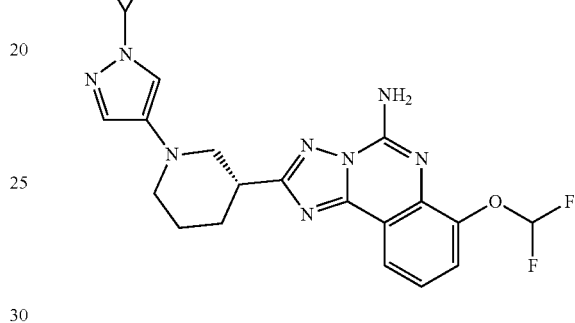
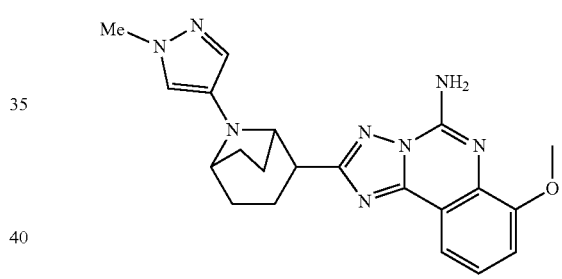
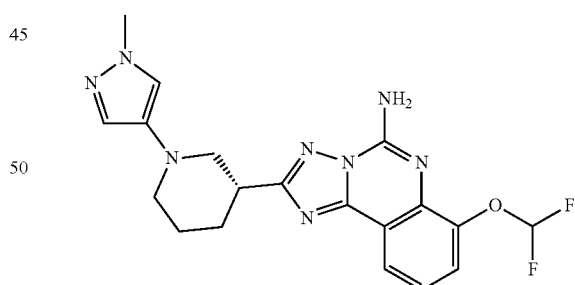
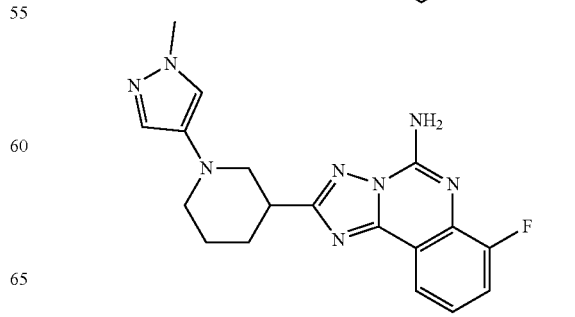

359
-continued
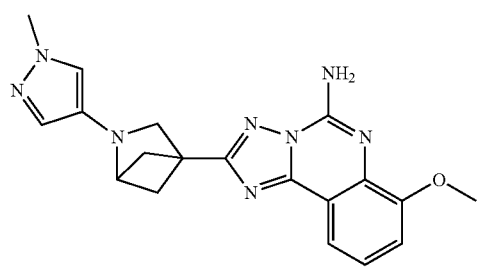
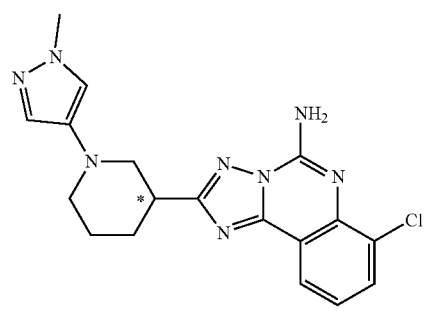
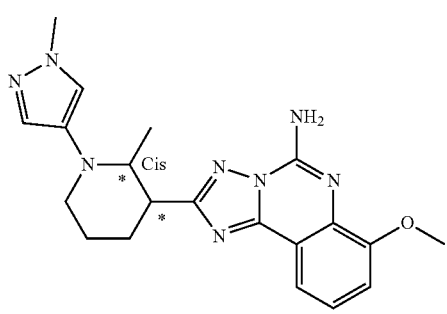
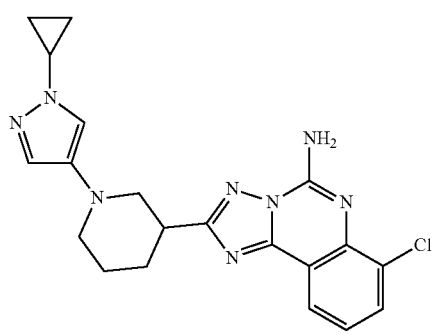
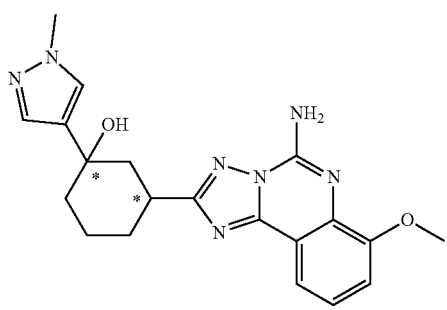
360
-continued
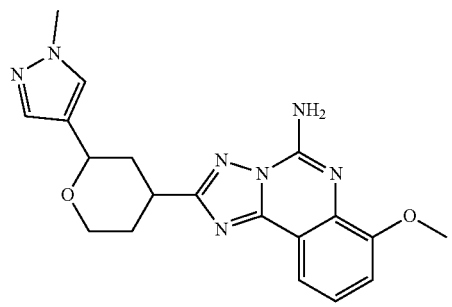
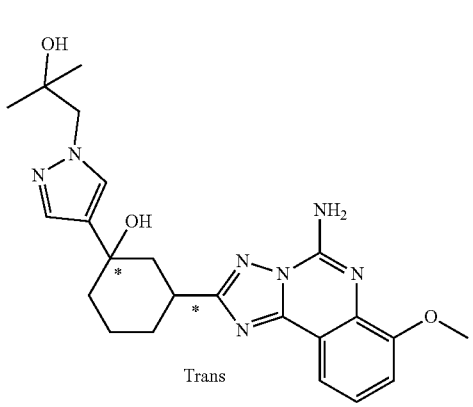
Trans
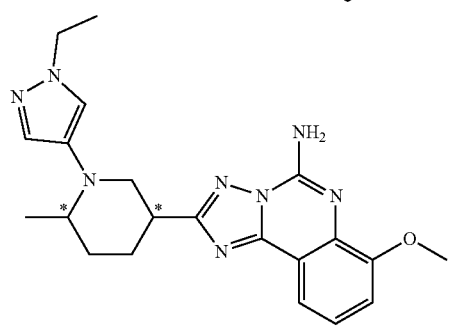
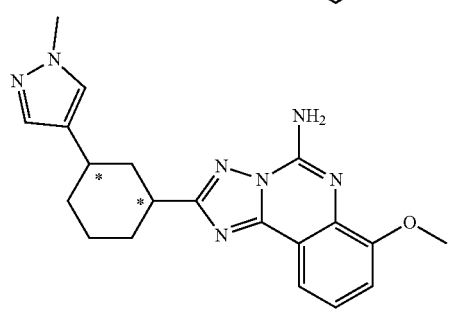
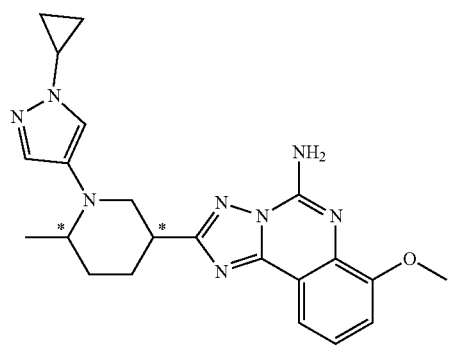

361
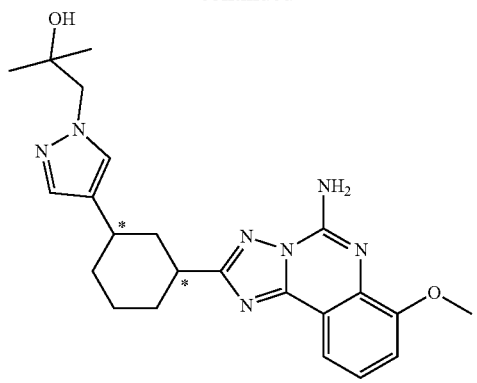
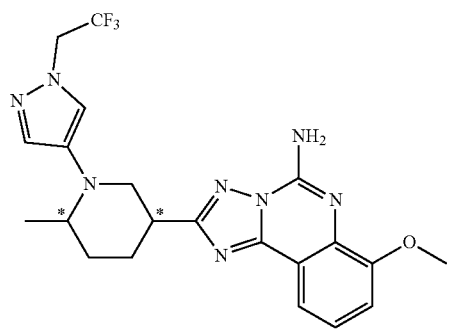
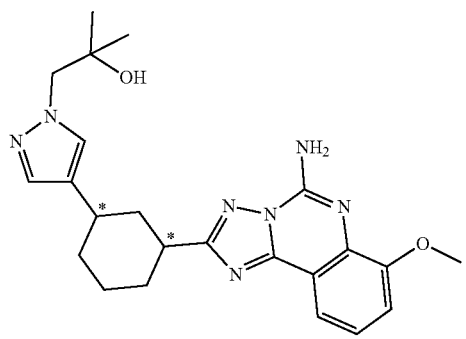
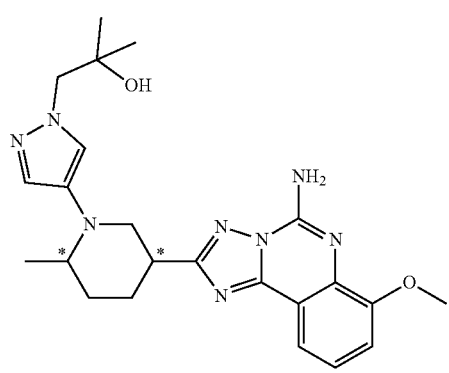
362
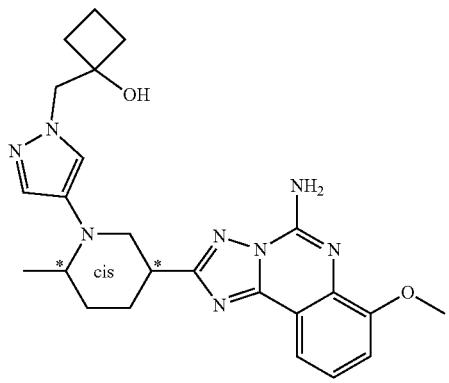
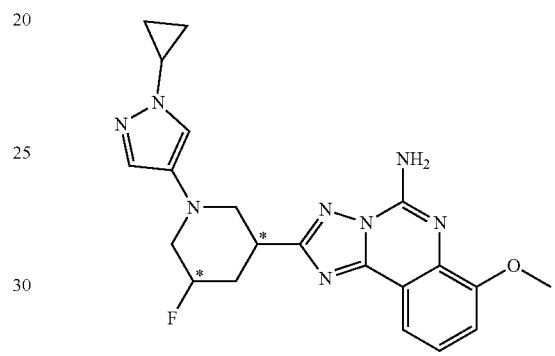
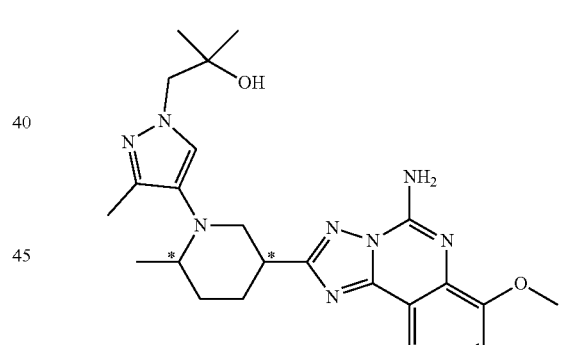
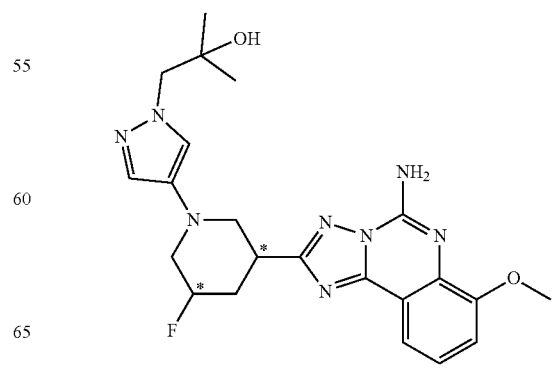

363
-continued
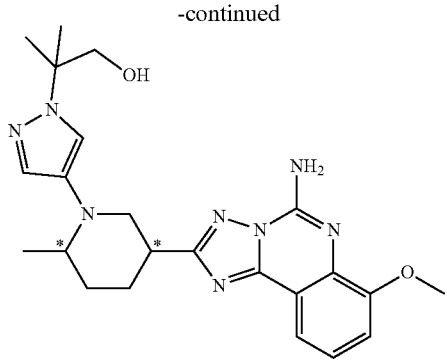
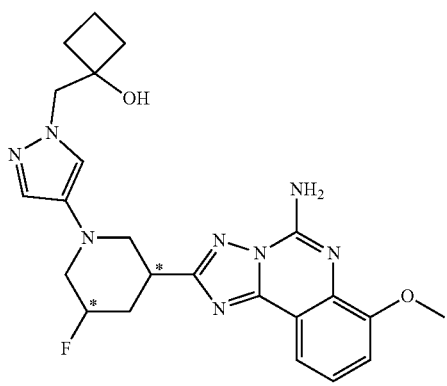
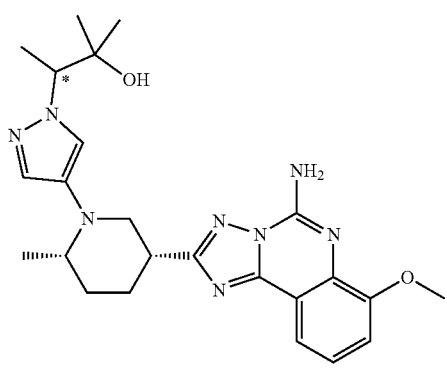
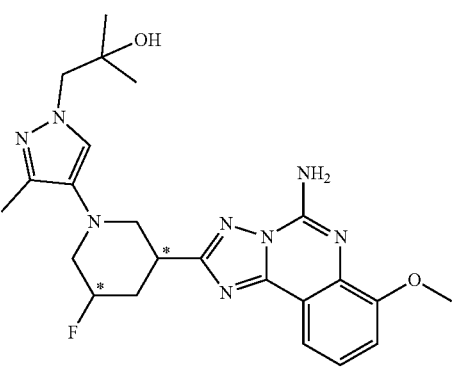
364
-continued
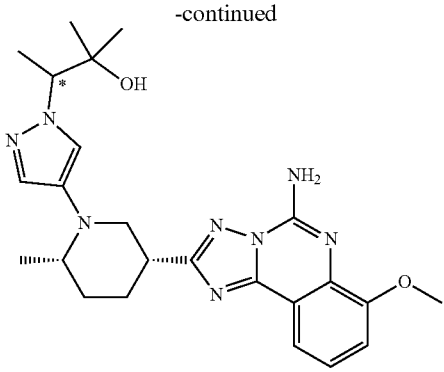
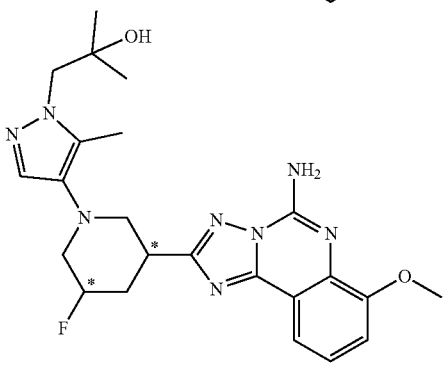
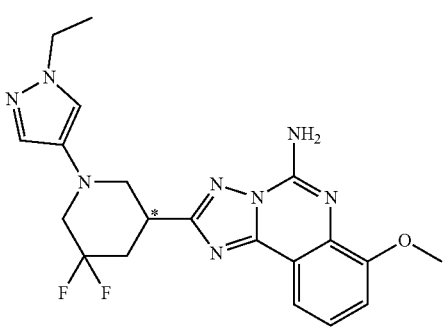
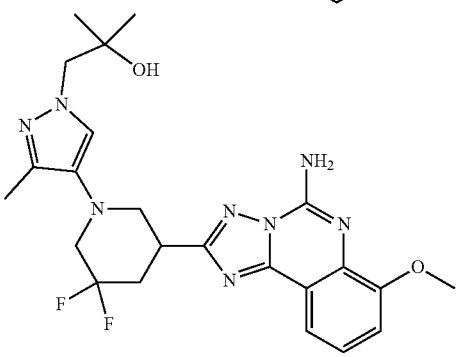
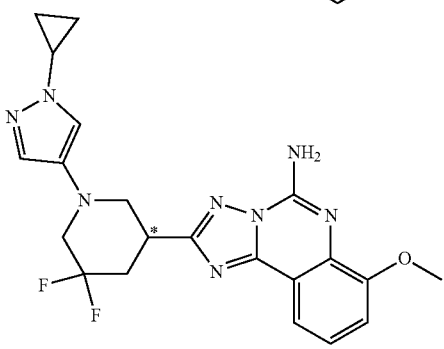

365
-continued
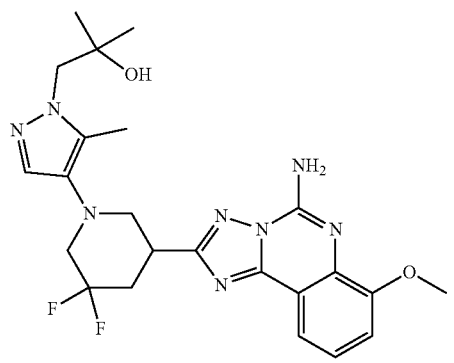
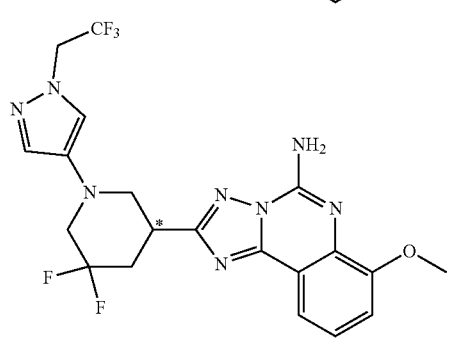
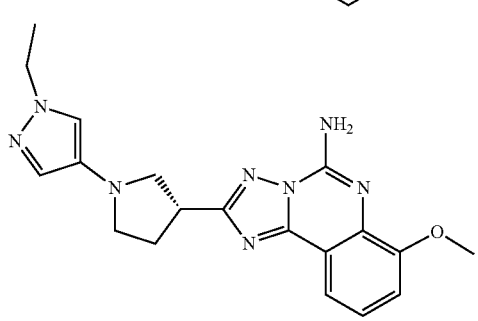
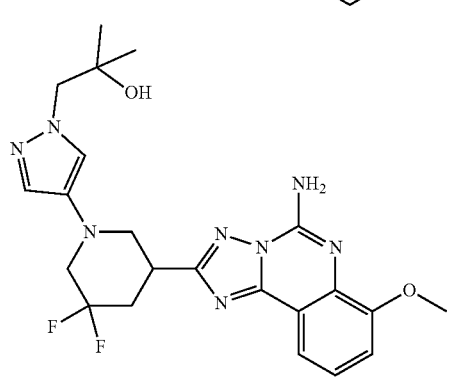
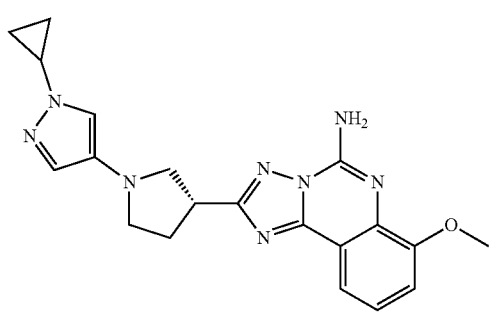
366
-continued
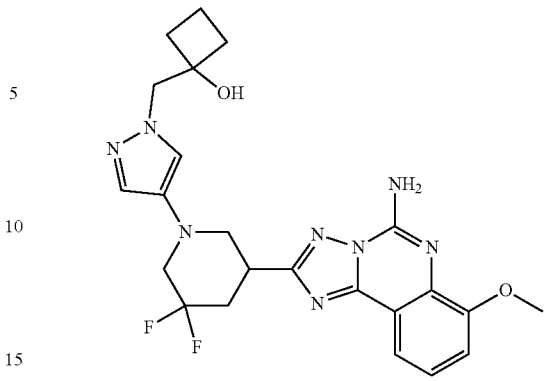
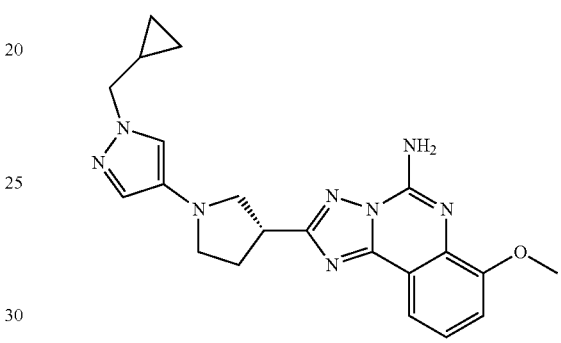
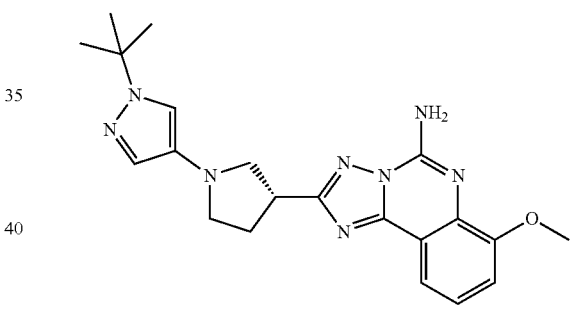
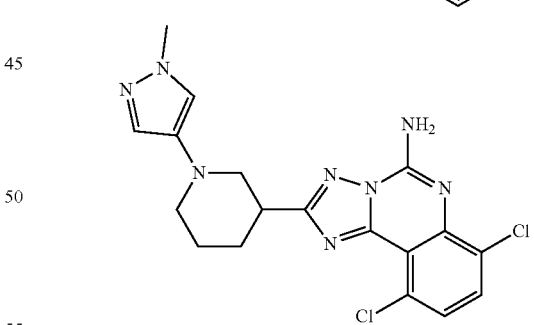
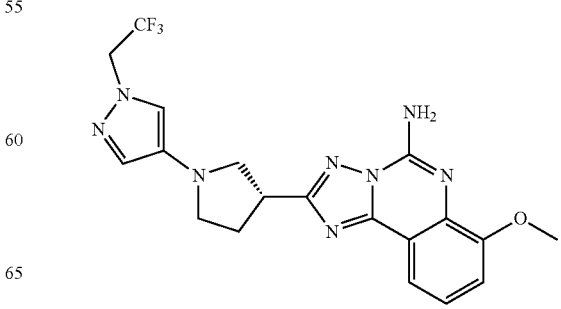

367
-continued
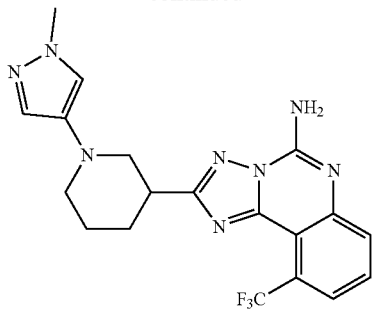
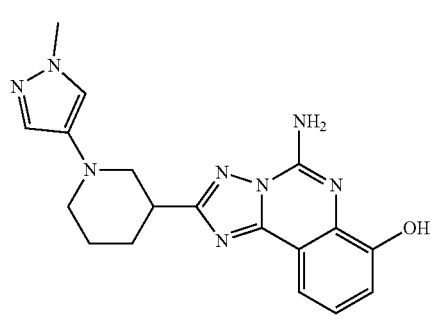
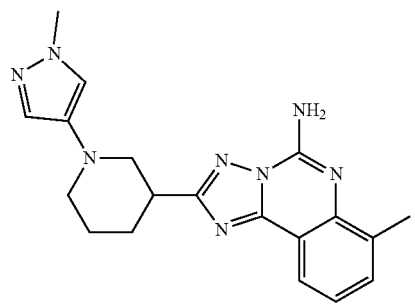
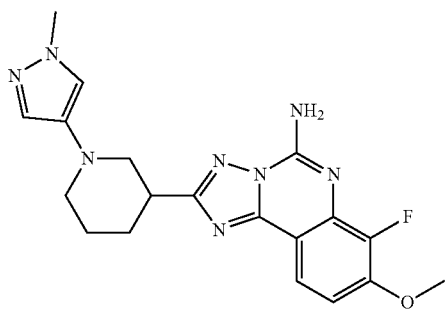
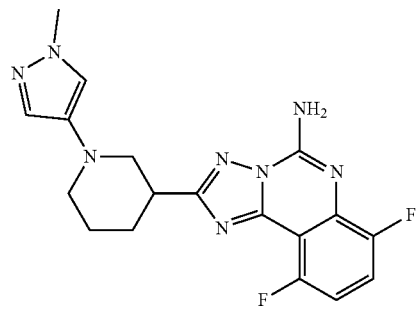
368
-continued
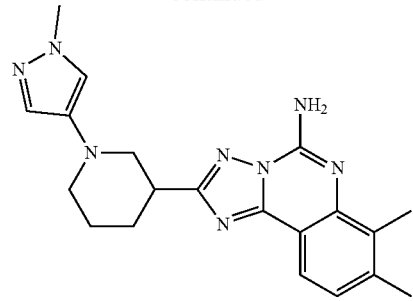
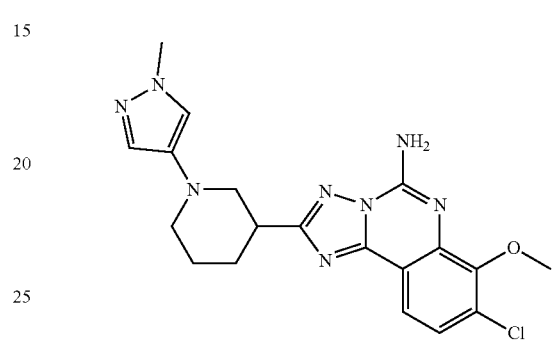
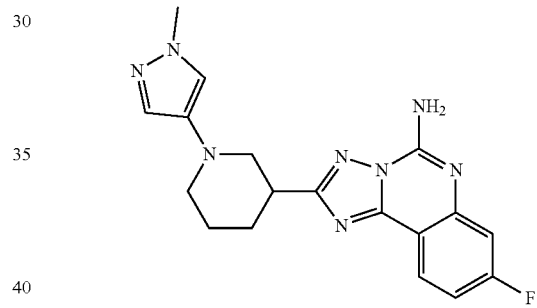
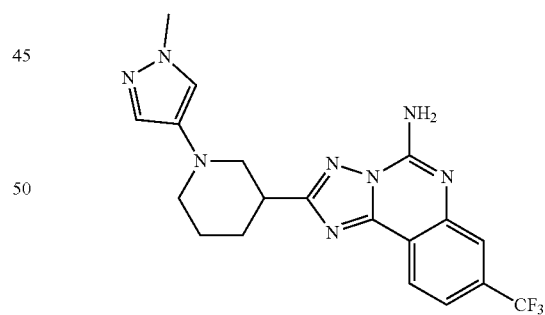
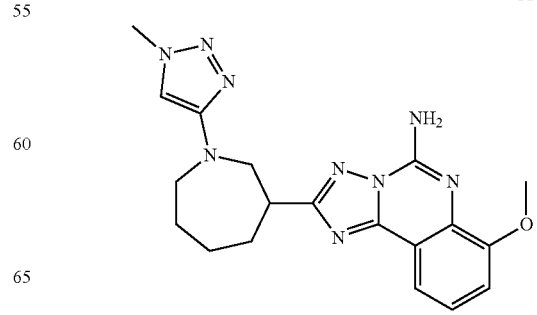

369
-continued
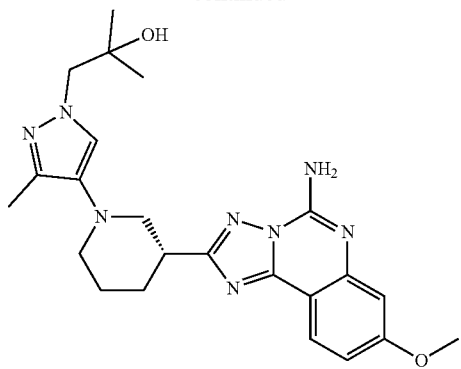
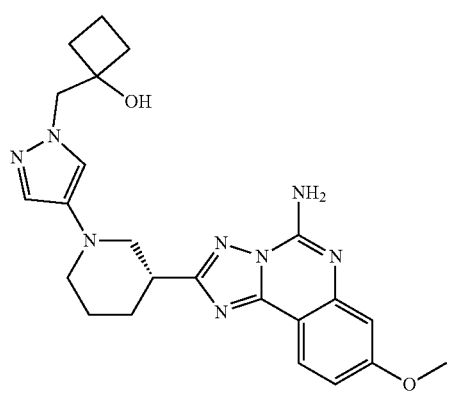
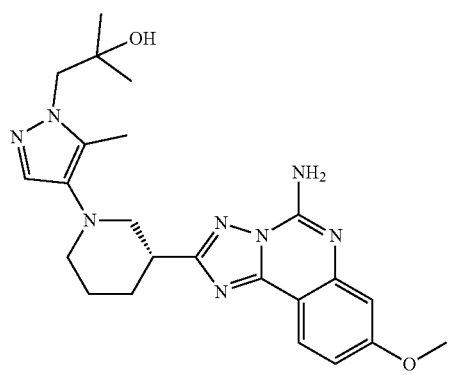
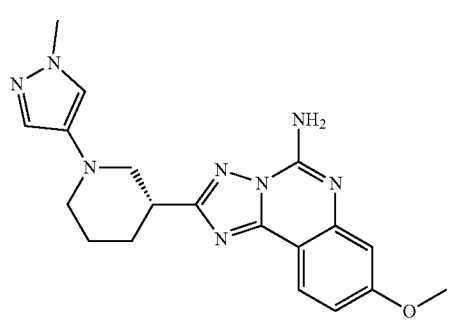
370
-continued
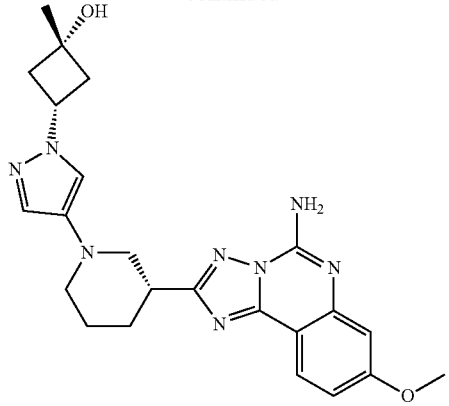
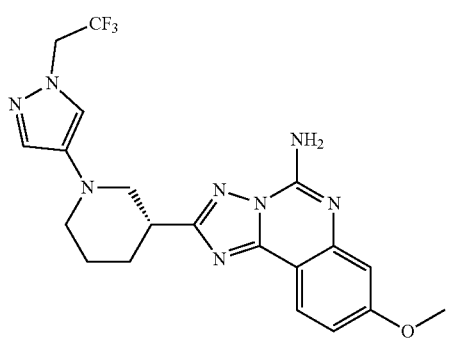
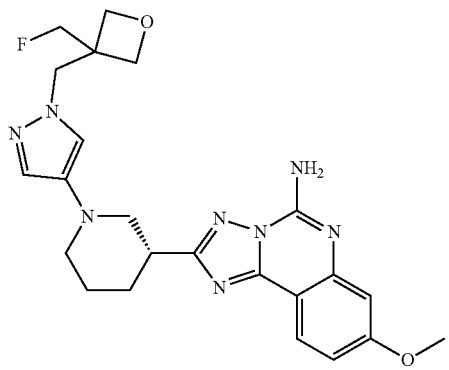
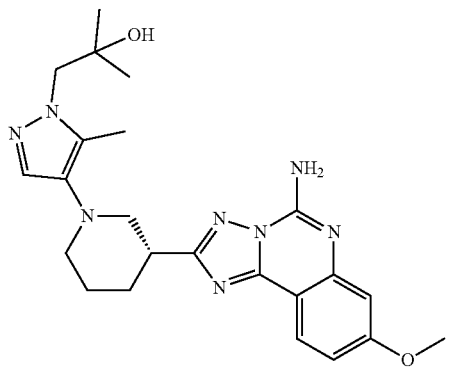

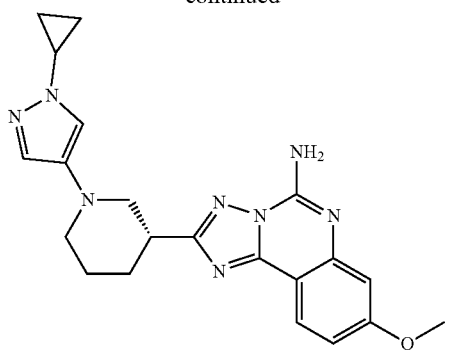
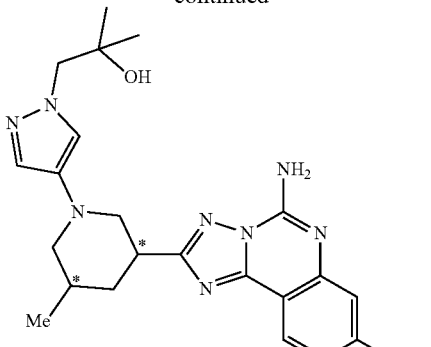
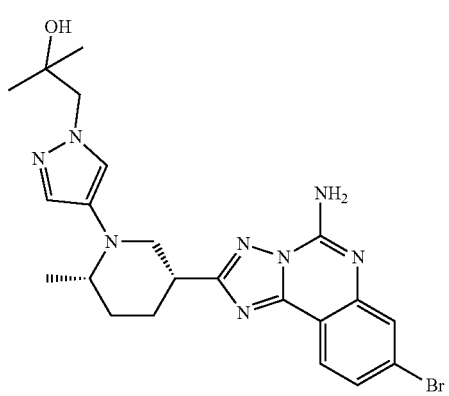
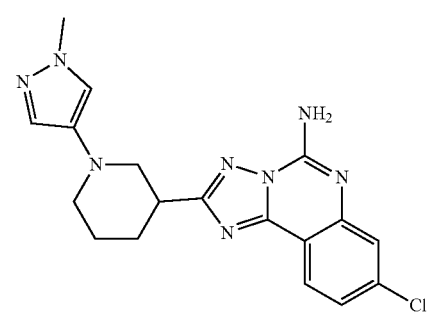
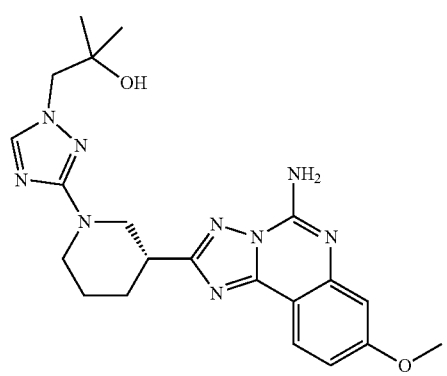
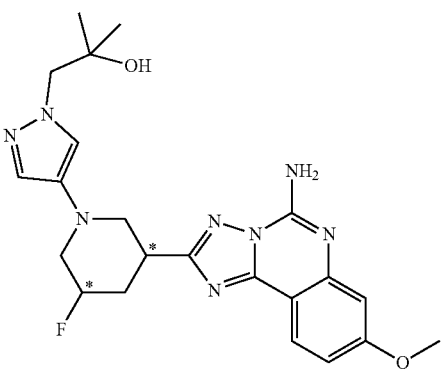
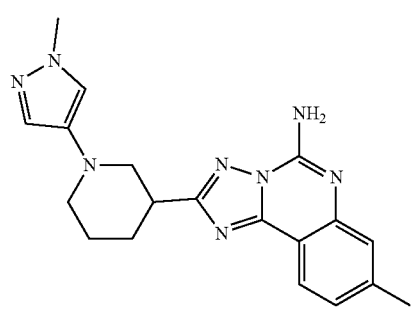
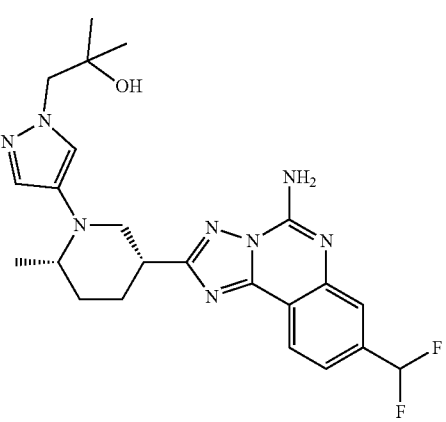

373
-continued
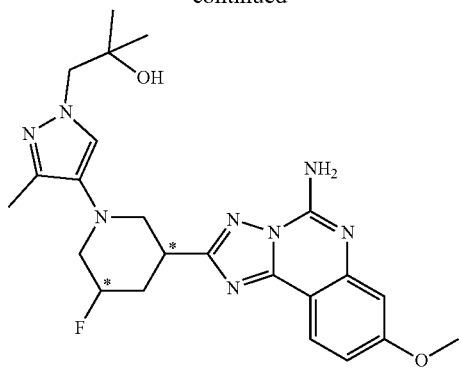
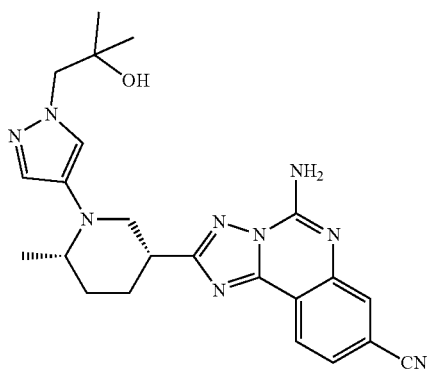
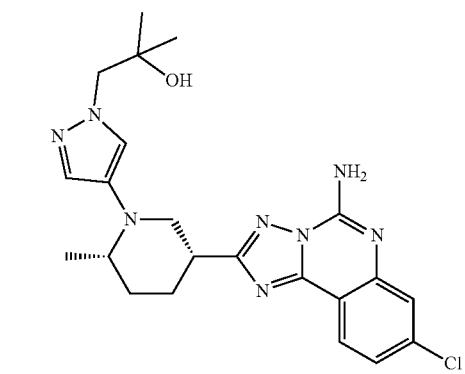
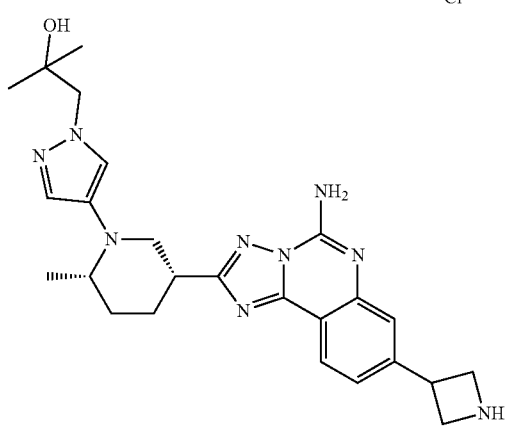
374
-continued
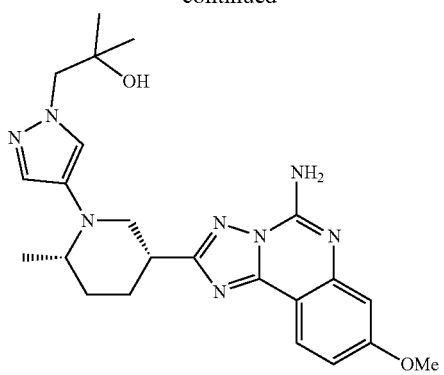
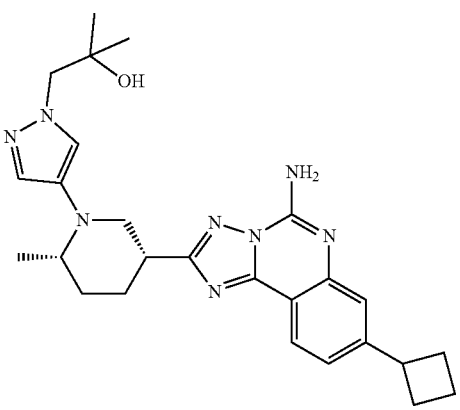
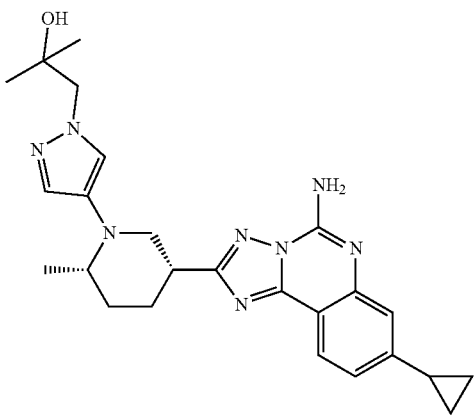
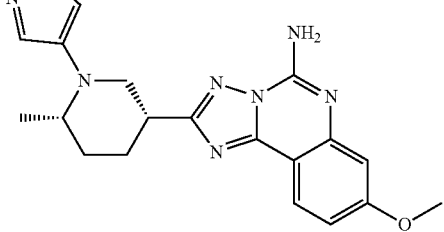

375
-continued
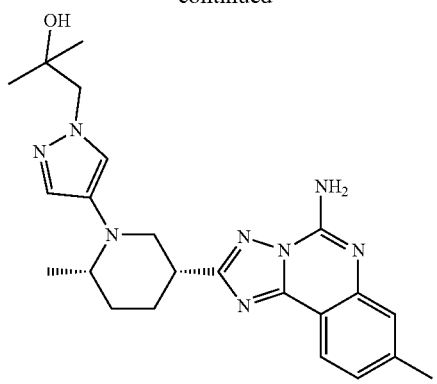
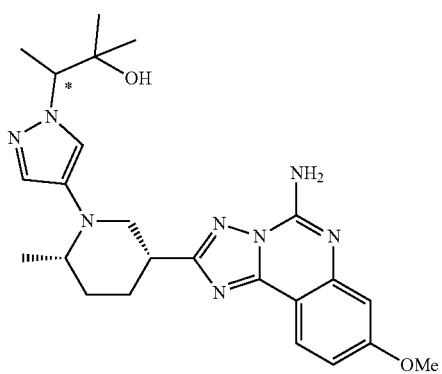
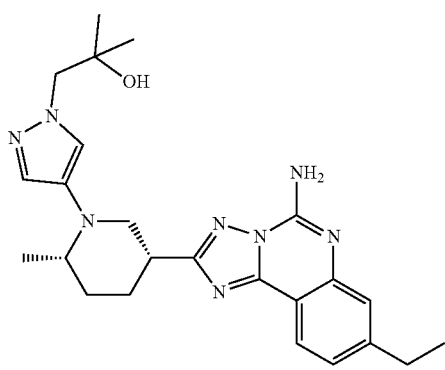
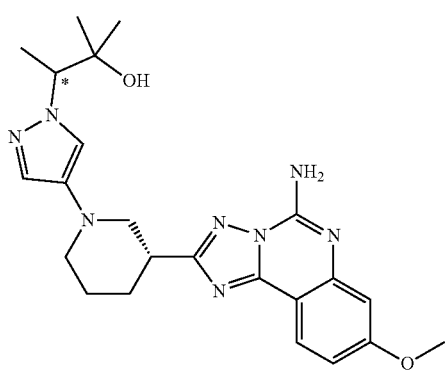
376
-continued
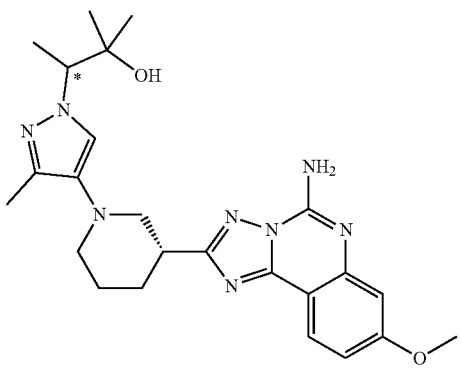
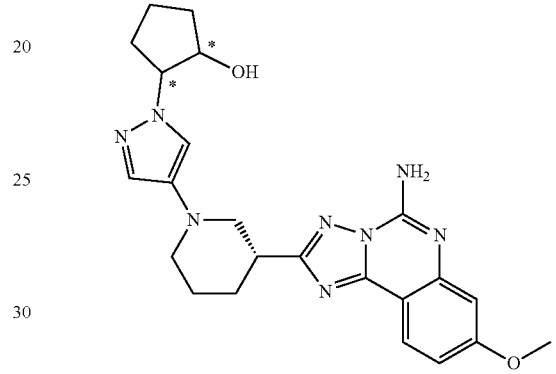
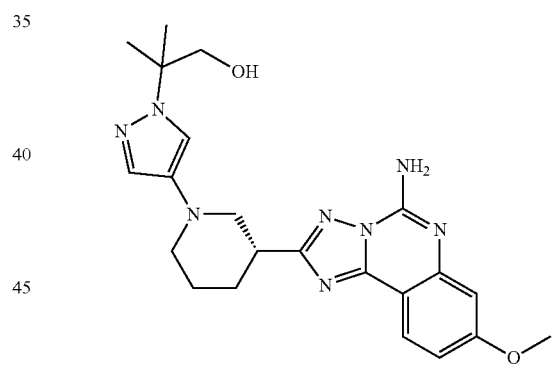
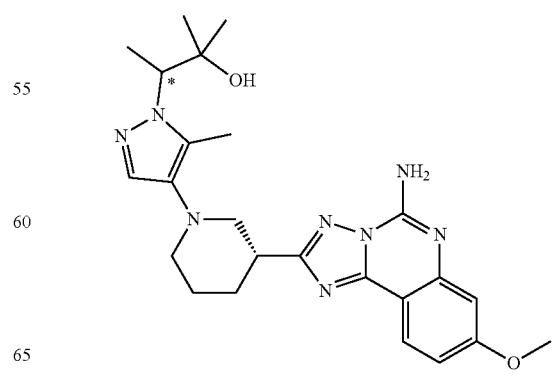

377
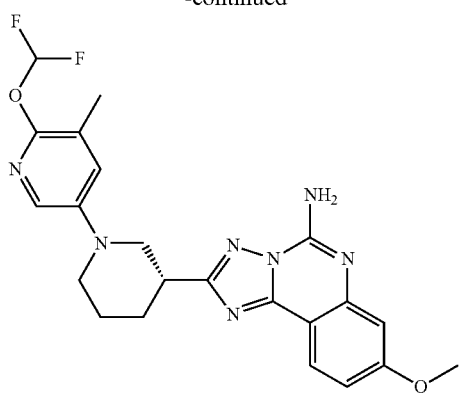
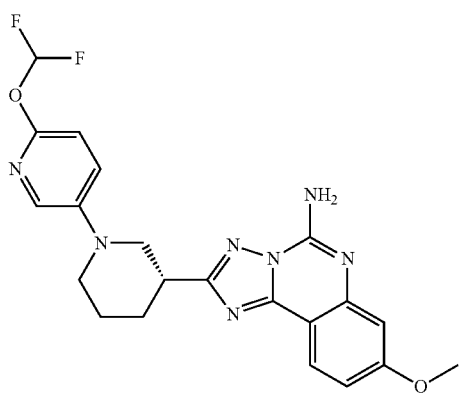
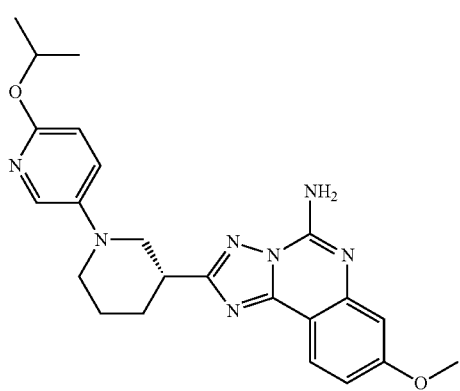
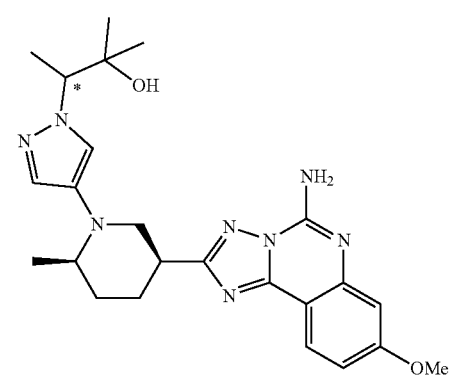
378
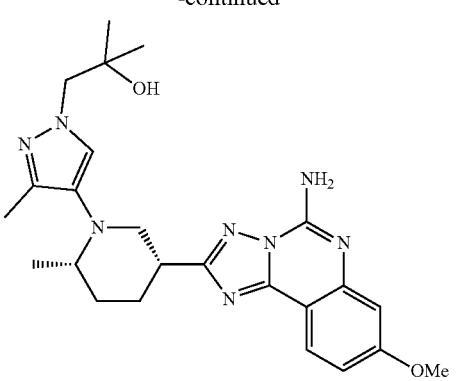
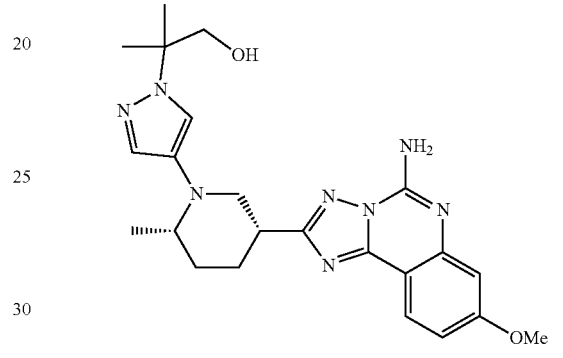
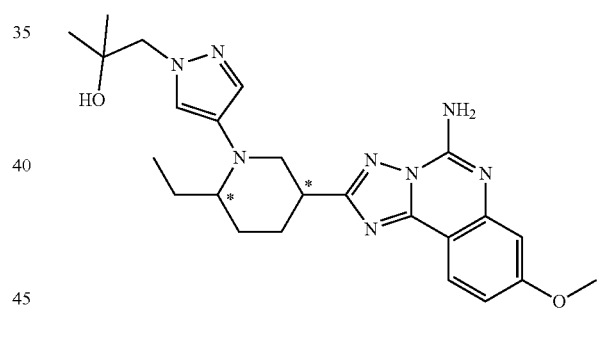
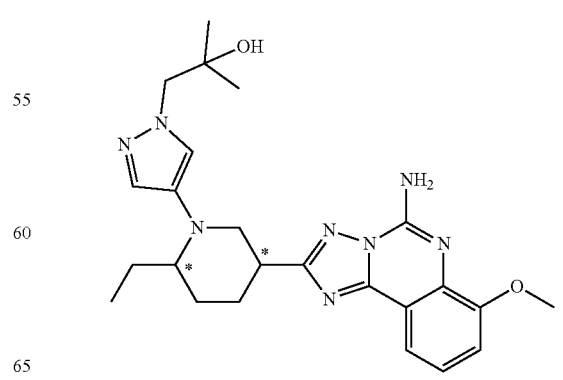

379
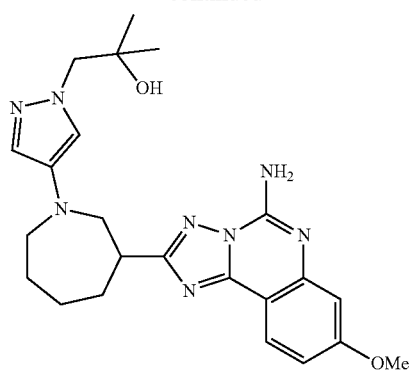
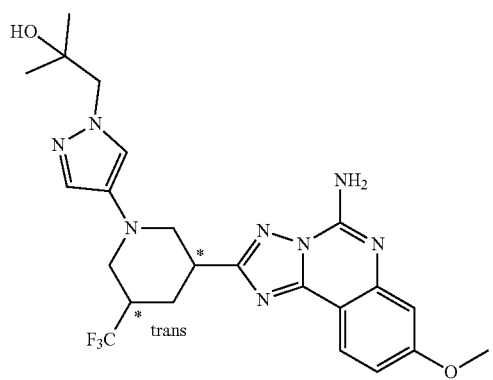
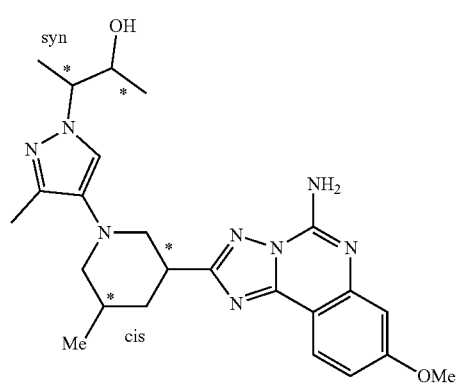
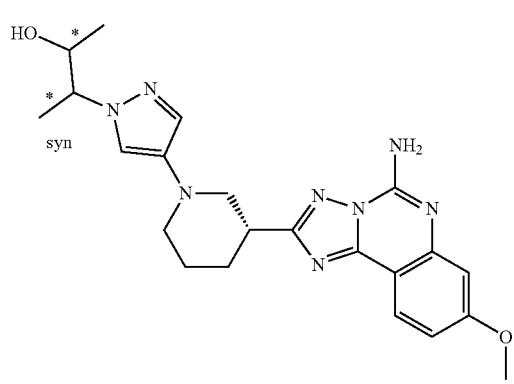
380
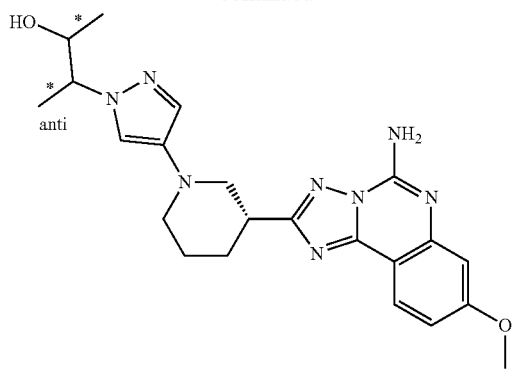
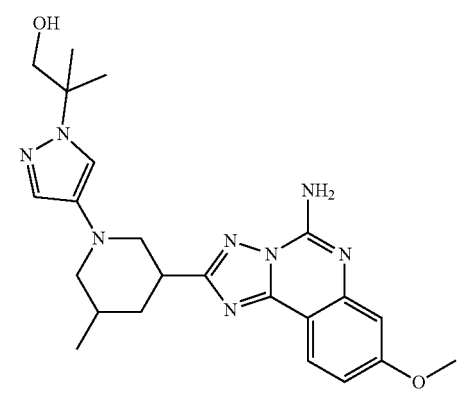
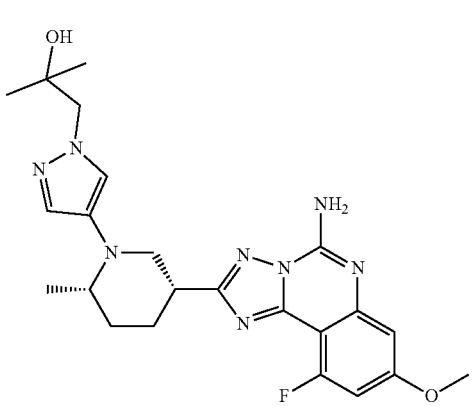
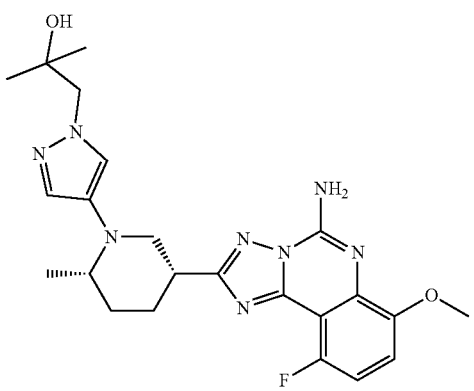

-continued

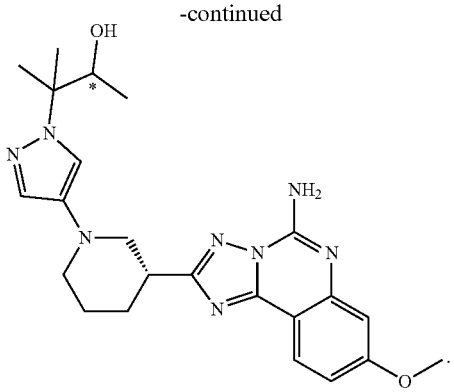

14. A pharmaceutical composition comprising a compound of claim 1, or a pharmaceutically acceptable salt thereof, and a pharmaceutically acceptable carrier.

15. A method of treating cancer wherein the cancer is mediated by the adenosine A2a receptor and/or the adenosine A2b receptor comprising administering an effective amount of a compound of claim 1, or a pharmaceutically acceptable salt thereof, to a person in need thereof.

16. The method of claim 15, wherein said cancer is selected from melanoma, head and neck cancer, classical Hodgkin lymphoma, urothelial carcinoma, gastric cancer, cervical cancer, primary mediastinal large-B-cell lymphoma, microsatellite instability-high cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, salivary cancer, prostate cancer, and metastatic castration resistant prostate cancer.

17. The method of claim 16, wherein said compound, or a pharmaceutically acceptable salt thereof, is administered in combination with another therapeutic agent.

18. The method of claim 17, wherein said additional therapeutic agent is a PD-1 antagonist.

19. The method of claim 18, wherein said additional therapeutic agent is selected from pembrolizumab, nivolumab, atezolizumab, durvalumab, and avelumab.

20. The method of claim 18, wherein said additional therapeutic agent is pembrolizumab.

* * * * *